US012410442B2

(12) United States Patent
Burns et al.

(10) Patent No.: US 12,410,442 B2
(45) Date of Patent: Sep. 9, 2025

(54) COMPOSITIONS AND METHODS FOR TREATING SENSORINEURAL HEARING LOSS USING OTOFERLIN DUAL VECTOR SYSTEMS

(71) Applicants: Decibel Therapeutics, Inc., Boston, MA (US); Regeneron Pharmaceuticals, Inc., Tarrytown, NY (US)

(72) Inventors: Joseph Burns, Newton, MA (US); Kathryn Ellis, Arlington, MA (US); Adam Palermo, Somerville, MA (US); Martin Schwander, Auburndale, MA (US); Jonathon Whitton, Cambridge, MA (US); Leah Sabin, Goldens Bridge, NY (US); Christos Kyratsous, Irvington, NY (US); Meghan Drummond Samuelson, Katonah, NY (US)

(73) Assignees: Regeneron Pharmaceuticals, Inc., Tarrytown, NY (US); Decibel Therapeutics, Inc., Boston, MA (US)

( * ) Notice: Subject to any disclaimer, the term of this patent is extended or adjusted under 35 U.S.C. 154(b) by 976 days.

(21) Appl. No.: 17/395,711

(22) Filed: Aug. 6, 2021

(65) Prior Publication Data

US 2021/0395781 A1     Dec. 23, 2021

Related U.S. Application Data

(63) Continuation of application No. PCT/US2020/017257, filed on Feb. 7, 2020.

(60) Provisional application No. 62/965,770, filed on Jan. 24, 2020, provisional application No. 62/928,279, filed on Oct. 30, 2019, provisional application No. 62/802,890, filed on Feb. 8, 2019.

(51) Int. Cl.
*C12N 15/80*   (2006.01)
*A61K 48/00*   (2006.01)
*C07K 14/705*  (2006.01)
*C12N 15/86*   (2006.01)

(52) U.S. Cl.
CPC ............ *C12N 15/86* (2013.01); *A61K 48/005* (2013.01); *C07K 14/705* (2013.01); *C12N 2800/40* (2013.01); *C12N 2830/008* (2013.01); *C12N 2840/44* (2013.01)

(58) Field of Classification Search
CPC .............. C12N 15/86; C12N 2800/40; C12N 2830/008; C12N 15/52; C12N 15/902; C12N 2750/14144; C12N 2830/50; C12N 2800/50; A61K 35/761; A61K 31/711; C07K 14/4716; C07K 14/50; C12Y 301/03001; C12Y 402/01011; C12Y 207/10001

USPC ........................................................ 435/320.1
See application file for complete search history.

(56) References Cited

U.S. PATENT DOCUMENTS

| 6,436,392 | B1 | 8/2002 | Engelhardt et al. |
|---|---|---|---|
| 6,544,786 | B1 | 4/2003 | Xiao et al. |
| 6,808,922 | B1 | 10/2004 | Bebbington et al. |
| 6,897,045 | B2 | 5/2005 | Engelhardt et al. |
| 7,803,622 | B2 | 9/2010 | Engelhardt et al. |
| 8,236,557 | B2 | 8/2012 | Dongsheng et al. |
| 8,298,818 | B2 | 10/2012 | Boye et al. |
| 10,214,572 | B2 | 2/2019 | Boye et al. |
| 11,325,956 | B2 | 5/2022 | Boye et al. |
| 11,525,139 | B2 | 12/2022 | Simons et al. |
| 11,660,353 | B2 | 5/2023 | Burns et al. |
| 11,781,145 | B2 | 10/2023 | Simons et al. |
| 11,807,867 | B2 | 11/2023 | Simons et al. |
| 12,188,041 | B2 | 1/2025 | Dyka et al. |
| 12,233,136 | B2 | 2/2025 | Burns et al. |
| 2003/0219741 | A1 | 11/2003 | Isogai et al. |
| 2004/0072154 | A1 | 4/2004 | Morris et al. |
| 2007/0161031 | A1 | 7/2007 | Trinklein et al. |
| 2007/0161110 | A1 | 7/2007 | Iida et al. |
| 2008/0249052 | A1 | 10/2008 | Duan et al. |
| 2010/0003218 | A1 | 1/2010 | Duan et al. |
| 2010/0266551 | A1 | 10/2010 | Richard et al. |
| 2012/0003190 | A1 | 1/2012 | Yamoah et al. |

(Continued)

FOREIGN PATENT DOCUMENTS

| WO | WO-01/25465 A1 | 4/2001 |
|---|---|---|
| WO | WO-2001/070972 A2 | 9/2001 |

(Continued)

OTHER PUBLICATIONS

Liang et al., "Characterization of the Human and Mouse Unconventional Myosin XV Genes Responsible for Hereditary Deafness DFNB3 and Shaker 2," Genomics. 61(3):243-258 (1999).

(Continued)

*Primary Examiner* — Robert B Mondesi
*Assistant Examiner* — Mohammad Y Meah
(74) *Attorney, Agent, or Firm* — Clark & Elbing LLP

(57) ABSTRACT

The disclosure features compositions and methods for the treatment of sensorineural hearing loss and auditory neuropathy, particularly forms of the disease that are associated with mutations in otoferlin (OTOF), by way of OTOF gene therapy. The disclosure provides a variety of compositions that include a first nucleic acid vector that contains a polynucleotide encoding an N-terminal portion of an OTOF protein and a second nucleic acid vector that contains a polynucleotide encoding a C-terminal portion of an OTOF protein. These vectors can be used to increase the expression of OTOF in a subject, such as a human subject suffering from sensorineural hearing loss.

19 Claims, 25 Drawing Sheets

Specification includes a Sequence Listing.

(56) References Cited

U.S. PATENT DOCUMENTS

| | | |
|---|---|---|
| 2012/0087862 A1 | 4/2012 | Hood et al. |
| 2013/0210895 A1 | 8/2013 | Boye et al. |
| 2014/0249208 A1 | 9/2014 | Bancel et al. |
| 2014/0256802 A1 | 9/2014 | Boye et al. |
| 2015/0065562 A1 | 3/2015 | Yazicioglu et al. |
| 2015/0209406 A1 | 7/2015 | Chen |
| 2016/0022836 A1 | 1/2016 | Banfi et al. |
| 2016/0076054 A1 | 3/2016 | Auricchio et al. |
| 2018/0015172 A1 | 1/2018 | Muzyczka et al. |
| 2018/0055908 A1 | 3/2018 | Petit et al. |
| 2018/0327779 A1 | 11/2018 | Colella et al. |
| 2019/0002916 A1 | 1/2019 | Kalatzis et al. |
| 2019/0153050 A1 | 5/2019 | Boye et al. |
| 2019/0185864 A1 | 6/2019 | Simons et al. |
| 2019/0309326 A1 | 10/2019 | Maclaren et al. |
| 2020/0155705 A1 | 5/2020 | Burns et al. |
| 2020/0157573 A1 | 5/2020 | Boye et al. |
| 2021/0130421 A1 | 5/2021 | Boye et al. |
| 2021/0236654 A1 | 8/2021 | Burns et al. |
| 2021/0388045 A1 | 12/2021 | Burns et al. |
| 2021/0395778 A1 | 12/2021 | Dyka et al. |
| 2022/0064671 A1 | 3/2022 | Maranga et al. |
| 2022/0265865 A1 | 8/2022 | Burns et al. |
| 2023/0149565 A1 | 5/2023 | Boye et al. |
| 2024/0011039 A1 | 1/2024 | Simons et al. |
| 2024/0131186 A1 | 4/2024 | Burns et al. |
| 2024/0148905 A1 | 5/2024 | Palermo et al. |
| 2024/0309399 A1 | 9/2024 | Hu et al. |

FOREIGN PATENT DOCUMENTS

| | | | |
|---|---|---|---|
| WO | WO-2008/088895 A2 | 7/2008 | |
| WO | WO-2009/100438 A2 | 8/2009 | |
| WO | WO-2013/075008 A1 | 5/2013 | |
| WO | WO-2013/158879 A1 | 10/2013 | |
| WO | WO-2014/140051 A1 | 9/2014 | |
| WO | WO-2014/170480 A1 | 10/2014 | |
| WO | WO-2014/193716 A2 | 12/2014 | |
| WO | WO-2016/131981 A1 | 8/2016 | |
| WO | WO-2016/139321 A1 | 9/2016 | |
| WO | WO-2017/049252 A1 | 3/2017 | |
| WO | WO-2017/100791 A1 | 6/2017 | |
| WO | WO-2017/216560 A1 | 12/2017 | |
| WO | WO-2018/039375 A1 | 3/2018 | |
| WO | WO-2018/145111 A1 | 8/2018 | |
| WO | WO-2018/162748 A1 | 9/2018 | |
| WO | WO-2018/204734 A1 | 11/2018 | |
| WO | WO-2019/162396 A1 | 8/2019 | |
| WO | WO-2019/165292 A1 | 8/2019 | |
| WO | WO-2019/183641 A1 | 9/2019 | |
| WO | WO-2020/093018 A1 | 5/2020 | |
| WO | WO-2020/097372 A1 | 5/2020 | |
| WO | WO-2020/148458 A1 | 7/2020 | |
| WO | WO-2021/087296 A1 | 5/2021 | |
| WO | WO-2024/173835 A2 | 8/2024 | |

OTHER PUBLICATIONS

Yuhe, Liu, "Preparation of adeno-associated virus vector and its application in cochlea transgenic research," Chinese Journal of Otology. 4(4):343-347 (2006) (6 pages).

Hirsch et al., "Delivering Transgenic DNA Exceeding the Carrying Capacity of AAV Vectors," available in PMC Aug. 3, 2016, published in final edited form as: Methods Mol Biol. 13382:21-39 (2016) (20 pages).

Majewski and Ott, "GT Repeats Are Associated with Recombination on Human Chromosome 22," Genome Res. 10(8): 1108-1144 (Aug. 2000) (7 pages).

Lostal et al., "Full-Length Dystrophin Reconstitution with Adeno-Associated Viral Vectors, " Human Gene Ther. 25(6): 552-562 (Jun. 2014) (11 pages).

Gao et al., "The Dystrophin Complex: structure, function and implications for therapy," available in PMC Jul. 1, 2016, published in final edited form as: Compr Physiol. 5(3): 1223-1239 (Jul. 2015) (33 pages).

Dyka et al., "Dual adeno-associated virus vectors result in efficient in vitro and in vivo expression of an oversized gene, MYO7A," Human Gene Ther Methods. 25(2): 166-77 (Apr. 2014) (12 pages).

Pryadkina et al., "A comparison of AAV strategies distinguishes overlapping vectors for efficient systemic delivery of the 6.2 kb Dysferlin coding sequence," Mol Ther Methods Clin Dev. 2: 15009 (Mar. 2015) (12 pages).

Geleoc et al., "Sound strategies for hearing restoration," available in PMC Aug. 29, 2014, published in final edited form as: Science. 344(6184):1241062 (May 2014) (20 pages).

Al-Moyed et al., "A dual-AAV approach restores fast exocytosis and partially rescues auditory function in deaf otoferlin knock-out mice," EMBO Mol Med. 11(1):e9396 (2019) (13 pages).

GenBank Accession No. JN953192.1, "Mus musculus targeted KO-first, conditional ready, lacZ-tagged mutant allele Myo15:tm1a(EUCOMM)Wtsi; transgenic," retrieved from <https://www.ncbi.nlm.nih.gov/nuccore/JN953192>, dated Nov. 5, 2011 (11 pages).

Caberlotto et al., "Usher type 1G protein sans is a critical component of the tip-link complex, a structure controlling actin polymerization in stereocilia," Proc Natl Acad Sci U S A. 108(14):5825-30 (2011) (14 pages).

Schlabach et al., "Synthetic design of strong promoters," Proc Natl Acad Sci U S A. 107(6):2538-43 (2010).

International Search Report and Written Opinion for International Application No. PCT/US2019/029366, mailed Sep. 10, 2019 (17 pages).

Boëda et al., "A specific promoter of the sensory cells of the inner ear defined by transgenesis," Hum Mol Genet. 10(15):1581-1589 (2001).

Belyantseva et al., "Myosin XVa localizes to the tips of inner ear sensory cell stereocilia and is essential for staircase formation of the hair bundle," Proc Natl Acad Sci U S A. 100(24):13958-63 (2003).

GenBank Accession No. JN957158.1, "Mus musculus targeted non-conditional, lacZ-tagged mutant allele Myo15:tm1e(EUCOMM) Wtsi; transgenic," retrieved from <https://www.ncbi.nlm.nih.gov/nucleotide/JN957158.1>, dated Nov. 5, 2011 (12 pages).

International Search Report and Written Opinion for International Patent Application No. PCT/US2020/017292, mailed Jun. 26, 2020 (18 pages).

Akil et al., "Dual AAV gene therapy restores hearing in a mouse model for human genetic Deafness," International Symposium on Inner Ear Therapies (ISIET), Marrakech, Morocco. 21 (2017) (Abstract only).

Akil et al., "Dual AAV-mediated gene therapy restores hearing in a DFNB9 mouse model," Proc Natl Acad Sci U S A. 116(10):4496-4501 (2019).

Al-Moyed et al., "A dual AAV viral vector approach partially restores exocytosis and rescues hearing in deaf otoferlin knock-out mice," ARO Abstracts. 41:76 (2018) (Abstract only).

Alemi, "Progress Report: AOS Research Grant: Restoration of Hearing in the Otoferlin Knockout Mouse using Viral Gene Therapy," 145th Annual Meeting of the American Otological Society, Inc, Apr. 21-22, San Diego, California. 68 (2012) (Abstract only).

Choi et al., "Identities and frequencies of mutations of the otoferlin gene (OTOF) causing DFNB9 deafness in Pakistan," available in PMC Oct. 1, 2012, published in final edited form as: Clin Genet. 75(3):237-243 (2009) (10 pages).

Duan et al., "Expanding AAV Packaging Capacity with Trans-splicing or Overlapping Vectors: A Quantitative Comparison," Mol Ther. 4(4):383-91 (2001).

McClements et al., "Adeno-associated Virus (AAV) Dual Vector Strategies for Gene Therapy Encoding Large Transgenes," Yale J Biol Med. 90(4):611-623 (2017).

Trapani et al., "Effective delivery of large genes to the retina by dual AAV vectors," EMBO Mol Med. 6(2):194-211 (2014).

Trapani et al., "Improved dual AAV vectors with reduced expression of truncated proteins are safe and effective in the retina of a mouse model of Stargardt disease," Hum Mol Genet. 24(23):6811-25 (2015).

(56) References Cited

OTHER PUBLICATIONS

Yasunaga et al., "*OTOF* Encodes Multiple Long and Short Isoforms: Genetic Evidence That the Long Ones Underlie Recessive Deafness DFNB9," Am J Hum Genet. 67(3):591-600 (2000).
International Search Report and Written Opinion for International Application No. PCT/US2020/017257, mailed Apr. 29, 2020 (22 pages).
Xu et al., "Trans-Splicing Adeno-Associated Viral Vector-Mediated Gene Therapy Is Limited by the Accumulation of Spliced mRNA but Not by Dual Vector Coinfection Efficiency," available in PMC Jun. 19, 2008, published in final edited form as: Hum Gene Ther. 15(9):896-905 (2004) (17 pages).
Ghosh et al., "A Hybrid Vector System Expands Adeno-associated Viral Vector Packaging Capacity in a Transgene-independent Manner," The American Society of Gene Therapy. 16(1):124-130 (2008).
Ghosh et al., "Efficient Transgene Reconstitution with Hybrid Dual AAV Vectors Carrying the Minimized Bridging Sequences," Hum Gene Ther. 22(1):77-83 (2011).
International Search Report and Written Opinion for International Patent Application No. PCT/US2020/058265, mailed Feb. 8, 2021 (15 pages).
Michalski et al., "Genetics of auditory mechano-electrical transduction," Pflugers Arch. 467(1):49-72 (2015).
Skarnes et al., "A conditional knockout resource for the genome-wide study of mouse gene function," available in PMC Feb. 14, 2013, published in final edited form as: Nature. 474(7351):337-342 (2011) (18 pages).
Boye et al., "Transduction and Tropism of an Abbreviated Form of CMV-Chicken B-Actin Promoter (CBA) With AAV in Mouse Retina," ARVO Annual Meeting Abstract May 2006, published in: Investigative Ophthalmology & Visual Science. 47: 852 (2006) (2 pages) (Abstract only).
Lovell, "Mouse DNA sequence from clone RP23-135F6 on chromosome 11," European Nucleotide Archive, EMBL-EBI. (2012) (15 pages).
Higashimoto et al., "The woodchuck hepatitis virus post-transcriptional regulatory element reduces readthrough transcription from retroviral vectors," Gene Ther. 14(17):1298-304 (2007).
Wang, Aihui, Dissertation: "Molecular Cloning of an Unconventional Myosin MYO15 and the Identification of Mutations of MYO15 Responsible for Human Nonsyndromic Deafness DFNB3," Doctor of Philosophy, Graduate Program in Genetics, Michigan State University (1999) (140 pages).
Corns et al., "Mechanotransduction is required for establishing and maintaining mature inner hair cells and regulating efferent innervation," Nat Commun. 9(1):4015 (Oct. 2018) (15 pages).
International Search Report and Written Opinion for PCT/US2022/017058, dated Jun. 14, 2022 (14 pages).
Yoshimura et al., "Enhanced viral-mediated cochlear gene delivery in adult mice by combining canal fenestration with round window membrane inoculation," Scientific Reports. 8:2980 (with supplemental material) (Feb. 2018) (14 pages).
Pangrsic et al., "Otoferlin: a multi-$C_2$ domain protein essential for hearing," Trends in Neurosciences. 35(11): 671-680 (2012) (10 pages).
Holt et al., "Split otoferlin reunited," EMBO Molecular Medicine. 11:(1)e9995 (Jan. 2019) (3 pages).
Suzuki et al., "Cochlear gene therapy with ancestral AAV in adult mice: complete transduction of inner hair cells without cochlear dysfunction," Scientific Reports. 7(1):45524 (Apr. 2017) (11 pages).
Tertrais et al., "Viral Transfer of Mini-Otoferlins Partially Restores the Fast Component of Exocytosis and Uncovers Ultrafast Endocytosis in Auditory Hair Cells of Otoferlin Knock-Out Mice," J. Neurosci. 39(18):3394-3411 (May 2019) (18 pages).
Petrs-Silva et al., "Novel Properties of Tyrosine-mutant AAV2 Vectors in the Mouse Retina," Molecular Therapy. 19(2):293-301 (Feb. 2011) (9 pages).
American Academy of Audiology, "Children's Hospital of Philadelphia Performs First Gene Therapy Procedure to Treat Genetic Hearing Loss in United States," <https://www.audiology.org/childrens-hospital-of-philadelphia-performs-first-gene-therapy-procedure-to-treat-genetic-hearing-loss-in-united-states/>, dated Jan. 26, 2024 (2 pages).
Yoshimura et al., "Targeted Allele Suppression Prevents Progressive Hearing Loss in the Mature Murine Model of Human *TMC1* Deafness," Molecular Therapy. 27(3):681-690 (with supplemental material) (Mar. 2019) (17 pages).
Akil et al., "Surgical Method for Virally Mediated Gene Delivery to the Mouse Inner Ear through the Round Window Membrane," Journal of Visualized Experiments. 97(1):e52187 (Mar. 2015) (7 pages).
Liu et al., "Specific and Efficient Transduction of *Cochlear* Inner Hair Cells with Recombinant Adeno-associated Virus Type 3 Vector," Molecular Therapy. 12(4):725-733 (Oct. 2005) (9 pages).
"Basics of sound, the Ear, and Hearing," *Hearing Loss: Determining Eligibility for Social Security Benefits*. Edited by Robert A. Dobie and Susan Van Hemel, 42-68 (2004) (61 pages).
Akil et al., "AAV-Mediated Gene Delivery to the Inner Ear," *Adeno-Associated Virus Vectors: Design and Delivery*. Methods in Molecular Biology. Edited by Michael J. Castle, 271-282 (2019) [published online on Jan. 1, 2019] (16 pages).
Langouet-Astrie et al., "Characterization of intravitreally delivered capsid mutant AAV2-Cre vector to induce tissue-specific mutations in murine retinal ganglion cells," Experimental Eye Research. 151(1):61-67 (Jul. 2016) (7 pages).
Li et al., "A novel bispecific molecule delivered by recombinant AAV2 suppresses ocular inflammation and choroidal neovascularization," J. Cell. Mol. Med. 21(8):1555-1571 (Aug. 2017) (17 pages).
Lopes-Pacheco et al., "Self-complementary and tyrosine-mutant rAAV vectors enhance transduction in cystic fibrosis bronchial epithelial cells," Experimental Cell Research. 372:99-107 (Sep. 2018) (9 pages).
Petrs-Silva et al., "High-efficiency Transduction of the Mouse Retina by Tyrosine-mutant AAV Serotype Vectors," Molecular Therapy. 17(3):463-471 (Mar. 2009) (9 pages).
Kilpatrick et al., "Adeno-associated virus-mediated gene delivery into the scala media of the normal and deafened adult mouse ear," Gene Therapy. 18(6):569-578 (Jan. 2011) (10 pages).
Tao et al., "Delivery of Adeno-Associated Virus Vectors in Adult Mammalian Inner-Ear Cell Subtypes Without Auditory Dysfunction," Human Gene Therapy. 29(4):492-506 (Nov. 2017) (15 pages).
Zhang et al., "Cochlear Gene Therapy for Sensorineural Hearing Loss: Current Status and Major Remaining Hurdles for Translational Success," Front. Mol. Neurosci. 11(221):1-15 (Jun. 2018) (15 pages).
Roux et al., "Otoferlin, Defective in a Human Deafness Form, Is Essential for Exocytosis at the Auditory Ribbon Synapse," Cell. 127(2):277-289 (Oct. 2006) (13 pages).
"Genetic Hearing Loss With No. Associated Abnormalities," *Hereditary Hearing Loss and Its Syndromes, Third Edition*. Helga V. Toriello and Shelley D. Smith. 164-165 (2013) (4 pages).
Ahmed et al., "Emerging Gene Therapies for Genetic Hearing Loss," JARO. 18(5):649-670 (Aug. 2017) (22 pages).
Zhang et al., "Temperature sensitive auditory neuropathy," Hearing Research. 335(1):53-63 (Jan. 2016) (11 pages).
Hamosh et al. "OTOFERLIN; OTOF," OMIM. (Apr. 2015) (8 pages) retrieved via The Wayback Machine on Jul. 29, 2015, URL: <https://web.archive.org/web/20150729163826/http://omim.org/entry/603681>.
International Search Report and Written Opinion for International Patent Application No. PCT/US2024/016218, mailed Jul. 12, 2024 (19 pages).
Kim et al., "Direct isolation and identification of promoters in the human genome," Genome Res. 15(6):830-9 (Jun. 2005) (11 pages).
U.S. Appl. No. 17/290,082, Dyka et al.
U.S. Appl. No. 16/952,016, Boye et al.
U.S. Appl. No. 17/916,308, Boye et al.
GenPept Accession NP_001274418.1, dated Apr. 23, 2017, (4 pages) retrieved from https://www.ncbi.nlm.nih.gov/protein/566559996?sat=46&satkey=73202094.
McClements et al., "A fragmented adeno-associated viral dual vector strategy for treatment of diseases caused by mutations in

(56) References Cited

OTHER PUBLICATIONS large genes leads to expression of hybrid transcripts," J Genet Syndr Gene Ther. 7(5):311 (Nov. 14, 2016) (16 pages).
Avraham, "What's hot about otoferlin," Embo J. 35(23):2502-4 (Dec. 1, 2016).
NCBI Reference Sequence: NM_001632.5, "Homo sapiens alkaline phosphatase, placental (ALPP), mRNA" (Apr. 4, 2024) (5 pages).
NCBI Reference Sequence: NP_000251.3, "unconventional myosin-VIIa isoform 1 [Homo sapiens]" (Dec. 11, 2024) (5 pages).
GenBank: U39226.1, "Human myosin Viia (USH1B) mRNA, complete cds" (Jul. 11, 1996) (4 pages).
Akil et al., "Restoration of Hearing in the VGLUT3 Knockout Mouse Using Virally Mediated Gene Therapy," Neuron. 75:283-293 (2012).
Al-Hussaini et al., "Mature retinal pigment epithelium cells are retained in the cell cycle and proliferate in vivo," Mol Vis. 14:1784-91 (2008).
Allocca et al., "Serotype-dependent packaging of large genes in adeno-associated viral vectors results in effective gene delivery in mice," J Clin Invest. 118(5):1955-64 (May 2008) (11 pages).
Chen et al., "Molecular cloning and domain structure of human myosin-VIIa, the gene product defective in Usher syndrome 1B," Genomics 36(3):440-8 (Sep. 15, 1996).
Daya et al., "Gene therapy using adeno-associated virus vectors," Clin Microbiol Rev. 21(4):583-93 (Oct. 2008).
Dong et al., "Characterization of genome integrity for oversized recombinant AAV vector," Mol Ther. 18(1):87-92 (Jan. 2010).
Duan et al., "Circular intermediates of recombinant adeno-associated virus have defined structural characteristics responsible for long-term episomal persistence in muscle tissue," J Virol. 72(11):8568-77 (Nov. 1998).
Hashimoto et al., "Lentiviral gene replacement therapy of retinas in a mouse model for Usher syndrome type 1B," Gene Ther. 14(7):584-94 (Apr. 2007) (21 pages).
Jacobson et al., "Usher syndromes due to MYO7A, PCDH15, USH2A or GPR98 mutations share retinal disease mechanism," Hum Mol Genet. 17(15):2405-15 (Aug. 1, 2008).
Lai et al., "Evidence for the failure of adeno-associated virus serotype 5 to package a viral genome > or = 8.2 kb," Mol Ther. 18(1): 75-9 (Jan. 2010).
Li et al., "High-efficiency transduction of fibroblasts and mesenchymal stem cells by tyrosine-mutant AAV2 vectors for their potential use in cellular therapy," Hum Gene Ther. 21(11):1527-43 (Nov. 2010) (18 pages).
Lopes et al., "Retinal gene therapy with a large MYO7A cDNA using adeno-associated virus," Gene Ther. 20(8):824-33 (Aug. 2013) (21 pages).
Weil et al., "Human myosin VIIA responsible for the Usher 1B syndrome: a predicted membrane-associated motor protein expressed in developing sensory epithelia," Proc Natl Acad Sci USA. 93(8):3232-7 (Apr. 16, 1996).
Wu et al., "Effect of genome size on AAV vector packaging," Mol Ther. 18(1):80-6 (Jan. 2010).
Yan et al., "Inverted terminal repeat sequences are important for intermolecular recombination and circularization of adeno-associated virus genomes," J Virol. 79(1):364-79 (Jan. 2005).
Freni et al., "Cochlear Implant Surgery: Endomeatal Approach versus Posterior Tympanotomy," Int. J. Environ. Res. Public Health 17:4187 (Jun. 2020) (9 pages).
"Types of CFTR Mutations," Cystic Fibrosis Foundation. < https://www.cff.org/research-clinical-trials/types-cftr-mutations#:-:text=>, accessed Mar. 1, 2025 (9 pages).
Barnes et al., "Remarkable Rigidity of the Single a-Helical Domain of Myosin-VI As Revealed by NMR Spectroscopy," J Am Chem Soc. 141(22):9004-9017 (Jun. 2019).
Laine et al., "Cell cycle regulation in the inner ear sensory epithelia: role of cyclin D1 and cyclin-dependent kinase inhibitors," Dev Biol. 337(1):134-46 (Jan. 2010).
Orthwein et al., "A mechanism for the suppression of homologous recombination in G1 cells," Nature. 528(7582):422-6 (Dec. 2015); retraction in: Nature. 638(8051):844 (Feb. 2025) (35 pages).
Regalado et al., "Some deaf children in China can hear after gene therapy treatment," MIT Technology Review. <https://www.technologyreview.com/2023/10/27/1082551/gene-treatment-deaf-children-hearing-china/>, published Oct. 27, 2023 (7 pages).
Zhang et al., "Single amino acid change alters specificity of the multi-allelic wheat stem rust resistance locus SR9," Nat Commun. 14(1):7354 (Nov. 2023) (12 pages).

Dual hybrid: Myo15-hOTOF

Overlapping : Myo15-hOTOF

SEQUENCE LISTING

<160> NUMBER OF SEQ ID NOS: 69

<210> SEQ ID NO 1
<211> LENGTH: 1997
<212> TYPE: PRT
<213> ORGANISM: Homo sapiens

<400> SEQUENCE: 1

Met Ala Leu Leu Ile His Leu Lys Thr Val Ser Glu Leu Arg Gly Arg
1               5                   10                  15

Gly Asp Arg Ile Ala Lys Val Thr Phe Arg Gly Gln Ser Phe Tyr Ser
            20                  25                  30

Arg Val Leu Glu Asn Cys Glu Asp Val Ala Asp Phe Asp Glu Thr Phe
        35                  40                  45

Arg Trp Pro Val Ala Ser Ser Ile Asp Arg Asn Glu Met Leu Glu Ile
    50                  55                  60

Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                85                  90                  95

Thr Asp Thr Leu Ile Asp Asp Asn Asn Ala Ile Ile Lys Thr Ser Leu
            100                 105                 110

Cys Val Glu Val Arg Tyr Gln Ala Thr Asp Gly Thr Val Gly Ser Trp
        115                 120                 125

Asp Asp Gly Asp Phe Leu Gly Asp Glu Ser Leu Gln Glu Glu Glu Lys
    130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
                165                 170                 175

Ser Ala Met Lys Leu Gly Lys Asn Arg Ser His Lys Glu Glu Pro Gln
            180                 185                 190

Arg Pro Asp Glu Pro Ala Val Leu Glu Met Glu Asp Leu Asp His Leu
        195                 200                 205

Ala Ile Arg Leu Gly Asp Gly Leu Asp Pro Asp Ser Val Ser Leu Ala
    210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
                245                 250                 255

Ser Ile Thr Val Ile Glu Ala Arg Gln Leu Val Gly Leu Asn Met Asp
            260                 265                 270

Pro Val Val Cys Val Glu Val Gly Asp Asp Lys Lys Tyr Thr Ser Met
        275                 280                 285

Lys Glu Ser Thr Asn Cys Pro Tyr Tyr Asn Glu Tyr Phe Val Phe Asp
    290                 295                 300

Phe His Val Ser Pro Asp Val Met Phe Asp Lys Ile Ile Lys Ile Ser
305                 310                 315                 320

Val Ile His Ser Lys Asn Leu Leu Arg Ser Gly Thr Leu Val Gly Ser
                325                 330                 335

Phe Lys Met Asp Val Gly Thr Val Tyr Ser Gln Pro Glu His Gln Phe
            340                 345                 350

His His Lys Trp Ala Ile Leu Ser Asp Pro Asp Asp Ile Ser Ser Gly
        355                 360                 365

-continued

```
Leu Lys Gly Tyr Val Lys Cys Asp Val Ala Val Gly Lys Gly Asp
370             375                 380

Asn Ile Lys Thr Pro His Lys Ala Asn Glu Thr Asp Glu Asp Ile
385                 390                 395                 400

Glu Gly Asn Leu Leu Leu Pro Glu Gly Val Pro Pro Glu Arg Gln Trp
            405                 410                 415

Ala Arg Phe Tyr Val Lys Ile Tyr Arg Ala Glu Gly Leu Pro Arg Met
            420                 425                 430

Asn Thr Ser Leu Met Ala Asn Val Lys Lys Ala Phe Ile Gly Glu Asn
        435                 440                 445

Lys Asp Leu Val Asp Pro Tyr Val Gln Val Phe Phe Ala Gly Gln Lys
450                 455                 460

Gly Lys Thr Ser Val Gln Lys Ser Ser Tyr Glu Pro Leu Trp Asn Glu
465                 470                 475                 480

Gln Val Val Phe Thr Asp Leu Phe Pro Pro Leu Cys Lys Arg Met Lys
                485                 490                 495

Val Gln Ile Arg Asp Ser Asp Lys Val Asn Asp Val Ala Ile Gly Thr
            500                 505                 510

His Phe Ile Asp Leu Arg Lys Ile Ser Asn Asp Gly Asp Lys Gly Phe
        515                 520                 525

Leu Pro Thr Leu Gly Pro Ala Trp Val Asn Met Tyr Gly Ser Thr Arg
530                 535                 540

Asn Tyr Thr Leu Leu Asp Glu His Gln Asp Leu Asn Glu Gly Leu Gly
545                 550                 555                 560

Glu Gly Val Ser Phe Arg Ala Arg Leu Leu Gly Leu Ala Val Glu
                565                 570                 575

Ile Val Asp Thr Ser Asn Pro Glu Leu Thr Ser Ser Thr Glu Val Gln
            580                 585                 590

Val Glu Gln Ala Thr Pro Ile Ser Glu Ser Cys Ala Gly Lys Met Glu
        595                 600                 605

Glu Phe Phe Leu Phe Gly Ala Phe Leu Glu Ala Ser Met Ile Asp Arg
610                 615                 620

Arg Asn Gly Asp Lys Pro Ile Thr Phe Glu Val Thr Ile Gly Asn Tyr
625                 630                 635                 640

Gly Asn Glu Val Asp Gly Leu Ser Arg Pro Gln Arg Pro Arg Pro Arg
                645                 650                 655

Lys Glu Pro Gly Asp Glu Glu Val Asp Leu Ile Gln Asn Ala Ser
            660                 665                 670

Asp Asp Glu Ala Gly Asp Ala Gly Asp Leu Ala Ser Val Ser Ser Thr
        675                 680                 685

Pro Pro Met Arg Pro Gln Val Thr Asp Arg Asn Tyr Phe His Leu Pro
690                 695                 700

Tyr Leu Glu Arg Lys Pro Cys Ile Tyr Ile Lys Ser Trp Trp Pro Asp
705                 710                 715                 720

Gln Arg Arg Arg Leu Tyr Asn Ala Asn Ile Met Asp His Ile Ala Asp
                725                 730                 735

Lys Leu Glu Glu Gly Leu Asn Asp Ile Gln Glu Met Ile Lys Thr Glu
            740                 745                 750

Lys Ser Tyr Pro Glu Arg Arg Leu Arg Gly Val Leu Glu Leu Ser
        755                 760                 765

Cys Gly Cys Cys Arg Phe Leu Ser Leu Ala Asp Lys Asp Gln Gly His
770                 775                 780

Ser Ser Arg Thr Arg Leu Asp Arg Glu Arg Leu Lys Ser Cys Met Arg
```

-continued

```
            785                 790                 795                 800
        Glu Leu Glu Asn Met Gly Gln Gln Ala Arg Met Leu Arg Ala Gln Val
                            805                 810                 815
        Lys Arg His Thr Val Arg Asp Lys Leu Arg Leu Cys Gln Asn Phe Leu
                            820                 825                 830
        Gln Lys Leu Arg Phe Leu Ala Asp Glu Pro Gln His Ser Ile Pro Asp
                            835                 840                 845
        Ile Phe Ile Trp Met Met Ser Asn Asn Lys Arg Val Ala Tyr Ala Arg
                            850                 855                 860
        Val Pro Ser Lys Asp Leu Leu Phe Ser Ile Val Glu Glu Thr Gly
        865                 870                 875                 880
        Lys Asp Cys Ala Lys Val Lys Thr Leu Phe Leu Lys Leu Pro Gly Lys
                            885                 890                 895
        Arg Gly Phe Gly Ser Ala Gly Trp Thr Val Gln Ala Lys Val Glu Leu
                            900                 905                 910
        Tyr Leu Trp Leu Gly Leu Ser Lys Gln Arg Lys Glu Phe Leu Cys Gly
                            915                 920                 925
        Leu Pro Cys Gly Phe Gln Glu Val Lys Ala Ala Gln Gly Leu Gly Leu
                            930                 935                 940
        His Ala Phe Pro Pro Val Ser Leu Val Tyr Thr Lys Lys Gln Ala Phe
        945                 950                 955                 960
        Gln Leu Arg Ala His Met Tyr Gln Ala Arg Ser Leu Phe Ala Ala Asp
                            965                 970                 975
        Ser Ser Gly Leu Ser Asp Pro Phe Ala Arg Val Phe Phe Ile Asn Gln
                            980                 985                 990
        Ser Gln Cys Thr Glu Val Leu Asn  Glu Thr Leu Cys Pro  Thr Trp Asp
                    995                 1000                1005
        Gln Met  Leu Val Phe Asp Asn  Leu Glu Leu Tyr Gly  Glu Ala His
            1010                1015                1020
        Glu Leu  Arg Asp Asp Pro Pro  Ile Ile Val Ile Glu  Ile Tyr Asp
            1025                1030                1035
        Gln Asp  Ser Met Gly Lys Ala  Asp Phe Met Gly Arg  Thr Phe Ala
            1040                1045                1050
        Lys Pro  Leu Val Lys Met Ala  Asp Glu Ala Tyr Cys  Pro Pro Arg
            1055                1060                1065
        Phe Pro  Pro Gln Leu Glu Tyr  Tyr Gln Ile Tyr Arg  Gly Asn Ala
            1070                1075                1080
        Thr Ala  Gly Asp Leu Leu Ala  Ala Phe Glu Leu Leu  Gln Ile Gly
            1085                1090                1095
        Pro Ala  Gly Lys Ala Asp Leu  Pro Pro Ile Asn Gly  Pro Val Asp
            1100                1105                1110
        Val Asp  Arg Gly Pro Ile Met  Pro Val Pro Met Gly  Ile Arg Pro
            1115                1120                1125
        Val Leu  Ser Lys Tyr Arg Val  Glu Val Leu Phe Trp  Gly Leu Arg
            1130                1135                1140
        Asp Leu  Lys Arg Val Asn Leu  Ala Gln Val Asp Arg  Pro Arg Val
            1145                1150                1155
        Asp Ile  Glu Cys Ala Gly Lys  Gly Val Gln Ser Ser  Leu Ile His
            1160                1165                1170
        Asn Tyr  Lys Lys Asn Pro Asn  Phe Asn Thr Leu Val  Lys Trp Phe
            1175                1180                1185
        Glu Val  Asp Leu Pro Glu Asn  Glu Leu Leu His Pro  Pro Leu Asn
            1190                1195                1200
```

-continued

```
Ile Arg Val Val Asp Cys Arg Ala Phe Gly Arg Tyr Thr Leu Val
1205                1210                1215

Gly Ser His Ala Val Ser Ser Leu Arg Arg Phe Ile Tyr Arg Pro
1220                1225                1230

Pro Asp Arg Ser Ala Pro Ser Trp Asn Thr Thr Val Arg Leu Leu
1235                1240                1245

Arg Arg Cys Arg Val Leu Cys Asn Gly Gly Ser Ser Ser His Ser
1250                1255                1260

Thr Gly Glu Val Val Val Thr Met Glu Pro Glu Val Pro Ile Lys
1265                1270                1275

Lys Leu Glu Thr Met Val Lys Leu Asp Ala Thr Ser Glu Ala Val
1280                1285                1290

Val Lys Val Asp Val Ala Glu Glu Lys Glu Lys Lys Lys
1295                1300                1305

Lys Lys Gly Thr Ala Glu Glu Pro Glu Glu Glu Pro Asp Glu
1310                1315                1320

Ser Met Leu Asp Trp Trp Ser Lys Tyr Phe Ala Ser Ile Asp Thr
1325                1330                1335

Met Lys Glu Gln Leu Arg Gln Gln Glu Pro Ser Gly Ile Asp Leu
1340                1345                1350

Glu Glu Lys Glu Glu Val Asp Asn Thr Glu Gly Leu Lys Gly Ser
1355                1360                1365

Met Lys Gly Lys Glu Lys Ala Arg Ala Ala Lys Glu Glu Lys Lys
1370                1375                1380

Lys Lys Thr Gln Ser Ser Gly Ser Gly Gln Gly Ser Glu Ala Pro
1385                1390                1395

Glu Lys Lys Pro Lys Ile Asp Glu Leu Lys Val Tyr Pro Lys
1400                1405                1410

Glu Leu Glu Ser Glu Phe Asp Asn Phe Glu Asp Trp Leu His Thr
1415                1420                1425

Phe Asn Leu Leu Arg Gly Lys Thr Gly Asp Asp Glu Asp Gly Ser
1430                1435                1440

Thr Glu Glu Glu Arg Ile Val Gly Arg Phe Lys Gly Ser Leu Cys
1445                1450                1455

Val Tyr Lys Val Pro Leu Pro Glu Asp Val Ser Arg Glu Ala Gly
1460                1465                1470

Tyr Asp Ser Thr Tyr Gly Met Phe Gln Gly Ile Pro Ser Asn Asp
1475                1480                1485

Pro Ile Asn Val Leu Val Arg Val Tyr Val Val Arg Ala Thr Asp
1490                1495                1500

Leu His Pro Ala Asp Ile Asn Gly Lys Ala Asp Pro Tyr Ile Ala
1505                1510                1515

Ile Arg Leu Gly Lys Thr Asp Ile Arg Asp Lys Glu Asn Tyr Ile
1520                1525                1530

Ser Lys Gln Leu Asn Pro Val Phe Gly Lys Ser Phe Asp Ile Glu
1535                1540                1545

Ala Ser Phe Pro Met Glu Ser Met Leu Thr Val Ala Val Tyr Asp
1550                1555                1560

Trp Asp Leu Val Gly Thr Asp Asp Leu Ile Gly Glu Thr Lys Ile
1565                1570                1575

Asp Leu Glu Asn Arg Phe Tyr Ser Lys His Arg Ala Thr Cys Gly
1580                1585                1590
```

```
Ile Ala Gln Thr Tyr Ser Thr His Gly Tyr Asn Ile Trp Arg Asp
1595                1600                1605

Pro Met Lys Pro Ser Gln Ile Leu Thr Arg Leu Cys Lys Asp Gly
1610                1615                1620

Lys Val Asp Gly Pro His Phe Gly Pro Pro Gly Arg Val Lys Val
1625                1630                1635

Ala Asn Arg Val Phe Thr Gly Pro Ser Glu Ile Glu Asp Glu Asn
1640                1645                1650

Gly Gln Arg Lys Pro Thr Asp Glu His Val Ala Leu Leu Ala Leu
1655                1660                1665

Arg His Trp Glu Asp Ile Pro Arg Ala Gly Cys Arg Leu Val Pro
1670                1675                1680

Glu His Val Glu Thr Arg Pro Leu Leu Asn Pro Asp Lys Pro Gly
1685                1690                1695

Ile Glu Gln Gly Arg Leu Glu Leu Trp Val Asp Met Phe Pro Met
1700                1705                1710

Asp Met Pro Ala Pro Gly Thr Pro Leu Asp Ile Ser Pro Arg Lys
1715                1720                1725

Pro Lys Lys Tyr Glu Leu Arg Val Ile Ile Trp Asn Thr Asp Glu
1730                1735                1740

Val Val Leu Glu Asp Asp Asp Phe Phe Thr Gly Glu Lys Ser Ser
1745                1750                1755

Asp Ile Phe Val Arg Gly Trp Leu Lys Gly Gln Gln Glu Asp Lys
1760                1765                1770

Gln Asp Thr Asp Val His Tyr His Ser Leu Thr Gly Glu Gly Asn
1775                1780                1785

Phe Asn Trp Arg Tyr Leu Phe Pro Phe Asp Tyr Leu Ala Ala Glu
1790                1795                1800

Glu Lys Ile Val Ile Ser Lys Lys Glu Ser Met Phe Ser Trp Asp
1805                1810                1815

Glu Thr Glu Tyr Lys Ile Pro Ala Arg Leu Thr Leu Gln Ile Trp
1820                1825                1830

Asp Ala Asp His Phe Ser Ala Asp Asp Phe Leu Gly Ala Ile Glu
1835                1840                1845

Leu Asp Leu Asn Arg Phe Pro Arg Gly Ala Lys Thr Ala Lys Gln
1850                1855                1860

Cys Thr Met Glu Met Ala Thr Gly Glu Val Asp Val Pro Leu Val
1865                1870                1875

Ser Ile Phe Lys Gln Lys Arg Val Lys Gly Trp Trp Pro Leu Leu
1880                1885                1890

Ala Arg Asn Glu Asn Asp Glu Phe Glu Leu Thr Gly Lys Val Glu
1895                1900                1905

Ala Glu Leu His Leu Leu Thr Ala Glu Glu Ala Glu Lys Asn Pro
1910                1915                1920

Val Gly Leu Ala Arg Asn Glu Pro Asp Pro Leu Glu Lys Pro Asn
1925                1930                1935

Arg Pro Asp Thr Ser Phe Ile Trp Phe Leu Asn Pro Leu Lys Ser
1940                1945                1950

Ala Arg Tyr Phe Leu Trp His Thr Tyr Arg Trp Leu Leu Leu Lys
1955                1960                1965

Leu Leu Leu Leu Leu Leu Leu Leu Leu Leu Ala Leu Phe Leu
1970                1975                1980

Tyr Ser Val Pro Gly Tyr Leu Val Lys Lys Ile Leu Gly Ala
```

```
            1985               1990              1995
```

<210> SEQ ID NO 2
<211> LENGTH: 1230
<212> TYPE: PRT
<213> ORGANISM: Homo sapiens

<400> SEQUENCE: 2

```
Met Ile Lys Thr Glu Lys Ser Tyr Pro Glu Arg Arg Leu Arg Gly Val
1               5                   10                  15

Leu Glu Glu Leu Ser Cys Gly Cys Arg Phe Leu Ser Leu Ala Asp
            20                  25                  30

Lys Asp Gln Gly His Ser Ser Arg Thr Arg Leu Asp Arg Glu Arg Leu
            35                  40                  45

Lys Ser Cys Met Arg Glu Leu Glu Asn Met Gly Gln Gln Ala Arg Met
        50                  55                  60

Leu Arg Ala Gln Val Lys Arg His Thr Val Arg Asp Lys Leu Arg Leu
65                  70                  75                  80

Cys Gln Asn Phe Leu Gln Lys Leu Arg Phe Leu Ala Asp Glu Pro Gln
                85                  90                  95

His Ser Ile Pro Asp Ile Phe Ile Trp Met Met Ser Asn Asn Lys Arg
            100                 105                 110

Val Ala Tyr Ala Arg Val Pro Ser Lys Asp Leu Leu Phe Ser Ile Val
            115                 120                 125

Glu Glu Glu Thr Gly Lys Asp Cys Ala Lys Val Lys Thr Leu Phe Leu
130                 135                 140

Lys Leu Pro Gly Lys Arg Gly Phe Gly Ser Ala Gly Trp Thr Val Gln
145                 150                 155                 160

Ala Lys Val Glu Leu Tyr Leu Trp Leu Gly Leu Ser Lys Gln Arg Lys
                165                 170                 175

Glu Phe Leu Cys Gly Leu Pro Cys Gly Phe Gln Glu Val Lys Ala Ala
            180                 185                 190

Gln Gly Leu Gly Leu His Ala Phe Pro Pro Val Ser Leu Val Tyr Thr
        195                 200                 205

Lys Lys Gln Ala Phe Gln Leu Arg Ala His Met Tyr Gln Ala Arg Ser
210                 215                 220

Leu Phe Ala Ala Asp Ser Ser Gly Leu Ser Asp Pro Phe Ala Arg Val
225                 230                 235                 240

Phe Phe Ile Asn Gln Ser Gln Cys Thr Glu Val Leu Asn Glu Thr Leu
                245                 250                 255

Cys Pro Thr Trp Asp Gln Met Leu Val Phe Asp Asn Leu Glu Leu Tyr
            260                 265                 270

Gly Glu Ala His Glu Leu Arg Asp Asp Pro Pro Ile Ile Val Ile Glu
        275                 280                 285

Ile Tyr Asp Gln Asp Ser Met Gly Lys Ala Asp Phe Met Gly Arg Thr
290                 295                 300

Phe Ala Lys Pro Leu Val Lys Met Ala Asp Glu Ala Tyr Cys Pro Pro
305                 310                 315                 320

Arg Phe Pro Pro Gln Leu Glu Tyr Tyr Gln Ile Tyr Arg Gly Asn Ala
                325                 330                 335

Thr Ala Gly Asp Leu Leu Ala Ala Phe Glu Leu Leu Gln Ile Gly Pro
            340                 345                 350

Ala Gly Lys Ala Asp Leu Pro Pro Ile Asn Gly Pro Val Asp Val Asp
        355                 360                 365
```

```
Arg Gly Pro Ile Met Pro Val Pro Met Gly Ile Arg Pro Val Leu Ser
    370             375                 380

Lys Tyr Arg Val Glu Val Leu Phe Trp Gly Leu Arg Asp Leu Lys Arg
385                 390                 395                 400

Val Asn Leu Ala Gln Val Asp Arg Pro Arg Val Asp Ile Glu Cys Ala
                405                 410                 415

Gly Lys Gly Val Gln Ser Ser Leu Ile His Asn Tyr Lys Lys Asn Pro
                420                 425                 430

Asn Phe Asn Thr Leu Val Lys Trp Phe Glu Val Asp Leu Pro Glu Asn
        435                 440                 445

Glu Leu Leu His Pro Pro Leu Asn Ile Arg Val Asp Cys Arg Ala
    450                 455                 460

Phe Gly Arg Tyr Thr Leu Val Gly Ser His Ala Val Ser Ser Leu Arg
465                 470                 475                 480

Arg Phe Ile Tyr Arg Pro Asp Arg Ser Ala Pro Ser Trp Asn Thr
                485                 490                 495

Thr Gly Glu Val Val Thr Met Glu Pro Glu Val Pro Ile Lys Lys
                500                 505                 510

Leu Glu Thr Met Val Lys Leu Asp Ala Thr Ser Glu Ala Val Val Lys
    515                 520                 525

Val Asp Val Ala Glu Glu Lys Glu Lys Lys Lys Lys Lys Gly
    530                 535                 540

Thr Ala Glu Glu Pro Glu Glu Glu Pro Asp Glu Ser Met Leu Asp
545                 550                 555                 560

Trp Trp Ser Lys Tyr Phe Ala Ser Ile Asp Thr Met Lys Glu Gln Leu
                565                 570                 575

Arg Gln Gln Glu Pro Ser Gly Ile Asp Leu Glu Glu Lys Glu Glu Val
                580                 585                 590

Asp Asn Thr Glu Gly Leu Lys Gly Ser Met Lys Gly Lys Glu Lys Ala
            595                 600                 605

Arg Ala Ala Lys Glu Glu Lys Lys Lys Thr Gln Ser Ser Gly Ser
    610                 615                 620

Gly Gln Gly Ser Glu Ala Pro Glu Lys Lys Pro Lys Ile Asp Glu
625                 630                 635                 640

Leu Lys Val Tyr Pro Lys Glu Leu Glu Ser Glu Phe Asp Asn Phe Glu
                645                 650                 655

Asp Trp Leu His Thr Phe Asn Leu Leu Arg Gly Lys Thr Gly Asp Asp
            660                 665                 670

Glu Asp Gly Ser Thr Glu Glu Arg Ile Val Gly Arg Phe Lys Gly
            675                 680                 685

Ser Leu Cys Val Tyr Lys Val Pro Leu Pro Glu Asp Val Ser Arg Glu
    690                 695                 700

Ala Gly Tyr Asp Ser Thr Tyr Gly Met Phe Gln Gly Ile Pro Ser Asn
705                 710                 715                 720

Asp Pro Ile Asn Val Leu Val Arg Val Tyr Val Arg Ala Thr Asp
                725                 730                 735

Leu His Pro Ala Asp Ile Asn Gly Lys Ala Asp Pro Tyr Ile Ala Ile
                740                 745                 750

Arg Leu Gly Lys Thr Asp Ile Arg Asp Lys Glu Asn Tyr Ile Ser Lys
            755                 760                 765

Gln Leu Asn Pro Val Phe Gly Lys Ser Phe Asp Ile Glu Ala Ser Phe
    770                 775                 780

Pro Met Glu Ser Met Leu Thr Val Ala Val Tyr Asp Trp Asp Leu Val
```

```
                785                 790                 795                 800
       Gly Thr Asp Asp Leu Ile Gly Glu Thr Lys Ile Asp Leu Glu Asn Arg
                       805                 810                 815

Phe Tyr Ser Lys His Arg Ala Thr Cys Gly Ile Ala Gln Thr Tyr Ser
                       820                 825                 830

Thr His Gly Tyr Asn Ile Trp Arg Asp Pro Met Lys Pro Ser Gln Ile
                       835                 840                 845

Leu Thr Arg Leu Cys Lys Asp Gly Lys Val Asp Gly Pro His Phe Gly
                       850                 855                 860

Pro Pro Gly Arg Val Lys Val Ala Asn Arg Val Phe Thr Gly Pro Ser
       865                 870                 875                 880

Glu Ile Glu Asp Glu Asn Gly Gln Arg Lys Pro Thr Asp Glu His Val
                       885                 890                 895

Ala Leu Leu Ala Leu Arg His Trp Glu Asp Ile Pro Arg Ala Gly Cys
                       900                 905                 910

Arg Leu Val Pro Glu His Val Glu Thr Arg Pro Leu Leu Asn Pro Asp
                       915                 920                 925

Lys Pro Gly Ile Glu Gln Gly Arg Leu Glu Leu Trp Val Asp Met Phe
                       930                 935                 940

Pro Met Asp Met Pro Ala Pro Gly Thr Pro Leu Asp Ile Ser Pro Arg
       945                 950                 955                 960

Lys Pro Lys Lys Tyr Glu Leu Arg Val Ile Ile Trp Asn Thr Asp Glu
                       965                 970                 975

Val Val Leu Glu Asp Asp Asp Phe Phe Thr Gly Glu Lys Ser Ser Asp
                       980                 985                 990

Ile Phe Val Arg Gly Trp Leu Lys Gly Gln Gln Glu Asp Lys Gln Asp
                       995                 1000                1005

Thr Asp Val His Tyr His Ser Leu Thr Gly Glu Gly Asn Phe Asn
                  1010                1015                1020

Trp Arg Tyr Leu Phe Pro Phe Asp Tyr Leu Ala Ala Glu Glu Lys
                  1025                1030                1035

Ile Val Ile Ser Lys Lys Glu Ser Met Phe Ser Trp Asp Glu Thr
                  1040                1045                1050

Glu Tyr Lys Ile Pro Ala Arg Leu Thr Leu Gln Ile Trp Asp Ala
                  1055                1060                1065

Asp His Phe Ser Ala Asp Asp Phe Leu Gly Ala Ile Glu Leu Asp
                  1070                1075                1080

Leu Asn Arg Phe Pro Arg Gly Ala Lys Thr Ala Lys Gln Cys Thr
                  1085                1090                1095

Met Glu Met Ala Thr Gly Glu Val Asp Val Pro Leu Val Ser Ile
                  1100                1105                1110

Phe Lys Gln Lys Arg Val Lys Gly Trp Trp Pro Leu Leu Ala Arg
                  1115                1120                1125

Asn Glu Asn Asp Glu Phe Glu Leu Thr Gly Lys Val Glu Ala Glu
                  1130                1135                1140

Leu His Leu Leu Thr Ala Glu Glu Ala Glu Lys Asn Pro Val Gly
                  1145                1150                1155

Leu Ala Arg Asn Glu Pro Asp Pro Leu Glu Lys Pro Asn Arg Pro
                  1160                1165                1170

Asp Thr Ser Phe Ile Trp Phe Leu Asn Pro Leu Lys Ser Ala Arg
                  1175                1180                1185

Tyr Phe Leu Trp His Thr Tyr Arg Trp Leu Leu Leu Lys Leu Leu
                  1190                1195                1200
```

```
Leu Leu Leu Leu Leu Leu Leu Leu Ala Leu Phe Leu Tyr Ser
    1205                1210                1215

Val Pro Gly Tyr Leu Val Lys Lys Ile Leu Gly Ala
    1220                1225                1230

<210> SEQ ID NO 3
<211> LENGTH: 1230
<212> TYPE: PRT
<213> ORGANISM: Homo sapiens

<400> SEQUENCE: 3

Met Ile Lys Thr Glu Lys Ser Tyr Pro Glu Arg Arg Leu Arg Gly Val
1               5                   10                  15

Leu Glu Glu Leu Ser Cys Gly Cys Cys Arg Phe Leu Ser Leu Ala Asp
                20                  25                  30

Lys Asp Gln Gly His Ser Ser Arg Thr Arg Leu Asp Arg Glu Arg Leu
            35                  40                  45

Lys Ser Cys Met Arg Glu Leu Glu Asn Met Gly Gln Gln Ala Arg Met
50                  55                  60

Leu Arg Ala Gln Val Lys Arg His Thr Val Arg Asp Lys Leu Arg Leu
65                  70                  75                  80

Cys Gln Asn Phe Leu Gln Lys Leu Arg Phe Leu Ala Asp Glu Pro Gln
                85                  90                  95

His Ser Ile Pro Asp Ile Phe Ile Trp Met Met Ser Asn Asn Lys Arg
            100                 105                 110

Val Ala Tyr Ala Arg Val Pro Ser Lys Asp Leu Leu Phe Ser Ile Val
        115                 120                 125

Glu Glu Glu Thr Gly Lys Asp Cys Ala Lys Val Lys Thr Leu Phe Leu
130                 135                 140

Lys Leu Pro Gly Lys Arg Gly Phe Gly Ser Ala Gly Trp Thr Val Gln
145                 150                 155                 160

Ala Lys Val Glu Leu Tyr Leu Trp Leu Gly Leu Ser Lys Gln Arg Lys
                165                 170                 175

Glu Phe Leu Cys Gly Leu Pro Cys Gly Phe Gln Glu Val Lys Ala Ala
            180                 185                 190

Gln Gly Leu Gly Leu His Ala Phe Pro Pro Val Ser Leu Val Tyr Thr
        195                 200                 205

Lys Lys Gln Ala Phe Gln Leu Arg Ala His Met Tyr Gln Ala Arg Ser
210                 215                 220

Leu Phe Ala Ala Asp Ser Ser Gly Leu Ser Asp Pro Phe Ala Arg Val
225                 230                 235                 240

Phe Phe Ile Asn Gln Ser Gln Cys Thr Glu Val Leu Asn Glu Thr Leu
                245                 250                 255

Cys Pro Thr Trp Asp Gln Met Leu Val Phe Asp Asn Leu Glu Leu Tyr
            260                 265                 270

Gly Glu Ala His Glu Leu Arg Asp Asp Pro Ile Ile Val Ile Glu
        275                 280                 285

Ile Tyr Asp Gln Asp Ser Met Gly Lys Ala Asp Phe Met Gly Arg Thr
290                 295                 300

Phe Ala Lys Pro Leu Val Lys Met Ala Asp Glu Ala Tyr Cys Pro Pro
305                 310                 315                 320

Arg Phe Pro Pro Gln Leu Glu Tyr Tyr Gln Ile Tyr Arg Gly Asn Ala
                325                 330                 335

Thr Ala Gly Asp Leu Leu Ala Ala Phe Glu Leu Leu Gln Ile Gly Pro
```

-continued

```
                340                 345                 350
Ala Gly Lys Ala Asp Leu Pro Pro Ile Asn Gly Pro Val Asp Val Asp
            355                 360                 365

Arg Gly Pro Ile Met Pro Val Pro Met Gly Ile Arg Pro Val Leu Ser
    370                 375                 380

Lys Tyr Arg Val Glu Val Leu Phe Trp Gly Leu Arg Asp Leu Lys Arg
385                 390                 395                 400

Val Asn Leu Ala Gln Val Asp Arg Pro Arg Val Asp Ile Glu Cys Ala
                405                 410                 415

Gly Lys Gly Val Gln Ser Ser Leu Ile His Asn Tyr Lys Lys Asn Pro
            420                 425                 430

Asn Phe Asn Thr Leu Val Lys Trp Phe Glu Val Asp Leu Pro Glu Asn
        435                 440                 445

Glu Leu Leu His Pro Pro Leu Asn Ile Arg Val Val Asp Cys Arg Ala
            450                 455                 460

Phe Gly Arg Tyr Thr Leu Val Gly Ser His Ala Val Ser Ser Leu Arg
465                 470                 475                 480

Arg Phe Ile Tyr Arg Pro Pro Asp Arg Ser Ala Pro Ser Trp Asn Thr
                485                 490                 495

Thr Gly Glu Val Val Thr Met Glu Pro Glu Val Pro Ile Lys Lys
            500                 505                 510

Leu Glu Thr Met Val Lys Leu Asp Ala Thr Ser Glu Ala Val Val Lys
        515                 520                 525

Val Asp Val Ala Glu Glu Lys Glu Lys Lys Lys Lys Lys Gly
    530                 535                 540

Thr Ala Glu Glu Pro Glu Glu Glu Pro Asp Glu Ser Met Leu Asp
545                 550                 555                 560

Trp Trp Ser Lys Tyr Phe Ala Ser Ile Asp Thr Met Lys Glu Gln Leu
                565                 570                 575

Arg Gln Gln Glu Pro Ser Gly Ile Asp Leu Glu Glu Lys Glu Glu Val
            580                 585                 590

Asp Asn Thr Glu Gly Leu Lys Gly Ser Met Lys Gly Lys Glu Lys Ala
        595                 600                 605

Arg Ala Ala Lys Glu Glu Lys Lys Lys Thr Gln Ser Ser Gly Ser
    610                 615                 620

Gly Gln Gly Ser Glu Ala Pro Glu Lys Lys Pro Lys Ile Asp Glu
625                 630                 635                 640

Leu Lys Val Tyr Pro Lys Glu Leu Glu Ser Glu Phe Asp Asn Phe Glu
                645                 650                 655

Asp Trp Leu His Thr Phe Asn Leu Leu Arg Gly Lys Thr Gly Asp Asp
            660                 665                 670

Glu Asp Gly Ser Thr Glu Glu Arg Ile Val Gly Arg Phe Lys Gly
        675                 680                 685

Ser Leu Cys Val Tyr Lys Val Pro Leu Pro Glu Asp Val Ser Arg Glu
    690                 695                 700

Ala Gly Tyr Asp Ser Thr Tyr Gly Met Phe Gln Gly Ile Pro Ser Asn
705                 710                 715                 720

Asp Pro Ile Asn Val Leu Val Arg Val Tyr Val Arg Ala Thr Asp
                725                 730                 735

Leu His Pro Ala Asp Ile Asn Gly Lys Ala Asp Pro Tyr Ile Ala Ile
            740                 745                 750

Arg Leu Gly Lys Thr Asp Ile Arg Asp Lys Glu Asn Tyr Ile Ser Lys
        755                 760                 765
```

```
Gln Leu Asn Pro Val Phe Gly Lys Ser Phe Asp Ile Glu Ala Ser Phe
    770             775                 780

Pro Met Glu Ser Met Leu Thr Val Ala Val Tyr Asp Trp Asp Leu Val
785                 790                 795                 800

Gly Thr Asp Asp Leu Ile Gly Glu Thr Lys Ile Asp Leu Glu Asn Arg
                805                 810                 815

Phe Tyr Ser Lys His Arg Ala Thr Cys Gly Ile Ala Gln Thr Tyr Ser
                820                 825                 830

Thr His Gly Tyr Asn Ile Trp Arg Asp Pro Met Lys Pro Ser Gln Ile
            835                 840                 845

Leu Thr Arg Leu Cys Lys Asp Gly Lys Val Asp Gly Pro His Phe Gly
    850                 855                 860

Pro Pro Gly Arg Val Lys Val Ala Asn Arg Val Phe Thr Gly Pro Ser
865                 870                 875                 880

Glu Ile Glu Asp Glu Asn Gly Gln Arg Lys Pro Thr Asp Glu His Val
                885                 890                 895

Ala Leu Leu Ala Leu Arg His Trp Glu Asp Ile Pro Arg Ala Gly Cys
            900                 905                 910

Arg Leu Val Pro Glu His Val Glu Thr Arg Pro Leu Leu Asn Pro Asp
    915                 920                 925

Lys Pro Gly Ile Glu Gln Gly Arg Leu Glu Leu Trp Val Asp Met Phe
    930                 935                 940

Pro Met Asp Met Pro Ala Pro Gly Thr Pro Leu Asp Ile Ser Pro Arg
945                 950                 955                 960

Lys Pro Lys Lys Tyr Glu Leu Arg Val Ile Ile Trp Asn Thr Asp Glu
                965                 970                 975

Val Val Leu Glu Asp Asp Asp Phe Phe Thr Gly Glu Lys Ser Ser Asp
                980                 985                 990

Ile Phe Val Arg Gly Trp Leu Lys Gly Gln Gln Glu Asp Lys Gln Asp
            995                 1000                1005

Thr Asp Val His Tyr His Ser Leu Thr Gly Glu Gly Asn Phe Asn
    1010                1015                1020

Trp Arg Tyr Leu Phe Pro Phe Asp Tyr Leu Ala Ala Glu Glu Lys
    1025                1030                1035

Ile Val Ile Ser Lys Lys Glu Ser Met Phe Ser Trp Asp Glu Thr
    1040                1045                1050

Glu Tyr Lys Ile Pro Ala Arg Leu Thr Leu Gln Ile Trp Asp Ala
    1055                1060                1065

Asp His Phe Ser Ala Asp Asp Phe Leu Gly Ala Ile Glu Leu Asp
    1070                1075                1080

Leu Asn Arg Phe Pro Arg Gly Ala Lys Thr Ala Lys Gln Cys Thr
    1085                1090                1095

Met Glu Met Ala Thr Gly Glu Val Asp Val Pro Leu Val Ser Ile
    1100                1105                1110

Phe Lys Gln Lys Arg Val Lys Gly Trp Trp Pro Leu Leu Ala Arg
    1115                1120                1125

Asn Glu Asn Asp Glu Phe Glu Leu Thr Gly Lys Val Glu Ala Glu
    1130                1135                1140

Leu His Leu Leu Thr Ala Glu Glu Ala Glu Lys Asn Pro Val Gly
    1145                1150                1155

Leu Ala Arg Asn Glu Pro Asp Pro Leu Glu Lys Pro Asn Arg Pro
    1160                1165                1170
```

```
Asp Thr Ala Phe Val Trp Phe Leu Asn Pro Leu Lys Ser Ile Lys
    1175                1180                1185

Tyr Leu Ile Cys Thr Arg Tyr Lys Trp Leu Ile Ile Lys Ile Val
    1190                1195                1200

Leu Ala Leu Leu Gly Leu Leu Met Leu Gly Leu Phe Leu Tyr Ser
    1205                1210                1215

Leu Pro Gly Tyr Met Val Lys Lys Leu Leu Gly Ala
    1220                1225                1230

<210> SEQ ID NO 4
<211> LENGTH: 1307
<212> TYPE: PRT
<213> ORGANISM: Homo sapiens

<400> SEQUENCE: 4

Met Met Thr Asp Thr Gln Asp Gly Pro Ser Glu Ser Ser Gln Ile Met
1               5                   10                  15

Arg Ser Leu Thr Pro Leu Ile Asn Arg Glu Glu Ala Phe Gly Glu Ala
                20                  25                  30

Gly Glu Ala Gly Leu Trp Pro Ser Ile Thr His Thr Pro Asp Ser Gln
            35                  40                  45

Glu Glu Gly Leu Asn Asp Ile Gln Glu Met Ile Lys Thr Glu Lys Ser
        50                  55                  60

Tyr Pro Glu Arg Arg Leu Arg Gly Val Leu Glu Leu Ser Cys Gly
65                  70                  75                  80

Cys Cys Arg Phe Leu Ser Leu Ala Asp Lys Asp Gln Gly His Ser Ser
                85                  90                  95

Arg Thr Arg Leu Asp Arg Glu Arg Leu Lys Ser Cys Met Arg Glu Leu
            100                 105                 110

Glu Asn Met Gly Gln Gln Ala Arg Met Leu Arg Ala Gln Val Lys Arg
        115                 120                 125

His Thr Val Arg Asp Lys Leu Arg Leu Cys Gln Asn Phe Leu Gln Lys
    130                 135                 140

Leu Arg Phe Leu Ala Asp Glu Pro Gln His Ser Ile Pro Asp Ile Phe
145                 150                 155                 160

Ile Trp Met Met Ser Asn Asn Lys Arg Val Ala Tyr Ala Arg Val Pro
                165                 170                 175

Ser Lys Asp Leu Leu Phe Ser Ile Val Glu Glu Thr Gly Lys Asp
            180                 185                 190

Cys Ala Lys Val Lys Thr Leu Phe Leu Lys Leu Pro Gly Lys Arg Gly
        195                 200                 205

Phe Gly Ser Ala Gly Trp Thr Val Gln Ala Lys Val Glu Leu Tyr Leu
    210                 215                 220

Trp Leu Gly Leu Ser Lys Gln Arg Lys Glu Phe Leu Cys Gly Leu Pro
225                 230                 235                 240

Cys Gly Phe Gln Glu Val Lys Ala Ala Gln Gly Leu Gly Leu His Ala
                245                 250                 255

Phe Pro Pro Val Ser Leu Val Tyr Thr Lys Lys Gln Ala Phe Gln Leu
            260                 265                 270

Arg Ala His Met Tyr Gln Ala Arg Ser Leu Phe Ala Ala Asp Ser Ser
        275                 280                 285

Gly Leu Ser Asp Pro Phe Ala Arg Val Phe Phe Ile Asn Gln Ser Gln
    290                 295                 300

Cys Thr Glu Val Leu Asn Glu Thr Leu Cys Pro Thr Trp Asp Gln Met
305                 310                 315                 320
```

```
Leu Val Phe Asp Asn Leu Glu Leu Tyr Gly Ala His Glu Leu Arg
                325                 330                 335

Asp Asp Pro Pro Ile Ile Val Ile Glu Ile Tyr Asp Gln Asp Ser Met
                340                 345                 350

Gly Lys Ala Asp Phe Met Gly Arg Thr Phe Ala Lys Pro Leu Val Lys
                355                 360                 365

Met Ala Asp Glu Ala Tyr Cys Pro Pro Arg Phe Pro Pro Gln Leu Glu
                370                 375                 380

Tyr Tyr Gln Ile Tyr Arg Gly Asn Ala Thr Ala Gly Asp Leu Leu Ala
385                 390                 395                 400

Ala Phe Glu Leu Leu Gln Ile Gly Pro Ala Gly Lys Ala Asp Leu Pro
                405                 410                 415

Pro Ile Asn Gly Pro Val Asp Val Asp Arg Gly Pro Ile Met Pro Val
                420                 425                 430

Pro Met Gly Ile Arg Pro Val Leu Ser Lys Tyr Arg Val Glu Val Leu
                435                 440                 445

Phe Trp Gly Leu Arg Asp Leu Lys Arg Val Asn Leu Ala Gln Val Asp
            450                 455                 460

Arg Pro Arg Val Asp Ile Glu Cys Ala Gly Lys Gly Val Gln Ser Ser
465                 470                 475                 480

Leu Ile His Asn Tyr Lys Lys Asn Pro Asn Phe Asn Thr Leu Val Lys
                485                 490                 495

Trp Phe Glu Val Asp Leu Pro Glu Asn Glu Leu Leu His Pro Pro Leu
                500                 505                 510

Asn Ile Arg Val Val Asp Cys Arg Ala Phe Gly Arg Tyr Thr Leu Val
                515                 520                 525

Gly Ser His Ala Val Ser Ser Leu Arg Arg Phe Ile Tyr Arg Pro Pro
                530                 535                 540

Asp Arg Ser Ala Pro Ser Trp Asn Thr Thr Val Arg Leu Leu Arg Arg
545                 550                 555                 560

Cys Arg Val Leu Cys Asn Gly Ser Ser Ser His Ser Thr Gly Glu
                565                 570                 575

Val Val Val Thr Met Glu Pro Glu Val Pro Ile Lys Lys Leu Glu Thr
                580                 585                 590

Met Val Lys Leu Asp Ala Thr Ser Glu Ala Val Val Lys Val Asp Val
                595                 600                 605

Ala Glu Glu Glu Lys Glu Lys Lys Lys Lys Lys Gly Thr Ala Glu
                610                 615                 620

Glu Pro Glu Glu Glu Pro Asp Glu Ser Met Leu Asp Trp Trp Ser
625                 630                 635                 640

Lys Tyr Phe Ala Ser Ile Asp Thr Met Lys Glu Gln Leu Arg Gln Gln
                645                 650                 655

Glu Pro Ser Gly Ile Asp Leu Glu Glu Lys Glu Glu Val Asp Asn Thr
                660                 665                 670

Glu Gly Leu Lys Gly Ser Met Lys Gly Lys Glu Lys Ala Arg Ala Ala
                675                 680                 685

Lys Glu Glu Lys Lys Lys Thr Gln Ser Ser Gly Ser Gly Gln Gly
                690                 695                 700

Ser Glu Ala Pro Glu Lys Lys Pro Lys Ile Asp Glu Leu Lys Val
705                 710                 715                 720

Tyr Pro Lys Glu Leu Glu Ser Glu Phe Asp Asn Phe Glu Asp Trp Leu
                725                 730                 735
```

```
His Thr Phe Asn Leu Leu Arg Gly Lys Thr Gly Asp Asp Glu Asp Gly
            740                 745                 750

Ser Thr Glu Glu Glu Arg Ile Val Gly Arg Phe Lys Gly Ser Leu Cys
            755                 760                 765

Val Tyr Lys Val Pro Leu Pro Glu Asp Val Ser Arg Glu Ala Gly Tyr
    770                 775                 780

Asp Ser Thr Tyr Gly Met Phe Gln Gly Ile Pro Ser Asn Asp Pro Ile
785                 790                 795                 800

Asn Val Leu Val Arg Val Tyr Val Val Arg Ala Thr Asp Leu His Pro
                805                 810                 815

Ala Asp Ile Asn Gly Lys Ala Asp Pro Tyr Ile Ala Ile Arg Leu Gly
            820                 825                 830

Lys Thr Asp Ile Arg Asp Lys Glu Asn Tyr Ile Ser Lys Gln Leu Asn
            835                 840                 845

Pro Val Phe Gly Lys Ser Phe Asp Ile Glu Ala Ser Phe Pro Met Glu
    850                 855                 860

Ser Met Leu Thr Val Ala Val Tyr Asp Trp Asp Leu Val Gly Thr Asp
865                 870                 875                 880

Asp Leu Ile Gly Glu Thr Lys Ile Asp Leu Glu Asn Arg Phe Tyr Ser
                885                 890                 895

Lys His Arg Ala Thr Cys Gly Ile Ala Gln Thr Tyr Ser Thr His Gly
            900                 905                 910

Tyr Asn Ile Trp Arg Asp Pro Met Lys Pro Ser Gln Ile Leu Thr Arg
            915                 920                 925

Leu Cys Lys Asp Gly Lys Val Asp Gly Pro His Phe Gly Pro Pro Gly
    930                 935                 940

Arg Val Lys Val Ala Asn Arg Val Phe Thr Gly Pro Ser Glu Ile Glu
945                 950                 955                 960

Asp Glu Asn Gly Gln Arg Lys Pro Thr Asp Glu His Val Ala Leu Leu
                965                 970                 975

Ala Leu Arg His Trp Glu Asp Ile Pro Arg Ala Gly Cys Arg Leu Val
            980                 985                 990

Pro Glu His Val Glu Thr Arg Pro  Leu Leu Asn Pro Asp  Lys Pro Gly
    995                 1000                1005

Ile Glu  Gln Gly Arg Leu Glu  Leu Trp Val Asp Met  Phe Pro Met
    1010                1015                1020

Asp Met  Pro Ala Pro Gly Thr  Pro Leu Asp Ile Ser  Pro Arg Lys
    1025                1030                1035

Pro Lys  Lys Tyr Glu Leu Arg  Val Ile Ile Trp Asn  Thr Asp Glu
    1040                1045                1050

Val Val  Leu Glu Asp Asp Asp  Phe Phe Thr Gly Glu  Lys Ser Ser
    1055                1060                1065

Asp Ile  Phe Val Arg Gly Trp  Leu Lys Gly Gln Gln  Glu Asp Lys
    1070                1075                1080

Gln Asp  Thr Asp Val His Tyr  His Ser Leu Thr Gly  Glu Gly Asn
    1085                1090                1095

Phe Asn  Trp Arg Tyr Leu Phe  Pro Phe Asp Tyr Leu  Ala Ala Glu
    1100                1105                1110

Glu Lys  Ile Val Ile Ser Lys  Lys Glu Ser Met Phe  Ser Trp Asp
    1115                1120                1125

Glu Thr  Glu Tyr Lys Ile Pro  Ala Arg Leu Thr Leu  Gln Ile Trp
    1130                1135                1140

Asp Ala  Asp His Phe Ser Ala  Asp Asp Phe Leu Gly  Ala Ile Glu
```

-continued

```
                1145                1150                1155

Leu Asp Leu Asn Arg Phe Pro Arg Gly Ala Lys Thr Ala Lys Gln
        1160                1165                1170

Cys Thr Met Glu Met Ala Thr Gly Glu Val Asp Val Pro Leu Val
    1175                1180                1185

Ser Ile Phe Lys Gln Lys Arg Val Lys Gly Trp Trp Pro Leu Leu
    1190                1195                1200

Ala Arg Asn Glu Asn Asp Glu Phe Glu Leu Thr Gly Lys Val Glu
    1205                1210                1215

Ala Glu Leu His Leu Leu Thr Ala Glu Glu Ala Glu Lys Asn Pro
    1220                1225                1230

Val Gly Leu Ala Arg Asn Glu Pro Asp Pro Leu Glu Lys Pro Asn
    1235                1240                1245

Arg Pro Asp Thr Ser Phe Ile Trp Phe Leu Asn Pro Leu Lys Ser
    1250                1255                1260

Ala Arg Tyr Phe Leu Trp His Thr Tyr Arg Trp Leu Leu Leu Lys
    1265                1270                1275

Leu Leu Leu Leu Leu Leu Leu Leu Leu Leu Ala Leu Phe Leu
    1280                1285                1290

Tyr Ser Val Pro Gly Tyr Leu Val Lys Lys Ile Leu Gly Ala
    1295                1300                1305

<210> SEQ ID NO 5
<211> LENGTH: 1997
<212> TYPE: PRT
<213> ORGANISM: Homo sapiens

<400> SEQUENCE: 5

Met Ala Leu Leu Ile His Leu Lys Thr Val Ser Glu Leu Arg Gly Arg
1               5                   10                  15

Gly Asp Arg Ile Ala Lys Val Thr Phe Arg Gly Gln Ser Phe Tyr Ser
                20                  25                  30

Arg Val Leu Glu Asn Cys Glu Asp Val Ala Asp Phe Asp Glu Thr Phe
            35                  40                  45

Arg Trp Pro Val Ala Ser Ser Ile Asp Arg Asn Glu Met Leu Glu Ile
        50                  55                  60

Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                85                  90                  95

Thr Asp Thr Leu Ile Asp Asp Asn Asn Ala Ile Ile Lys Thr Ser Leu
            100                 105                 110

Cys Val Glu Val Arg Tyr Gln Ala Thr Asp Gly Thr Val Gly Ser Trp
        115                 120                 125

Asp Asp Gly Asp Phe Leu Gly Asp Glu Ser Leu Gln Glu Glu Glu Lys
    130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
                165                 170                 175

Ser Ala Met Lys Leu Gly Lys Asn Arg Ser His Lys Glu Glu Pro Gln
            180                 185                 190

Arg Pro Asp Glu Pro Ala Val Leu Glu Met Glu Asp Leu Asp His Leu
        195                 200                 205
```

-continued

```
Ala Ile Arg Leu Gly Asp Gly Leu Asp Pro Asp Ser Val Ser Leu Ala
    210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
                245                 250                 255

Ser Ile Thr Val Ile Glu Ala Arg Gln Leu Val Gly Leu Asn Met Asp
                260                 265                 270

Pro Val Cys Val Glu Val Gly Asp Asp Lys Lys Tyr Thr Ser Met
            275                 280                 285

Lys Glu Ser Thr Asn Cys Pro Tyr Tyr Asn Glu Tyr Phe Val Phe Asp
290                 295                 300

Phe His Val Ser Pro Asp Val Met Phe Asp Lys Ile Ile Lys Ile Ser
305                 310                 315                 320

Val Ile His Ser Lys Asn Leu Leu Arg Ser Gly Thr Leu Val Gly Ser
                325                 330                 335

Phe Lys Met Asp Val Gly Thr Val Tyr Ser Gln Pro Glu His Gln Phe
                340                 345                 350

His His Lys Trp Ala Ile Leu Ser Asp Pro Asp Asp Ile Ser Ser Gly
            355                 360                 365

Leu Lys Gly Tyr Val Lys Cys Asp Val Ala Val Val Gly Lys Gly Asp
    370                 375                 380

Asn Ile Lys Thr Pro His Lys Ala Asn Glu Thr Asp Glu Asp Asp Ile
385                 390                 395                 400

Glu Gly Asn Leu Leu Pro Glu Gly Val Pro Pro Glu Arg Gln Trp
                405                 410                 415

Ala Arg Phe Tyr Val Lys Ile Tyr Arg Ala Glu Gly Leu Pro Arg Met
                420                 425                 430

Asn Thr Ser Leu Met Ala Asn Val Lys Lys Ala Phe Ile Gly Glu Asn
            435                 440                 445

Lys Asp Leu Val Asp Pro Tyr Val Gln Val Phe Phe Ala Gly Gln Lys
    450                 455                 460

Gly Lys Thr Ser Val Gln Lys Ser Ser Tyr Glu Pro Leu Trp Asn Glu
465                 470                 475                 480

Gln Val Val Phe Thr Asp Leu Phe Pro Pro Leu Cys Lys Arg Met Lys
                485                 490                 495

Val Gln Ile Arg Asp Ser Asp Lys Val Asn Asp Val Ala Ile Gly Thr
                500                 505                 510

His Phe Ile Asp Leu Arg Lys Ile Ser Asn Asp Gly Asp Lys Gly Phe
            515                 520                 525

Leu Pro Thr Leu Gly Pro Ala Trp Val Asn Met Tyr Gly Ser Thr Arg
    530                 535                 540

Asn Tyr Thr Leu Leu Asp Glu His Gln Asp Leu Asn Glu Gly Leu Gly
545                 550                 555                 560

Glu Gly Val Ser Phe Arg Ala Arg Leu Leu Gly Leu Ala Val Glu
                565                 570                 575

Ile Val Asp Thr Ser Asn Pro Glu Leu Thr Ser Ser Thr Glu Val Gln
                580                 585                 590

Val Glu Gln Ala Thr Pro Ile Ser Glu Ser Cys Ala Gly Lys Met Glu
            595                 600                 605

Glu Phe Phe Leu Phe Gly Ala Phe Leu Glu Ala Ser Met Ile Asp Arg
    610                 615                 620

Arg Asn Gly Asp Lys Pro Ile Thr Phe Glu Val Thr Ile Gly Asn Tyr
```

-continued

```
         625                 630                 635                 640
Gly Asn Glu Val Asp Gly Leu Ser Arg Pro Gln Arg Pro Arg Pro Arg
                    645                 650                 655

Lys Glu Pro Gly Asp Glu Glu Val Asp Leu Ile Gln Asn Ala Ser
            660                 665                 670

Asp Asp Glu Ala Gly Asp Ala Gly Asp Leu Ala Ser Val Ser Ser Thr
                675                 680                 685

Pro Pro Met Arg Pro Gln Val Thr Asp Arg Asn Tyr Phe His Leu Pro
        690                 695                 700

Tyr Leu Glu Arg Lys Pro Cys Ile Tyr Ile Lys Ser Trp Trp Pro Asp
705                 710                 715                 720

Gln Arg Arg Arg Leu Tyr Asn Ala Asn Ile Met Asp His Ile Ala Asp
                    725                 730                 735

Lys Leu Glu Glu Gly Leu Asn Asp Ile Gln Glu Met Ile Lys Thr Glu
                740                 745                 750

Lys Ser Tyr Pro Glu Arg Arg Leu Arg Gly Val Leu Glu Glu Leu Ser
        755                 760                 765

Cys Gly Cys Cys Arg Phe Leu Ser Leu Ala Asp Lys Asp Gln Gly His
770                 775                 780

Ser Ser Arg Thr Arg Leu Asp Arg Glu Arg Leu Lys Ser Cys Met Arg
785                 790                 795                 800

Glu Leu Glu Asn Met Gly Gln Gln Ala Arg Met Leu Arg Ala Gln Val
                805                 810                 815

Lys Arg His Thr Val Arg Asp Lys Leu Arg Leu Cys Gln Asn Phe Leu
                820                 825                 830

Gln Lys Leu Arg Phe Leu Ala Asp Glu Pro Gln His Ser Ile Pro Asp
            835                 840                 845

Ile Phe Ile Trp Met Met Ser Asn Asn Lys Arg Val Ala Tyr Ala Arg
            850                 855                 860

Val Pro Ser Lys Asp Leu Leu Phe Ser Ile Val Glu Glu Thr Gly
865                 870                 875                 880

Lys Asp Cys Ala Lys Val Lys Thr Leu Phe Leu Lys Leu Pro Gly Lys
                885                 890                 895

Arg Gly Phe Gly Ser Ala Gly Trp Thr Val Gln Ala Lys Val Glu Leu
        900                 905                 910

Tyr Leu Trp Leu Gly Leu Ser Lys Gln Arg Lys Glu Phe Leu Cys Gly
    915                 920                 925

Leu Pro Cys Gly Phe Gln Glu Val Lys Ala Ala Gln Gly Leu Gly Leu
    930                 935                 940

His Ala Phe Pro Pro Val Ser Leu Val Tyr Thr Lys Lys Gln Ala Phe
945                 950                 955                 960

Gln Leu Arg Ala His Met Tyr Gln Ala Arg Ser Leu Phe Ala Ala Asp
                965                 970                 975

Ser Ser Gly Leu Ser Asp Pro Phe Ala Arg Val Phe Ile Asn Gln
            980                 985                 990

Ser Gln Cys Thr Glu Val Leu Asn  Glu Thr Leu Cys Pro  Thr Trp Asp
        995                 1000                1005

Gln Met  Leu Val Phe Asp Asn  Leu Glu Leu Tyr Gly  Glu Ala His
        1010                1015                1020

Glu Leu  Arg Asp Asp Pro  Ile Ile Val Ile Glu  Ile Tyr Asp
        1025                1030                1035

Gln Asp  Ser Met Gly Lys Ala  Asp Phe Met Gly Arg  Thr Phe Ala
        1040                1045                1050
```

-continued

```
Lys Pro Leu Val Lys Met Ala Asp Glu Ala Tyr Cys Pro Pro Arg
    1055                1060                1065
Phe Pro Pro Gln Leu Glu Tyr Tyr Gln Ile Tyr Arg Gly Asn Ala
    1070                1075                1080
Thr Ala Gly Asp Leu Leu Ala Ala Phe Glu Leu Leu Gln Ile Gly
    1085                1090                1095
Pro Ala Gly Lys Ala Asp Leu Pro Pro Ile Asn Gly Pro Val Asp
    1100                1105                1110
Val Asp Arg Gly Pro Ile Met Pro Val Pro Met Gly Ile Arg Pro
    1115                1120                1125
Val Leu Ser Lys Tyr Arg Val Glu Val Leu Phe Trp Gly Leu Arg
    1130                1135                1140
Asp Leu Lys Arg Val Asn Leu Ala Gln Val Asp Arg Pro Arg Val
    1145                1150                1155
Asp Ile Glu Cys Ala Gly Lys Gly Val Gln Ser Ser Leu Ile His
    1160                1165                1170
Asn Tyr Lys Lys Asn Pro Asn Phe Asn Thr Leu Val Lys Trp Phe
    1175                1180                1185
Glu Val Asp Leu Pro Glu Asn Glu Leu Leu His Pro Pro Leu Asn
    1190                1195                1200
Ile Arg Val Val Asp Cys Arg Ala Phe Gly Arg Tyr Thr Leu Val
    1205                1210                1215
Gly Ser His Ala Val Ser Ser Leu Arg Arg Phe Ile Tyr Arg Pro
    1220                1225                1230
Pro Asp Arg Ser Ala Pro Ser Trp Asn Thr Thr Val Arg Leu Leu
    1235                1240                1245
Arg Arg Cys Arg Val Leu Cys Asn Gly Gly Ser Ser Ser His Ser
    1250                1255                1260
Thr Gly Glu Val Val Val Thr Met Glu Pro Glu Val Pro Ile Lys
    1265                1270                1275
Lys Leu Glu Thr Met Val Lys Leu Asp Ala Thr Ser Glu Ala Val
    1280                1285                1290
Val Lys Val Asp Val Ala Glu Glu Glu Lys Glu Lys Lys Lys Lys
    1295                1300                1305
Lys Lys Gly Thr Ala Glu Pro Glu Glu Glu Pro Asp Glu
    1310                1315                1320
Ser Met Leu Asp Trp Trp Ser Lys Tyr Phe Ala Ser Ile Asp Thr
    1325                1330                1335
Met Lys Glu Gln Leu Arg Gln Gln Glu Pro Ser Gly Ile Asp Leu
    1340                1345                1350
Glu Glu Lys Glu Glu Val Asp Asn Thr Glu Gly Leu Lys Gly Ser
    1355                1360                1365
Met Lys Gly Lys Glu Lys Ala Arg Ala Ala Lys Glu Glu Lys Lys
    1370                1375                1380
Lys Lys Thr Gln Ser Ser Gly Ser Gly Gln Gly Ser Glu Ala Pro
    1385                1390                1395
Glu Lys Lys Lys Pro Lys Ile Asp Glu Leu Lys Val Tyr Pro Lys
    1400                1405                1410
Glu Leu Glu Ser Glu Phe Asp Asn Phe Glu Asp Trp Leu His Thr
    1415                1420                1425
Phe Asn Leu Leu Arg Gly Lys Thr Gly Asp Asp Glu Asp Gly Ser
    1430                1435                1440
```

```
Thr Glu Glu Glu Arg Ile Val Gly Arg Phe Lys Gly Ser Leu Cys
    1445                1450                1455

Val Tyr Lys Val Pro Leu Pro Glu Asp Val Ser Arg Glu Ala Gly
    1460                1465                1470

Tyr Asp Ser Thr Tyr Gly Met Phe Gln Gly Ile Pro Ser Asn Asp
    1475                1480                1485

Pro Ile Asn Val Leu Val Arg Val Tyr Val Val Arg Ala Thr Asp
    1490                1495                1500

Leu His Pro Ala Asp Ile Asn Gly Lys Ala Asp Pro Tyr Ile Ala
    1505                1510                1515

Ile Arg Leu Gly Lys Thr Asp Ile Arg Asp Lys Glu Asn Tyr Ile
    1520                1525                1530

Ser Lys Gln Leu Asn Pro Val Phe Gly Lys Ser Phe Asp Ile Glu
    1535                1540                1545

Ala Ser Phe Pro Met Glu Ser Met Leu Thr Val Ala Val Tyr Asp
    1550                1555                1560

Trp Asp Leu Val Gly Thr Asp Asp Leu Ile Gly Glu Thr Lys Ile
    1565                1570                1575

Asp Leu Glu Asn Arg Phe Tyr Ser Lys His Arg Ala Thr Cys Gly
    1580                1585                1590

Ile Ala Gln Thr Tyr Ser Thr His Gly Tyr Asn Ile Trp Arg Asp
    1595                1600                1605

Pro Met Lys Pro Ser Gln Ile Leu Thr Arg Leu Cys Lys Asp Gly
    1610                1615                1620

Lys Val Asp Gly Pro His Phe Gly Pro Pro Gly Arg Val Lys Val
    1625                1630                1635

Ala Asn Arg Val Phe Thr Gly Pro Ser Glu Ile Glu Asp Glu Asn
    1640                1645                1650

Gly Gln Arg Lys Pro Thr Asp Glu His Val Ala Leu Leu Ala Leu
    1655                1660                1665

Arg His Trp Glu Asp Ile Pro Arg Ala Gly Cys Arg Leu Val Pro
    1670                1675                1680

Glu His Val Glu Thr Arg Pro Leu Leu Asn Pro Asp Lys Pro Gly
    1685                1690                1695

Ile Glu Gln Gly Arg Leu Glu Leu Trp Val Asp Met Phe Pro Met
    1700                1705                1710

Asp Met Pro Ala Pro Gly Thr Pro Leu Asp Ile Ser Pro Arg Lys
    1715                1720                1725

Pro Lys Lys Tyr Glu Leu Arg Val Ile Ile Trp Asn Thr Asp Glu
    1730                1735                1740

Val Val Leu Glu Asp Asp Asp Phe Phe Thr Gly Glu Lys Ser Ser
    1745                1750                1755

Asp Ile Phe Val Arg Gly Trp Leu Lys Gly Gln Gln Glu Asp Lys
    1760                1765                1770

Gln Asp Thr Asp Val His Tyr His Ser Leu Thr Gly Glu Gly Asn
    1775                1780                1785

Phe Asn Trp Arg Tyr Leu Phe Pro Phe Asp Tyr Leu Ala Ala Glu
    1790                1795                1800

Glu Lys Ile Val Ile Ser Lys Lys Glu Ser Met Phe Ser Trp Asp
    1805                1810                1815

Glu Thr Glu Tyr Lys Ile Pro Ala Arg Leu Thr Leu Gln Ile Trp
    1820                1825                1830

Asp Ala Asp His Phe Ser Ala Asp Asp Phe Leu Gly Ala Ile Glu
```

```
                          1835                1840                1845

Leu Asp Leu Asn Arg Phe Pro Arg Gly Ala Lys Thr Ala Lys Gln
        1850                1855                1860

Cys Thr Met Glu Met Ala Thr Gly Glu Val Asp Val Pro Leu Val
    1865                1870                1875

Ser Ile Phe Lys Gln Lys Arg Val Lys Gly Trp Trp Pro Leu Leu
    1880                1885                1890

Ala Arg Asn Glu Asn Asp Glu Phe Glu Leu Thr Gly Lys Val Glu
    1895                1900                1905

Ala Glu Leu His Leu Leu Thr Ala Glu Glu Ala Glu Lys Asn Pro
    1910                1915                1920

Val Gly Leu Ala Arg Asn Glu Pro Asp Pro Leu Glu Lys Pro Asn
    1925                1930                1935

Arg Pro Asp Thr Ala Phe Val Trp Phe Leu Asn Pro Leu Lys Ser
    1940                1945                1950

Ile Lys Tyr Leu Ile Cys Thr Arg Tyr Lys Trp Leu Ile Ile Lys
    1955                1960                1965

Ile Val Leu Ala Leu Leu Gly Leu Leu Met Leu Gly Leu Phe Leu
    1970                1975                1980

Tyr Ser Leu Pro Gly Tyr Met Val Lys Lys Leu Leu Gly Ala
    1985                1990                1995

<210> SEQ ID NO 6
<211> LENGTH: 1997
<212> TYPE: PRT
<213> ORGANISM: Mus musculus

<400> SEQUENCE: 6

Met Ala Leu Ile Val His Leu Lys Thr Val Ser Glu Leu Arg Gly Lys
1               5                   10                  15

Gly Asp Arg Ile Ala Lys Val Thr Phe Arg Gly Gln Ser Phe Tyr Ser
                20                  25                  30

Arg Val Leu Glu Asn Cys Glu Gly Val Ala Asp Phe Asp Glu Thr Phe
            35                  40                  45

Arg Trp Pro Val Ala Ser Ser Ile Asp Arg Asn Glu Val Leu Glu Ile
        50                  55                  60

Gln Ile Phe Asn Tyr Ser Lys Val Phe Ser Asn Lys Leu Ile Gly Thr
65                  70                  75                  80

Phe Cys Met Val Leu Gln Lys Val Val Glu Glu Asn Arg Val Glu Val
                85                  90                  95

Thr Asp Thr Leu Met Asp Asp Ser Asn Ala Ile Ile Lys Thr Ser Leu
            100                 105                 110

Ser Met Glu Val Arg Tyr Gln Ala Thr Asp Gly Thr Val Gly Pro Trp
        115                 120                 125

Asp Asp Gly Asp Phe Leu Gly Asp Glu Ser Leu Gln Glu Glu Lys Asp
    130                 135                 140

Ser Gln Glu Thr Asp Gly Leu Leu Pro Gly Ser Arg Pro Ser Thr Arg
145                 150                 155                 160

Ile Ser Gly Glu Lys Ser Phe Arg Arg Ala Gly Arg Ser Val Phe Ser
                165                 170                 175

Ala Met Lys Leu Gly Lys Thr Arg Ser His Lys Glu Glu Pro Gln Arg
            180                 185                 190

Gln Asp Glu Pro Ala Val Leu Glu Met Glu Asp Leu Asp His Leu Ala
        195                 200                 205
```

-continued

```
Ile Gln Leu Gly Asp Gly Leu Asp Pro Asp Ser Val Ser Leu Ala Ser
            210                 215                 220
Val Thr Ala Leu Thr Ser Asn Val Ser Asn Lys Arg Ser Lys Pro Asp
225                 230                 235                 240
Ile Lys Met Glu Pro Ser Ala Gly Arg Pro Met Asp Tyr Gln Val Ser
                245                 250                 255
Ile Thr Val Ile Glu Ala Arg Gln Leu Val Gly Leu Asn Met Asp Pro
            260                 265                 270
Val Val Cys Val Glu Val Gly Asp Asp Lys Lys Tyr Thr Ser Met Lys
                275                 280                 285
Glu Ser Thr Asn Cys Pro Tyr Tyr Asn Glu Tyr Phe Val Phe Asp Phe
290                 295                 300
His Val Ser Pro Asp Val Met Phe Asp Lys Ile Ile Lys Ile Ser Val
305                 310                 315                 320
Ile His Ser Lys Asn Leu Leu Arg Ser Gly Thr Leu Val Gly Ser Phe
                325                 330                 335
Lys Met Asp Val Gly Thr Val Tyr Ser Gln Pro Glu His Gln Phe His
                340                 345                 350
His Lys Trp Ala Ile Leu Ser Asp Pro Asp Asp Ile Ser Ala Gly Leu
            355                 360                 365
Lys Gly Tyr Val Lys Cys Asp Val Ala Val Val Gly Lys Gly Asp Asn
370                 375                 380
Ile Lys Thr Pro His Lys Ala Asn Glu Thr Asp Glu Asp Asp Ile Glu
385                 390                 395                 400
Gly Asn Leu Leu Leu Pro Glu Gly Val Pro Pro Glu Arg Gln Trp Ala
                405                 410                 415
Arg Phe Tyr Val Lys Ile Tyr Arg Ala Glu Gly Leu Pro Arg Met Asn
            420                 425                 430
Thr Ser Leu Met Ala Asn Val Lys Lys Ala Phe Ile Gly Glu Asn Lys
            435                 440                 445
Asp Leu Val Asp Pro Tyr Val Gln Val Phe Phe Ala Gly Gln Lys Gly
            450                 455                 460
Lys Thr Ser Val Gln Lys Ser Ser Tyr Glu Pro Leu Trp Asn Glu Gln
465                 470                 475                 480
Val Val Phe Thr Asp Leu Phe Pro Pro Leu Cys Lys Arg Met Lys Val
                485                 490                 495
Gln Ile Arg Asp Ser Asp Lys Val Asn Asp Val Ala Ile Gly Thr His
                500                 505                 510
Phe Ile Asp Leu Arg Lys Ile Ser Asn Asp Gly Asp Lys Gly Phe Leu
            515                 520                 525
Pro Thr Leu Gly Pro Ala Trp Val Asn Met Tyr Gly Ser Thr Arg Asn
530                 535                 540
Tyr Thr Leu Leu Asp Glu His Gln Asp Leu Asn Glu Gly Leu Gly Glu
545                 550                 555                 560
Gly Val Ser Phe Arg Ala Arg Leu Met Leu Gly Leu Ala Val Glu Ile
                565                 570                 575
Leu Asp Thr Ser Asn Pro Glu Leu Thr Ser Ser Thr Glu Val Gln Val
            580                 585                 590
Glu Gln Ala Thr Pro Val Ser Glu Ser Cys Thr Gly Arg Met Glu Glu
                595                 600                 605
Phe Phe Leu Phe Gly Ala Phe Leu Glu Ala Ser Met Ile Asp Arg Lys
            610                 615                 620
Asn Gly Asp Lys Pro Ile Thr Phe Glu Val Thr Ile Gly Asn Tyr Gly
```

-continued

```
            625                 630                 635                 640
Asn Glu Val Asp Gly Met Ser Arg Pro Leu Arg Pro Arg Pro Arg Lys
                    645                 650                 655

Glu Pro Gly Asp Glu Glu Val Asp Leu Ile Gln Asn Ser Ser Asp
                660                 665                 670

Asp Glu Gly Asp Glu Ala Gly Asp Leu Ala Ser Val Ser Ser Thr Pro
            675                 680                 685

Pro Met Arg Pro Gln Ile Thr Asp Arg Asn Tyr Phe His Leu Pro Tyr
        690                 695                 700

Leu Glu Arg Lys Pro Cys Ile Tyr Ile Lys Ser Trp Trp Pro Asp Gln
705                 710                 715                 720

Arg Arg Arg Leu Tyr Asn Ala Asn Ile Met Asp His Ile Ala Asp Lys
                725                 730                 735

Leu Glu Glu Gly Leu Asn Asp Val Gln Glu Met Ile Lys Thr Glu Lys
                740                 745                 750

Ser Tyr Pro Glu Arg Arg Leu Arg Gly Val Leu Glu Glu Leu Ser Cys
        755                 760                 765

Gly Cys His Arg Phe Leu Ser Leu Ser Asp Lys Asp Gln Gly Arg Ser
        770                 775                 780

Ser Arg Thr Arg Leu Asp Arg Glu Arg Leu Lys Ser Cys Met Arg Glu
785                 790                 795                 800

Leu Glu Ser Met Gly Gln Gln Ala Lys Ser Leu Arg Ala Gln Val Lys
                805                 810                 815

Arg His Thr Val Arg Asp Lys Leu Arg Ser Cys Gln Asn Phe Leu Gln
                820                 825                 830

Lys Leu Arg Phe Leu Ala Asp Glu Pro Gln His Ser Ile Pro Asp Val
            835                 840                 845

Phe Ile Trp Met Met Ser Asn Asn Lys Arg Ile Ala Tyr Ala Arg Val
        850                 855                 860

Pro Ser Lys Asp Leu Leu Phe Ser Ile Val Glu Glu Leu Gly Lys
865                 870                 875                 880

Asp Cys Ala Lys Val Lys Thr Leu Phe Leu Lys Leu Pro Gly Lys Arg
                885                 890                 895

Gly Phe Gly Ser Ala Gly Trp Thr Val Gln Ala Lys Leu Glu Leu Tyr
            900                 905                 910

Leu Trp Leu Gly Leu Ser Lys Gln Arg Lys Asp Phe Leu Cys Gly Leu
        915                 920                 925

Pro Cys Gly Phe Glu Glu Val Lys Ala Ala Gln Gly Leu Gly Leu His
    930                 935                 940

Ser Phe Pro Pro Ile Ser Leu Val Tyr Thr Lys Lys Gln Ala Phe Gln
945                 950                 955                 960

Leu Arg Ala His Met Tyr Gln Ala Arg Ser Leu Phe Ala Ala Asp Ser
                965                 970                 975

Ser Gly Leu Ser Asp Pro Phe Ala Arg Val Phe Phe Ile Asn Gln Ser
            980                 985                 990

Gln Cys Thr Glu Val Leu Asn Glu Thr Leu Cys Pro Thr Trp Asp Gln
        995                 1000                1005

Met Leu Val Phe Asp Asn Leu Glu Leu Tyr Gly Glu Ala His Glu
    1010                1015                1020

Leu Arg Asp Asp Pro Pro Ile Ile Val Ile Glu Ile Tyr Asp Gln
    1025                1030                1035

Asp Ser Met Gly Lys Ala Asp Phe Met Gly Arg Thr Phe Ala Lys
    1040                1045                1050
```

```
Pro Leu Val Lys Met Ala Asp Glu Ala Tyr Cys Pro Pro Arg Phe
    1055            1060            1065

Pro Pro Gln Leu Glu Tyr Tyr Gln Ile Tyr Arg Gly Ser Ala Thr
    1070            1075            1080

Ala Gly Asp Leu Leu Ala Ala Phe Glu Leu Leu Gln Ile Gly Pro
    1085            1090            1095

Ser Gly Lys Ala Asp Leu Pro Pro Ile Asn Gly Pro Val Asp Met
    1100            1105            1110

Asp Arg Gly Pro Ile Met Pro Val Pro Val Gly Ile Arg Pro Val
    1115            1120            1125

Leu Ser Lys Tyr Arg Val Glu Val Leu Phe Trp Gly Leu Arg Asp
    1130            1135            1140

Leu Lys Arg Val Asn Leu Ala Gln Val Asp Arg Pro Arg Val Asp
    1145            1150            1155

Ile Glu Cys Ala Gly Lys Gly Val Gln Ser Ser Leu Ile His Asn
    1160            1165            1170

Tyr Lys Lys Asn Pro Asn Phe Asn Thr Leu Val Lys Trp Phe Glu
    1175            1180            1185

Val Asp Leu Pro Glu Asn Glu Leu Leu His Pro Pro Leu Asn Ile
    1190            1195            1200

Arg Val Val Asp Cys Arg Ala Phe Gly Arg Tyr Thr Leu Val Gly
    1205            1210            1215

Ser His Ala Val Ser Ser Leu Arg Arg Phe Ile Tyr Arg Pro Pro
    1220            1225            1230

Asp Arg Ser Ala Pro Asn Trp Asn Thr Thr Val Arg Leu Leu Arg
    1235            1240            1245

Gly Cys His Arg Leu Arg Asn Gly Gly Pro Ser Ser Arg Pro Thr
    1250            1255            1260

Gly Glu Val Val Val Ser Met Glu Pro Glu Pro Val Lys Lys
    1265            1270            1275

Leu Glu Thr Met Val Lys Leu Asp Ala Thr Ser Asp Ala Val Val
    1280            1285            1290

Lys Val Asp Val Ala Glu Asp Glu Lys Glu Arg Lys Lys Lys Lys
    1295            1300            1305

Lys Lys Gly Pro Ser Glu Glu Pro Glu Glu Glu Pro Asp Glu
    1310            1315            1320

Ser Met Leu Asp Trp Trp Ser Lys Tyr Phe Ala Ser Ile Asp Thr
    1325            1330            1335

Met Lys Glu Gln Leu Arg Gln His Glu Thr Ser Gly Thr Asp Leu
    1340            1345            1350

Glu Glu Lys Glu Glu Met Ser Ala Glu Gly Leu Lys Gly Pro
    1355            1360            1365

Met Lys Ser Lys Glu Lys Ser Arg Ala Ala Lys Glu Glu Lys Lys
    1370            1375            1380

Lys Lys Asn Gln Ser Pro Gly Pro Gly Gln Gly Ser Glu Ala Pro
    1385            1390            1395

Glu Lys Lys Lys Ala Lys Ile Asp Glu Leu Lys Val Tyr Pro Lys
    1400            1405            1410

Glu Leu Glu Ser Glu Phe Asp Ser Phe Glu Asp Trp Leu His Thr
    1415            1420            1425

Phe Asn Leu Leu Arg Gly Lys Thr Gly Asp Asp Glu Asp Gly Ser
    1430            1435            1440
```

```
Thr Glu Glu Glu Arg Ile Val Gly Arg Phe Lys Gly Ser Leu Cys
    1445                1450                1455

Val Tyr Lys Val Pro Leu Pro Glu Asp Val Ser Arg Glu Ala Gly
    1460                1465                1470

Tyr Asp Pro Thr Tyr Gly Met Phe Gln Gly Ile Pro Ser Asn Asp
    1475                1480                1485

Pro Ile Asn Val Leu Val Arg Ile Tyr Val Val Arg Ala Thr Asp
    1490                1495                1500

Leu His Pro Ala Asp Ile Asn Gly Lys Ala Asp Pro Tyr Ile Ala
    1505                1510                1515

Ile Lys Leu Gly Lys Thr Asp Ile Arg Asp Lys Glu Asn Tyr Ile
    1520                1525                1530

Ser Lys Gln Leu Asn Pro Val Phe Gly Lys Ser Phe Asp Ile Glu
    1535                1540                1545

Ala Ser Phe Pro Met Glu Ser Met Leu Thr Val Ala Val Tyr Asp
    1550                1555                1560

Trp Asp Leu Val Gly Thr Asp Asp Leu Ile Gly Glu Thr Lys Ile
    1565                1570                1575

Asp Leu Glu Asn Arg Phe Tyr Ser Lys His Arg Ala Thr Cys Gly
    1580                1585                1590

Ile Ala Gln Thr Tyr Ser Ile His Gly Tyr Asn Ile Trp Arg Asp
    1595                1600                1605

Pro Met Lys Pro Ser Gln Ile Leu Thr Arg Leu Cys Lys Glu Gly
    1610                1615                1620

Lys Val Asp Gly Pro His Phe Gly Pro His Gly Arg Val Arg Val
    1625                1630                1635

Ala Asn Arg Val Phe Thr Gly Pro Ser Glu Ile Glu Asp Glu Asn
    1640                1645                1650

Gly Gln Arg Lys Pro Thr Asp Glu His Val Ala Leu Ser Ala Leu
    1655                1660                1665

Arg His Trp Glu Asp Ile Pro Arg Val Gly Cys Arg Leu Val Pro
    1670                1675                1680

Glu His Val Glu Thr Arg Pro Leu Leu Asn Pro Asp Lys Pro Gly
    1685                1690                1695

Ile Glu Gln Gly Arg Leu Glu Leu Trp Val Asp Met Phe Pro Met
    1700                1705                1710

Asp Met Pro Ala Pro Gly Thr Pro Leu Asp Ile Ser Pro Arg Lys
    1715                1720                1725

Pro Lys Lys Tyr Glu Leu Arg Val Ile Val Trp Asn Thr Asp Glu
    1730                1735                1740

Val Val Leu Glu Asp Asp Asp Phe Phe Thr Gly Glu Lys Ser Ser
    1745                1750                1755

Asp Ile Phe Val Arg Gly Trp Leu Lys Gly Gln Gln Glu Asp Lys
    1760                1765                1770

Gln Asp Thr Asp Val His Tyr His Ser Leu Thr Gly Glu Gly Asn
    1775                1780                1785

Phe Asn Trp Arg Tyr Leu Phe Pro Phe Asp Tyr Leu Ala Ala Glu
    1790                1795                1800

Glu Lys Ile Val Met Ser Lys Lys Glu Ser Met Phe Ser Trp Asp
    1805                1810                1815

Glu Thr Glu Tyr Lys Ile Pro Ala Arg Leu Thr Leu Gln Ile Trp
    1820                1825                1830

Asp Ala Asp His Phe Ser Ala Asp Asp Phe Leu Gly Ala Ile Glu
```

```
                     1835                1840                1845

Leu  Asp  Leu  Asn  Arg  Phe  Pro  Arg  Gly  Ala  Lys  Thr  Ala  Lys  Gln
        1850                1855                1860

Cys  Thr  Met  Glu  Met  Ala  Thr  Gly  Glu  Val  Asp  Val  Pro  Leu  Val
        1865                1870                1875

Ser  Ile  Phe  Lys  Gln  Lys  Arg  Val  Lys  Gly  Trp  Trp  Pro  Leu  Leu
        1880                1885                1890

Ala  Arg  Asn  Glu  Asn  Asp  Glu  Phe  Glu  Leu  Thr  Gly  Lys  Val  Glu
        1895                1900                1905

Ala  Glu  Leu  His  Leu  Leu  Thr  Ala  Glu  Glu  Ala  Glu  Lys  Asn  Pro
        1910                1915                1920

Val  Gly  Leu  Ala  Arg  Asn  Glu  Pro  Asp  Pro  Leu  Glu  Lys  Pro  Asn
        1925                1930                1935

Arg  Pro  Asp  Thr  Ser  Phe  Ile  Trp  Phe  Leu  Asn  Pro  Leu  Lys  Ser
        1940                1945                1950

Ala  Arg  Tyr  Phe  Leu  Trp  His  Thr  Tyr  Arg  Trp  Leu  Leu  Leu  Lys
        1955                1960                1965

Phe  Leu  Leu  Leu  Phe  Leu  Leu  Leu  Leu  Phe  Ala  Leu  Phe  Leu
        1970                1975                1980

Tyr  Ser  Leu  Pro  Gly  Tyr  Leu  Ala  Lys  Lys  Ile  Leu  Gly  Ala
        1985                1990                1995

<210> SEQ ID NO 7
<211> LENGTH: 1977
<212> TYPE: PRT
<213> ORGANISM: Mus musculus

<400> SEQUENCE: 7

Met  Ala  Leu  Ile  Val  His  Leu  Lys  Thr  Val  Ser  Glu  Leu  Arg  Gly  Lys
1                   5                   10                  15

Gly  Asp  Arg  Ile  Ala  Lys  Val  Thr  Phe  Arg  Gly  Gln  Ser  Phe  Tyr  Ser
                20                  25                  30

Arg  Val  Leu  Glu  Asn  Cys  Glu  Gly  Val  Ala  Asp  Phe  Asp  Glu  Thr  Phe
            35                  40                  45

Arg  Trp  Pro  Val  Ala  Ser  Ser  Ile  Asp  Arg  Asn  Glu  Val  Leu  Glu  Ile
        50                  55                  60

Gln  Ile  Phe  Asn  Tyr  Ser  Lys  Val  Phe  Ser  Asn  Lys  Leu  Ile  Gly  Thr
65                  70                  75                  80

Phe  Cys  Met  Val  Leu  Gln  Lys  Val  Val  Glu  Glu  Asn  Arg  Val  Glu  Val
                85                  90                  95

Thr  Asp  Thr  Leu  Met  Asp  Asp  Ser  Asn  Ala  Ile  Ile  Lys  Thr  Ser  Leu
            100                 105                 110

Ser  Met  Glu  Val  Arg  Tyr  Gln  Ala  Thr  Asp  Gly  Thr  Val  Gly  Pro  Trp
        115                 120                 125

Asp  Asp  Gly  Asp  Phe  Leu  Gly  Asp  Glu  Ser  Leu  Gln  Glu  Glu  Lys  Asp
    130                 135                 140

Ser  Gln  Glu  Thr  Asp  Gly  Leu  Leu  Pro  Gly  Ser  Arg  Pro  Ser  Thr  Arg
145                 150                 155                 160

Ile  Ser  Gly  Glu  Lys  Ser  Phe  Arg  Arg  Ala  Gly  Arg  Ser  Val  Phe  Ser
                165                 170                 175

Ala  Met  Lys  Leu  Gly  Lys  Thr  Arg  Ser  His  Lys  Glu  Glu  Pro  Gln  Arg
            180                 185                 190

Gln  Asp  Glu  Pro  Ala  Val  Leu  Glu  Met  Glu  Asp  Leu  Asp  His  Leu  Ala
        195                 200                 205
```

-continued

```
Ile Gln Leu Gly Asp Gly Leu Asp Pro Asp Ser Val Ser Leu Ala Ser
210                 215                 220
Val Thr Ala Leu Thr Ser Asn Val Ser Asn Lys Arg Ser Lys Pro Asp
225                 230                 235                 240
Ile Lys Met Glu Pro Ser Ala Gly Arg Pro Met Asp Tyr Gln Val Ser
                245                 250                 255
Ile Thr Val Ile Glu Ala Arg Gln Leu Val Gly Leu Asn Met Asp Pro
            260                 265                 270
Val Val Cys Val Glu Val Gly Asp Asp Lys Lys Tyr Thr Ser Met Lys
            275                 280                 285
Glu Ser Thr Asn Cys Pro Tyr Tyr Asn Glu Tyr Phe Val Phe Asp Phe
290                 295                 300
His Val Ser Pro Asp Val Met Phe Asp Lys Ile Ile Lys Ile Ser Val
305                 310                 315                 320
Ile His Ser Lys Asn Leu Leu Arg Ser Gly Thr Leu Val Gly Ser Phe
                325                 330                 335
Lys Met Asp Val Gly Thr Val Tyr Ser Gln Pro Glu His Gln Phe His
            340                 345                 350
His Lys Trp Ala Ile Leu Ser Asp Pro Asp Asp Ile Ser Ala Gly Leu
            355                 360                 365
Lys Gly Tyr Val Lys Cys Asp Val Ala Val Val Gly Lys Gly Asp Asn
370                 375                 380
Ile Lys Thr Pro His Lys Ala Asn Glu Thr Asp Glu Asp Asp Ile Glu
385                 390                 395                 400
Gly Asn Leu Leu Leu Pro Glu Gly Val Pro Pro Glu Arg Gln Trp Ala
                405                 410                 415
Arg Phe Tyr Val Lys Ile Tyr Arg Ala Glu Gly Leu Pro Arg Met Asn
            420                 425                 430
Thr Ser Leu Met Ala Asn Val Lys Lys Ala Phe Ile Gly Glu Asn Lys
            435                 440                 445
Asp Leu Val Asp Pro Tyr Val Gln Val Phe Phe Ala Gly Gln Lys Gly
450                 455                 460
Lys Thr Ser Val Gln Lys Ser Ser Tyr Glu Pro Leu Trp Asn Glu Gln
465                 470                 475                 480
Val Val Phe Thr Asp Leu Phe Pro Pro Leu Cys Lys Arg Met Lys Val
                485                 490                 495
Gln Ile Arg Asp Ser Asp Lys Val Asn Asp Val Ala Ile Gly Thr His
            500                 505                 510
Phe Ile Asp Leu Arg Lys Ile Ser Asn Asp Gly Asp Lys Gly Phe Leu
            515                 520                 525
Pro Thr Leu Gly Pro Ala Trp Val Asn Met Tyr Gly Ser Thr Arg Asn
530                 535                 540
Tyr Thr Leu Leu Asp Glu His Gln Asp Leu Asn Glu Gly Leu Gly Glu
545                 550                 555                 560
Gly Val Ser Phe Arg Ala Arg Leu Met Leu Gly Leu Ala Val Glu Ile
                565                 570                 575
Leu Asp Thr Ser Asn Pro Glu Leu Thr Ser Ser Thr Glu Val Gln Val
            580                 585                 590
Glu Gln Ala Thr Pro Val Ser Glu Ser Cys Thr Gly Arg Met Glu Glu
            595                 600                 605
Phe Phe Leu Phe Gly Ala Phe Leu Glu Ala Ser Met Ile Asp Arg Lys
610                 615                 620
Asn Gly Asp Lys Pro Ile Thr Phe Glu Val Thr Ile Gly Asn Tyr Gly
```

```
                625                630                635                640
Asn Glu Val Asp Gly Met Ser Arg Pro Leu Arg Pro Arg Pro Arg Lys
                    645                650                655
Glu Pro Gly Asp Glu Glu Val Asp Leu Ile Gln Asn Ser Ser Asp
                660                665                670
Asp Glu Gly Asp Glu Ala Gly Asp Leu Ala Ser Val Ser Ser Thr Pro
            675                680                685
Pro Met Arg Pro Gln Ile Thr Asp Arg Asn Tyr Phe His Leu Pro Tyr
        690                695                700
Leu Glu Arg Lys Pro Cys Ile Tyr Ile Lys Ser Trp Trp Pro Asp Gln
705                710                715                720
Arg Arg Arg Leu Tyr Asn Ala Asn Ile Met Asp His Ile Ala Asp Lys
                725                730                735
Leu Glu Glu Gly Leu Asn Asp Val Gln Glu Met Ile Lys Thr Glu Lys
                740                745                750
Ser Tyr Pro Glu Arg Arg Leu Arg Gly Val Leu Glu Glu Leu Ser Cys
        755                760                765
Gly Cys His Arg Phe Leu Ser Leu Ser Asp Lys Asp Gln Gly Arg Ser
        770                775                780
Ser Arg Thr Arg Leu Asp Arg Glu Arg Leu Lys Ser Cys Met Arg Glu
785                790                795                800
Leu Glu Ser Met Gly Gln Gln Ala Lys Ser Leu Arg Ala Gln Val Lys
                805                810                815
Arg His Thr Val Arg Asp Lys Leu Arg Ser Cys Gln Asn Phe Leu Gln
                820                825                830
Lys Leu Arg Phe Leu Ala Asp Glu Pro Gln His Ser Ile Pro Asp Val
        835                840                845
Phe Ile Trp Met Met Ser Asn Asn Lys Arg Ile Ala Tyr Ala Arg Val
        850                855                860
Pro Ser Lys Asp Leu Leu Phe Ser Ile Val Glu Glu Leu Gly Lys
865                870                875                880
Asp Cys Ala Lys Val Lys Thr Leu Phe Leu Lys Leu Pro Gly Lys Arg
                885                890                895
Gly Phe Gly Ser Ala Gly Trp Thr Val Gln Ala Lys Leu Glu Leu Tyr
                900                905                910
Leu Trp Leu Gly Leu Ser Lys Gln Arg Lys Asp Phe Leu Cys Gly Leu
        915                920                925
Pro Cys Gly Phe Glu Glu Val Lys Ala Ala Gln Gly Leu Gly Leu His
        930                935                940
Ser Phe Pro Pro Ile Ser Leu Val Tyr Thr Lys Lys Gln Ala Phe Gln
945                950                955                960
Leu Arg Ala His Met Tyr Gln Ala Arg Ser Leu Phe Ala Ala Asp Ser
                965                970                975
Ser Gly Leu Ser Asp Pro Phe Ala Arg Val Phe Phe Ile Asn Gln Ser
            980                985                990
Gln Cys Thr Glu Val Leu Asn Glu  Thr Leu Cys Pro Thr Trp Asp Gln
        995                1000                1005
Met Leu Val Phe Asp Asn Leu  Glu Leu Tyr Gly Glu  Ala His Glu
    1010                1015                1020
Leu Arg Asp Asp Pro Pro Ile  Ile Val Ile Glu Ile  Tyr Asp Gln
    1025                1030                1035
Asp Ser Met Gly Lys Ala Asp  Phe Met Gly Arg Thr  Phe Ala Lys
    1040                1045                1050
```

```
Pro Leu Val Lys Met Ala Asp Glu Ala Tyr Cys Pro Pro Arg Phe
    1055            1060                1065

Pro Pro Gln Leu Glu Tyr Tyr Gln Ile Tyr Arg Gly Ser Ala Thr
    1070            1075                1080

Ala Gly Asp Leu Leu Ala Ala Phe Glu Leu Leu Gln Ile Gly Pro
    1085            1090                1095

Ser Gly Lys Ala Asp Leu Pro Pro Ile Asn Gly Pro Val Asp Met
    1100            1105                1110

Asp Arg Gly Pro Ile Met Pro Val Pro Val Gly Ile Arg Pro Val
    1115            1120                1125

Leu Ser Lys Tyr Arg Val Glu Val Leu Phe Trp Gly Leu Arg Asp
    1130            1135                1140

Leu Lys Arg Val Asn Leu Ala Gln Val Asp Arg Pro Arg Val Asp
    1145            1150                1155

Ile Glu Cys Ala Gly Lys Gly Val Gln Ser Ser Leu Ile His Asn
    1160            1165                1170

Tyr Lys Lys Asn Pro Asn Phe Asn Thr Leu Val Lys Trp Phe Glu
    1175            1180                1185

Val Asp Leu Pro Glu Asn Glu Leu Leu His Pro Pro Leu Asn Ile
    1190            1195                1200

Arg Val Val Asp Cys Arg Ala Phe Gly Arg Tyr Thr Leu Val Gly
    1205            1210                1215

Ser His Ala Val Ser Ser Leu Arg Arg Phe Ile Tyr Arg Pro Pro
    1220            1225                1230

Asp Arg Ser Ala Pro Asn Trp Asn Thr Thr Gly Glu Val Val Val
    1235            1240                1245

Ser Met Glu Pro Glu Glu Pro Val Lys Lys Leu Glu Thr Met Val
    1250            1255                1260

Lys Leu Asp Ala Thr Ser Asp Ala Val Val Lys Val Asp Val Ala
    1265            1270                1275

Glu Asp Glu Lys Glu Arg Lys Lys Lys Lys Lys Gly Pro Ser
    1280            1285                1290

Glu Glu Pro Glu Glu Glu Pro Asp Glu Ser Met Leu Asp Trp
    1295            1300                1305

Trp Ser Lys Tyr Phe Ala Ser Ile Asp Thr Met Lys Glu Gln Leu
    1310            1315                1320

Arg Gln His Glu Thr Ser Gly Thr Asp Leu Glu Glu Lys Glu Glu
    1325            1330                1335

Met Glu Ser Ala Glu Gly Leu Lys Gly Pro Met Lys Ser Lys Glu
    1340            1345                1350

Lys Ser Arg Ala Ala Lys Glu Glu Lys Lys Lys Asn Gln Ser
    1355            1360                1365

Pro Gly Pro Gly Gln Gly Ser Glu Ala Pro Glu Lys Lys Lys Ala
    1370            1375                1380

Lys Ile Asp Glu Leu Lys Val Tyr Pro Lys Glu Leu Glu Ser Glu
    1385            1390                1395

Phe Asp Ser Phe Glu Asp Trp Leu His Thr Phe Asn Leu Leu Arg
    1400            1405                1410

Gly Lys Thr Gly Asp Asp Glu Asp Gly Ser Thr Glu Glu Glu Arg
    1415            1420                1425

Ile Val Gly Arg Phe Lys Gly Ser Leu Cys Val Tyr Lys Val Pro
    1430            1435                1440
```

```
Leu Pro Glu Asp Val Ser Arg Glu Ala Gly Tyr Asp Pro Thr Tyr
    1445                1450                1455

Gly Met Phe Gln Gly Ile Pro Ser Asn Asp Pro Ile Asn Val Leu
    1460                1465                1470

Val Arg Ile Tyr Val Val Arg Ala Thr Asp Leu His Pro Ala Asp
    1475                1480                1485

Ile Asn Gly Lys Ala Asp Pro Tyr Ile Ala Ile Lys Leu Gly Lys
    1490                1495                1500

Thr Asp Ile Arg Asp Lys Glu Asn Tyr Ile Ser Lys Gln Leu Asn
    1505                1510                1515

Pro Val Phe Gly Lys Ser Phe Asp Ile Glu Ala Ser Phe Pro Met
    1520                1525                1530

Glu Ser Met Leu Thr Val Ala Val Tyr Asp Trp Asp Leu Val Gly
    1535                1540                1545

Thr Asp Asp Leu Ile Gly Glu Thr Lys Ile Asp Leu Glu Asn Arg
    1550                1555                1560

Phe Tyr Ser Lys His Arg Ala Thr Cys Gly Ile Ala Gln Thr Tyr
    1565                1570                1575

Ser Ile His Gly Tyr Asn Ile Trp Arg Asp Pro Met Lys Pro Ser
    1580                1585                1590

Gln Ile Leu Thr Arg Leu Cys Lys Glu Gly Lys Val Asp Gly Pro
    1595                1600                1605

His Phe Gly Pro His Gly Arg Val Arg Val Ala Asn Arg Val Phe
    1610                1615                1620

Thr Gly Pro Ser Glu Ile Glu Asp Glu Asn Gly Gln Arg Lys Pro
    1625                1630                1635

Thr Asp Glu His Val Ala Leu Ser Ala Leu Arg His Trp Glu Asp
    1640                1645                1650

Ile Pro Arg Val Gly Cys Arg Leu Val Pro Glu His Val Glu Thr
    1655                1660                1665

Arg Pro Leu Leu Asn Pro Asp Lys Pro Gly Ile Glu Gln Gly Arg
    1670                1675                1680

Leu Glu Leu Trp Val Asp Met Phe Pro Met Asp Met Pro Ala Pro
    1685                1690                1695

Gly Thr Pro Leu Asp Ile Ser Pro Arg Lys Pro Lys Lys Tyr Glu
    1700                1705                1710

Leu Arg Val Ile Val Trp Asn Thr Asp Glu Val Val Leu Glu Asp
    1715                1720                1725

Asp Asp Phe Phe Thr Gly Glu Lys Ser Ser Asp Ile Phe Val Arg
    1730                1735                1740

Gly Trp Leu Lys Gly Gln Gln Glu Asp Lys Gln Asp Thr Asp Val
    1745                1750                1755

His Tyr His Ser Leu Thr Gly Glu Gly Asn Phe Asn Trp Arg Tyr
    1760                1765                1770

Leu Phe Pro Phe Asp Tyr Leu Ala Ala Glu Glu Lys Ile Val Met
    1775                1780                1785

Ser Lys Lys Glu Ser Met Phe Ser Trp Asp Glu Thr Glu Tyr Lys
    1790                1795                1800

Ile Pro Ala Arg Leu Thr Leu Gln Ile Trp Asp Ala Asp His Phe
    1805                1810                1815

Ser Ala Asp Asp Phe Leu Gly Ala Ile Glu Leu Asp Leu Asn Arg
    1820                1825                1830

Phe Pro Arg Gly Ala Lys Thr Ala Lys Gln Cys Thr Met Glu Met
```

```
                1835                1840                1845

Ala Thr Gly Glu Val Asp Val Pro Leu Val Ser Ile Phe Lys Gln
    1850                1855                1860

Lys Arg Val Lys Gly Trp Trp Pro Leu Leu Ala Arg Asn Glu Asn
1865                1870                1875

Asp Glu Phe Glu Leu Thr Gly Lys Val Glu Ala Glu Leu His Leu
    1880                1885                1890

Leu Thr Ala Glu Glu Ala Glu Lys Asn Pro Val Gly Leu Ala Arg
    1895                1900                1905

Asn Glu Pro Asp Pro Leu Glu Lys Pro Asn Arg Pro Asp Thr Ser
    1910                1915                1920

Phe Ile Trp Phe Leu Asn Pro Leu Lys Ser Ala Arg Tyr Phe Leu
    1925                1930                1935

Trp His Thr Tyr Arg Trp Leu Leu Leu Lys Phe Leu Leu Leu Phe
    1940                1945                1950

Leu Leu Leu Leu Leu Phe Ala Leu Phe Leu Tyr Ser Leu Pro Gly
    1955                1960                1965

Tyr Leu Ala Lys Lys Ile Leu Gly Ala
    1970                1975

<210> SEQ ID NO 8
<211> LENGTH: 1992
<212> TYPE: PRT
<213> ORGANISM: Mus musculus

<400> SEQUENCE: 8

Met Ala Leu Ile Val His Leu Lys Thr Val Ser Glu Leu Arg Gly Lys
1               5                   10                  15

Gly Asp Arg Ile Ala Lys Val Thr Phe Arg Gly Gln Ser Phe Tyr Ser
                20                  25                  30

Arg Val Leu Glu Asn Cys Glu Gly Val Ala Asp Phe Asp Glu Thr Phe
            35                  40                  45

Arg Trp Pro Val Ala Ser Ser Ile Asp Arg Asn Glu Val Leu Glu Ile
        50                  55                  60

Gln Ile Phe Asn Tyr Ser Lys Val Phe Ser Asn Lys Leu Ile Gly Thr
65                  70                  75                  80

Phe Cys Met Val Leu Gln Lys Val Val Glu Glu Asn Arg Val Glu Val
                85                  90                  95

Thr Asp Thr Leu Met Asp Asp Ser Asn Ala Ile Ile Lys Thr Ser Leu
            100                 105                 110

Ser Met Glu Val Arg Tyr Gln Ala Thr Asp Gly Thr Val Gly Pro Trp
        115                 120                 125

Asp Asp Gly Asp Phe Leu Gly Asp Glu Ser Leu Gln Glu Glu Lys Asp
    130                 135                 140

Ser Gln Glu Thr Asp Gly Leu Leu Pro Gly Ser Arg Pro Ser Thr Arg
145                 150                 155                 160

Ile Ser Gly Glu Lys Ser Phe Arg Ser Lys Gly Arg Glu Lys Thr Lys
                165                 170                 175

Gly Gly Arg Asp Gly Glu His Lys Ala Gly Arg Ser Val Phe Ser Ala
            180                 185                 190

Met Lys Leu Gly Lys Thr Arg Ser His Lys Glu Glu Pro Gln Arg Gln
        195                 200                 205

Asp Glu Pro Ala Val Leu Glu Met Glu Asp Leu Asp His Leu Ala Ile
    210                 215                 220
```

```
Gln Leu Gly Asp Gly Leu Asp Pro Asp Ser Val Ser Leu Ala Ser Val
225                 230                 235                 240

Thr Ala Leu Thr Ser Asn Val Ser Asn Lys Arg Ser Lys Pro Asp Ile
            245                 250                 255

Lys Met Glu Pro Ser Ala Gly Arg Pro Met Asp Tyr Gln Val Ser Ile
        260                 265                 270

Thr Val Ile Glu Ala Arg Gln Leu Val Gly Leu Asn Met Asp Pro Val
    275                 280                 285

Val Cys Val Glu Val Gly Asp Asp Lys Lys Tyr Thr Ser Met Lys Glu
    290                 295                 300

Ser Thr Asn Cys Pro Tyr Tyr Asn Glu Tyr Phe Val Phe Asp Phe His
305                 310                 315                 320

Val Ser Pro Asp Val Met Phe Asp Lys Ile Ile Lys Ile Ser Val Ile
                325                 330                 335

His Ser Lys Asn Leu Leu Arg Ser Gly Thr Leu Val Gly Ser Phe Lys
                340                 345                 350

Met Asp Val Gly Thr Val Tyr Ser Gln Pro Glu His Gln Phe His His
            355                 360                 365

Lys Trp Ala Ile Leu Ser Asp Pro Asp Asp Ile Ser Ala Gly Leu Lys
370                 375                 380

Gly Tyr Val Lys Cys Asp Val Ala Val Val Gly Lys Gly Asp Asn Ile
385                 390                 395                 400

Lys Thr Pro His Lys Ala Asn Glu Thr Asp Glu Asp Ile Glu Gly
                405                 410                 415

Asn Leu Leu Leu Pro Glu Gly Val Pro Pro Glu Arg Gln Trp Ala Arg
            420                 425                 430

Phe Tyr Val Lys Ile Tyr Arg Ala Glu Gly Leu Pro Arg Met Asn Thr
        435                 440                 445

Ser Leu Met Ala Asn Val Lys Lys Ala Phe Ile Gly Glu Asn Lys Asp
450                 455                 460

Leu Val Asp Pro Tyr Val Gln Val Phe Phe Ala Gly Gln Lys Gly Lys
465                 470                 475                 480

Thr Ser Val Gln Lys Ser Ser Tyr Glu Pro Leu Trp Asn Glu Gln Val
            485                 490                 495

Val Phe Thr Asp Leu Phe Pro Pro Leu Cys Lys Arg Met Lys Val Gln
            500                 505                 510

Ile Arg Asp Ser Asp Lys Val Asn Asp Val Ala Ile Gly Thr His Phe
        515                 520                 525

Ile Asp Leu Arg Lys Ile Ser Asn Asp Gly Lys Gly Phe Leu Pro
        530                 535                 540

Thr Leu Gly Pro Ala Trp Val Asn Met Tyr Gly Ser Thr Arg Asn Tyr
545                 550                 555                 560

Thr Leu Leu Asp Glu His Gln Asp Leu Asn Glu Gly Leu Gly Glu Gly
                565                 570                 575

Val Ser Phe Arg Ala Arg Leu Met Leu Gly Leu Ala Val Glu Ile Leu
            580                 585                 590

Asp Thr Ser Asn Pro Glu Leu Thr Ser Ser Thr Glu Val Gln Val Glu
        595                 600                 605

Gln Ala Thr Pro Val Ser Glu Ser Cys Thr Gly Arg Met Glu Glu Phe
        610                 615                 620

Phe Leu Phe Gly Ala Phe Leu Glu Ala Ser Met Ile Asp Arg Lys Asn
625                 630                 635                 640

Gly Asp Lys Pro Ile Thr Phe Glu Val Thr Ile Gly Asn Tyr Gly Asn
```

-continued

```
            645                 650                 655
Glu Val Asp Gly Met Ser Arg Pro Leu Arg Pro Arg Pro Arg Lys Glu
                660                 665                 670
Pro Gly Asp Glu Glu Val Asp Leu Ile Gln Asn Ser Ser Asp Asp
                675                 680                 685
Glu Gly Asp Glu Ala Gly Asp Leu Ala Ser Val Ser Ser Thr Pro Pro
    690                 695                 700
Met Arg Pro Gln Ile Thr Asp Arg Asn Tyr Phe His Leu Pro Tyr Leu
705                 710                 715                 720
Glu Arg Lys Pro Cys Ile Tyr Ile Lys Ser Trp Trp Pro Asp Gln Arg
                725                 730                 735
Arg Arg Leu Tyr Asn Ala Asn Ile Met Asp His Ile Ala Asp Lys Leu
                740                 745                 750
Glu Glu Gly Leu Asn Asp Val Gln Glu Met Ile Lys Thr Glu Lys Ser
                755                 760                 765
Tyr Pro Glu Arg Arg Leu Arg Gly Val Leu Glu Glu Leu Ser Cys Gly
    770                 775                 780
Cys His Arg Phe Leu Ser Leu Ser Asp Lys Asp Gln Gly Arg Ser Ser
785                 790                 795                 800
Arg Thr Arg Leu Asp Arg Glu Arg Leu Lys Ser Cys Met Arg Glu Leu
                805                 810                 815
Glu Ser Met Gly Gln Gln Ala Lys Ser Leu Arg Ala Gln Val Lys Arg
                820                 825                 830
His Thr Val Arg Asp Lys Leu Arg Ser Cys Gln Asn Phe Leu Gln Lys
                835                 840                 845
Leu Arg Phe Leu Ala Asp Glu Pro Gln His Ser Ile Pro Asp Val Phe
    850                 855                 860
Ile Trp Met Met Ser Asn Asn Lys Arg Ile Ala Tyr Ala Arg Val Pro
865                 870                 875                 880
Ser Lys Asp Leu Leu Phe Ser Ile Val Glu Glu Leu Gly Lys Asp
                885                 890                 895
Cys Ala Lys Val Lys Thr Leu Phe Leu Lys Leu Pro Gly Lys Arg Gly
                900                 905                 910
Phe Gly Ser Ala Gly Trp Thr Val Gln Ala Lys Leu Glu Leu Tyr Leu
                915                 920                 925
Trp Leu Gly Leu Ser Lys Gln Arg Lys Asp Phe Leu Cys Gly Leu Pro
    930                 935                 940
Cys Gly Phe Glu Glu Val Lys Ala Ala Gln Gly Leu Gly Leu His Ser
945                 950                 955                 960
Phe Pro Pro Ile Ser Leu Val Tyr Thr Lys Lys Gln Ala Phe Gln Leu
                965                 970                 975
Arg Ala His Met Tyr Gln Ala Arg Ser Leu Phe Ala Ala Asp Ser Ser
                980                 985                 990
Gly Leu Ser Asp Pro Phe Ala Arg  Val Phe Phe Ile Asn  Gln Ser Gln
    995                 1000                1005
Cys Thr  Glu Val Leu Asn Glu  Thr Leu Cys Pro Thr  Trp Asp Gln
    1010                1015                1020
Met Leu  Val Phe Asp Asn Leu  Glu Leu Tyr Gly Glu  Ala His Glu
    1025                1030                1035
Leu Arg  Asp Asp Pro Pro Ile  Ile Val Ile Glu Ile  Tyr Asp Gln
    1040                1045                1050
Asp Ser  Met Gly Lys Ala Asp  Phe Met Gly Arg Thr  Phe Ala Lys
    1055                1060                1065
```

-continued

```
Pro Leu Val Lys Met Ala Asp Glu Ala Tyr Cys Pro Pro Arg Phe
    1070                1075                1080

Pro Pro Gln Leu Glu Tyr Tyr Gln Ile Tyr Arg Gly Ser Ala Thr
    1085                1090                1095

Ala Gly Asp Leu Leu Ala Ala Phe Glu Leu Leu Gln Ile Gly Pro
    1100                1105                1110

Ser Gly Lys Ala Asp Leu Pro Pro Ile Asn Gly Pro Val Asp Met
    1115                1120                1125

Asp Arg Gly Pro Ile Met Pro Val Pro Val Gly Ile Arg Pro Val
    1130                1135                1140

Leu Ser Lys Tyr Arg Val Glu Val Leu Phe Trp Gly Leu Arg Asp
    1145                1150                1155

Leu Lys Arg Val Asn Leu Ala Gln Val Asp Arg Pro Arg Val Asp
    1160                1165                1170

Ile Glu Cys Ala Gly Lys Gly Val Gln Ser Ser Leu Ile His Asn
    1175                1180                1185

Tyr Lys Lys Asn Pro Asn Phe Asn Thr Leu Val Lys Trp Phe Glu
    1190                1195                1200

Val Asp Leu Pro Glu Asn Glu Leu Leu His Pro Pro Leu Asn Ile
    1205                1210                1215

Arg Val Val Asp Cys Arg Ala Phe Gly Arg Tyr Thr Leu Val Gly
    1220                1225                1230

Ser His Ala Val Ser Ser Leu Arg Arg Phe Ile Tyr Arg Pro Pro
    1235                1240                1245

Asp Arg Ser Ala Pro Asn Trp Asn Thr Thr Gly Glu Val Val Val
    1250                1255                1260

Ser Met Glu Pro Glu Glu Pro Val Lys Lys Leu Glu Thr Met Val
    1265                1270                1275

Lys Leu Asp Ala Thr Ser Asp Ala Val Val Lys Val Asp Val Ala
    1280                1285                1290

Glu Asp Glu Lys Glu Arg Lys Lys Lys Lys Lys Gly Pro Ser
    1295                1300                1305

Glu Glu Pro Glu Glu Glu Pro Asp Glu Ser Met Leu Asp Trp
    1310                1315                1320

Trp Ser Lys Tyr Phe Ala Ser Ile Asp Thr Met Lys Glu Gln Leu
    1325                1330                1335

Arg Gln His Glu Thr Ser Gly Thr Asp Leu Glu Glu Lys Glu Glu
    1340                1345                1350

Met Glu Ser Ala Glu Gly Leu Lys Gly Pro Met Lys Ser Lys Glu
    1355                1360                1365

Lys Ser Arg Ala Ala Lys Glu Glu Lys Lys Lys Asn Gln Ser
    1370                1375                1380

Pro Gly Pro Gly Gln Gly Ser Glu Ala Pro Glu Lys Lys Ala
    1385                1390                1395

Lys Ile Asp Glu Leu Lys Val Tyr Pro Lys Glu Leu Glu Ser Glu
    1400                1405                1410

Phe Asp Ser Phe Glu Asp Trp Leu His Thr Phe Asn Leu Leu Arg
    1415                1420                1425

Gly Lys Thr Gly Asp Asp Glu Asp Gly Ser Thr Glu Glu Glu Arg
    1430                1435                1440

Ile Val Gly Arg Phe Lys Gly Ser Leu Cys Val Tyr Lys Val Pro
    1445                1450                1455
```

```
Leu Pro Glu Asp Val Ser Arg Glu Ala Gly Tyr Asp Pro Thr Tyr
    1460            1465                1470

Gly Met Phe Gln Gly Ile Pro Ser Asn Asp Pro Ile Asn Val Leu
    1475            1480                1485

Val Arg Ile Tyr Val Val Arg Ala Thr Asp Leu His Pro Ala Asp
    1490            1495                1500

Ile Asn Gly Lys Ala Asp Pro Tyr Ile Ala Ile Lys Leu Gly Lys
    1505            1510                1515

Thr Asp Ile Arg Asp Lys Glu Asn Tyr Ile Ser Lys Gln Leu Asn
    1520            1525                1530

Pro Val Phe Gly Lys Ser Phe Asp Ile Glu Ala Ser Phe Pro Met
    1535            1540                1545

Glu Ser Met Leu Thr Val Ala Val Tyr Asp Trp Asp Leu Val Gly
    1550            1555                1560

Thr Asp Asp Leu Ile Gly Glu Thr Lys Ile Asp Leu Glu Asn Arg
    1565            1570                1575

Phe Tyr Ser Lys His Arg Ala Thr Cys Gly Ile Ala Gln Thr Tyr
    1580            1585                1590

Ser Ile His Gly Tyr Asn Ile Trp Arg Asp Pro Met Lys Pro Ser
    1595            1600                1605

Gln Ile Leu Thr Arg Leu Cys Lys Glu Gly Lys Val Asp Gly Pro
    1610            1615                1620

His Phe Gly Pro His Gly Arg Val Arg Val Ala Asn Arg Val Phe
    1625            1630                1635

Thr Gly Pro Ser Glu Ile Glu Asp Glu Asn Gly Gln Arg Lys Pro
    1640            1645                1650

Thr Asp Glu His Val Ala Leu Ser Ala Leu Arg His Trp Glu Asp
    1655            1660                1665

Ile Pro Arg Val Gly Cys Arg Leu Val Pro Glu His Val Glu Thr
    1670            1675                1680

Arg Pro Leu Leu Asn Pro Asp Lys Pro Gly Ile Glu Gln Gly Arg
    1685            1690                1695

Leu Glu Leu Trp Val Asp Met Phe Pro Met Asp Met Pro Ala Pro
    1700            1705                1710

Gly Thr Pro Leu Asp Ile Ser Pro Arg Lys Pro Lys Lys Tyr Glu
    1715            1720                1725

Leu Arg Val Ile Val Trp Asn Thr Asp Glu Val Val Leu Glu Asp
    1730            1735                1740

Asp Asp Phe Phe Thr Gly Glu Lys Ser Ser Asp Ile Phe Val Arg
    1745            1750                1755

Gly Trp Leu Lys Gly Gln Gln Glu Asp Lys Gln Asp Thr Asp Val
    1760            1765                1770

His Tyr His Ser Leu Thr Gly Glu Gly Asn Phe Asn Trp Arg Tyr
    1775            1780                1785

Leu Phe Pro Phe Asp Tyr Leu Ala Ala Glu Glu Lys Ile Val Met
    1790            1795                1800

Ser Lys Lys Glu Ser Met Phe Ser Trp Asp Glu Thr Glu Tyr Lys
    1805            1810                1815

Ile Pro Ala Arg Leu Thr Leu Gln Ile Trp Asp Ala Asp His Phe
    1820            1825                1830

Ser Ala Asp Asp Phe Leu Gly Ala Ile Glu Leu Asp Leu Asn Arg
    1835            1840                1845

Phe Pro Arg Gly Ala Lys Thr Ala Lys Gln Cys Thr Met Glu Met
```

```
                    1850                1855                1860

Ala  Thr  Gly  Glu  Val  Asp  Val  Pro  Leu  Val  Ser  Ile  Phe  Lys  Gln
          1865                1870                1875

Lys  Arg  Val  Lys  Gly  Trp  Trp  Pro  Leu  Leu  Ala  Arg  Asn  Glu  Asn
     1880                1885                1890

Asp  Glu  Phe  Glu  Leu  Thr  Gly  Lys  Val  Glu  Ala  Glu  Leu  His  Leu
1895                1900                1905

Leu  Thr  Ala  Glu  Glu  Ala  Glu  Lys  Asn  Pro  Val  Gly  Leu  Ala  Arg
          1910                1915                1920

Asn  Glu  Pro  Asp  Pro  Leu  Glu  Lys  Pro  Asn  Arg  Pro  Asp  Thr  Ala
     1925                1930                1935

Phe  Val  Trp  Phe  Leu  Asn  Pro  Leu  Lys  Ser  Ile  Lys  Tyr  Leu  Ile
1940                1945                1950

Cys  Thr  Arg  Tyr  Lys  Trp  Leu  Ile  Ile  Lys  Ile  Val  Leu  Ala  Leu
          1955                1960                1965

Leu  Gly  Leu  Leu  Met  Leu  Ala  Leu  Phe  Leu  Tyr  Ser  Leu  Pro  Gly
     1970                1975                1980

Tyr  Met  Val  Lys  Lys  Leu  Leu  Gly  Ala
1985                1990

<210> SEQ ID NO 9
<211> LENGTH: 1977
<212> TYPE: PRT
<213> ORGANISM: Mus musculus

<400> SEQUENCE: 9

Met  Ala  Leu  Ile  Val  His  Leu  Lys  Thr  Val  Ser  Glu  Leu  Arg  Gly  Lys
1                  5                   10                  15

Gly  Asp  Arg  Ile  Ala  Lys  Val  Thr  Phe  Arg  Gly  Gln  Ser  Phe  Tyr  Ser
               20                  25                  30

Arg  Val  Leu  Glu  Asn  Cys  Glu  Gly  Val  Ala  Asp  Phe  Asp  Glu  Thr  Phe
                    35                  40                  45

Arg  Trp  Pro  Val  Ala  Ser  Ser  Ile  Asp  Arg  Asn  Glu  Val  Leu  Glu  Ile
          50                  55                  60

Gln  Ile  Phe  Asn  Tyr  Ser  Lys  Val  Phe  Ser  Asn  Lys  Leu  Ile  Gly  Thr
65                  70                  75                  80

Phe  Cys  Met  Val  Leu  Gln  Lys  Val  Val  Glu  Glu  Asn  Arg  Val  Glu  Val
                    85                  90                  95

Thr  Asp  Thr  Leu  Met  Asp  Asp  Ser  Asn  Ala  Ile  Ile  Lys  Thr  Ser  Leu
               100                 105                 110

Ser  Met  Glu  Val  Arg  Tyr  Gln  Ala  Thr  Asp  Gly  Thr  Val  Gly  Pro  Trp
               115                 120                 125

Asp  Asp  Gly  Asp  Phe  Leu  Gly  Asp  Glu  Ser  Leu  Gln  Glu  Glu  Lys  Asp
          130                 135                 140

Ser  Gln  Glu  Thr  Asp  Gly  Leu  Leu  Pro  Gly  Ser  Arg  Pro  Ser  Thr  Arg
145                 150                 155                 160

Ile  Ser  Gly  Glu  Lys  Ser  Phe  Arg  Arg  Ala  Gly  Arg  Ser  Val  Phe  Ser
                    165                 170                 175

Ala  Met  Lys  Leu  Gly  Lys  Thr  Arg  Ser  His  Lys  Glu  Glu  Pro  Gln  Arg
               180                 185                 190

Gln  Asp  Glu  Pro  Ala  Val  Leu  Glu  Met  Glu  Asp  Leu  Asp  His  Leu  Ala
               195                 200                 205

Ile  Gln  Leu  Gly  Asp  Gly  Leu  Asp  Pro  Asp  Ser  Val  Ser  Leu  Ala  Ser
          210                 215                 220
```

```
Val Thr Ala Leu Thr Ser Asn Val Ser Asn Lys Arg Ser Lys Pro Asp
225                 230                 235                 240

Ile Lys Met Glu Pro Ser Ala Gly Arg Pro Met Asp Tyr Gln Val Ser
            245                 250                 255

Ile Thr Val Ile Glu Ala Arg Gln Leu Val Gly Leu Asn Met Asp Pro
        260                 265                 270

Val Val Cys Val Glu Val Gly Asp Asp Lys Lys Tyr Thr Ser Met Lys
    275                 280                 285

Glu Ser Thr Asn Cys Pro Tyr Tyr Asn Glu Tyr Phe Val Phe Asp Phe
290                 295                 300

His Val Ser Pro Asp Val Met Phe Asp Lys Ile Ile Lys Ile Ser Val
305                 310                 315                 320

Ile His Ser Lys Asn Leu Leu Arg Ser Gly Thr Leu Val Gly Ser Phe
            325                 330                 335

Lys Met Asp Val Gly Thr Val Tyr Ser Gln Pro Glu His Gln Phe His
        340                 345                 350

His Lys Trp Ala Ile Leu Ser Asp Pro Asp Asp Ile Ser Ala Gly Leu
    355                 360                 365

Lys Gly Tyr Val Lys Cys Asp Val Ala Val Val Gly Lys Gly Asp Asn
370                 375                 380

Ile Lys Thr Pro His Lys Ala Asn Glu Thr Asp Glu Asp Ile Glu
385                 390                 395                 400

Gly Asn Leu Leu Leu Pro Glu Gly Val Pro Pro Glu Arg Gln Trp Ala
            405                 410                 415

Arg Phe Tyr Val Lys Ile Tyr Arg Ala Glu Gly Leu Pro Arg Met Asn
        420                 425                 430

Thr Ser Leu Met Ala Asn Val Lys Lys Ala Phe Ile Gly Glu Asn Lys
    435                 440                 445

Asp Leu Val Asp Pro Tyr Val Gln Val Phe Phe Ala Gly Gln Lys Gly
450                 455                 460

Lys Thr Ser Val Gln Lys Ser Ser Tyr Glu Pro Leu Trp Asn Glu Gln
465                 470                 475                 480

Val Val Phe Thr Asp Leu Phe Pro Pro Leu Cys Lys Arg Met Lys Val
            485                 490                 495

Gln Ile Arg Asp Ser Asp Lys Val Asn Asp Val Ala Ile Gly Thr His
        500                 505                 510

Phe Ile Asp Leu Arg Lys Ile Ser Asn Asp Gly Asp Lys Gly Phe Leu
    515                 520                 525

Pro Thr Leu Gly Pro Ala Trp Val Asn Met Tyr Gly Ser Thr Arg Asn
530                 535                 540

Tyr Thr Leu Leu Asp Glu His Gln Asp Leu Asn Glu Gly Leu Gly Glu
545                 550                 555                 560

Gly Val Ser Phe Arg Ala Arg Leu Met Leu Gly Leu Ala Val Glu Ile
            565                 570                 575

Leu Asp Thr Ser Asn Pro Glu Leu Thr Ser Ser Thr Glu Val Gln Val
        580                 585                 590

Glu Gln Ala Thr Pro Val Ser Glu Ser Cys Thr Gly Arg Met Glu Glu
    595                 600                 605

Phe Phe Leu Phe Gly Ala Phe Leu Glu Ala Ser Met Ile Asp Arg Lys
610                 615                 620

Asn Gly Asp Lys Pro Ile Thr Phe Glu Val Thr Ile Gly Asn Tyr Gly
625                 630                 635                 640

Asn Glu Val Asp Gly Met Ser Arg Pro Leu Arg Pro Arg Pro Arg Lys
```

-continued

```
                645                 650                 655
Glu Pro Gly Asp Glu Glu Val Asp Leu Ile Gln Asn Ser Ser Asp
            660                 665                 670

Asp Glu Gly Asp Glu Ala Gly Asp Leu Ala Ser Val Ser Ser Thr Pro
            675                 680                 685

Pro Met Arg Pro Gln Ile Thr Asp Arg Asn Tyr Phe His Leu Pro Tyr
    690                 695                 700

Leu Glu Arg Lys Pro Cys Ile Tyr Ile Lys Ser Trp Trp Pro Asp Gln
705                 710                 715                 720

Arg Arg Arg Leu Tyr Asn Ala Asn Ile Met Asp His Ile Ala Asp Lys
                725                 730                 735

Leu Glu Glu Gly Leu Asn Asp Val Gln Glu Met Ile Lys Thr Glu Lys
            740                 745                 750

Ser Tyr Pro Glu Arg Arg Leu Arg Gly Val Leu Glu Glu Leu Ser Cys
            755                 760                 765

Gly Cys His Arg Phe Leu Ser Leu Ser Asp Lys Asp Gln Gly Arg Ser
    770                 775                 780

Ser Arg Thr Arg Leu Asp Arg Glu Arg Leu Lys Ser Cys Met Arg Glu
785                 790                 795                 800

Leu Glu Ser Met Gly Gln Gln Ala Lys Ser Leu Arg Ala Gln Val Lys
                805                 810                 815

Arg His Thr Val Arg Asp Lys Leu Arg Ser Cys Gln Asn Phe Leu Gln
            820                 825                 830

Lys Leu Arg Phe Leu Ala Asp Glu Pro Gln His Ser Ile Pro Asp Val
            835                 840                 845

Phe Ile Trp Met Met Ser Asn Asn Lys Arg Ile Ala Tyr Ala Arg Val
    850                 855                 860

Pro Ser Lys Asp Leu Leu Phe Ser Ile Val Glu Glu Leu Gly Lys
865                 870                 875                 880

Asp Cys Ala Lys Val Lys Thr Leu Phe Leu Lys Leu Pro Gly Lys Arg
                885                 890                 895

Gly Phe Gly Ser Ala Gly Trp Thr Val Gln Ala Lys Leu Glu Leu Tyr
            900                 905                 910

Leu Trp Leu Gly Leu Ser Lys Gln Arg Lys Asp Phe Leu Cys Gly Leu
    915                 920                 925

Pro Cys Gly Phe Glu Glu Val Lys Ala Ala Gln Gly Leu Gly Leu His
    930                 935                 940

Ser Phe Pro Pro Ile Ser Leu Val Tyr Thr Lys Lys Gln Ala Phe Gln
945                 950                 955                 960

Leu Arg Ala His Met Tyr Gln Ala Arg Ser Leu Phe Ala Ala Asp Ser
                965                 970                 975

Ser Gly Leu Ser Asp Pro Phe Ala Arg Val Phe Ile Asn Gln Ser
            980                 985                 990

Gln Cys Thr Glu Val Leu Asn Glu Thr Leu Cys Pro Thr Trp Asp Gln
            995                 1000                1005

Met Leu Val Phe Asp Asn Leu Glu Leu Tyr Gly Glu Ala His Glu
    1010                1015                1020

Leu Arg Asp Asp Pro Pro Ile Ile Val Ile Glu Ile Tyr Asp Gln
    1025                1030                1035

Asp Ser Met Gly Lys Ala Asp Phe Met Gly Arg Thr Phe Ala Lys
    1040                1045                1050

Pro Leu Val Lys Met Ala Asp Glu Ala Tyr Cys Pro Pro Arg Phe
    1055                1060                1065
```

-continued

Pro Pro Gln Leu Glu Tyr Tyr Gln Ile Tyr Arg Gly Ser Ala Thr
    1070            1075            1080

Ala Gly Asp Leu Leu Ala Ala Phe Glu Leu Leu Gln Ile Gly Pro
    1085            1090            1095

Ser Gly Lys Ala Asp Leu Pro Pro Ile Asn Gly Pro Val Asp Met
    1100            1105            1110

Asp Arg Gly Pro Ile Met Pro Val Pro Val Gly Ile Arg Pro Val
    1115            1120            1125

Leu Ser Lys Tyr Arg Val Glu Val Leu Phe Trp Gly Leu Arg Asp
    1130            1135            1140

Leu Lys Arg Val Asn Leu Ala Gln Val Asp Arg Pro Arg Val Asp
    1145            1150            1155

Ile Glu Cys Ala Gly Lys Gly Val Gln Ser Ser Leu Ile His Asn
    1160            1165            1170

Tyr Lys Lys Asn Pro Asn Phe Asn Thr Leu Val Lys Trp Phe Glu
    1175            1180            1185

Val Asp Leu Pro Glu Asn Glu Leu Leu His Pro Pro Leu Asn Ile
    1190            1195            1200

Arg Val Val Asp Cys Arg Ala Phe Gly Arg Tyr Thr Leu Val Gly
    1205            1210            1215

Ser His Ala Val Ser Ser Leu Arg Arg Phe Ile Tyr Arg Pro Pro
    1220            1225            1230

Asp Arg Ser Ala Pro Asn Trp Asn Thr Thr Gly Glu Val Val Val
    1235            1240            1245

Ser Met Glu Pro Glu Glu Pro Val Lys Lys Leu Glu Thr Met Val
    1250            1255            1260

Lys Leu Asp Ala Thr Ser Asp Ala Val Val Lys Val Asp Val Ala
    1265            1270            1275

Glu Asp Glu Lys Glu Arg Lys Lys Lys Lys Lys Gly Pro Ser
    1280            1285            1290

Glu Glu Pro Glu Glu Glu Pro Asp Glu Ser Met Leu Asp Trp
    1295            1300            1305

Trp Ser Lys Tyr Phe Ala Ser Ile Asp Thr Met Lys Glu Gln Leu
    1310            1315            1320

Arg Gln His Glu Thr Ser Gly Thr Asp Leu Glu Glu Lys Glu Glu
    1325            1330            1335

Met Glu Ser Ala Glu Gly Leu Lys Gly Pro Met Lys Ser Lys Glu
    1340            1345            1350

Lys Ser Arg Ala Ala Lys Glu Glu Lys Lys Lys Asn Gln Ser
    1355            1360            1365

Pro Gly Pro Gly Gln Gly Ser Glu Ala Pro Glu Lys Lys Ala
    1370            1375            1380

Lys Ile Asp Glu Leu Lys Val Tyr Pro Lys Glu Leu Glu Ser Glu
    1385            1390            1395

Phe Asp Ser Phe Glu Asp Trp Leu His Thr Phe Asn Leu Leu Arg
    1400            1405            1410

Gly Lys Thr Gly Asp Asp Glu Asp Gly Ser Thr Glu Glu Arg
    1415            1420            1425

Ile Val Gly Arg Phe Lys Gly Ser Leu Cys Val Tyr Lys Val Pro
    1430            1435            1440

Leu Pro Glu Asp Val Ser Arg Glu Ala Gly Tyr Asp Pro Thr Tyr
    1445            1450            1455

-continued

```
Gly Met Phe Gln Gly Ile Pro Ser Asn Asp Pro Ile Asn Val Leu
    1460                1465                1470

Val Arg Ile Tyr Val Val Arg Ala Thr Asp Leu His Pro Ala Asp
    1475                1480                1485

Ile Asn Gly Lys Ala Asp Pro Tyr Ile Ala Ile Lys Leu Gly Lys
    1490                1495                1500

Thr Asp Ile Arg Asp Lys Glu Asn Tyr Ile Ser Lys Gln Leu Asn
    1505                1510                1515

Pro Val Phe Gly Lys Ser Phe Asp Ile Glu Ala Ser Phe Pro Met
    1520                1525                1530

Glu Ser Met Leu Thr Val Ala Val Tyr Asp Trp Asp Leu Val Gly
    1535                1540                1545

Thr Asp Asp Leu Ile Gly Glu Thr Lys Ile Asp Leu Glu Asn Arg
    1550                1555                1560

Phe Tyr Ser Lys His Arg Ala Thr Cys Gly Ile Ala Gln Thr Tyr
    1565                1570                1575

Ser Ile His Gly Tyr Asn Ile Trp Arg Asp Pro Met Lys Pro Ser
    1580                1585                1590

Gln Ile Leu Thr Arg Leu Cys Lys Glu Gly Lys Val Asp Gly Pro
    1595                1600                1605

His Phe Gly Pro His Gly Arg Val Arg Val Ala Asn Arg Val Phe
    1610                1615                1620

Thr Gly Pro Ser Glu Ile Glu Asp Glu Asn Gly Gln Arg Lys Pro
    1625                1630                1635

Thr Asp Glu His Val Ala Leu Ser Ala Leu Arg His Trp Glu Asp
    1640                1645                1650

Ile Pro Arg Val Gly Cys Arg Leu Val Pro Glu His Val Glu Thr
    1655                1660                1665

Arg Pro Leu Leu Asn Pro Asp Lys Pro Gly Ile Glu Gln Gly Arg
    1670                1675                1680

Leu Glu Leu Trp Val Asp Met Phe Pro Met Asp Met Pro Ala Pro
    1685                1690                1695

Gly Thr Pro Leu Asp Ile Ser Pro Arg Lys Pro Lys Lys Tyr Glu
    1700                1705                1710

Leu Arg Val Ile Val Trp Asn Thr Asp Glu Val Val Leu Glu Asp
    1715                1720                1725

Asp Asp Phe Phe Thr Gly Glu Lys Ser Ser Asp Ile Phe Val Arg
    1730                1735                1740

Gly Trp Leu Lys Gly Gln Gln Glu Asp Lys Gln Asp Thr Asp Val
    1745                1750                1755

His Tyr His Ser Leu Thr Gly Glu Gly Asn Phe Asn Trp Arg Tyr
    1760                1765                1770

Leu Phe Pro Phe Asp Tyr Leu Ala Ala Glu Glu Lys Ile Val Met
    1775                1780                1785

Ser Lys Lys Glu Ser Met Phe Ser Trp Asp Glu Thr Glu Tyr Lys
    1790                1795                1800

Ile Pro Ala Arg Leu Thr Leu Gln Ile Trp Asp Ala Asp His Phe
    1805                1810                1815

Ser Ala Asp Asp Phe Leu Gly Ala Ile Glu Leu Asp Leu Asn Arg
    1820                1825                1830

Phe Pro Arg Gly Ala Lys Thr Ala Lys Gln Cys Thr Met Glu Met
    1835                1840                1845

Ala Thr Gly Glu Val Asp Val Pro Leu Val Ser Ile Phe Lys Gln
```

|  | 1850 |  |  |  | 1855 |  |  |  | 1860 |  |
| --- | --- | --- | --- | --- | --- | --- | --- | --- | --- | --- |

Lys Arg Val Lys Gly Trp Trp Pro Leu Leu Ala Arg Asn Glu Asn
    1865                                1870                        1875

Asp Glu Phe Glu Leu Thr Gly Lys Val Glu Ala Glu Leu His Leu
    1880                                1885                            1890

Leu Thr Ala Glu Glu Ala Glu Lys Asn Pro Val Gly Leu Ala Arg
    1895                                1900                           1905

Asn Glu Pro Asp Pro Leu Glu Lys Pro Asn Arg Pro Asp Thr Ala
    1910                                1915                           1920

Phe Val Trp Phe Leu Asn Pro Leu Lys Ser Ile Lys Tyr Leu Ile
    1925                                1930                           1935

Cys Thr Arg Tyr Lys Trp Leu Ile Ile Lys Ile Val Leu Ala Leu
    1940                                1945                           1950

Leu Gly Leu Leu Met Leu Ala Leu Phe Leu Tyr Ser Leu Pro Gly
    1955                                1960                           1965

Tyr Met Val Lys Lys Leu Leu Gly Ala
    1970                                1975

<210> SEQ ID NO 10
<211> LENGTH: 7171
<212> TYPE: DNA
<213> ORGANISM: Homo sapiens

<400> SEQUENCE: 10

| | |
|---|---:|
| atcggagggg ggtcgggagg aggaggagga ggcagcggca gagaagagag aggcgtgtga | 60 |
| gccgtgctcc accggctagc tccttcccgc tgctcctgcc tggcagtgcc aggcagccca | 120 |
| caccagcatg gccttgctca tccacctcaa gacagtctcg gagctgcggg cagggggcga | 180 |
| ccggatcgcc aaagtgactt tccgagggca atccttctac tctcgggtcc tggagaactg | 240 |
| tgaggatgtg gctgactttg atgagacatt tcggtggccg gtggccagca gcatcgacag | 300 |
| aaatgagatg ctggagattc aggttttcaa ctacagcaaa gtcttcagca caagctcat | 360 |
| cgggaccttc cgcatggtgc tgcagaaggt ggtagaggag agccatgtgg aggtgactga | 420 |
| cacgctgatt gatgacaaca atgctatcat caagaccagc ctgtgcgtgg aggtccggta | 480 |
| tcaggccact gacggcacag tgggctcctg gacgatggg gacttcctgg agatgagtc | 540 |
| tcttcaagag gaagagaagg acagccaaga gacggatgga ctgctcccag gctcccggcc | 600 |
| cagctcccgg cccccaggag agaagagctt ccggagagcc gggaggagcg tgttctccgc | 660 |
| catgaagctc ggcaaaaacc ggtctcacaa ggagagccc caaagaccag atgaaccggc | 720 |
| ggtgctggag atgaagacc ttgaccatct ggccattcgg ctaggagatg gactggatcc | 780 |
| cgactcggtt tctctagcct cagtcacagc tctcaccact aatgtctcca acaagcgatc | 840 |
| taagccagac attaagatgg agccaagtgc tgggcggccc atggattacc aggtcagcat | 900 |
| cacggtgatc gaggcccggc agctggtggg cttgaacatg gaccctgtgg tgtgcgtgga | 960 |
| ggtgggtgac acaagaagt acacatccat gaaggagtcc actaactgcc cctattacaa | 1020 |
| cgagtacttc gtcttcgact tccatgtctc tccggatgtc atgtttgaca agatcatcaa | 1080 |
| gatttcggtg attcactcca gaacctgctg cgcagtggc accctggtgg gctccttcaa | 1140 |
| aatggacgtg ggaaccgtgt actcgcagcc agagcaccag ttccatcaca gtgggccat | 1200 |
| cctgtctgac cccgatgaca tctcctcggg gctgaagggc tacgtgaagt gtgacgttgc | 1260 |
| cgtggtgggc aaagggggaca acatcaagac gccccacaag gccaatgaga ccgacgaaga | 1320 |
| tgacattgag gggaacttgc tgctccccga gggggtgccc ccgaacgcc agtgggcccg | 1380 |

| | |
|---|---|
| gttctatgtg aaaatttacc gagcagaggg gctgccccgt atgaacacaa gcctcatggc | 1440 |
| caatgtaaag aaggctttca tcggtgaaaa caaggacctc gtggacccct acgtgcaagt | 1500 |
| cttctttgct ggccagaagg gcaagacttc agtgcagaag agcagctatg agcccctgtg | 1560 |
| gaatgagcag gtcgtctttaca gacctcttcccccactctgcaaacgcatgaaggtgca | 1620 |
| gatccgagac tcggacaagg tcaacgacgt ggccatcggc acccacttca ttgacctgcg | 1680 |
| caagatttct aatgacggag acaaaggctt cctgcccaca ctgggccag cctgggtgaa | 1740 |
| catgtacggc tccacacgta actacacgct gctggatgag catcaggacc tgaacgaggg | 1800 |
| cctggggag ggtgtgtcct tccgggcccg gctcctgctg ggcctggctg tggagatcgt | 1860 |
| agacacctcc aaccctgagc tcaccagctc cacagaggtg caggtggagc aggccacgcc | 1920 |
| catctcggag agctgtgcag gtaaaatgga agaattcttt ctctttggag ccttcctgga | 1980 |
| ggcctcaatg atcgaccgga gaaacggaga caagcccatc acctttgagg tcaccatagg | 2040 |
| caactatggg aacgaagttg atggcctgtc ccggccccag cggcctcggc cccggaagga | 2100 |
| gccgggggat gaggaagaag tagacctgat tcagaacgca agtgatgacg aggccggtga | 2160 |
| tgccggggac ctggcctcag tctcctccac tccaccaatg cggcccccagg tcaccgacag | 2220 |
| gaactacttc catctgccct acctggagcg aaagccctgc atctacatca gagctggtg | 2280 |
| gccggaccag cgccgccgcc tctacaatgc caacatcatg gaccacattg ccgacaagct | 2340 |
| ggaagaaggc ctgaacgaca tacaggagat gatcaaaacg gagaagtcct accctgagcg | 2400 |
| tcgcctgcgg ggcgtcctgg aggagctgag ctgtggctgc tgccgcttcc tctccctcgc | 2460 |
| tgacaaggac cagggccact catcccgcac caggcttgac cgggagcgcc tcaagtcctg | 2520 |
| catgagggag ctgaaaaca tggggcagca ggccaggatg ctgcgggccc aggtgaagcg | 2580 |
| gcacacggtg cgggacaagc tgaggctgtg ccagaacttc ctgcagaagc tgcgcttcct | 2640 |
| ggcggacgag ccccagcaca gcattcccga catcttcatc tggatgatga gcaacaacaa | 2700 |
| gcgtgtcgcc tatgcccgtg tgccctccaa ggacctgctc ttctccatcg tggaggagga | 2760 |
| gactggcaag gactgcgcca aggtcaagac gctcttcctt aagctgccag ggaagcgggg | 2820 |
| cttcggctcg gcaggctgga cagtgcaggc caaggtggag ctgtacctgt ggctgggcct | 2880 |
| cagcaaacag cgcaaggagt tcctgtgcgg cctgccctgt ggcttccagg aggtcaaggc | 2940 |
| agcccagggc ctgggcctgc atgccttccc accgtcagc ctggtctaca ccaagaagca | 3000 |
| ggcgttccag ctccgagcgc acatgtacca ggcccgcagc ctctttgccg ccgacagcag | 3060 |
| cggactctca gaccccttg cccgcgtctt cttcatcaat cagagtcagt gcacagaggt | 3120 |
| gctgaatgag accctgtgtc ccacctggga ccagatgctg gtgttcgaca acctggagct | 3180 |
| ctatggtgaa gctcatgagc tgaggacga tccgcccatc attgtcattg aaatctatga | 3240 |
| ccaggattcc atgggcaaag ctgacttcat gggccggacc ttcgccaaac ccctggtgaa | 3300 |
| gatggcagac gaggcgtact gcccaccccg cttcccacct cagctcgagt actaccagat | 3360 |
| ctaccgtggc aacgccacag ctggagacct gctggcggcc ttcgagctgc tgcagattgg | 3420 |
| accagcaggg aaggctgacc tgccccccat caatggcccg gtggacgtgg accgaggtcc | 3480 |
| catcatgccc gtgcccatgg gcatccgcc cgtgctcagc aagtaccgag tggaggtgct | 3540 |
| gttctggggc ctacgggacc taaagcgggt gaacctggcc caggtggacc ggccacgggt | 3600 |
| ggacatcgag tgtgcaggga agggggtgca gtcgtccctg atccacaatt ataagaagaa | 3660 |
| ccccaacttc aacacccctcg tcaagtggtt tgaagtggac ctcccagaga cgagctgct | 3720 |

```
gcacccgccc ttgaacatcc gtgtggtgga ctgccgggcc ttcggtcgct acacactggt   3780
gggctcccat gccgtcagct ccctgcgacg cttcatctac cggcccccag accgctcggc   3840
ccccagctgg aacaccacgg tcaggcttct ccggcgctgc cgtgtgctgt gcaatggggg   3900
ctcctcctct cactccacag gggaggttgt ggtgactatg gagccagagg tacccatcaa   3960
gaaactggag accatggtga agctggacgc gacttctgaa gctgttgtca aggtggatgt   4020
ggctgaggag gagaaggaga agaagaagaa gaagaagggc actgcggagg agccagagga   4080
ggaggagcca gacgagagca tgctggactg gtggtccaag tactttgcct ccattgacac   4140
catgaaggag caacttcgac aacaagagcc ctctggaatt gacttggagg agaaggagga   4200
agtggacaat accgagggcc tgaaggggtc aatgaagggc aaggagaagg caagggctgc   4260
caaagaggag aagaagaaga aaactcagag ctctggctct ggccagggt ccgaggcccc   4320
cgagaagaag aaacccaaga ttgatgagct taaggtatac cccaaagagc tggagtccga   4380
gtttgataac tttgaggact ggctgcacac tttcaacttg cttcggggca agaccgggga   4440
tgatgaggat ggctccaccg aggaggagcg cattgtggga cgcttcaagg gctccctctg   4500
cgtgtacaaa gtgccactcc cagaggacgt gtcccgggaa gccggctacg actccaccta   4560
cggcatgttc cagggcatcc cgagcaatga ccccatcaat gtgctggtcc gagtctatgt   4620
ggtccgggcc acggacctgc accctgctga catcaacggc aaagctgacc cctacatcgc   4680
catccggcta ggcaagactg acatccgcga caaggagaac tacatctcca gcagctcaa   4740
ccctgtcttt gggaagtcct ttgacatcga ggcctccttc cccatggaat ccatgctgac   4800
ggtggctgtg tatgactggg acctggtggg cactgatgac ctcattgggg aaaccaagat   4860
cgacctggag aaccgcttct acagcaagca ccgcgccacc tgcggcatcg cccagaccta   4920
ctccacacat ggctacaata tctggcggga ccccatgaag cccagccaga tcctgacccg   4980
cctctgcaaa gacggcaaag tggacggccc ccactttggg cccctggga gagtgaaggt   5040
ggccaaccgc gtcttcactg ggccctctga gattgaggac gagaacggtc agaggaagcc   5100
cacagacgag catgtggcgc tgttggccct gaggcactgg gaggacatcc ccgcgcagg   5160
ctgccgcctg gtgccagagc atgtggagac gaggccgctg ctcaacccg acaagccggg   5220
catcgagcag ggccgcctgg agctgtgggt ggacatgttc cccatggaca tgccagcccc   5280
tgggacgcct ctggacatct cacctcggaa gcccaagaag tacgagctgc gggtcatcat   5340
ctggaacaca gatgaggtgg tcttggagga cgacgacttc ttcacagggg agaagtccag   5400
tgacatcttc gtgaggggt ggctgaaggg ccagcaggag acaagcagg acacagacgt   5460
ccactaccac tccctcactg gcgagggcaa cttcaactgg cgctacctgt cccccttcga   5520
ctacctggcg gcgaggaga agatcgtcat ctccaagaag gagtccatgt tctcctggga   5580
cgagaccgag tacaagatcc ccgcgcggct caccctgcag atctgggatg cggaccactt   5640
ctccgctgac gacttcctgg gggccatcga gctggaccg aaccggttcc gcgggggcgc   5700
aaagacagcc aagcagtgca ccatggagat ggccaccggg gaggtggacg tgcccctcgt   5760
gtccatcttc aagcaaaagc gcgtcaaagg ctggtggccc ctcctggccc gcaatgagaa   5820
cgatgagttt gagctcacgg gcaaggtgga ggctgagctg catttactga cagcaggaa   5880
ggcagagaag aacccagtgg gcctggcccg caatgaacct gaccccctag agaaacccaa   5940
ccggcccgac acgagcttca tctggttcct gaaccctctc aagtcggctc gctacttctt   6000
gtggcacacg tatcgctggc tgctcctcaa actgttgctg ctcctgctgc tgctcctcct   6060
cctcgccctg ttcctctact ctgtgcctgg ctacctggtc aagaaaatcc tcgggccctg   6120
```

```
agcccagtgg cctcctggcc ggcccgacac ggccttcgtc tggttcctca accctctcaa    6180
gtccatcaag tacctcatct gcacccggta caagtggctc atcatcaaga tcgtgctggc    6240
gctgttgggg ctgctcatgt tggggctctt cctctacagc ctccctggct acatggtcaa    6300
aaagctcctt ggggcatgaa ggccgccagc tcccgccagc cgctcccag ccctgccgca     6360 tttcctttca gtggcttgga ctctttccca tctcccctgg ggagcctgag gagcccagcg    6420
tccactcttc atgccttggg ccgagcctgc ctcctgcttg cggggccgc ctgtcctcac     6480 tgccccaggc tgcggcttgc ccagtcccgc ccctctgacc cctgcctgtg ggctggggag    6540
ccttggatgg ggtggggacc tggaatgggt ctctcttgcc ccacctggct gaggcgccac    6600
ccttcttcag gcccaggctc cagaggaaga ctcctgaaac cctccccagg tcttccaagt    6660
acaggattga agctttagtg aaattaacca aggaccatgg gtcagtgccc agggctttaa    6720
aaagaatgaa cgagcaaaag gtatccccgc cgtgacccct gcagatagca ccggtctttg    6780
atccgcagca ggggccagac cctgcccaca gtcccagcg cggctgcttc tgccactgct     6840
gggctccact tggctcctct cacttcccag ggggtcgcct gtcctgcctg tgggtttcca    6900
tggcttccca gagctccctc tgccccagcc agcgcctcca ggcccagctg aggagctgtg    6960
agaagcagca gagggactc cccatcccgg gcacaccctg tcctcccacc cctgccccct     7020
tgcccttcca gcccttttcag ctgcagctgg gagctggccc gtcaagtgct gcccctgcct   7080
gtgtctgggt ttctgttggc tgttttctt ttcttgagtg gtgatttttc tctaaataaa     7140
agaagtcaag cactgaaaaa aaaaaaaaa a                                    7171
```

<210> SEQ ID NO 11
<211> LENGTH: 4969
<212> TYPE: DNA
<213> ORGANISM: Homo sapiens

<400> SEQUENCE: 11

```
ccgtgagttc tgcccaggcc ctgtgagctc accagagcca cagactcaca gcccagaggt      60
ggcttcttcc ttcaggaact gaagaacccc catgaacacc aacatctcca ggttctgaga    120
acagaacctg ggaaattgat gacttcctca tgatgaccga tactcaggat ggccctagcg    180
agagctccca gatcatgagg aagaaggcct gaacgacata caggagatga tcaaaacgga    240
gaagtcctac cctgagcgtc gcctgcgggg cgtcctggag gagctgagct gtggctgctg    300
ccgcttcctc tccctcgctg acaaggacca gggccactca tcccgcacca ggcttgaccg    360
ggagcgcctc aagtcctgca tgagggagct ggaaaacatg gggcagcagg ccaggatgct    420
gcgggcccag gtgaagcggc acacggtgcg ggacaagctg aggctgtgcc agaacttcct    480
gcagaagctc gcttcctgg cggacgagcc ccagcacagc attcccgaca tcttcatctg     540
gatgatgagc aacaacaagc gtgtcgccta tgcccgtgtg ccctccaagg acctgctctt    600
ctccatcgtg gaggaggaga ctggcaagga ctgcgcaag gtcaagacgc tcttccttaa     660
gctgccaggg aagcggggct tcggctcggc aggctggaca gtgcaggcca aggtggagct    720
gtacctgtgg ctgggcctca gcaaacagcg caaggagttc ctgtgcggcc tgccctgtgg    780
cttccaggag gtcaaggcag cccagggcct gggcctgcat gccttccac ccgtcagcct     840 ggtctacacc aagaagcagg cgttccagct ccgagcgcac atgtaccagg cccgcagcct    900
ctttgccgcc gacagcagcg gactctcaga cccctttgcc ccgtcttctc tcatcaatca    960
gagtcagtgc acagaggtgc tgaatgagac cctgtgtccc acctgggacc agatgctggt   1020
```

```
gttcgacaac ctggagctct atggtgaagc tcatgagctg agggacgatc cgccatcat    1080 tgtcattgaa atctatgacc aggattccat gggcaaagct gacttcatgg gccggacctt    1140
cgccaaaccc ctggtgaaga tggcagacga ggcgtactgc ccaccccgct tcccacctca    1200
gctcgagtac taccagatct accgtggcaa cgccacagct ggagacctgc tggcggcctt    1260
cgagctgctg cagattggac cagcagggaa ggctgacctg cccccatca atggcccggt    1320 ggacgtggac cgaggtccca tcatgcccgt gccatgggc atccggcccg tgctcagcaa    1380
gtaccgagtg gaggtgctgt tctggggcct acgggaccta aagcgggtga acctggccca    1440
ggtggaccgg ccacgggtgg acatcgagtg tgcagggaag ggggtgcagt cgtccctgat    1500
ccacaattat aagaagaacc ccaacttcaa caccctcgtc aagtggtttg aagtggacct    1560
cccagagaac gagctgctgc acccgccctt gaacatccgt gtggtggact gccgggcctt    1620
cggtcgctac acactggtgg gctccatgc cgtcagctcc ctgcgacgct tcatctaccg    1680
gcccccagac cgctcggccc ccagctggaa caccacgggg gaggttgtgg tgactatgga    1740
gccagaggta cccatcaaga aactggagac catggtgaag ctggacgcga cttctgaagc    1800
tgttgtcaag gtggatgtgg ctgaggagga aaggagaag aagaagaaga gaaagggcac    1860
tgcggaggag ccagaggagg aggagccaga cgagagcatg ctggactggt ggtccaagta    1920
ctttgcctcc attgacacca tgaaggagca acttcgacaa caagagccct ctggaattga    1980
cttggaggag aaggaggaag tggacaatac cgagggcctg aagggggtcaa tgaagggcaa    2040 ggagaaggca agggctgcca agaggagaa gaagaagaaa actcagagct ggctctctgg    2100
ccaggggtcc gaggcccccg agaagaagaa acccaagatt gatgagctta aggtataccc    2160
caaagagctg gagtccgagt ttgataactt tgaggactgg ctgcacactt tcaacttgct    2220
tcggggcaag accggggatg atgaggatgg ctccaccgag gaggagcgca ttgtgggacg    2280
cttcaagggc tccctctgcg tgtacaaagt gccactccca gaggacgtgt cccgggaagc    2340
cggctacgac tccaccctacg gcatgttcca gggcatcccg agcaatgacc ccatcaatgt    2400
gctggtccga gtctatgtgg tccgggccac ggacctgcac cctgctgaca tcaacggcaa    2460
agctgacccc tacatcgcca tccggctagg caagactgac atccgcgaca aggagaacta    2520
catctccaag cagctcaacc ctgtctttgg gaagtccttt gacatcgagg cctccttccc    2580
catggaatcc atgctgacgg tggctgtgta tgactgggac ctggtgggca ctgatgacct    2640
cattggggaa accaagatcg acctggagaa ccgcttctac agcaagcacc gcgccacctg    2700
cggcatcgcc cagacctact ccacacatgg ctacaatatc tggcgggacc ccatgaagcc    2760
cagccagatc ctgacccgcc tctgcaaaga cggcaaagtg gacggccccc actttgggcc    2820
ccctgggaga gtgaaggtgg ccaaccgcgt cttcactggg ccctctgaga ttgaggacga    2880
gaacggtcag aggaagccca cagacgagca tgtggcgctg ttggccctga ggcactggga    2940
ggacatcccc cgcgcaggct gccgcctggt gccagagcat gtggagacga ggccgctgct    3000
caaccccgac aagccgggca tcgagcaggg ccgcctggag ctgtgggtgg acatgttccc    3060
catggacatg ccagcccctg ggacgcctct ggacatctca cctcggaagc ccaagaagta    3120
cgagctgcgg gtcatcatct ggaacacaga tgaggtggtc ttggaggacg acgacttctt    3180
cacaggggag aagtccagtg acatcttcgt gaggggggtgg ctgaagggcc agcaggagga    3240
caagcaggac acagacgtcc actaccactc cctcactggc gagggcaact tcaactggcg    3300
ctacctgttc cccttcgact acctggcggc ggaggagaag atcgtcatct ccaagaagga    3360
gtccatgttc tcctgggacg agaccgagta caagatcccc gcgcggctca ccctgcagat    3420
```

```
ctgggatgcg gaccacttct ccgctgacga cttcctgggg gccatcgagc tggacctgaa    3480
ccggttcccg cggggcgcaa agacagccaa gcagtgcacc atggagatgg ccaccgggga    3540
ggtggacgtg cccctcgtgt ccatcttcaa gcaaaagcgc gtcaaaggct ggtggcccct    3600
cctggcccgc aatgagaacg atgagtttga gctcacgggc aaggtggagg ctgagctgca    3660
tttactgaca gcagaggagg cagagaagaa cccagtgggc ctggcccgca atgaacctga    3720
cccctagag aaacccaacc ggcccgacac gagcttcatc tggttcctga accctctcaa     3780
gtcggctcgc tacttcttgt ggcacacgta tcgctggctg ctcctcaaac tgttgctgct    3840
cctgctgctg ctcctcctcc tcgccctgtt cctctactct gtgcctggct acctggtcaa    3900
gaaaatcctc ggggcctgag cccagtggcc tcctggccgg cccgacacgg ccttcgtctg    3960
gttcctcaac cctctcaagt ccatcaagta cctcatctgc acccggtaca agtggctcat    4020
catcaagatc gtgctggcgc tgttggggct gctcatgttg gggctcttcc tctacagcct    4080
ccctggctac atggtcaaaa agctccttgg ggcatgaagg ccgccagctc ccgccagccg    4140
ctccccagcc ctgccgcatt tcctttcagt ggcttggact ctttcccatc tccctggggg    4200
agcctgagga gccagcgtc cactcttcat gccttgggcc gagcctgcct cctgcttgcg     4260
ggggccgcct gtcctcactg ccccaggctg cggcttgccc agtcccgccc ctctgacccc    4320
tgcctgtggg ctggggagcc ttggatgggg tggggacctg gaatgggtct ctcttgcccc    4380
acctggctga ggcgccaccc ttcttcaggc ccaggctcca gaggaagact cctgaaaccc    4440
tccccaggtc ttccaagtac aggattgaag ctttagtgaa attaaccaag gaccatgggt    4500
cagtgcccag ggctttaaaa agaatgaacg agcaaaaggt atccccgccg tgaccctgc     4560
agatagcacc ggtctttgat ccgcagcagg ggccagaccc tgcccacaag tcccagcgcg    4620
gctgcttctg ccactgctgg gctccacttg gctcctctca cttcccaggg ggtcgcctgt    4680
cctgcctgtg ggtttccatg gcttcccaga gctccctctg ccccagccag cgcctccagg    4740
cccagctgag gagctgtgag aagcagcaga ggggactccc catcccgggc acaccctgtc    4800
ctcccacccc tgcccccttg cccttccagc cctttcagct gcagctggga gctggcccgt    4860
caagtgctgc ccctgcctgt gtctgggttt ctgttggctg tttttctttt cttgagtggt    4920
gattttctc taaataaaag aagtcaagca ctgaaaaaaa aaaaaaaaa                 4969
```

<210> SEQ ID NO 12
<211> LENGTH: 4771
<212> TYPE: DNA
<213> ORGANISM: Homo sapiens

<400> SEQUENCE: 12

```
ccgtgagttc tgcccaggcc ctgtgagctc accagagcca cagactcaca gcccagaggt      60
ggcttcttcc ttcaggaact gaagaacccc catgaacacc aacatctcca ggttctgaga     120
acagaacctg ggaaattgat gacttcctca tgatgaccga tactcaggat ggccctagcg     180
agagctccca gatcatgagg aagaaggcct gaacgacata caggagatga tcaaaacgga     240
gaagtcctac cctgagcgtc gcctgcgggg cgtcctggag gagctgagct gtggctgctg     300
ccgcttcctc tccctcgctg acaaggacca gggccactca tcccgcacca ggcttgaccg     360
ggagcgcctc aagtcctgca tgagggagct ggaaaacatg gggcagcagg ccaggatgct     420
gcgggcccag gtgaagcggc acacggtgcg ggacaagctg aggctgtgcc agaacttcct     480
gcagaagctg cgcttcctgg cggacgagcc ccagcacagc attcccgaca tcttcatctg     540
```

```
gatgatgagc aacaacaagc gtgtcgccta tgcccgtgtg ccctccaagg acctgctctt    600
ctccatcgtg gaggaggaga ctggcaagga ctgcgccaag gtcaagacgc tcttccttaa    660
gctgccaggg aagcggggct tcggctcggc aggctggaca gtgcaggcca aggtggagct    720
gtacctgtgg ctgggcctca gcaaacagcg caaggagttc ctgtgcggcc tgccctgtgg    780
cttccaggag gtcaaggcag cccagggcct gggcctgcat gccttcccac ccgtcagcct    840
ggtctacacc aagaagcagg cgttccagct ccgagcgcac atgtaccagg cccgcagcct    900
cttagccgcc gacagcagcg gactctcaga ccccttagcc cgcgtcttct tcatcaatca    960
gagtcagtgc acagaggtgc tgaatgagac cctgtgtccc acctgggacc agatgctggt   1020
gttcgacaac ctggagctct atggtgaagc tcatgagctg agggacgatc cgcccatcat   1080
tgtcattgaa atctatgacc aggattccat gggcaaagct gacttcatgg gccgaccctt   1140
cgccaaaccc ctggtgaaga tggcagacga ggcgtactgc ccaccccgct tcccacctca   1200
gctcgagtac taccagatct accgtggcaa cgccacagct ggagacctgc tggcggcctt   1260
cgagctgctg cagattggac cagcaggaa  ggctgacctg cccccatca  atggcccggt   1320
ggacgtggac cgaggtccca tcatgcccgt gcccatgggc atccggcccg tgctcagcaa   1380
gtaccgagtg gaggtgctgt tctggggcct acgggaccta agcgggtga  acctggccca   1440
ggtggaccgg ccacgggtgg acatcgagtg tgcaggaag  ggggtgcagt cgtccctgat   1500
ccacaattat aagaagaacc ccaacttcaa caccctcgtc aagtggtttg aagtggacct   1560
cccagagaac gagctgctgc acccgccctt gaacatccgt gtggtggact gccgggcctt   1620
cggtcgctac acactggtgg gctcccatgc cgtcagctcc ctgcgacgct tcatctaccg   1680
gcccccagac cgctcggccc ccagctggaa caccacgggg gaggttgtgg tgactatgga   1740
gccagaggta cccatcaaga aactggagac catggtgaag ctggacgcga cttctgaagc   1800
tgttgtcaag gtggatgtgg ctgaggagga aaggagaag  aagaagaaga agaagggcac   1860
tgcggaggag ccagaggagg aggagccaga cgagagcatg ctggactggt ggtccaagta   1920
cttgcctcc  attgacacca tgaaggagca acttcgacaa caagagccct ctggaattga   1980
cttggaggag aaggaggaag tggacaatac cgagggcctg aaggggtcaa tgaagggcaa   2040
ggagaaggca agggctgcca agaggagaa  gaagaagaaa actcagagct ctggctctgg   2100
ccagggggtcc gaggcccccg agaagaagaa acccaagatt gatgagctta aggtatacccc   2160
caaagagctg gagtccgagt ttgataactt tgaggactgg ctgcacactt tcaacttgct   2220
tcggggcaag accggggatg atgaggatgg ctccaccgag gaggagcgca ttgtgggacg   2280
cttcaagggc tccctctgcg tgtacaaagt gccactccca gaggacgtgt cccgggaagc   2340
cggctacgac tccaccctacg gcatgttcca gggcatcccg agcaatgacc catcaatgt    2400
gctggtccga gtctatgtgg tccgggccac ggacctgcac cctgctgaca tcaacggcaa   2460
agctgacccc tacatcgcca tccggctagg caagactgac atccgcgaca aggagaacta   2520
catctccaag cagctcaacc ctgtctttgg gaagtccttt gacatcgagg cctccttccc   2580
catggaatcc atgctgacgg tggctgtgta tgactgggac ctggtgggca ctgatgacct   2640
cattgggaa  accaagatcg acctggagaa ccgcttctac agcaagcacc gcgccacctg   2700
cggcatcgcc cagacctact ccacacatgg ctacaatatc tggcgggacc ccatgaagcc   2760
cagccagatc ctgacccgcc tctgcaaaga cggcaaagtg gacggccccc actttgggcc   2820
ccctgggaga gtgaaggtgg ccaaccgcgt cttcactggg ccctctgaga ttgaggacga   2880
gaacggtcag aggaagccca cagacgagca tgtggcgctg ttggccctga ggcactggga   2940
```

-continued

```
ggacatcccc cgcgcaggct gccgcctggt gccagagcat gtggagacga ggccgctgct    3000
caaccccgac aagccgggca tcgagcaggg ccgcctggag ctgtgggtgg acatgttccc    3060
catggacatg ccagcccctg ggacgcctct ggacatctca cctcggaagc ccaagaagta    3120
cgagctgcgg gtcatcatct ggaacacaga tgaggtggtc ttggaggacg acgacttctt    3180
cacaggggag aagtccagtg acatcttcgt gaggggtggg ctgaagggcc agcaggagga    3240
caagcaggac acagacgtcc actaccactc cctcactggc gagggcaact tcaactggcg    3300
ctacctgttc cccttcgact acctggcggc ggaggagaag atcgtcatct ccaagaagga    3360
gtccatgttc tcctgggacg agaccgagta caagatcccc cgcgcggctca ccctgcagat    3420 ctgggatgcg gaccacttct ccgctgacga cttcctgggg gccatcgagc tggacctgaa    3480
ccggttcccg cggggcgcaa agacagccaa gcagtgcacc atggagatgg ccaccgggga    3540
ggtggacgtg cccctcgtgt ccatcttcaa gcaaaagcgc gtcaaaggct ggtggcccct    3600 cctgcccgc aatgagaacg atgagtttga gctcacgggc aaggtggagg ctgagctgca    3660
tttactgaca gcagaggagg cagagaagaa cccagtgggc ctggcccgca atgaacctga    3720 cccctagag aaacccaacc ggcccgacac ggccttcgtc tggttcctca accctctcaa    3780
gtccatcaag tacctcatct gcacccggta caagtggctc atcatcaaga tcgtgctggc    3840
gctgttgggg ctgctcatgt gggggctctt cctctacagc ctccctggct acatggtcaa    3900
aaagctcctt ggggcatgaa ggccgccagc tcccgccagc cgctccccag ccctgccgca    3960
tttcctttca gtggcttgga ctctttccca tctccctgg ggagcctgag gagcccagcg    4020
tccactcttc atgccttggg ccgagcctgc ctcctgcttg cgggggccgc ctgtcctcac    4080
tgccccaggc tgcggcttgc ccagtcccgc ccctctgacc cctgcctgtg gctggggag    4140 ccttggatgg ggtggggacc tggaatgggt ctctcttgcc ccacctggct gaggcgccac    4200
ccttcttcag gcccaggctc cagaggaaga ctcctgaaaac cctccccagg tcttccaagt    4260
acaggattga agctttagtg aaattaacca aggaccatgg gtcagtgccc agggctttaa    4320
aaagaatgaa cgagcaaaag gtatcccgc cgtgacccct gcagatagca ccggtctttg    4380
atccgcagca ggggccagac cctgcccaca agtcccagcg cggctgcttc tgccactgct    4440
gggctccact tggctcctct cacttcccag ggggtcgcct gtcctgcctg tgggtttcca    4500
tggcttccca gagctccctc tgccccagcc agcgcctcca ggcccagctg aggagctgtg    4560
agaagcagca gagggactc cccatcccgg gcacaccctg tcctcccacc cctgccccct    4620
tgcccttcca gcccttttcag ctgcagctgg gagctggccc gtcaagtgct gcccctgcct    4680
gtgtctgggt ttctgttggc tgtttttctt ttcttgagtg gtgatttttc tctaaataaa    4740
agaagtcaag cactgaaaaa aaaaaaaaaa a                                   4771
```

<210> SEQ ID NO 13
<211> LENGTH: 5123
<212> TYPE: DNA
<213> ORGANISM: Homo sapiens

<400> SEQUENCE: 13

```
ccgtgagttc tgcccaggcc ctgtgagctc accagagcca cagactcaca gcccagaggt     60
ggcttcttcc ttcaggaact gaagaacccc catgaacacc aacatctcca ggttctgaga    120
acagaacctg ggaaattgat gacttcctca tgatgaccga tactcaggat ggccctagcg    180
agagctccca gatcatgagg tccctcactc ccctgatcaa cagggaggag gcatttgggg    240
```

```
aggctgggga ggcggggctg tgccccagca tcacccacac tcctgattca caggaagaag    300
gcctgaacga catacaggag atgatcaaaa cggagaagtc ctaccctgag cgtcgcctgc    360
ggggcgtcct ggaggagctg agctgtggct gctgccgctt cctctccctc gctgacaagg    420
accagggcca ctcatcccgc accaggcttg accgggagcg cctcaagtcc tgcatgaggg    480
agctggaaaa catggggcag caggccagga tgctgcgggc ccaggtgaag cggcacacgg    540
tgcgggacaa gctgaggctg tgccagaact tcctgcagaa gctgcgcttc ctggcggacg    600
agccccagca cagcattccc gacatcttca tctggatgat gagcaacaac aagcgtgtcg    660
cctatgcccg tgtgcctcc aaggacctgc tcttctccat cgtggaggag gagactggca    720
aggactgcgc caaggtcaag acgctcttcc ttaagctgcc agggaagcgg ggcttcggct    780
cggcaggctg acagtgcag gccaaggtgg agctgtacct gtggctgggc ctcagcaaac    840
agcgcaagga gttcctgtgc ggcctgccct gtggcttcca ggaggtcaag gcagcccagg    900
gcctgggcct gcatgccttc ccacccgtca gcctggtcta caccaagaag caggcgttcc    960
agctccgagc gcacatgtac caggcccgca gcctctttgc cgccgacagc agcggactct   1020
cagacccctt tgcccgcgtc ttcttcatca atcagagtca gtgcacagag gtgctgaatg   1080
agaccctgtg tcccacctgg gaccagatgc tggtgttcga caacctggag ctctatggtg   1140
aagctcatga gctgagggac gatccgccca tcattgtcat tgaaatctat gaccaggatt   1200
ccatgggcaa agctgacttc atgggccgga ccttcgccaa cccctggtg aagatggcag   1260 acgaggcgta ctgcccaccc cgcttcccac ctcagctcga gtactaccag atctaccgtg   1320
gcaacgccac agctggagac ctgctggcgg ccttcgagct gctgcagatt ggaccagcag   1380
ggaaggctga cctgcccccc atcaatggcc cggtggacgt ggaccgaggt cccatcatgc   1440
ccgtgcccat gggcatccgg cccgtgctca gcaagtaccg agtggaggtg ctgttctggg   1500
gcctacggga cctaaagcgg gtgaacctgg cccaggtgga ccggccacgg gtggacatcg   1560
agtgtgcagg gaaggggggtg cagtcgtccc tgatccacaa ttataagaag aaccccaact   1620
tcaacaccct cgtcaagtgg tttgaagtgg acctcccaga gaacgagctg ctgcacccgc   1680
ccttgaacat ccgtgtggtg gactgccggg ccttcggtcg ctacacactg gtgggctccc   1740
atgccgtcag ctccctgcga cgcttcatct accggccccc agaccgctcg ccccccagct   1800
ggaacaccac ggtcaggctt ctccggcgct gccgtgtgct gtgcaatggg ggctcctcct   1860
ctcactccac aggggaggtt gtggtgacta tggagccaga ggtacccatc aagaaactgg   1920
agaccatggt gaagctggac gcgacttctg aagctgttgt caaggtggat gtggctgagg   1980
aggagaagga gaagaagaag aagaagaagg gcactgcgga ggagccagag gaggaggagc   2040
cagacgagag catgctggac tggtggtcca agtactttgc ctccattgac accatgaagg   2100
agcaacttcg acaacaagag ccctctggaa ttgacttgga ggagaaggag gaagtggaca   2160
ataccgaggg cctgaagggg tcaatgaagg gcaaggagaa ggcaagggct gccaaagagg   2220
agaagaagaa gaaaactcag agctctggct ctggccaggg gtccgaggcc cccgagaaga   2280
agaaacccaa gattgatgag cttaaggtat accccaaaga gctggagtcc gagtttgata   2340
actttgagga ctggctgcac actttcaact tgcttcgggg caagaccggg gatgatgagg   2400
atggctccac cgaggaggag cgcattgtgg gacgcttcaa gggctccctc tgcgtgtaca   2460
aagtgccact cccagaggac gtgtcccggg aagccggcta cgactccacc tacggcatgt   2520
tccagggcat cccgagcaat gaccccatca atgtgctggt ccgagtctat gtggtccggg   2580
ccacggacct gcaccctgct gacatcaacg gcaaagctga cccctacatc gccatccggc   2640
```

```
taggcaagac tgacatccgc gacaaggaga actacatctc caagcagctc aaccctgtct   2700
ttgggaagtc ctttgacatc gaggcctcct tccccatgga atccatgctg acggtggctg   2760
tgtatgactg ggacctggtg ggcactgatg acctcattgg ggaaaccaag atcgacctgg   2820
agaaccgctt ctacagcaag caccgcgcca cctgcggcat cgcccagacc tactccacac   2880
atggctacaa tatctggcgg gaccccatga agcccagcca gatcctgacc cgcctctgca   2940
aagacggcaa agtggacggc ccccactttg gccccctggg agagtgaag gtggccaacc    3000 gcgtcttcac tgggccctct gagattgagg acgagaacgg tcagaggaag cccacagacg   3060
agcatgtggc gctgttggcc ctgaggcact gggaggacat ccccgcgca ggctgccgcc     3120 tggtgccaga gcatgtggag acgaggccgc tgctcaaccc cgacaagccg gcatcgagc    3180 agggccgcct ggagctgtgg gtggacatgt tccccatgga catgccagcc cctgggacgc    3240
ctctggacat ctcacctcgg aagcccaaga agtacgagct gcgggtcatc atctggaaca    3300
cagatgaggt ggtcttggag gacgacgact tcttcacagg ggagaagtcc agtgacatct    3360
tcgtgagggg gtggctgaag ggccagcagg aggacaagca ggacacagac gtccactacc    3420
actccctcac tggcgagggc aacttcaact ggcgctacct gttccccttc gactacctgg    3480
cggcggagga aagatcgtc atctccaaga aggagtccat gttctcctgg gacgagaccg     3540
agtacaagat ccccgcgcgg ctcaccctgc agatctggga tgcggaccac ttctccgctg    3600
acgacttcct gggggccatc gagctggacc tgaaccggtt cccgcggggc gcaaagacag    3660
ccaagcagtg caccatggag atggccaccg gggaggtgga cgtgccctc gtgtccatct     3720 tcaagcaaaa gcgcgtcaaa ggctggtggc ccctcctggc ccgcaatgag aacgatgagt    3780
ttgagctcac gggcaaggtg gaggctgagc tgcatttact gacagcagag gaggcagaga    3840
agaacccagt gggcctggcc cgcaatgaac ctgaccccct agagaaaccc aaccggcccg    3900
acacgagctt catctggttc ctgaaccctc tcaagtcggc tcgctacttc ttgtggcaca    3960
cgtatcgctg gctgctcctc aaactgttgc tgctcctgct gctgctcctc ctcctcgccc    4020
tgttcctcta ctctgtgcct ggctacctgg tcaagaaaat cctcgggggcc tgagcccagt    4080 ggcctcctgg ccggcccgac acggccttcg tctggttcct caaccctctc aagtccatca    4140
agtacctcat ctgcacccgg tacaagtggc tcatcatcaa gatcgtgctg gcgctgttgg    4200
ggctgctcat gttggggctc ttcctctaca gcctccctgg ctacatggtc aaaaagctcc    4260
ttggggcatg aaggccgcca gctcccgcca gccgctcccc agccctgccg catttccttt    4320
cagtggcttg gactctttcc catctcccct ggggagcctg aggagcccag cgtccactct    4380
tcatgccttg ggccgagcct gcctcctgct tgcgggggcc gcctgtcctc actgccccag    4440
gctgcggctt gcccagtccc gccccctctga ccctgcctg tgggctgggg agccttggat    4500
ggggtgggga cctggaatgg gtctctcttg ccccacctgg ctgaggcgcc accttcttc     4560 aggcccaggc tccagaggaa gactcctgaa accctcccca ggtcttccaa gtacaggatt    4620
gaagctttag tgaaattaac caaggaccat gggtcagtgc ccagggcttt aaaaagaatg    4680
aacgagcaaa aggtatcccc gccgtgaccc ctgcagatag caccggtctt tgatccgcag    4740
caggggccag accctgccca aagtcccag cgcggctgct tctgccactg ctgggctcca     4800
cttggctcct ctcacttccc aggggtcgc ctgtcctgcc tgtgggtttc catggcttcc      4860
cagagctccc tctgccccag ccagcgcctc caggcccagc tgaggagctg tgagaagcag    4920
cagaggggac tccccatccc gggcacaccc tgtcctccca cccctgcccc cttgcccttc    4980
```

-continued

| | |
|---|---|
| cagcccttc agctgcagct gggagctggc ccgtcaagtg ctgcccctgc ctgtgtctgg | 5040 |
| gtttctgttg gctgtttttc ttttcttgag tggtgatttt tctctaaata aaagaagtca | 5100 |
| agcactgaaa aaaaaaaaaa aaa | 5123 |

<210> SEQ ID NO 14
<211> LENGTH: 6973
<212> TYPE: DNA
<213> ORGANISM: Homo sapiens

<400> SEQUENCE: 14

| | |
|---|---|
| atcggagggg ggtcgggagg aggaggagga ggcagcggca gagaagagag aggcgtgtga | 60 |
| gccgtgctcc accggctagc tccttcccgc tgctcctgcc tggcagtgcc aggcagccca | 120 |
| caccagcatg gccttgctca tccacctcaa gacagtctcg gagctgcggg caggggcga | 180 |
| ccggatcgcc aaagtgactt tccgagggca atccttctac tctcgggtcc tggagaactg | 240 |
| tgaggatgtg gctgactttg atgagacatt tcggtggccg gtggccagca gcatcgacag | 300 |
| aaatgagatg ctggagattc aggttttcaa ctacagcaaa gtcttcagca caagctcat | 360 |
| cgggaccttc cgcatggtgc tgcagaaggt ggtagaggag agccatgtgg aggtgactga | 420 |
| cacgctgatt gatgacaaca atgctatcat caagaccagc ctgtgcgtgg aggtccggta | 480 |
| tcaggccact gacggcacag tgggctcctg ggacgatggg gacttcctgg agatgagtc | 540 |
| tcttcaagag gaagagaagg acagccaaga gacggatgga ctgctcccag ctcccggcc | 600 |
| cagctcccgg cccccaggag agaagagctt ccggagagcc gggaggagcg tgttctccgc | 660 |
| catgaagctc ggcaaaaacc ggtctcacaa ggaggagccc caaagaccag atgaaccggc | 720 |
| ggtgctggag atggaagacc ttgaccatct ggccattcgg ctaggagatg gactggatcc | 780 |
| cgactcggtg tctctagcct cagtcacagc tctcaccact aatgtctcca caagcgatc | 840 |
| taagccagac attaagatgg agccaagtgc tgggcggccc atggattacc aggtcagcat | 900 |
| cacggtgatc gaggcccggc agctggtggg cttgaacatg gaccctgtgg tgtgcgtgga | 960 |
| ggtgggtgac gacaagaagt acacatccat gaaggagtcc actaactgcc cctattacaa | 1020 |
| cgagtacttc gtcttcgact tccatgtctc tccggatgtc atgtttgaca agatcatcaa | 1080 |
| gatttcggtg attcactcca agaacctgct gcgcagtggc accctggtgg ctccttcaa | 1140 |
| aatggacgtg ggaaccgtgt actcgcagcc agagcaccag ttccatcaca gtgggccat | 1200 |
| cctgtctgac cccgatgaca tctcctcggg gctgaagggc tacgtgaagt gtgacgttgc | 1260 |
| cgtggtgggc aaaggggaca acatcaagac gccccacaag gccaatgaga ccgacgaaga | 1320 |
| tgacattgag gggaacttgc tgctccccga gggggtgccc ccgaacgcc agtgggcccg | 1380 |
| gttctatgtg aaaattacc gagcagaggg gctgccccgt atgaacacaa gcctcatggc | 1440 |
| caatgtaaag aaggctttca tcggtgaaaa caaggacctc gtggacccct acgtgcaagt | 1500 |
| cttctttgct ggccagaagg gcaagacttc agtgcagaag agcagctatg agccctgtg | 1560 |
| gaatgagcag gtcgtcttta cagacctctt ccccccactc tgcaaacgca tgaaggtgca | 1620 |
| gatccgagac tcggacaagg tcaacgacgt ggccatcggc acccacttca ttgacctgcg | 1680 |
| caagatttct aatgacggag acaaaggctt cctgcccaca ctgggcccag cctgggtgaa | 1740 |
| catgtacggc tccacacgta actacacgct gctggatgag catcaggacc tgaacgaggg | 1800 |
| cctgggggag ggtgtgtcct tccgggcccg gctcctgctg ggcctggctg tggagatcgt | 1860 |
| agacacctcc aaccctgagc tcaccagctc cacagaggtg caggtggagc aggccacgcc | 1920 |
| catctcggag agctgtgcag gtaaaatgga agaattcttt ctctttggag ccttcctgga | 1980 |

```
ggcctcaatg atcgaccgga gaaacggaga caagcccatc acctttgagg tcaccatagg    2040
caactatggg aacgaagttg atggcctgtc ccggccccag cggcctcggc cccgaagga    2100 gccgggggat gaggaagaag tagacctgat tcagaacgca agtgatgacg aggccggtga    2160
tgccggggac ctggcctcag tctcctccac tccaccaatg cggcccccag tcaccgacag    2220
gaactacttc catctgccct acctggagcg aaagccctgc atctacatca gagctggtg    2280 gccggaccag cgccgccgcc tctacaatgc caacatcatg gacccacattg ccgacaagct    2340 ggaagaaggc ctgaacgaca tacaggagat gatcaaaacg gagaagtcct accctgagcg    2400
tcgcctgcgg ggcgtcctgg aggagctgag ctgtggctgc tgccgcttcc tctccctcgc    2460
tgacaaggac cagggccact catcccgcac caggcttgac cgggagcgcc tcaagtcctg    2520
catgagggag ctgaaaaaca tggggcagca ggccaggatg ctgcgggccc aggtgaagcg    2580
gcacacggtg cgggacaagc tgaggctgtg ccagaacttc ctgcagaagc tgcgcttcct    2640
ggcggacgag ccccagcaca gcattcccga catcttcatc tggatgatga gcaacaacaa    2700
gcgtgtcgcc tatgcccgtg tgccctccaa ggacctgctc ttctccatcg tggaggagga    2760
gactggcaag gactgcgcca aggtcaagac gctcttcctt aagctgccag ggaagcgggg    2820
cttcggctcg gcaggctgga cagtgcaggc caaggtggag ctgtacctgt ggctgggcct    2880
cagcaaacag cgcaaggagt tcctgtgcgg cctgccctgt ggcttccagg aggtcaaggc    2940
agcccagggc ctgggcctgc atgccttccc acccgtcagc ctggtctaca ccaagaagca    3000
ggcgttccag ctccgagcgc acatgtacca ggcccgcagc ctctttgccg ccgacagcag    3060
cggactctca gacccctttg cccgcgtctt cttcatcaat cagagtcagt gcacagaggt    3120
gctgaatgag accctgtgtc ccacctggga ccagatgctg gtgttcgaca acctggagct    3180
ctatggtgaa gctcatgagc tgagggacga tccgcccatc attgtcattg aaatctatga    3240
ccaggattcc atgggcaaag ctgacttcat gggccggacc ttcgccaaac ccctggtgaa    3300
gatggcagac gaggcgtact gcccaccccg cttcccacct cagctcgagt actaccagat    3360
ctaccgtggc aacgccacag ctggagacct gctggcggcc ttcgagctgc tgcagattgg    3420
accagcaggg aaggctgacc tgccccccat caatggcccg gtgacgtgg accgaggtcc    3480 catcatgccc gtgcccatgg gcatccggcc cgtgctcagc aagtaccgag tggaggtgct    3540
gttctggggc ctacgggacc taaagcgggt gaacctggcc caggtggacc ggccacgggt    3600
ggacatcgag tgtgcaggga aggggtgca gtcgtccctg atccacaatt ataagaagaa    3660
ccccaacttc aacaccctcg tcaagtggtt tgaagtggac ctcccagaga cgagctgct    3720 gcacccgccc ttgaacatcc gtgtggtgga ctgccgggcc ttcggtcgct acacactggt    3780
gggctcccat gccgtcagct ccctgcgacg cttcatctac cggcccccag accgctcggc    3840
ccccagctgg aacaccacgg tcaggcttct ccggcgctgc cgtgtgctgt gcaatggggg    3900
ctcctcctct cactccacag gggaggttgt ggtgactatg gagccagagg tacccatcaa    3960
gaaactggag accatggtga agctggacgc gacttctgaa gctgttgtca aggtggatgt    4020
ggctgaggag gagaaggaga agaagaagaa gaagaagggc actgcggagg agccagagga    4080
ggaggagcca gacgagagca tgctggactg gtggtccaag tactttgcct ccattgacac    4140
catgaaggag caacttcgac aacaagagcc ctctggaatt gacttggagg agaaggagga    4200
agtggacaat accgagggcc tgaagggtc aatgaagggc aaggagaagg caaggggctgc    4260 caaagaggag aagaagaaga aaactcagag ctctggctct ggccaggggt ccgaggcccc    4320
```

```
cgagaagaag aaacccaaga ttgatgagct taaggtatac cccaaagagc tggagtccga    4380
gtttgataac tttgaggact ggctgcacac tttcaacttg cttcggggca agaccgggga    4440
tgatgaggat ggctccaccg aggaggagcg cattgtggga cgcttcaagg gctccctctg    4500
cgtgtacaaa gtgccactcc cagaggacgt gtcccgggaa gccggctacg actccaccta    4560
cggcatgttc cagggcatcc cgagcaatga ccccatcaat gtgctggtcc gagtctatgt    4620
ggtccgggcc acggacctgc accctgctga catcaacggc aaagctgacc cctacatcgc    4680
catccggcta ggcaagactg acatccgcga caaggagaac tacatctcca agcagctcaa    4740
ccctgtcttt gggaagtcct ttgacatcga ggcctccttc cccatggaat ccatgctgac    4800
ggtggctgtg tatgactggg acctggtggg cactgatgac ctcattgggg aaaccaagat    4860
cgacctggag aaccgcttct acagcaagca ccgcgccacc tgcggcatcg cccagaccta    4920
ctccacacat ggctacaata tctggcggga ccccatgaag cccagccaga tcctgacccg    4980
cctctgcaaa gacggcaaag tggacggcc ccactttggg ccccctggga gagtgaaggt    5040
ggccaaccgc gtcttcactg ggccctctga gattgaggac gagaacggtc agaggaagcc    5100
cacagacgag catgtggcgc tgttggccct gaggcactgg gaggacatcc ccgcgcagg    5160 ctgccgcctg gtgccagagc atgtggagac gaggccgctg ctcaacccccg acaagccggg    5220 catcgagcag ggccgcctgg agctgtgggt ggacatgttc cccatggaca tgccagcccc    5280
tgggacgcct ctggacatct cacctcggaa gcccaagaag tacgagctgc gggtcatcat    5340
ctggaacaca gatgaggtgg tcttggagga cgacgacttc ttcacagggg agaagtccag    5400
tgacatcttc gtgaggggt ggctgaaggg ccagcaggag gacaagcagg acacagacgt    5460
ccactaccac tccctcactg gcgagggcaa cttcaactgg cgctacctgt tccccttcga    5520
ctacctggcg gcggaggaga agatcgtcat ctccaagaag gagtccatgt tctcctggga    5580
cgagaccgag tacaagatcc ccgcgcggct caccctgcag atctgggatg cggaccactt    5640
ctccgctgac gacttcctgg gggccatcga gctggacctg aaccggttcc gcgggggcgc    5700
aaagacagcc aagcagtgca ccatggagat ggccaccggg gaggtggacg tgcccctcgt    5760
gtccatcttc aagcaaaagc gcgtcaaagg ctggtggccc ctcctggccc gcaatgagaa    5820
cgatgagttt gagctcacgg gcaaggtgga ggctgagctg cattttactga cagcagagga    5880 ggcagagaag aacccagtgg gcctggcccg caatgaacct gaccccctag agaaacccaa    5940
ccggcccgac acggccttcg tctggttcct caaccctctc aagtccatca gtacctcat    6000 ctgcacccgg tacaagtggc tcatcatcaa gatcgtgctg cgcgctgttgg ggctgctcat    6060 gttggggctc ttcctctaca gcctccctgg ctacatggtc aaaaagctcc ttggggcatg    6120
aaggccgcca gctcccgcca gccgctcccc agccctgccg catttccttt cagtggcttg    6180
gactctttcc catctcccct ggggagcctg aggagcccag cgtccactct tcatgccttg    6240
ggccgagcct gcctcctgct tgcggggcc gcctgtcctc actgccccag gctgcggctt    6300
gcccagtccc gcccctctga cccctgcctg tgggctgggg agcttggat ggggtgggga    6360 cctggaatgg gtctctcttg ccccaccgg ctgaggcgcc acccttcttc aggcccaggc    6420
tccagaggaa gactcctgaa accctcccca gtcttccaa gtacaggatt gaagctttag    6480
tgaaattaac caaggaccat gggtcagtgc ccagggcttt aaaaagaatg aacgagcaaa    6540 aggtatccc gccgtgaccc ctgcagatag caccggtctt tgatccgcag cagggggcag    6600
accctgccca caagtcccag cgcggctgct tctgccactg ctgggctcca cttggctcct    6660
ctcacttccc aggggggtcgc ctgtcctgcc tgtgggtttc catggcttcc cagagctccc    6720
```

-continued

| | |
|---|---|
| tctgccccag ccagcgcctc caggcccagc tgaggagctg tgagaagcag cagaggggac | 6780 |
| tccccatccc gggcacaccc tgtcctccca ccctgccccc cttgcccttc cagccctttc | 6840 |
| agctgcagct gggagctggc ccgtcaagtg ctgcccctgc ctgtgtctgg gtttctgttg | 6900 |
| gctgtttttc ttttcttgag tggtgatttt tctctaaata aagaagtca agcactgaaa | 6960 |
| aaaaaaaaaa aaa | 6973 |

<210> SEQ ID NO 15
<211> LENGTH: 7125
<212> TYPE: DNA
<213> ORGANISM: Mus musculus
<400> SEQUENCE: 15

| | |
|---|---|
| ttggttgcct tggtctctgt gggcagcagc aggaggaggc ggcagcagcc agagaagagg | 60 |
| gaggcgtgtg agccacactc caccagcgag cttcttcccg ctgctctgga actgcccagg | 120 |
| ctctccccac cagcatggcc ctgattgttc acctcaagac tgtctcagag ctccgaggca | 180 |
| aaggtgaccg gattgccaaa gtcactttcc gagggcagtc tttctactcc cgggtcctgg | 240 |
| agaactgcga gggtgtggct gactttgatg agacgttccg gtggccagtg ccagcagca | 300 |
| tcgaccggaa tgaagtgttg gagattcaga ttttcaacta cagcaaagtc ttcagcaaca | 360 |
| agctgatagg gaccttctgc atggtgctgc agaaagtggt ggaggagaat cgggtagagg | 420 |
| tgaccgacac gctgatggat gacagcaatg ctatcatcaa gaccagcctg agcatggagg | 480 |
| tccggtatca ggccacagat ggcactgtgg gcccctggga tgatggagac ttcctgggag | 540 |
| atgaatccct ccaggaggag aaggacagcc aggagacaga tgggctgcta cctggttccc | 600 |
| gacccagcac ccggatatct ggcgagaaga gctttcgcag agcgggaagg agtgtgttct | 660 |
| cggccatgaa actcggcaaa actcggtccc acaaagagga gccccaaaga caagatgagc | 720 |
| cagcagtgct ggagatggag gacctggacc acctagccat tcagctgggg gatgggctgg | 780 |
| atcctgactc cgtgtctcta gcctcggtca ccgctctcac cagcaatgtc tccaacaaac | 840 |
| ggtctaagcc agatattaag atggagccca gtgctggaag gcccatggat taccaggtca | 900 |
| gcatcacagt gattgaggct cggcagctgg tgggcttgaa catggaccct gtggtgtgtg | 960 |
| tggaggtggg tgatgacaag aaatacacgt caatgaagga gtccacaaac tgcccttact | 1020 |
| acaacgagta ctttgtcttc gacttccatg tctctcctga tgtcatgttt gacaagatca | 1080 |
| tcaagatctc ggttatccat tctaagaacc tgcttcggag cggcacccat gtgggttcct | 1140 |
| tcaaaatgga tgtggggact gtgtattccc agcctgaaca ccagttccat cacaaatggg | 1200 |
| ccatcctgtc agaccccgat gacatctctg ctgggttgaa gggttatgta aagtgtgatg | 1260 |
| tcgctgtggt gggcaaggga gacaaacatca agacacccca caaggccaac gagacggatg | 1320 |
| aggacgacat tgaagggaac ttgctgctcc ccgagggcgt gcccccgaa cggcagtggg | 1380 |
| cacggttcta tgtgaaaatt taccgagcag agggactgcc ccggatgaac acaagcctca | 1440 |
| tggccaacgt gaagaaggcg ttcatcggtg agaacaagga cctcgtcgac ccctatgtgc | 1500 |
| aagtcttctt tgctggacaa aagggcaaaa catcagtgca gaagagcagc tatgagccgc | 1560 |
| tatgaatga gcaggtcgtc ttcacagact tgttcccccc actctgcaaa cgcatgaagg | 1620 |
| tgcagatccg ggactctgac aaggtcaatg atgtggccat cggcacccac ttcatcgacc | 1680 |
| tgcgcaagat ttccaacgat ggagacaaag gcttcctgcc tacccctcggt ccagcctggg | 1740 |
| tgaacatgta cggctccacg cgcaactaca cactgctgga cgagcaccag gacttgaatg | 1800 |

```
aaggcctggg ggagggtgtg tccttccggg cccgcctcat gttgggacta gctgtggaga    1860
tcctggacac ctccaaccca gagctcacca gctccacgga ggtgcaggtg gagcaggcca    1920
cgcctgtctc ggagagctgc acagggagaa tggaagaatt ttttctattt ggagccttct    1980
tggaagcctc aatgattgac cggaaaaatg gggacaagcc aattaccttt gaggtgacca    2040
taggaaacta cggcaatgaa gtcgatggta tgtcccggcc cctgaggcct cggccccgga    2100
aagagcctgg ggatgaagaa gaggtagacc tgattcagaa ctccagtgac gatgaaggtg    2160
acgaagccgg ggacctggcc tcggtgtcct ccaccccacc tatgcggccc cagatcacgg    2220
acaggaacta tttccacctg ccctacctgg agcgcaagcc ctgcatctat atcaagagct    2280
ggtggcctga ccagaggcgg cgcctctaca atgccaacat catggatcac attgctgaca    2340
agctggaaga aggcctgaat gatgtacagg agatgatcaa aacggagaag tcctacccgg    2400
agcgccgcct gcggggtgtg ctagaggaac tcagctgtgg ctgccaccgc ttcctctccc    2460
tctcggacaa ggaccagggc cgctcgtccc gcaccaggct ggatcgagag cgtcttaagt    2520
cctgtatgag ggagttggag agcatgggac agcaggccaa gagcctgagg gctcaggtga    2580
agcggcacac tgttcgggac aagctgaggt catgccagaa cttttctgcag aagctacgct    2640 tcctggcgga tgagccccag cacagcattc ctgatgtgtt catttggatg atgagcaaca    2700
acaaacgtat cgcctatgcc cgcgtgcctt ccaaagacct gctcttctcc atcgtggagg    2760
aggaactggg caaggactgc gccaaagtca agaccctctt cctgaagctg ccagggaaga    2820
ggggcttcgg ctcggcaggc tggacagtac aggccaagct ggagctctac ctgtggctgg    2880
gcctcagcaa gcagcgaaag gacttcctgt gtggtctgcc ctgtggcttc gaggaggtca    2940
aggcagccca aggcctgggc ctgcattcct ttccgcccat cagcctagtc tacaccaaga    3000
agcaagcctt ccagctccga gcacacatgt atcaggcccg aagcctcttt gctgctgaca    3060
gcagtgggct ctctgatccc tttgcccgtg tcttcttcat caaccagagc caatgcactg    3120
aggttctaaa cgagacactg tgtcccacct gggaccagat gctggtattt gacaacctgg    3180
agctgtacgg tgaagctcac gagttacgag atgatccccc catcattgtc attgaaatct    3240
acgaccagga cagcatgggc aaagccgact tcatgggccg gaccttcgcc aagcccctgg    3300
tgaagatggc agatgaagca tactgcccac ctcgcttccc gccgcagctt gagtactacc    3360
agatctaccg aggcagtgcc actgccggag acctactggc tgccttcgag ctgctgcaga    3420
ttgggccatc agggaaggct gacctgccac ccatcaatgg cccagtggac atggacagag    3480
ggcccatcat gcctgtgccc gtgggaatcc ggccagtgct cagcaagtac cgagtggagg    3540
tgctgttctg gggcctgagg gacctaaaga gggtgaacct ggcccaggtg gaccgaccac    3600
gggtggacat cgagtgtgca ggaaaggggg tacaatcctc cctgattcac aattataaga    3660
agaaccccaa cttcaacacg ctggtcaagt ggtttgaagt ggacctcccg gagaatgagc    3720
tcctgcaccc acccttgaac atccgagtgg tagattgccg ggcctttgga cgatacaccc    3780
tggtgggttc ccacgcagtc agctcactga ggcgcttcat ctaccgacct ccagaccgct    3840 cagccccca ctggaacacc acagtcaggc tgctccgggg ctgccacagg ctgcgcaatg    3900
ggggcccctc ttctcgcccc acaggggagg ttgtagtaag catggagcct gaggagccag    3960
ttaagaagct ggagaccatg gtgaaactgg atgcgacttc tgatgctgtg gtcaaggtgg    4020
atgtggctga agatgagaag gaaaggaaga agaagaaaaa gaaaggcccg tcagaggagc    4080
cagaggagga gagccgat gagagcatgc tggattggtg gtccaagtac ttcgcctcca    4140
tcgacacaat gaaggagcaa cttcgacaac atgagacctc tggaactgac ttggaagaga    4200
```

```
aggaagagat ggaaagcgct gagggcctga agggaccaat gaagagcaag gagaagtcca      4260
gagctgcaaa ggaggagaaa aagaagaaaa accagagccc tggccctggc cagggatcgg      4320
aggctcctga gaagaagaaa gccaagatcg atgagcttaa ggtgtacccc aaggagctgg      4380
aatcggagtt tgacagcttt gaggactggc tgcacacctt caacctgttg aggggcaaga      4440
cgggagatga tgaggatggc tccacagagg aggagcgcat agtaggccga ttcaagggct      4500
ccctctgtgt gtacaaagtg ccactcccag aagatgtatc tcgagaagct ggctatgatc      4560
ccacctatgg aatgttccag ggcatcccaa gcaatgaccc catcaatgtg ctggtccgaa      4620
tctatgtggt ccgggccaca gacctgcacc cggccgacat caatggcaaa gctgacccct      4680
atattgccat caagttaggc aagaccgaca tccgagacaa ggagaactac atctccaagc      4740
agctcaaccc tgtgtttggg aagtcctttg acattgaggc ctccttcccc atggagtcca      4800
tgttgacagt ggccgtgtac gactgggatc tggtgggcac tgatgacctc atcggagaaa      4860
ccaagattga cctggaaaac cgcttctaca gcaagcatcg cgccacctgc ggcatcgcac      4920
agacctattc catacatggc tacaatatct ggagggaccc catgaagccc agccagatcc      4980
tgacacgcct ctgtaaagag ggcaaagtgg acggccccca cttttggtcc catgggagag      5040
tgagggttgc caaccgtgtc ttcacggggc cttcagaaat agaggatgag aatggtcaga      5100
ggaagcccac agatgagcac gtggcactgt ctgctctgag acactgggag gacatccccc      5160
gggtgggctg ccgccttgtg ccggaacacg tggagaccag gccgctgctc aaccctgaca      5220
agccaggcat tgagcagggc cgcctggagc tgtgggtgga catgttcccc atggacatgc      5280
cagcccctgg gacacctctg gatatatccc ccaggaaacc caagaagtac gagctgcggg      5340
tcatcgtgtg gaacacagac gaggtggtcc tggaagacga tgatttcttc acggagagaa      5400
agtccagtga cattttttgtg agggggtggc tgaagggcca gcaggaggac aaacaggaca      5460
cagatgtcca ctatcactcc ctcacggggg agggcaactt caactggaga tacctcttcc      5520
ccttcgacta cctagcggcc gaagagaaga tcgttatgtc caaaaaggag tctatgttct      5580
cctgggatga cacggagtac aagatccctg cgcggctcac cctgcagatc tgggacgctg      5640
accacttctc ggctgacgac ttcctggggg ctatcgagct ggacctgaac cggttcccga      5700
ggggcgctaa gacagccaag cagtgcacca tggagatggc caccggggag gtggacgtac      5760
ccctggtttc catcttttaaa cagaaacgtg tcaaaggctg gtggcccctc ctggcccgca      5820
atgagaatga tgagtttgag ctcacaggca agtggaggc ggagctacac ctactcacgg      5880
cagaggaggc agagaagaac cctgtgggcc tggctcgcaa tgaacctgat cccctagaaa      5940
aacccaatcg gccggacaca agcttcatct ggttcttgaa ccctctcaag tctgcccgct      6000
acttcctgtg gcatacctac cgctggctac tcctcaaatt cctgctgctc ttcctcctgc      6060
tgctgctctt cgccctgttt ctctactctc tgcctggcta cctggccaag aagatccttg      6120
gggcctgagc cctgcagtcg cctaggcctg ccggcctgac acggcattcg tctggttcct      6180
gaacccactc aaatctatca agtacctcat ctgcacccgg tacaagtggc tgatcatcaa      6240
gatcgtgctg gcgctgctgg ggctgctcat gctggccctc ttcctttaca gcctcccagg      6300
ctacatggtc aagaagctcc taggggcctg aagtgtgccc caccccagcc cgctccagca      6360
tccctccagg ggctgctgcg tattttgcct tccctcacct ggactctctc ccaactccct      6420
gaggagccct cccacgcctg ccagccttga gcaagacacc tgcttgctgg acttcatccc      6480
caccccacac ccaaactgtt gcttgcctga tcttgtccca ggcctgcctg gggtttgggg      6540
```

| | |
|---|---|
| cacagttggc ctccaaaacc agatacccto ttgtctaaag taccaggttc ctctgcccaa | 6600 |
| ccccaagagt ggtagtggcc caaccctccc tgtgctttcc aaatcttgtc ttaaggcacc | 6660 |
| agtgaaatta accaagaaac gcggagcaat gcccaaggct ctgatgagta ggaacacgtg | 6720 |
| gaaagcacca ggaatgccag cagaggcgag gcggcacacc tctctgcaga gcatccaggc | 6780 |
| cgagcggcgg gcagcggcca gctgcttctg cgcatgctct cctcttggct ctgcttcttt | 6840 |
| ctcacagtca cagtcacttc acagcttagc cttgggcttc ccatcacttc caggggtgcc | 6900 |
| tctgccttgg ccagtgtgtg tcagctagta cacaagctcc aagtgtgaat caggtgtact | 6960 |
| ggccgtcctg aagactgact gccctgtcct tcctgccgac agccacaccc gagtgtacac | 7020 |
| ttaaagcggt gcccttctgc ctctgtgggc ctgctggctg ctgttccttt cttgagtgtg | 7080 |
| atttttttt tctctccctc aataaaataa atcaaactct gagac | 7125 |

<210> SEQ ID NO 16
<211> LENGTH: 7065
<212> TYPE: DNA
<213> ORGANISM: Mus musculus

<400> SEQUENCE: 16

| | |
|---|---|
| ttggttgcct tggtctctgt gggcagcagc aggaggaggc ggcagcagcc agagaagagg | 60 |
| gaggcgtgtg agccacactc caccagcgag cttcttcccg ctgctctgga actgcccagg | 120 |
| ctctccccac cagcatggcc ctgattgttc acctcaagac tgtctcagag ctccgaggca | 180 |
| aaggtgaccg gattgccaaa gtcactttcc gagggcagtc tttctactcc cgggtcctgg | 240 |
| agaactgcga gggtgtggct gactttgatg agacgttccg gtggccagtg ccagcagca | 300 |
| tcgaccggaa tgaagtgttg gagattcaga ttttcaacta cagcaaagtc ttcagcaaca | 360 |
| agctgatagg gaccttctgc atggtgctgc agaaaagtggt ggaggagaat cgggtagagg | 420 |
| tgaccgacac gctgatggat gacagcaatg ctatcatcaa gaccagcctg agcatggagg | 480 |
| tccggtatca ggccacagat ggcactgtgg gcccctggga tgatggagac ttcctgggag | 540 |
| atgaatccct ccaggaggag aaggacagcc aggagacaga tgggctgcta cctggttccc | 600 |
| gacccagcac ccggatatct ggcgagaaga gctttcgcag agcgggaagg agtgtgttct | 660 |
| cggccatgaa actcggcaaa actcggtccc acaaagagga gccccaaaga caagatgagc | 720 |
| cagcagtgct ggagatggag gacctggacc acctagccat tcagctgggg gatgggctgg | 780 |
| atcctgactc cgtgtctcta gcctcggtca ccgctctcac cagcaatgtc tccaacaaac | 840 |
| ggtctaagcc agatattaag atggagccca gtgctggaag gcccatggat taccaggtca | 900 |
| gcatcacagt gattgaggct cggcagctgg tgggcttgaa catggaccct gtggtgtgtg | 960 |
| tggaggtggg tgatgacaag aaatacacgt caatgaagga gtccacaaac tgcccttact | 1020 |
| acaacgagta ctttgtcttc gacttccatg tctctcctga tgtcatgttt gacaagatca | 1080 |
| tcaagatctc ggttatccat tctaagaacc tgcttcggag cggcacccta gtgggttcct | 1140 |
| tcaaaatgga tgtggggact gtgtattccc agcctgaaca ccagttccat cacaaatggg | 1200 |
| ccatcctgtc agaccccgat gacatctctg ctgggttgaa gggttatgta aagtgtgatg | 1260 |
| tcgctgtggt gggcaaggga gacaacatca agacacccca caaggccaac gagacggatg | 1320 |
| aggacgacat tgaagggaac ttgctgctcc ccgagggcgt gccccccgaa cggcagtggg | 1380 |
| cacggttcta tgtgaaaatt taccgagcag agggactgcc ccggatgaac acaagcctca | 1440 |
| tggccaacgt gaagaaggcg ttcatcgtg agaacaagga cctcgtcgac ccctatgtgc | 1500 |
| aagtcttctt tgctggacaa aagggcaaaa catcagtgca gaagagcagc tatgagccgc | 1560 |

```
tatggaatga gcaggtcgtc ttcacagact tgttcccccc actctgcaaa cgcatgaagg    1620
tgcagatccg ggactctgac aaggtcaatg atgtggccat cggcacccac ttcatcgacc    1680
tgcgcaagat ttccaacgat ggagacaaag gcttcctgcc taccctcggt ccagcctggg    1740
tgaacatgta cggctccacg cgcaactaca cactgctgga cgagcaccag gacttgaatg    1800
aaggcctggg ggagggtgtg tccttccggg cccgcctcat gttgggacta gctgtggaga    1860
tcctggacac ctccaaccca gagctcacca gctccacgga ggtgcaggtg agcaggcca    1920 cgcctgtctc ggagagctgc acagggagaa tggaagaatt ttttctattt ggagccttct    1980
tggaagcctc aatgattgac cggaaaaatg gggacaagcc aattaccttt gaggtgacca    2040
taggaaacta cggcaatgaa gtcgatggta tgtcccggcc cctgaggcct cggccccgga    2100
aagagcctgg ggatgaagaa gaggtagacc tgattcagaa ctccagtgac gatgaaggtg    2160
acgaagccgg ggacctggcc tcggtgtcct ccaccccacc tatgcggccc cagatcacgg    2220
acaggaacta tttccacctg ccctacctgg agcgcaagcc ctgcatctat atcaagagct    2280
ggtggcctga ccagaggcgg cgcctctaca atgccaacat catggatcac attgctgaca    2340
agctggaaga aggcctgaat gatgtacagg agatgatcaa aacggagaag tcctacccgg    2400
agcgccgcct gcggggtgtg ctagaggaac tcagctgtgg ctgccaccgc ttcctctccc    2460
tctcggacaa ggaccagggc cgctcgtccc gcaccaggct ggatcgagag cgtcttaagt    2520
cctgtatgag ggagttggag agcatgggac agcaggccaa gagcctgagg gctcaggtga    2580
agcggcacac tgttcgggac aagctgaggt catgccagaa cttctgcag aagctacgct    2640 tcctggcgga tgagccccag cacagcattc ctgatgtgtt catttggatg atgagcaaca    2700
acaaacgtat cgcctatgcc cgcgtgcctt ccaaagacct gctcttctcc atcgtggagg    2760
aggaactggg caaggactgc gccaaagtca agaccctctt cctgaagctg ccagggaaga    2820
ggggcttcgg ctcggcaggc tggacagtac aggccaagct ggagctctac ctgtggctgg    2880
gcctcagcaa gcagcgaaag gacttcctgt gtggtctgcc ctgtggcttc gaggaggtca    2940
aggcagccca aggcctgggc ctgcattcct ttccgcccat cagcctagtc tacaccaaga    3000
agcaagcctt ccagctccga gcacacatgt atcaggcccg aagcctcttt gctgctgaca    3060
gcagtgggct ctctgatccc tttgcccgtg tcttcttcat caaccagagc caatgcactg    3120
aggttctaaa cgagacactg tgtcccacct gggaccagat gctggtattt gacaacctgg    3180
agctgtacgg tgaagctcac gagttacgag atgatccccc catcattgtc attgaaatct    3240
acgaccagga cagcatgggc aaagccgact tcatgggccg gaccttcgcc aagcccctgg    3300
tgaagatggc agatgaagca tactgcccac ctcgcttccc gccgcagctt gagtactacc    3360
agatctaccg aggcagtgcc actgccggag acctactggc tgccttcgag ctgctgcaga    3420
ttgggccatc agggaaggct gacctgccac ccatcaatgg cccagtggac atggacagag    3480
ggcccatcat gcctgtgccc gtgggaatcc ggccagtgct cagcaagtac cgagtggagg    3540
tgctgttctg gggcctgagg gacctaaaga gggtgaacct ggcccaggtg gaccgaccac    3600
gggtggacat cgagtgtgca ggaaaggggg tacaatcctc cctgattcac aattataaga    3660
agaaccccaa cttcaacacg ctggtcaagt ggtttgaagt ggacctccgc gagaatgagc    3720
tcctgcaccc acccttgaac atccgagtgg tagattgccg ggcctttgga cgatacaccc    3780
tggtgggttc ccacgcagtc agctcactga ggcgcttcat ctaccgacct ccagaccgct    3840
cagcccccaa ctggaacacc acaggggagg ttgtagtaag catggagcct gaggagccag    3900
```

-continued

```
ttaagaagct ggagaccatg gtgaaactgg atgcgacttc tgatgctgtg gtcaaggtgg      3960
atgtggctga agatgagaag gaaaggaaga agaagaaaaa gaaaggcccg tcagaggagc      4020
cagaggagga agagcccgat gagagcatgc tggattggtg gtccaagtac ttcgcctcca      4080
tcgacacaat gaaggagcaa cttcgacaac atgagacctc tggaactgac ttggaagaga      4140
aggaagagat ggaaagcgct gagggcctga agggaccaat gaagagcaag gagaagtcca      4200
gagctgcaaa ggaggagaaa aagaagaaaa accagagccc tggccctggc cagggatcgg      4260
aggctcctga agaagagaaa gccaagatcg atgagcttaa ggtgtacccc aaggagctgg      4320
aatcggagtt tgacagcttt gaggactggc tgcacacctt caacctgttg aggggcaaga      4380
cgggagatga tgaggatggc tccacagagg aggagcgcat agtaggccga ttcaagggct      4440
ccctctgtgt gtacaaagtg ccactcccag aagatgtatc tcgagaagct ggctatgatc      4500
ccacctatgg aatgttccag ggcatcccaa gcaatgaccc catcaatgtg ctggtccgaa      4560
tctatgtggt ccgggccaca gacctgcacc cggccgacat caatggcaaa gctgacccct      4620
atattgccat caagttaggc aagaccgaca tccgagacaa ggagaactac atctccaagc      4680
agctcaaccc tgtgtttggg aagtcctttg acattgaggc ctccttcccc atggagtcca      4740
tgttgacagt ggccgtgtac gactgggatc tggtgggcac tgatgacctc atcggagaaa      4800
ccaagattga cctggaaaac cgcttctaca gcaagcatcg cgccacctgc ggcatcgcac      4860
agacctattc catacatggc tacaatatct ggagggaccc catgaagccc agccagatcc      4920
tgacacgcct ctgtaaagag ggcaaagtgg acggccccca ctttggtccc catgggagag      4980 tgaggggttgc caaccgtgtc ttcacggggc cttcagaaat agaggatgag aatggtcaga      5040
ggaagcccac agatgagcac gtggcactgt ctgctctgag acactgggag gacatccccc      5100
gggtgggctg ccgccttgtg ccggaacacg tggagaccag gccgctgctc aaccctgaca      5160
agccaggcat tgagcagggc cgcctggagc tgtgggtgga catgttcccc atggacatgc      5220
cagcccctgg gacacctctg gatatatccc ccaggaaacc caagaagtac gagctgcggg      5280
tcatcgtgtg gaacacagac gaggtggtcc tggaagacga tgatttcttc acgggagaga      5340
agtccagtga catttttgtg aggggggtggc tgaaggccca gcaggaggac aaacaggaca      5400
cagatgtcca ctatcactcc ctcacggggg agggcaactt caactggaga tacctcttcc      5460
ccttcgacta cctagcggcc gaagagaaga tcgttatgtc caaaaaggag tctatgttct      5520
cctgggatga gacggagtac aagatccctg cgcggctcac cctgcagatc tgggacgctg      5580
accacttctc ggctgacgac ttcctggggg ctatcgagct ggacctgaac cggttcccga      5640
ggggcgctaa gacagccaag cagtgcacca tggagatggc caccggggag gtggacgtac      5700 ccctggttc catctttaaa cagaaacgtg tcaaaggctg gtggcccctc ctggcccgca      5760
atgagaatga tgagtttgag ctcacaggca agtggaggc ggagctacac ctactcacgg      5820
cagaggaggc agagaagaac cctgtgggcc tggctcgcaa tgaacctgat ccctagaaa      5880 aacccaatcg gccggacaca agcttcatct ggttcttgaa ccctctcaag tctgcccgct      5940
acttcctgtg gcatacctac cgctggctac tcctcaaatt cctgctgctc ttcctcctgc      6000
tgctgctctt cgcccgtttt ctctactctc tgcctggcta cctggccaag aagatccttg      6060
gggcctgagc cctgcagtcg cctaggcctg ccggcctgac acggcattcg tctggttcct      6120
gaacccactc aaatctatca agtacctcat ctgcacccgg tacaagtggc tgatcatcaa      6180
gatcgtgctg cgcgctgctgg ggctgctcat gctggcccttc ttcctttaca gcctcccagg      6240
ctacatggtc aagaagctcc tagggggcctg aagtgtgccc caccccagcc cgctccagca      6300
```

```
tccctccagg ggctgctgcg tattttgcct tccctcacct ggactctctc ccaactccct    6360
gaggagccct cccacgcctg ccagccttga gcaagacacc tgcttgctgg acttcatccc    6420
caccccacac ccaaactgtt gcttgcctga tcttgtccca ggcctgcctg gggtttgggg    6480
cacagttggc ctccaaaacc agatacccto ttgtctaaag taccaggttc ctctgcccaa    6540
ccccaagagt ggtagtggcc caaccctccc tgtgctttcc aaatcttgtc ttaaggcacc    6600
agtgaaatta accaagaaac gcggagcaat gcccaaggct ctgatgagta ggaacacgtg    6660
gaaagcacca ggaatgccag cagaggcgag gcggcacacc tctctgcaga gcatccaggc    6720
cgagcggcgg gcagcggcca gctgcttctg cgcatgctct cctcttggct ctgcttcttt    6780
ctcacagtca cagtcacttc acagcttagc cttgggcttc ccatcacttc caggggtgcc    6840
tctgccttgg ccagtgtgtg tcagctagta cacaagctcc aagtgtgaat caggtgtact    6900
ggccgtcctg aagactgact gccctgtcct tcctgccgac agccacaccc gagtgtacac    6960
ttaaagcggt gcccttctgc ctctgtgggc ctgctggctg ctgttccttt cttgagtgtg    7020 atttttttt tctctccctc aataaaataa atcaaactct gagac                    7065

<210> SEQ ID NO 17
<211> LENGTH: 6907
<212> TYPE: DNA
<213> ORGANISM: Mus musculus

<400> SEQUENCE: 17
ttggttgcct tggtctctgt gggcagcagc aggaggaggc ggcagcagcc agagaagagg      60
gaggcgtgtg agccacactc caccagcgag cttcttcccg ctgctctgga actgcccagg     120
ctctccccac cagcatggcc ctgattgttc acctcaagac tgtctcagag ctccgaggca     180 aggtgaccg gattgccaaa gtcacttttcc gagggcagtc tttctactcc cgggtcctgg     240
agaactgcga gggtgtggct gactttgatg agacgttccg gtggccagtg ccagcagca     300 tcgaccggaa tgaagtgttg gagattcaga ttttcaacta cagcaaagtc ttcagcaaca     360
agctgatagg gaccttctgc atggtgctgc agaaagtggt ggaggagaat cgggtagagg     420
tgaccgacac gctgatggat gacagcaatg ctatcatcaa gccagcctg agcatggagg     480 tccggtatca ggccacagat ggcactgtgg gcccctggga tgatggagac ttcctgggag     540
atgaatccct ccaggaggag aaggacagcc aggagacaga tgggctgcta cctggttccc     600
gacccagcac ccggatatct ggcgagaaga gctttcgcag caaaggcaga gagaagacca     660
agggaggcag agatggcgag cacaaagcgg gaaggagtgt gttctcggcc atgaaactcg     720
gcaaaactcg gtcccacaaa gaggagcccc aaagacaaga tgagccagca gtgctggaga     780
tggaggacct ggaccaccta gccattcagc tgggggatgg gctggatcct gactccgtgt     840
ctctagcctc ggtcaccgct ctcaccagca atgtctccaa caaacggtct aagccagata     900
ttaagatgga gcccagtgct ggaaggccca tggattacca ggtcagcatc acagtgattg     960
aggctcggca gctggtgggc ttgaacatgg accctgtggt gtgtgtggag gtgggtgatg    1020
acaagaaata cacgtcaatg aaggagtcca caaactgccc ttactacaac gagtactttg    1080
tcttcgactt ccatgtctct cctgatgtca tgtttgacaa gatcatcaag atctcggtta    1140
tccattctaa gaacctgctt cggagcggca ccctggtggg ttccttcaaa atggatgtgg    1200
ggactgtgta ttcccagcct gaacaccagt tccatcacaa atgggccatc ctgtcagacc    1260
ccgatgacat ctctgctggg ttgaagggtt atgtaaagtg tgatgtcgct gtggtgggca    1320
```

```
agggagacaa catcaagaca ccccacaagg ccaacgagac ggatgaggac gacattgaag    1380
ggaacttgct gctccccgag ggcgtgcccc ccgaacggca gtgggcacgg ttctatgtga    1440
aaatttaccg agcagaggga ctgccccgga tgaacacaag cctcatggcc aacgtgaaga    1500
aggcgttcat cggtgagaac aaggacctcg tcgacccta  tgtgcaagtc ttctttgctg    1560
gacaaaaggg caaaacatca gtgcagaaga gcagctatga gccgctatgg aatgagcagg    1620
tcgtcttcac agacttgttc cccccactct gcaaacgcat gaaggtgcag atccgggact    1680
ctgacaaggt caatgatgtg ccatcggca  cccacttcat cgacctgcgc aagatttcca    1740
acgatggaga caaaggcttc ctgcctaccc tcggtccagc ctgggtgaac atgtacggct    1800
ccacgcgcaa ctacacactg ctggacgagc accaggactt gaatgaaggc ctggggagg     1860 gtgtgtcctt ccgggcccgc tcatgttgg  gactagctgt ggagatcctg gacacctcca    1920
acccagagct caccagctcc acggaggtgc aggtggagca ggccacgcct gtctcggaga    1980
gctgcacagg gagaatggaa gaatttttc  tatttggagc cttcttggaa gcctcaatga    2040
ttgaccggaa aaatggggac aagccaatta cctttgaggt gaccatagga aactacggca    2100
atgaagtcga tggtatgtcc cggcccctga ggcctcggcc ccggaaagag cctggggatg    2160
aagaagaggt agacctgatt cagaactcca gtgacgatga aggtgacgaa gccggggacc    2220
tggcctcggt gtcctccacc ccacctatgc ggccccagat cacggacagg aactatttcc    2280
acctgcccta cctggagcgc aagccctgca tctatatcaa gagctggtgg cctgaccaga    2340
ggcggcgcct ctacaatgcc aacatcatgg atcacattgc tgacaagctg aagaaggcc     2400 tgaatgatgt acaggagatg atcaaaacgg agaagtccta cccggagcgc cgcctgcggg    2460
gtgtgctaga ggaactcagc tgtggctgcc accgcttcct ctccctctcg gacaaggacc    2520
agggccgctc gtcccgcacc aggctggatc gagagcgtct taagtcctgt atgagggagt    2580
tggagagcat gggacagcag gccaagagcc tgagggctca ggtgaagcgg cacactgttc    2640
gggacaagct gaggtcatgc cagaactttc tgcagaagct acgcttcctg gcggatgagc    2700
cccagcacag cattcctgat gtgttcattt ggatgatgag caacaacaaa cgtatcgcct    2760
atgcccgcgt gccttccaaa gacctgctct tctccatcgt ggaggaggaa ctgggcaagg    2820
actgcgccaa agtcaagacc ctcttcctga agctgccagg gaagagggc  ttcggctcgg    2880 caggctggac agtacaggcc aagctggagc tctacctgtg gctgggcctc agcaagcagc    2940
gaaaggactt cctgtgtggt ctgccctgtg gcttcgagga ggtcaaggca gcccaaggcc    3000
tgggcctgca ttcctttccg cccatcagcc tagtctacac caagaagcaa gccttccagc    3060
tccgagcaca catgtatcag gcccgaagcc tctttgctgc tgacagcagt gggctctctg    3120
atccctttgc ccgtgtcttc ttcatcaacc agagccaatg cactgaggtt ctaaacgaga    3180
cactgtgtcc cacctgggac cagatgctgg tatttgacaa cctggagctg tacggtgaag    3240
ctcacgagtt acgagatgat cccccatca  ttgtcattga aatctacgac caggacagca    3300
tgggcaaagc cgacttcatg ggccggacct tcgccaagcc cctggtgaag atggcagatg    3360
aagcatactg cccacctcgc ttcccgccgc agcttgagta ctaccagatc taccgaggca    3420
gtgccactgc cggagaccta ctggctgcct tcgagctgct gcagattggg ccatcaggga    3480
aggctgacct gccacccatc aatggcccag tggacatgga cagagggccc atcatgcctg    3540
tgcccgtggg aatccggcca gtgctcagca agtaccgagt ggaggtgctg ttctggggcc    3600
tgagggacct aaagagggtg aacctggccc aggtggaccg accacgggtg gacatcgagt    3660
gtgcaggaaa gggggtacaa tcctcccctga ttcacaatta taagaagaac cccaacttca    3720
```

-continued

```
acacgctggt caagtggttt gaagtggacc tcccggagaa tgagctcctg cacccaccct    3780
tgaacatccg agtggtagat tgccgggcct ttggacgata caccctggtg ggttcccacg    3840
cagtcagctc actgaggcgc ttcatctacc gacctccaga ccgctcagcc cccaactgga    3900
acaccacagg ggaggttgta gtaagcatgg agcctgagga gccagttaag aagctggaga    3960
ccatggtgaa actggatgcg acttctgatg ctgtggtcaa ggtggatgtg gctgaagatg    4020
agaaggaaag gaagaagaag aaaaagaaag gcccgtcaga ggagccagag gaggaagagc    4080
ccgatgagag catgctggat tggtggtcca agtacttcgc ctccatcgac acaatgaagg    4140
agcaacttcg acaacatgag acctctggaa ctgacttgga agagaaggaa gagatggaaa    4200
gcgctgaggg cctgaaggga ccaatgaaga gcaaggagaa gtccagagct gcaaaggagg    4260
agaaaaagaa gaaaaaccag agccctggcc ctggccaggg atcggaggct cctgagaaga    4320
agaaagccaa gatcgatgag cttaaggtgt accccaagga gctggaatcg agtttgaca    4380
gctttgagga ctggctgcac accttcaacc tgttgagggg caagacggga gatgatgagg    4440
atggctccac agaggaggag cgcatagtag gccgattcaa gggctccctc tgtgtgtaca    4500
aagtgccact cccagaagat gtatctcgag aagctggcta tgatcccacc tatggaatgt    4560
tccagggcat cccaagcaat gaccccatca atgtgctggt ccgaatctat gtggtccggg    4620
ccacagacct gcacccggcc gacatcaatg caaagctga ccctatatt gccatcaagt    4680
taggcaagac cgacatccga gacaaggaga actacatctc caagcagctc aaccctgtgt    4740
ttgggaagtc ctttgacatt gaggcctcct tccccatgga gtccatgttg acagtggccg    4800
tgtacgactg ggatctggtg ggcactgatg acctcatcgg agaaaccaag attgacctgg    4860
aaaaccgctt ctacagcaag catcgcgcca cctgcggcat cgcacagacc tattccatac    4920
atggctacaa tatctggagg gaccccatga agcccagcca gatcctgaca cgcctctgta    4980
aagagggcaa agtggacggc ccccactttg gtccccatgg gagagtgagg gttgccaacc    5040
gtgtcttcac ggggccttca gaaatagagg atgagaatgg tcagaggaag cccacagatg    5100
agcacgtggc actgtctgct ctgagacact ggggaggacat cccccgggtg ggctgccgcc    5160
ttgtgccgga acacgtggag accaggccgc tgctcaaccc tgacaagcca ggcattgagc    5220
agggccgcct ggagctgtgg gtggacatgt tccccatgga catgccagcc cctgggacac    5280
ctctggatat atcccccagg aaacccaaga agtacgagct gcgggtcatc gtgtggaaca    5340
cagacgaggt ggtcctggaa gacgatgatt tcttcacggg agagaagtcc agtgacattt    5400
ttgtgagggg gtggctgaag gccagcagg aggacaaaca ggacacagat gtccactatc    5460
actccctcac gggggagggc aacttcaact ggagatacct cttcccttc gactacctag    5520
cggccgaaga gaagatcgtt atgtccaaaa aggagtctat gttctcctgg gatgagacgg    5580
agtacaagat ccctgcgcgg ctcacccctc agatctggga cgctgaccac ttctcggctg    5640
acgacttcct gggggctatc gagctggacc tgaaccggtt cccagggggc gctaagacag    5700
ccaagcagtg caccatggag atggccaccg gggaggtgga cgtacccctg gtttccatct    5760
ttaaacagaa acgtgtcaaa ggctggtggc ccctcctggc ccgcaatgag aatgatgagt    5820
ttgagctcac aggcaaagtg gaggcggagc tacacctact cacggcagag gaggcagaga    5880
agaaccctgt gggcctggct cgcaatgaac ctgatccct agaaaaaccc aaccggcctg    5940
acacggcatt cgtctggttc ctgaacccac tcaaatctat caagtacctc atctgcaccc    6000
ggtacaagtg gctgatcatc aagatcgtgc tggcgctgct ggggctgctc atgctggccc    6060
```

| | |
|---|---:|
| tcttccttta cagcctccca ggctacatgg tcaagaagct cctaggggcc tgaagtgtgc | 6120 |
| cccaccccag cccgctccag catccctcca ggggctgctg cgtattttgc cttccctcac | 6180 |
| ctggactctc tcccaactcc ctgaggagcc ctcccacgcc tgccagcctt gagcaagaca | 6240 |
| cctgcttgct ggacttcatc cccaccccac acccaaactg ttgcttgcct gatcttgtcc | 6300 |
| caggcctgcc tggggtttgg ggcacagttg gcctccaaaa ccagataccc tcttgtctaa | 6360 |
| agtaccaggt tcctctgccc aaccccaaga gtggtagtgg cccaaccctc cctgtgcttt | 6420 |
| ccaaatcttg tcttaaggca ccagtgaaat taaccaagaa acgcggagca atgcccaagg | 6480 |
| ctctgatgag taggaacacg tggaaagcac caggaatgcc agcagaggcg aggcggcaca | 6540 |
| cctctctgca gagcatccag gccgagcggc gggcagcggc cagctgcttc tgcgcatgct | 6600 |
| ctcctcttgg ctctgcttct ttctcacagt cacagtcact tcacagctta gccttgggct | 6660 |
| tcccatcact tccaggggtg cctctgcctt ggccagtgtg tgtcagctag tacacaagct | 6720 |
| ccaagtgtga atcaggtgta ctggccgtcc tgaagactga ctgccctgtc cttcctgccg | 6780 |
| acagccacac ccgagtgtac acttaaagcg gtgcccttct gcctcgtgtg gcctgctggc | 6840 |
| tgctgttcct tcttgagtg tgattttttt tttctctccc tcaataaaat aaatcaaact | 6900 |
| ctgagac | 6907 |

<210> SEQ ID NO 18
<211> LENGTH: 6862
<212> TYPE: DNA
<213> ORGANISM: Mus musculus

<400> SEQUENCE: 18

| | |
|---|---:|
| ttggttgcct tggtctctgt gggcagcagc aggaggaggc ggcagcagcc agagaagagg | 60 |
| gaggcgtgtg agccacactc caccagcgag cttcttcccg ctgctctgga actgcccagg | 120 |
| ctctccccac cagcatggcc ctgattgttc acctcaagac tgtctcagag ctccgaggca | 180 |
| aaggtgaccg gattgccaaa gtcactttcc gagggcagtc tttctactcc cgggtcctgg | 240 |
| agaactgcga gggtgtggct gactttgatg agacgttccg gtggccagtg ccagcagca | 300 |
| tcgaccggaa tgaagtgttg gagattcaga ttttcaacta cagcaaagtc ttcagcaaca | 360 |
| agctgatagg gaccttctgc atggtgctgc agaaagtggt ggaggagaat cgggtagagg | 420 |
| tgaccgacac gctgatggat gacagcaatg ctatcatcaa gaccagcctg agcatggagg | 480 |
| tccggtatca ggccacagat ggcactgtgg gcccctggga tgatggagac ttcctgggag | 540 |
| atgaatccct ccaggaggag aaggacagcc aggagacaga tgggctgcta cctggttccc | 600 |
| gacccagcac ccggatatct ggcgagaaga gctttcgcag agcgggaagg agtgtgttct | 660 |
| cggccatgaa actcggcaaa actcggtccc acaaagagga gccccaaaga caagatgagc | 720 |
| cagcagtgct ggagatggag gacctggacc acctagccat tcagctgggg gatgggctgg | 780 |
| atcctgactc cgtgtctcta gcctcggtca ccgctctcac cagcaatgtc tccaacaaac | 840 |
| ggtctaagcc agatattaag atggagccca gtgctggaag gcccatggat taccaggtca | 900 |
| gcatcacagt gattgaggct cggcagctgg tgggcttgaa catggaccct gtggtgtgtg | 960 |
| tggaggtggg tgatgacaag aaatacacgt caatgaagga gtccacaaac tgcccttact | 1020 |
| acaacgagta ctttgtcttc gacttccatg tctctcctga tgtcatgttt gacaagatca | 1080 |
| tcaagatctc ggttatccat tctaagaacc tgcttcggag cggcacctg gtgggttcct | 1140 |
| tcaaaatgga tgtggggact gtgtattccc agcctgaaca ccagttccat cacaaatggg | 1200 |
| ccatcctgtc agacccgat gacatctctg ctgggttgaa gggttatgta aagtgtgatg | 1260 |

```
tcgctgtggt gggcaaggga gacaacatca agacacccca caaggccaac gagacggatg    1320
aggacgacat tgaagggaac ttgctgctcc ccgagggcgt gcccccgaa cggcagtggg     1380 cacggttcta tgtgaaaatt taccgagcag agggactgcc ccggatgaac acaagcctca    1440
tggccaacgt gaagaaggcg ttcatcggtg agaacaagga cctcgtcgac ccctatgtgc    1500
aagtcttctt tgctggacaa aagggcaaaa catcagtgca gaagagcagc tatgagccgc    1560 tatgaatga gcaggtcgtc ttcacagact tgttcccccc actctgcaaa cgcatgaagg     1620
tgcagatccg ggactctgac aaggtcaatg atgtggccat cggcacccac ttcatcgacc    1680
tgcgcaagat ttccaacgat ggagacaaag gcttcctgcc tacccctcggt ccagcctggg   1740 tgaacatgta cggctccacg cgcaactaca cactgctgga cgagcaccag gacttgaatg    1800
aaggcctggg ggagggtgtg tccttccggg cccgcctcat gttgggacta gctgtggaga    1860
tcctggacac ctccaaccca gagctcacca gctccacgga ggtgcaggtg gagcaggcca    1920
cgcctgtctc ggagagctgc acaggggaaa tggaagaatt ttttctattt ggagccttct    1980
tggaagcctc aatgattgac cggaaaaatg gggacaagcc aattacccttt gaggtgacca    2040 taggaaacta cggcaatgaa gtcgatggta tgtcccggcc cctgaggcct cggccccgga   2100
aagagcctgg ggatgaagaa gaggtagacc tgattcagaa ctccagtgac gatgaaggtg    2160
acgaagccgg ggacctggcc tcggtgtcct ccaccccacc tatgcggccc cagatcacgg    2220
acaggaacta tttccacctg ccctacctgg agcgcaagcc ctgcatctat atcaagagct    2280
ggtggcctga ccagaggcgg cgcctctaca atgccaacat catggatcac attgctgaca    2340
agctggaaga aggcctgaat gatgtacagg agatgatcaa aacggagaag tcctacccgg    2400
agcgccgcct gcggggtgtg ctagaggaac tcagctgtgg ctgccaccgc ttcctctccc    2460
tctcggacaa ggaccagggc cgctcgtccc gcaccaggc ggatcgagag cgtcttaagt     2520
cctgtatgag ggagttggag agcatggac agcaggccaa gagcctgagg gctcaggtga     2580
agcggcacac tgttcgggac aagctgaggt catgccagaa cttctgcag aagctacgct     2640 tcctggcgga tgagccccag cacagcattc ctgatgtgtt catttggatg atgagcaaca    2700
acaaacgtat cgcctatgcc cgcgtgcctt ccaaagacct gctcttctcc atcgtggagg    2760
aggaactggg caaggactgc gccaaagtca gaccctctt cctgaagctg ccagggaaga     2820
ggggcttcgg ctcggcaggc tggacagtac aggccaagct ggagctctac ctgtggctgg    2880
gcctcagcaa gcagcgaaag gacttcctgt gtggtctgcc ctgtggcttc gaggaggtca    2940
aggcagccca aggcctgggc ctgcattcct ttccgcccat cagcctagtc tacaccaaga    3000
agcaagcctt ccagctccga gcacacatgt atcaggcccg aagcctctttt gctgctgaca    3060 gcagtgggct ctctgatccc tttgcccgtg tcttcttcat caaccagagc caatgcactg    3120
aggttctaaa cgagacactg tgtccacct gggaccagat gctggtattt gacaacctgg     3180
agctgtacgg tgaagctcac gagttacgag atgatccccc catcattgtc attgaaatct    3240
acgaccagga cagcatgggc aaagccgact tcatgggccg gaccttcgcc aagcccctgg    3300
tgaagatggc agatgaagca tactgcccac ctcgcttccc gccgcagctt gagtactacc    3360
agatctaccg aggcagtgcc actgccggag acctactgg tgccttcgag ctgctgcaga    3420
ttgggccatc agggaaggct gacctgccac ccatcaatgg cccagtggac atggacagag    3480
ggcccatcat gcctgtgccc gtgggaatcc ggccagtgct cagcaagtac cgagtggagg    3540
tgctgttctg gggcctgagg gacctaaaga gggtgaacct ggcccaggtg gaccgaccac    3600
```

```
gggtggacat cgagtgtgca ggaaagggg tacaatcctc cctgattcac aattataaga    3660
agaaccccaa cttcaacacg ctggtcaagt ggtttgaagt ggacctcccg gagaatgagc    3720
tcctgcaccc acccttgaac atccgagtgg tagattgccg ggcctttgga cgatacaccc    3780
tggtgggttc ccacgcagtc agctcactga ggcgcttcat ctaccgacct ccagaccgct    3840
cagcccccaa ctggaacacc acaggggagg ttgtagtaag catggagcct gaggagccag    3900
ttaagaagct ggagaccatg gtgaaactgg atgcgacttc tgatgctgtg gtcaaggtgg    3960
atgtggctga agatgagaag gaaaggaaga agaagaaaaa gaaaggcccg tcagaggagc    4020
cagaggagga agagcccgat gagagcatgc tggattggtg gtccaagtac ttcgcctcca    4080
tcgacacaat gaaggagcaa cttcgacaac atgagacctc tggaactgac ttggaagaga    4140
aggaagagat ggaaagcgct gagggcctga agggaccaat gagagcaag gagaagtcca    4200
gagctgcaaa ggaggagaaa aagaagaaaa accagagccc tggccctggc cagggatcgg    4260
aggctcctga agaagaaa gccaagatcg atgagcttaa ggtgtacccc aaggagctgg    4320
aatcggagtt tgacagcttt gaggactggc tgcacacctt caacctgttg aggggcaaga    4380
cgggagatga tgaggatggc tccacagagg aggagcgcat agtaggccga ttcaagggct    4440
ccctctgtgt gtacaaagtg ccactcccag aagatgtatc tcgagaagct ggctatgatc    4500
ccacctatgg aatgttccag ggcatcccaa gcaatgaccc catcaatgtg ctggtccgaa    4560
tctatgtggt ccgggccaca gacctgcacc cggccgacat caatggcaaa gctgacccct    4620
atattgccat caagttaggc aagaccgaca tccgagacaa ggagaactac atctccaagc    4680
agctcaaccc tgtgtttggg aagtcctttg acattgaggc ctccttcccc atggagtcca    4740
tgttgacagt ggccgtgtac gactgggatc tggtgggcac tgatgacctc atcggagaaa    4800
ccaagattga cctggaaac cgcttctaca gcaagcatcg cgccacctgc ggcatcgcac    4860
agacctattc catacatggc tacaatatct ggagggaccc catgaagccc agccagatcc    4920
tgacacgcct ctgtaaagag ggcaaagtgg acggcccca cttggtccc catgggagag    4980
tgagggttgc caaccgtgtc ttcacggggc cttcagaaat agaggatgag aatggtcaga    5040
ggaagcccac agatgagcac gtggcactgt ctgctctgag acactgggag gacatccccc    5100
gggtgggctg ccgccttgtg ccggaacacg tggagaccag gccgctgctc aaccctgaca    5160
agccaggcat tgagcagggc cgcctggagc tgtgggtgga catgttcccc atggacatgc    5220
cagcccctgg gacacctctg gatatatccc ccaggaaacc caagaagtac gagctgcggg    5280
tcatcgtgtg gaacacagac gaggtggtcc tggaagacga tgatttcttc acggagaga    5340
agtccagtga cattttgtg aggggtggc tgaagggcca gcaggaggac aaacaggaca    5400
cagatgtcca ctatcactcc ctcacggggg agggcaactt caactggaga tacctcttcc    5460
ccttcgacta cctagcggcc gaagagaaga tcgttatgtc caaaaaggag tctatgttct    5520
cctgggatga gacggagtac aagatccctg cgcggctcac cctgcagatc tgggacgctg    5580
accacttctc ggctgacgac ttcctgggg ctatcgagct ggacctgaac cggttcccga    5640
ggggcgctaa gacagccaag cagtgcacca tggagatggc caccggggag gtggacgtac    5700
ccctggtttc catctttaaa cagaaacgtg tcaaaggctg gtggcccctc ctggcccgca    5760
atgagaatga tgagtttgag ctcacaggca agtggaggc ggagctacac ctactcacgg    5820
cagaggaggc agagaagaac cctgtggcc tggctcgcaa tgaacctgat cccctagaaa    5880
aacccaaccg gcctgacacg gcattcgtct ggttcctgaa cccactcaaa tctatcaagt    5940
acctcatctg cacccggtac aagtggctga tcatcaagat cgtgctggcg ctgctggggc    6000
```

```
tgctcatgct ggccctcttc ctttacagcc tcccaggcta catggtcaag aagctcctag    6060
gggcctgaag tgtgcccac cccagcccgc tccagcatcc ctccaggggc tgctgcgtat     6120
tttgccttcc ctcacctgga ctctctccca actccctgag gagccctccc acgcctgcca    6180
gccttgagca agacacctgc ttgctggact tcatccccac cccacaccca aactgttgct    6240
tgcctgatct tgtcccaggc ctgcctgggg tttggggcac agttggcctc caaaaccaga    6300
taccctcttg tctaaagtac caggttcctc tgcccaaccc caagagtggt agtgcccaa     6360 ccctccctgt gctttccaaa tcttgtctta aggcaccagt gaaattaacc aagaaacgcg    6420
gagcaatgcc caaggctctg atgagtagga acacgtggaa agcaccagga atgccagcag    6480
aggcgaggcg gcacacctct ctgcagagca tccaggccga gcggcgggca gcggccagct    6540
gcttctgcgc atgctctcct cttggctctg cttctttctc acagtcacag tcacttcaca    6600
gcttagcctt gggcttccca tcacttccag gggtgcctct gccttggcca gtgtgtgtca    6660
gctagtacac aagctccaag tgtgaatcag gtgtactggc cgtcctgaag actgactgcc    6720
ctgtccttcc tgccgacagc cacacccgag tgtacactta aagcggtgcc cttctgcctc    6780
tgtgggcctg ctggctgctg ttcctttctt gagtgtgatt ttttttttct ctccctcaat    6840
aaaataaatc aaactctgag ac                                            6862

<210> SEQ ID NO 19
<211> LENGTH: 77
<212> TYPE: DNA
<213> ORGANISM: Artificial Sequence
<220> FEATURE:
<223> OTHER INFORMATION: Synthetic Construct

<400> SEQUENCE: 19
gggattttgc cgatttcggc ctattggtta aaaaatgagc tgatttaaca aaaatttaac    60
gcgaatttta acaaaat                                                   77

<210> SEQ ID NO 20
<211> LENGTH: 82
<212> TYPE: DNA
<213> ORGANISM: Artificial Sequence
<220> FEATURE:
<223> OTHER INFORMATION: Synthetic Construct

<400> SEQUENCE: 20
gtaagtatca aggttacaag acaggtttaa ggagaccaat agaaactggg cttgtcgaga    60
cagagaagac tcttgcgttt ct                                             82

<210> SEQ ID NO 21
<211> LENGTH: 51
<212> TYPE: DNA
<213> ORGANISM: Artificial Sequence
<220> FEATURE:
<223> OTHER INFORMATION: Synthetic Construct

<400> SEQUENCE: 21
gataggcacc tattggtctt actgacatcc actttgcctt tctctccaca g             51

<210> SEQ ID NO 22
<211> LENGTH: 48
<212> TYPE: DNA
<213> ORGANISM: Artificial Sequence
<220> FEATURE:
<223> OTHER INFORMATION: Synthetic Construct
```

```
<400> SEQUENCE: 22
gcctgcaaga actggttcag cagcctgagc cacttcgtga tccacctg                48

<210> SEQ ID NO 23
<211> LENGTH: 548
<212> TYPE: DNA
<213> ORGANISM: Artificial Sequence
<220> FEATURE:
<223> OTHER INFORMATION: Synthetic Construct

<400> SEQUENCE: 23
gatccaatca acctctggat tacaaaattt gtgaaagatt gactggtatt cttaactatg    60
ttgctccttt tacgctatgt ggatacgctg ctttaatgcc tttgtatcat gctattgctt   120
cccgtatggc tttcattttc tcctccttgt ataaatcctg gttgctgtct ctttatgagg   180
agttgtggcc cgttgtcagg caacgtggcg tggtgtgcac tgtgtttgct gacgcaaccc   240
ccactggttg gggcattgcc accacctgtc agctcctttc cggactttc gctttccccc    300 tccctattgc cacggcggaa ctcatcgccg cctgccttgc ccgctgctgg acaggggctc   360
ggctgttggg cactgacaat tccgtggtgt tgtcggggaa atcatcgtcc tttccttggc   420
tgctcgcctg tgttgccacc tggattctgc gcgggacgtc cttctgctac gtcccttcgg   480
ccctcaatcc agcggacctt ccttcccgcg gcctgctgcc ggctctgcgg cctcttccgc   540
gtcttcga                                                            548

<210> SEQ ID NO 24
<211> LENGTH: 454
<212> TYPE: DNA
<213> ORGANISM: Mus musculus

<400> SEQUENCE: 24
ctgcagctca gcctactact tgctttccag gctgttccta gttcccatgt cagctgcttg    60
tgctttccag agacaaaaca ggaataatag atgtcattaa atatacattg gccccaggc    120 ggtcaatgtg gcagcctgag cctcctttcc atctctgtgg aggcagacat aggacccca    180 acaaacagca tgcaggttgg gagccagcca caggacccag gtaaggggcc ctgggtcctt   240
aagcttctgc cactggctcc ggcattgcag agagaagaga aggggcggca gagctgaacc   300
ttagccttgc cttcctgggt acccttctga gcctcactgt cttctgtgag atgggcaaag   360
tgcgggtgtg actccttggc aacggtgtta ccagggca ggtaaagttg tagttatttg    420
tggggtacac caggactgtt aaaggtgtaa ctat                               454

<210> SEQ ID NO 25
<211> LENGTH: 1157
<212> TYPE: DNA
<213> ORGANISM: Mus musculus

<400> SEQUENCE: 25
ggtctcaccc agcattttca cttctaataa gttcaaatgt gatacggcac ctttctaaaa    60
attagttttc agggaaatag ggttcaaaac tggtagtggt agggtccatt ctcacgaccc   120
ccaggcctgc taaccctgac caagctacct attacttacc ctcctctttc tcctcctcct   180
cttctccctt ctcctgcttc ccctcttcct tctccctccc ttcctctccc tcctcccct    240 ccttggctgt gatcagatcc agagcctgaa tgagcctcct gaccccacac ccccactagc   300
atgggcctgc aagtgcccag aagtccctcc tgcctcctaa actgcccagc cgatccatta   360
gctcttcctt cttcccagtg aaagaagcag gcacagcctg tccctcccgt tctacagaaa   420
```

-continued

```
ggaagctaca gcacagggag ggccaaaggc cttcctggga ctagacagtt gatcaacagc      480
aggactggag agctgggctc cattttttgtt ccttggtgcc ctgcccctcc ccatgacctg      540
cagagacatt cagcctgcca ggctttatga ggtgggagct gggctctccc tgatgtatta      600
ttcagctccc tggagttggc cagctcctgt tacactggcc acagccctgg gcatccgctt      660
ctcacttcta gtttcccctc caaggtaatg tggtgggtca tgatcattct atcctggctt      720
cagggaccta actccacttt ggggccattc gaggggtcta gggtagatga tgtccccctg      780
tggggattaa tgtcctgctc tgtaaaactg agctagctga gatccaggag ggcttggcca      840
gagacagcaa gttgttgcca tggtgacttt aaagccaggt tgctgcccca gcacaggcct      900
cccagtctac cctcactaga aaacaacacc caggcacttt ccaccacctc tcaaaggtga      960
aacccaaggc tggtctagag aatgaattat ggatcctcgc tgtccgtgcc acccagctag     1020
tcccagcggc tcagacactg aggagagact gtaggttcag ctacaagcaa aaagacctag     1080
ctggtctcca agcagtgtct ccaagtccct gaacctgtga cacctgcccc aggcatcatc     1140
aggcacagag ggccacc                                                    1157
```

<210> SEQ ID NO 26
<211> LENGTH: 76
<212> TYPE: DNA
<213> ORGANISM: Mus musculus

<400> SEQUENCE: 26

```
cccatgtcag ctgcttgtgc tttccagaga caaaacagga ataatagatg tcattaaata      60
tacattgggc cccagg                                                       76
```

<210> SEQ ID NO 27
<211> LENGTH: 95
<212> TYPE: DNA
<213> ORGANISM: Mus musculus

<400> SEQUENCE: 27

```
agcctgagcc tcctttccat ctctgtggag gcagacatag gaccccccaac aaacagcatg      60 caggttggga gccagccaca ggacccaggt aaggg                                  95
```

<210> SEQ ID NO 28
<211> LENGTH: 171
<212> TYPE: DNA
<213> ORGANISM: Artificial Sequence
<220> FEATURE:
<223> OTHER INFORMATION: Synthetic Construct

<400> SEQUENCE: 28

```
cccatgtcag ctgcttgtgc tttccagaga caaaacagga ataatagatg tcattaaata      60
tacattgggc cccaggagcc tgagcctcct ttccatctct gtggaggcag acataggacc     120
cccaacaaac agcatgcagg ttgggagcca gccacaggac ccaggtaagg g              171
```

<210> SEQ ID NO 29
<211> LENGTH: 171
<212> TYPE: DNA
<213> ORGANISM: Artificial Sequence
<220> FEATURE:
<223> OTHER INFORMATION: Synthetic Construct

<400> SEQUENCE: 29

```
agcctgagcc tcctttccat ctctgtggag gcagacatag gaccccccaac aaacagcatg      60
```

```
caggttggga gccagccaca ggacccaggt aagggcccat gtcagctgct tgtgctttcc         120
agagacaaaa caggaataat agatgtcatt aaatatacat tgggccccag g                  171

<210> SEQ ID NO 30
<211> LENGTH: 184
<212> TYPE: DNA
<213> ORGANISM: Mus musculus

<400> SEQUENCE: 30
cccatgtcag ctgcttgtgc tttccagaga caaaacagga ataatagatg tcattaaata         60
tacattgggc ccaggcggt caatgtggca gcctgagcct cctttccatc tctgtggagg          120
cagacatagg accccaaca aacagcatgc aggttgggag ccagccacag acccaggta          180 aggg                                                                      184

<210> SEQ ID NO 31
<211> LENGTH: 82
<212> TYPE: DNA
<213> ORGANISM: Mus musculus

<400> SEQUENCE: 31
tgaggtggga gctgggctct ccctgatgta ttattcagct ccctggagtt ggccagctcc         60
tgttacactg gccacagccc tg                                                  82

<210> SEQ ID NO 32
<211> LENGTH: 106
<212> TYPE: DNA
<213> ORGANISM: Mus musculus

<400> SEQUENCE: 32
cacaggcctc ccagtctacc ctcactagaa acaacaccc aggcactttc caccacctct         60
caaaggtgaa acccaaggct ggtctagaga atgaattatg gatcct                       106

<210> SEQ ID NO 33
<211> LENGTH: 188
<212> TYPE: DNA
<213> ORGANISM: Artificial Sequence
<220> FEATURE:
<223> OTHER INFORMATION: Synthetic Construct

<400> SEQUENCE: 33
tgaggtggga gctgggctct ccctgatgta ttattcagct ccctggagtt ggccagctcc         60
tgttacactg gccacagccc tgcacaggcc tcccagtcta ccctcactag aaaacaacac        120
ccaggcactt tccaccacct ctcaaaggtg aaacccaagg ctggtctaga gaatgaatta        180
tggatcct                                                                  188

<210> SEQ ID NO 34
<211> LENGTH: 188
<212> TYPE: DNA
<213> ORGANISM: Artificial Sequence
<220> FEATURE:
<223> OTHER INFORMATION: Synthetic Construct

<400> SEQUENCE: 34
cacaggcctc ccagtctacc ctcactagaa acaacaccc aggcactttc caccacctct         60
caaaggtgaa acccaaggct ggtctagaga atgaattatg gatccttgag gtgggagctg        120
ggctctccct gatgtattat tcagctccct ggagttggcc agctcctgtt acactggcca        180
cagccctg                                                                  188
```

<210> SEQ ID NO 35
<211> LENGTH: 430
<212> TYPE: DNA
<213> ORGANISM: Mus musculus

<400> SEQUENCE: 35

| | | | | |
|---|---|---|---|---|
| tgaggtggga gctgggctct ccctgatgta ttattcagct ccctggagtt ggccagctcc | 60 |
| tgttacactg gccacagccc tgggcatccg cttctcactt ctagtttccc ctccaaggta | 120 |
| atgtggtggg tcatgatcat tctatcctgg cttcagggac ctgactccac tttggggcca | 180 |
| ttcgaggggt ctagggtaga tgatgtcccc ctgtggggat taatgtcctg ctctgtaaaa | 240 |
| ctgagctagc tgagatccag gagggcttgg ccagagacag caagttgttg ccatggtgac | 300 |
| tttaaagcca ggttgctgcc ccagcacagg cctcccagtc taccctcact agaaaacaac | 360 |
| acccaggcac tttccaccac ctctcaaagg tgaaacccaa ggctggtcta gagaatgaat | 420 |
| tatggatcct | 430 |

<210> SEQ ID NO 36
<211> LENGTH: 1611
<212> TYPE: DNA
<213> ORGANISM: Artificial Sequence
<220> FEATURE:
<223> OTHER INFORMATION: Synthetic Construct

<400> SEQUENCE: 36

| | |
|---|---|
| ctgcagctca gcctactact tgcttttcag gctgttccta gttcccatgt cagctgcttg | 60 |
| tgcttttcag agacaaaaca ggaataatag atgtcattaa atatacattg gccccaggc | 120 |
| ggtcaatgtg gcagcctgag cctcctttcc atctctgtgg aggcagacat aggaccccca | 180 |
| acaaacagca tgcaggttgg gagccagcca caggacccag gtaaggggcc ctgggtcctt | 240 |
| aagcttctgc cactggctcc ggcattgcag agagaagaga aggggcggca gagctgaacc | 300 |
| ttagccttgc cttcctgggt acccttctga gcctcactgt cttctgtgag atgggcaaag | 360 |
| tgcgggtgtg actccttggc aacggtgtta caccagggca ggtaaagttg tagttatttg | 420 |
| tggggtacac caggactgtt aaaggtgtaa ctatggtctc acccagcatt ttcacttcta | 480 |
| ataagttcaa atgtgatacg gcacctttct aaaaattagt tttcaggaa atagggttca | 540 |
| aaactggtag tggtagggtc cattctcacg accccaggc ctgctaaccc tgaccaagct | 600 |
| acctattact taccctcctc tttctcctcc tcctcttct ccttctcctg cttcccctct | 660 |
| tccttctccc tcccttcctc tccctcctcc ccctccttgg ctgtgatcag atccagagcc | 720 |
| tgaatgagcc tcctgacccc acaccccac tagcatgggc ctgcaagtgc ccagaagtcc | 780 |
| ctcctgcctc ctaaactgcc cagccgatcc attagctctt ccttcttccc agtgaaagaa | 840 |
| gcaggcacag cctgtccctc ccgttctaca gaaaggaagc tacagcacag ggagggccaa | 900 |
| aggccttcct gggactagac agttgatcaa cagcaggact ggagagctgg gctccatttt | 960 |
| tgttccttgg tgccctgccc ctccccatga cctgcagaga cattcagcct gccaggcttt | 1020 |
| atgaggtggg agctgggctc tccctgatgt attattcagc tccctggagt tggccagctc | 1080 |
| ctgttacact ggccacagcc ctgggcatcc gcttctcact tctagtttcc cctccaaggt | 1140 |
| aatgtggtgg gtcatgatca ttctatcctg gcttcaggga cctgactcca ctttggggcc | 1200 |
| attcgagggg tctagggtag atgatgtccc cctgtgggga ttaatgtcct gctctgtaaa | 1260 |
| actgagctag ctgagatcca ggagggcttg gccagagaca gcaagttgtt gccatggtga | 1320 |

| | |
|---|---|
| ctttaaagcc aggttgctgc cccagcacag gcctcccagt ctaccctcac tagaaaacaa | 1380 |
| cacccaggca ctttccacca cctctcaaag gtgaaaccca aggctggtct agagaatgaa | 1440 |
| ttatggatcc tcgctgtccg tgccacccag ctagtcccag cggctcagac actgaggaga | 1500 |
| gactgtaggt tcagctacaa gcaaaaagac ctagctggtc tccaagcagt gtctccaagt | 1560 |
| ccctgaacct gtgacacctg ccccaggcat catcaggcac agagggccac c | 1611 |

<210> SEQ ID NO 37
<211> LENGTH: 1611
<212> TYPE: DNA
<213> ORGANISM: Artificial Sequence
<220> FEATURE:
<223> OTHER INFORMATION: Synthetic Construct

<400> SEQUENCE: 37

| | |
|---|---|
| ggtctcaccc agcattttca cttctaataa gttcaaatgt gatacggcac cttttctaaaa | 60 |
| attagttttc agggaaatag ggttcaaaac tggtagtggt agggtccatt ctcacgaccc | 120 |
| ccaggcctgc taaccctgac caagctacct attacttacc ctcctctttc tcctcctcct | 180 |
| ctttctcctt ctcctgcttc ccctcttcct tctccctccc ttcctctccc tcctccccct | 240 |
| ccttggctgt gatcagatcc agagcctgaa tgagcctcct gaccccacac ccccactagc | 300 |
| atgggcctgc aagtgcccag aagtccctcc tgcctcctaa actgcccagc cgatccatta | 360 |
| gctcttcctt cttcccagtg aaagaagcag gcacagcctg tccctcccgt tctacagaaa | 420 |
| ggaagctaca gcacagggag ggccaaaggc cttcctggga ctagacagtt gatcaacagc | 480 |
| aggactggag agctgggctc cattttttgtt ccttggtgcc ctgcccctcc ccatgacctg | 540 |
| cagagacatt cagcctgcca ggctttatga ggtgggagct gggctctccc tgatgtatta | 600 |
| ttcagctccc tggagttggc cagctcctgt tacactggcc acagccctgg gcatccgctt | 660 |
| ctcacttcta gtttccccctc caaggtaatg tggtgggtca tgatcattct atcctggctt | 720 |
| cagggacctg actccacttt ggggccattc gagggtcta gggtagatga tgtcccctg | 780 |
| tggggattaa tgtcctgctc tgtaaaactg agctagctga gatccaggag ggcttggcca | 840 |
| gagacagcaa gttgttgcca tggtgacttt aaagccaggt tgctgcccca gcacaggcct | 900 |
| cccagtctac cctcactaga aaacaacacc caggcacttt ccaccacctc tcaaaggtga | 960 |
| aacccaaggc tggtctagag aatgaattat ggatcctcgc tgtccgtgcc acccagctag | 1020 |
| tcccagcggc tcagacactg aggagagact gtaggttcag ctacaagcaa aaagacctag | 1080 |
| ctggtctcca gcagtgtct ccaagtccct gaacctgtga cacctgcccc aggcatcatc | 1140 |
| aggcacagag ggccaccctg cagctcagcc tactacttgc tttccaggct gttcctagtt | 1200 |
| cccatgtcag ctgcttgtgc tttcagaga caaaacagga ataatagatg tcattaaata | 1260 |
| tacattgggc cccaggcggt caatgtggca gcctgagcct cctttccatc tctgtggagg | 1320 |
| cagacatagg accccaaca aacagcatgc aggttgggag ccagccacag gacccaggta | 1380 |
| aggggccctg ggtccttaag cttctgccac tggctccggc attgcagaga gaagagaagg | 1440 |
| ggcggcagag ctgaaccttag gccttgcctt cctgggtacc cttctgagcc tcactgtctt | 1500 |
| ctgtgagatg ggcaaagtgc gggtgtgact ccttggcaac ggtgttacac cagggcaggt | 1560 |
| aaagttgtag ttatttgtgg ggtacaccag gactgttaaa ggtgtaacta t | 1611 |

<210> SEQ ID NO 38
<211> LENGTH: 965
<212> TYPE: DNA
<213> ORGANISM: Artificial Sequence

```
<220> FEATURE:
<223> OTHER INFORMATION: Synthetic Construct

<400> SEQUENCE: 38
ctgcagctca gcctactact tgctttccag gctgttccta gttcccatgt cagctgcttg      60
tgctttccag agacaaaaca ggaataatag atgtcattaa atatacattg ggccccaggc     120
ggtcaatgtg gcagcctgag cctcctttcc atctctgtgg aggcagacat aggacccca     180
acaaacagca tgcaggttgg agccagcca caggacccag gtaaggggcc ctgggtcctt     240
aagcttctgc cactggctcc ggcattgcag agagaagaga aggggcggca gactggagag     300
ctgggctcca tttttgttcc ttggtgccct gcccctcccc atgacctgca gagacattca     360
gcctgccagg ctttatgagg tgggagctgg gctctccctg atgtattatt cagctccctg     420
gagttggcca gctcctgtta cactggccac agccctgggc atccgcttct cacttctagt     480
ttcccctcca aggtaatgtg gtgggtcatg atcattctat cctggcttca gggacctgac     540
tccactttgg ggccattcga ggggtctagg gtagatgatg tccccctgtg gggattaatg     600
tcctgctctg taaaactgag ctagctgaga tccaggaggg cttggccaga gacagcaagt     660
tgttgccatg gtgactttaa agccaggttg ctgccccagc acaggcctcc cagtctaccc     720
tcactagaaa acaacaccca ggcactttcc accacctctc aaaggtgaaa cccaaggctg     780
gtctagagaa tgaattatgg atcctcgctg tccgtgccac ccagctagtc ccagcggctc     840
agacactgag gagagactgt aggttcagct acaagcaaaa agacctagct ggtctccaag     900
cagtgtctcc aagtccctga acctgtgaca cctgccccag gcatcatcag gcacagaggg     960
ccacc                                                                  965

<210> SEQ ID NO 39
<211> LENGTH: 520
<212> TYPE: DNA
<213> ORGANISM: Artificial Sequence
<220> FEATURE:
<223> OTHER INFORMATION: Synthetic Construct

<400> SEQUENCE: 39
ctgcagctca gcctactact tgctttccag gctgttccta gttcccatgt cagctgcttg      60
tgctttccag agacaaaaca ggaataatag atgtcattaa atatacattg ggccccaggc     120
ggtcaatgtg gcagcctgag cctcctttcc atctctgtgg aggcagacat aggacccca     180
acaaacagca tgcaggttgg agccagcca caggacccag gtaaggggcc ctgggtcctt     240
tttatgaggt gggagctggg ctctccctga tgtattattc agctccctgg agttggccag     300
ctcctgttac actggccaca gccctgggca tccgctgcca tggtgacttt aaagccaggt     360
tgctgcccca gcacaggcct cccagtctac cctcactaga aaacaacacc caggcacttt     420
ccaccacctc tcaaaggtga aacccaaggc tggtctagag aatgaattat ggatcctcgc     480
tgtccgtgcc acccagctag tcccagcggc tcagacactg                            520

<210> SEQ ID NO 40
<211> LENGTH: 235
<212> TYPE: DNA
<213> ORGANISM: Homo sapiens

<400> SEQUENCE: 40
gtatgccttt tgagatggat gcagcaggtt ctgtgaggct gccaggaggg gtagagttcc      60
cggggggcctc gggccccgct ggagtgtgga gcaggcccat gctcagctct ccaggctgtt     120
```
cgtggctccc ctgtcagctg ctcactcctt tccagagaca aaacaggaat aatagacatc    180
attaaatata catagggccc caggcggtcg gcgtggtggg ctgggcctcc cttcc    235

<210> SEQ ID NO 41
<211> LENGTH: 688
<212> TYPE: DNA
<213> ORGANISM: Homo sapiens

<400> SEQUENCE: 41
tgccctgcct tctgagccgg cagcctggct ccccacccca tgtattattc agctcctgag    60
agccagccag ctcctgttac actgaccgca gccagcacc tgctctgccc attccctcc    120 tcccttgcct aggacctaga gggttcaaag ttctcctcca agatgacttg gtgggctttg    180
gccatcccac cctaggcccc acttctggcc cagtgcaggt gtgctggtga tttagggcag    240
gtggcattcc atctctgtgg ctcaatgtct tcctctgtga agccgaagtg acccaagggc    300
tcccttcatg gggttgagcc agctgtggcc caggagggc ctaaccagga tgagcactga    360
tgttgccatg acgactccga ggccagaatg tctcccccag cacaggcctc ataggcaggc    420
ttccccatcc tggtaaacaa cacccacaca ctttctacta ctgctctagg gtgaaaccca    480
aggcgctcta gaggagatga attatggatc cgccctcccg gaatcctggc tcggccctcc    540
ccacgccacc cagggccagt cgggtctgct cacagcccga ggaggccgcg tgtccagccg    600
cgggcaagag acagagcagg tccctgtgtc tccaagtccc tgagcccgtg acaccggccc    660
caggccctgt agagagcagg cagccacc    688

<210> SEQ ID NO 42
<211> LENGTH: 77
<212> TYPE: DNA
<213> ORGANISM: Homo sapiens

<400> SEQUENCE: 42
cccctgtcag ctgctcactc ctttccagag acaaaacagg aataatagac atcattaaat    60
atacataggg ccccagg    77

<210> SEQ ID NO 43
<211> LENGTH: 82
<212> TYPE: DNA
<213> ORGANISM: Homo sapiens

<400> SEQUENCE: 43
tgagccggca gcctggctcc caccccatg tattattcag ctcctgagag ccagccagct    60
cctgttacac tgaccgcagc cc    82

<210> SEQ ID NO 44
<211> LENGTH: 111
<212> TYPE: DNA
<213> ORGANISM: Homo sapiens

<400> SEQUENCE: 44
cacaggcctc ataggcaggc ttccccatcc tggtaaacaa cacccacaca ctttctacta    60
ctgctctagg gtgaaaccca aggcgctcta gaggagatga attatggatc c    111

<210> SEQ ID NO 45
<211> LENGTH: 193
<212> TYPE: DNA
<213> ORGANISM: Artificial Sequence
<220> FEATURE:
<223> OTHER INFORMATION: Synthetic Construct

<400> SEQUENCE: 45

```
tgagccggca gcctggctcc caccccatg tattattcag ctcctgagag ccagccagct    60
cctgttacac tgaccgcagc cccacaggcc tcataggcag gcttccccat cctggtaaac   120
aacacccaca cactttctac tactgctcta gggtgaaacc caaggcgctc tagaggagat   180
gaattatgga tcc                                                      193
```

<210> SEQ ID NO 46
<211> LENGTH: 193
<212> TYPE: DNA
<213> ORGANISM: Artificial Sequence
<220> FEATURE:
<223> OTHER INFORMATION: Synthetic Construct

<400> SEQUENCE: 46

```
cacaggcctc ataggcaggc ttccccatcc tggtaaacaa cacccacaca ctttctacta    60
ctgctctagg gtgaaaccca aggcgctcta gaggagatga attatggatc ctgagccggc   120
agcctggctc cccaccccat gtattattca gctcctgaga ccagccagc tcctgttaca   180
ctgaccgcag ccc                                                      193
```

<210> SEQ ID NO 47
<211> LENGTH: 499
<212> TYPE: DNA
<213> ORGANISM: Homo sapiens

<400> SEQUENCE: 47

```
tgagccggca gcctggctcc caccccatg tattattcag ctcctgagag ccagccagct    60
cctgttacac tgaccgcagc ccagcacctg ctctgcccat tcccctcctc ccttgcctag   120
gacctagagg gttcaaagtt ctcctccaag atgacttggt gggctttggc catcccaccc   180
taggccccac ttctggccca gtgcaggtgt gctggtgatt tagggcaggt ggcattccat   240
ctctgtggct caatgtcttc ctctgtgaag ccgaagtgac ccaagggctc ccttcatggg   300
gttgagccag ctgtggccca gggagggcct aaccaggatg agcactgatg ttgccatgac   360
gactccgagg ccagaatgtc tcccccagca caggcctcat aggcaggctt ccccatcctg   420
gtaaacaaca cccacacact ttctactact gctctagggt gaaacccaag gcgctctaga   480
ggagatgaat tatggatcc                                                499
```

<210> SEQ ID NO 48
<211> LENGTH: 1262
<212> TYPE: DNA
<213> ORGANISM: Artificial Sequence
<220> FEATURE:
<223> OTHER INFORMATION: Synthetic Construct

<400> SEQUENCE: 48

```
gtatgccttt tgagatggat gcagcaggtt ctgtgaggct gccaggaggg gtagagttcc    60
cgggggcctc gggccccgct ggagtgtgga gcaggcccat gctcagctct ccaggctgtt   120
cgtggctccc ctgtcagctg ctcactcctt tccagagaca aaacaggaat aatagacatc   180
attaaatata catagggccc caggcggtcg gcgtggtggg ctgggcctcc cttccccata   240
acactgagct gctctgctgg gccaaccgtg ctcctgggcc agccagagga ccccatgag   300
gcggcatgca ggcggggagc aggccacaga acgcaggtaa ggagacctta gcctagagtc   360
cttggggtct gtcactggcc accctcgcat cccaggctgc aggaaactga ggcccagaga   420
```

```
ggacaaggac tttcctggac ccacacagcc agtcagtgac agagcctagg gtctgagcca    480
ggcctgaccc aacctccatt tctgcctctc taccccctgcc cccgcccccaa cacacacaca    540 cacacaagtg gagttccact gaaacgcccc tccttgccct gccttctgag ccggcagcct    600
ggctccccac cccatgtatt attcagctcc tgagagccag ccagctcctg ttacactgac    660
cgcagcccag cacctgctct gcccattccc ctcctccctt gcctaggacc tagagggttc    720
aaagttctcc tccaagatga cttggtgggc tttggccatc ccaccctagg ccccacttct    780
ggcccagtgc aggtgtgctg gtgatttagg gcaggtggca ttccatctct gtggctcaat    840
gtcttcctct gtgaagccga agtgacccaa gggctccctt catggggttg agccagctgt    900
ggcccaggga gggcctaacc aggatgagca ctgatgttgc catgacgact ccgaggccag    960
aatgtctccc ccagcacagg cctcataggc aggcttcccc atcctggtaa acaacaccca   1020
cacactttct actactgctc tagggtgaaa cccaaggcgc tctagaggag atgaattatg   1080
gatccgccct cccggaatcc tggctcggcc ctccccacgc cacccagggc cagtcgggtc   1140
tgctcacagc ccgaggaggc cgcgtgtcca gccgcgggga agagacagag caggtccctg   1200
tgtctccaag tccctgagcc cgtgacaccg gccccaggcc ctgtagagag caggcagcca   1260
cc                                                                  1262

<210> SEQ ID NO 49
<211> LENGTH: 649
<212> TYPE: DNA
<213> ORGANISM: Artificial Sequence
<220> FEATURE:
<223> OTHER INFORMATION: Synthetic Construct

<400> SEQUENCE: 49
gcaggcccat gctcagctct ccaggctgtt cgtggctccc ctgtcagctg ctcactcctt     60
tccagagaca aaacaggaat aatagacatc attaaatata catagggccc caggcggtcg    120
gcgtggtggg ctgggcctcc cttccccata acactgagct gctctgctgg gccaaccgtg    180
ctcctgggcc agccagagga cccccatgag gcggcatgca ggcggggagc aggccacaga    240
acgcaggtaa ggagaccttg ccttctgagc cggcagcctg gctccccacc ccatgtatta    300
ttcagctcct gagagccagc cagctcctgt tacactgacc gcagcccagc acctgctctg    360
cccattcccc tcctcccttg cctaggacct agagggttca aagttctcct ccaagatgac    420
ttggtgggct ttggccatcg gcctaaccag gatgagcact gatgttgcca tgacgactc     480 cgaggccaga atgtctcccc cagcacaggc ctcataggca ggcttcccca tcctggtaaa    540
caacacccac acactttcta ctactgctct agggtgaaac ccaaggcgct ctagaggaga    600
tgaattatgg atccgccctc ccggaatcct ggctcggccc tccccacgc                649

<210> SEQ ID NO 50
<211> LENGTH: 240
<212> TYPE: DNA
<213> ORGANISM: Mus musculus

<400> SEQUENCE: 50
ctgcagctca gcctactact tgctttccag gctgttccta gttcccatgt cagctgcttg     60
tgctttccag agacaaaaca ggaataatag atgtcattaa atatacattg ggccccaggc    120
ggtcaatgtg gcagcctgag cctcctttcc atctctgtgg aggcagacat aggacccca    180 acaaacagca tgcaggttgg gagccagcca caggacccag gtaaggggcc ctgggtcctt    240
```

```
<210> SEQ ID NO 51
<211> LENGTH: 95
<212> TYPE: DNA
<213> ORGANISM: Mus musculus

<400> SEQUENCE: 51
tttatgaggt gggagctggg ctctccctga tgtattattc agctccctgg agttggccag      60
ctcctgttac actggccaca gccctgggca tccgc                                 95

<210> SEQ ID NO 52
<211> LENGTH: 185
<212> TYPE: DNA
<213> ORGANISM: Mus musculus

<400> SEQUENCE: 52
tgccatggtg actttaaagc caggttgctg ccccagcaca ggcctcccag tctaccctca      60
ctagaaaaca acacccaggc actttccacc acctctcaaa ggtgaaaccc aaggctggtc     120
tagagaatga attatggatc ctcgctgtcc gtgccaccca gctagtccca gcggctcaga     180
cactg                                                                185

<210> SEQ ID NO 53
<211> LENGTH: 335
<212> TYPE: DNA
<213> ORGANISM: Artificial Sequence
<220> FEATURE:
<223> OTHER INFORMATION: Synthetic Construct

<400> SEQUENCE: 53
ctgcagctca gcctactact tgctttccag gctgttccta gttcccatgt cagctgcttg      60
tgctttccag agacaaaaca ggaataatag atgtcattaa atatacattg gccccaggc     120 ggtcaatgtg gcagcctgag cctcctttcc atctctgtgg aggcagacat aggaccccca     180
acaaacagca tgcaggttgg gagccagcca caggacccag gtaaggggcc ctgggtcctt     240
tttatgaggt gggagctggg ctctccctga tgtattattc agctccctgg agttggccag     300
ctcctgttac actggccaca gccctgggca tccgc                                335

<210> SEQ ID NO 54
<211> LENGTH: 425
<212> TYPE: DNA
<213> ORGANISM: Artificial Sequence
<220> FEATURE:
<223> OTHER INFORMATION: Synthetic Construct

<400> SEQUENCE: 54
ctgcagctca gcctactact tgctttccag gctgttccta gttcccatgt cagctgcttg      60
tgctttccag agacaaaaca ggaataatag atgtcattaa atatacattg gccccaggc     120 ggtcaatgtg gcagcctgag cctcctttcc atctctgtgg aggcagacat aggaccccca     180
acaaacagca tgcaggttgg gagccagcca caggacccag gtaaggggcc ctgggtcctt     240
tgccatggtg actttaaagc caggttgctg ccccagcaca ggcctcccag tctaccctca     300
ctagaaaaca acacccaggc actttccacc acctctcaaa ggtgaaaccc aaggctggtc     360
tagagaatga attatggatc ctcgctgtcc gtgccaccca gctagtccca gcggctcaga     420
cactg                                                                425

<210> SEQ ID NO 55
<211> LENGTH: 280
<212> TYPE: DNA
```

<213> ORGANISM: Mus musculus

<400> SEQUENCE: 55

```
tttatgaggt gggagctggg ctctccctga tgtattattc agctccctgg agttggccag    60
ctcctgttac actggccaca gccctgggca tccgctgcca tggtgacttt aaagccaggt   120
tgctgcccca gcacaggcct cccagtctac cctcactaga aaacaacacc caggcacttt   180
ccaccacctc tcaaaggtga aacccaaggc tggtctagag aatgaattat ggatcctcgc   240
tgtccgtgcc acccagctag tcccagcggc tcagacactg                         280
```

<210> SEQ ID NO 56
<211> LENGTH: 520
<212> TYPE: DNA
<213> ORGANISM: Artificial Sequence
<220> FEATURE:
<223> OTHER INFORMATION: Synthetic Construct

<400> SEQUENCE: 56

```
tttatgaggt gggagctggg ctctccctga tgtattattc agctccctgg agttggccag    60
ctcctgttac actggccaca gccctgggca tccgcctgca gctcagccta ctacttgctt   120
tccaggctgt tcctagttcc catgtcagct gcttgtgctt ccagagaca aaacaggaat    180
aatagatgtc attaaatata cattgggccc caggcggtca atgtggcagc ctgagcctcc   240
tttccatctc tgtggaggca gacataggac ccccaacaaa cagcatgcag gttgggagcc   300
agccacagga cccaggtaag gggccctggg tcctttgcca tggtgacttt aaagccaggt   360
tgctgcccca gcacaggcct cccagtctac cctcactaga aaacaacacc caggcacttt   420
ccaccacctc tcaaaggtga aacccaaggc tggtctagag aatgaattat ggatcctcgc   480
tgtccgtgcc acccagctag tcccagcggc tcagacactg                         520
```

<210> SEQ ID NO 57
<211> LENGTH: 520
<212> TYPE: DNA
<213> ORGANISM: Artificial Sequence
<220> FEATURE:
<223> OTHER INFORMATION: Synthetic Construct

<400> SEQUENCE: 57

```
tgccatggtg actttaaagc caggttgctg ccccagcaca ggcctcccag tctaccctca    60
ctagaaaaca cacccaggc actttccacc acctctcaaa ggtgaaaccc aaggctggtc   120
tagagaatga attatggatc ctcgctgtcc gtgccaccca gctagtccca gcggctcaga   180
cactgctgca gctcagccta ctacttgctt tccaggctgt tcctagttcc catgtcagct   240
gcttgtgctt ccagagaca aaacaggaat aatagatgtc attaaatata cattgggccc    300
caggcggtca atgtggcagc ctgagcctcc tttccatctc tgtggaggca gacataggac   360
ccccaacaaa cagcatgcag gttgggagcc agccacagga cccaggtaag gggccctggg   420
tccttttttat gaggtgggag ctgggctctc cctgatgtat tattcagctc cctggagttg   480
gccagctcct gttacactgg ccacagccct gggcatccgc                         520
```

<210> SEQ ID NO 58
<211> LENGTH: 520
<212> TYPE: DNA
<213> ORGANISM: Artificial Sequence
<220> FEATURE:
<223> OTHER INFORMATION: Synthetic Construct

<400> SEQUENCE: 58
```

```
tttatgaggt gggagctggg ctctccctga tgtattattc agctccctgg agttggccag    60
ctcctgttac actggccaca gccctgggca tccgctgcca tggtgacttt aaagccaggt   120
tgctgcccca gcacaggcct cccagtctac cctcactaga aaacaacacc caggcacttt   180
ccaccacctc tcaaaggtga aacccaaggc tggtctagag aatgaattat ggatcctcgc   240
tgtccgtgcc acccagctag tcccagcggc tcagacactg ctgcagctca gcctactact   300
tgctttccag gctgttccta gttcccatgt cagctgcttg tgctttccag agacaaaaca   360
ggaataatag atgtcattaa atatacattg gccccaggc ggtcaatgtg gcagcctgag    420 cctccttttcc atctctgtgg aggcagacat aggaccccca acaaacagca tgcaggttgg   480
gagccagcca caggacccag gtaaggggcc ctgggtcctt                        520
```

<210> SEQ ID NO 59
<211> LENGTH: 964
<212> TYPE: DNA
<213> ORGANISM: Artificial Sequence
<220> FEATURE:
<223> OTHER INFORMATION: Synthetic Construct

<400> SEQUENCE: 59

```
tgcagctcag cctactactt gctttccagg ctgttcctag ttcccatgtc agctgcttgt    60
gctttccaga gacaaaacag gaataataga tgtcattaaa tatacattgg ccccaggcg    120 gtcaatgtgg cagcctgagc ctccttttcca tctctgtgga ggcagacata ggaccccaa   180 caaacagcat gcaggttggg agccagccac aggacccagg taaggggccc tgggtcctta   240
agcttctgcc actggctccg gcattgcaga gagaagagaa ggggcggcag actggagagc   300
tgggctccat ttttgttcct tggtgccctg ccctccccca tgacctgcag agacattcag   360
cctgccaggc tttatgaggt gggagctggg ctctccctga tgtattattc agctccctgg   420
agttggccag ctcctgttac actggccaca gccctgggca tccgcttctc acttctagtt   480
tcccctccaa ggtaatgtgg tgggtcatga tcattctatc ctggcttcag ggacctgact   540
ccactttggg gccattcgag gggtctaggg tagatgatgt cccctgtgg ggattaatgt    600 cctgctctgt aaaactgagc tagctgagat ccaggagggc ttggcagag acagcaagtt    660 gttgccatgg tgactttaaa gccaggttgc tgccccagca caggcctccc agtctaccct   720
cactagaaaa caacacccag gcactttcca ccacctctca aggtgaaaac ccaaggctgg   780
tctagagaat gaattatgga tcctcgctgt ccgtgccacc cagctagtcc cagcggctca   840
gacactgagc agagactgta ggttcagcta caagcaaaaa gacctagctg gtctccaagc   900
agtgtctcca agtccctgaa cctgtgacac ctgccccagg catcatcagg cacagagggc   960
cacc                                                                964
```

<210> SEQ ID NO 60
<211> LENGTH: 519
<212> TYPE: DNA
<213> ORGANISM: Artificial Sequence
<220> FEATURE:
<223> OTHER INFORMATION: Synthetic Construct

<400> SEQUENCE: 60

```
tgcagctcag cctactactt gctttccagg ctgttcctag ttcccatgtc agctgcttgt    60
gctttccaga gacaaaacag gaataataga tgtcattaaa tatacattgg ccccaggcg    120 gtcaatgtgg cagcctgagc ctccttttcca tctctgtgga ggcagacata ggaccccaa   180
```

```
caaacagcat gcaggttggg agccagccac aggacccagg taaggggccc tgggtccttt      240
ttatgaggtg ggagctgggc tctccctgat gtattattca gctccctgga gttggccagc      300
tcctgttaca ctggccacag ccctgggcat ccgctgccat ggtgactttta aagccaggtt     360 gctgccccag cacaggcctc ccagtctacc ctcactagaa acaacaccc aggcactttc       420 caccacctct caaaggtgaa acccaaggct ggtctagaga atgaattatg gatcctcgct      480
gtccgtgcca cccagctagt cccagcggct cagacactg                             519
```

<210> SEQ ID NO 61
<211> LENGTH: 425
<212> TYPE: DNA
<213> ORGANISM: Artificial Sequence
<220> FEATURE:
<223> OTHER INFORMATION: Synthetic Construct

<400> SEQUENCE: 61

```
aatcaacctc tggattacaa aatttgtgaa agattgactg gtattcttaa ctatgttgct       60 cctttacgc tatgtggata cgctgcttta atgcctttgt atcatgctat tgcttcccgt      120
atggctttca ttttctcctc cttgtataaa tcctggttag ttcttgccac ggcggaactc      180
atcgccgcct gccttgcccg ctgctggaca ggggctcggc tgttgggcac tgacaattcc      240
gtggtgttta tttgtgaaat ttgtgatgct attgctttat tgtaaccat ctagctttat       300 ttgtgaaatt tgtgatgcta ttgctttatt tgtaaccatt ataagctgca ataaacaagt      360
taacaacaac aattgcattc attttatgtt tcaggttcag ggggagatgt gggaggtttt      420
ttaaa                                                                   425
```

<210> SEQ ID NO 62
<211> LENGTH: 865
<212> TYPE: DNA
<213> ORGANISM: Homo sapiens

<400> SEQUENCE: 62

```
ccccgggtgc gcggcgtcgg tggtgccggc gggggggcgcc aggtcgcagg cggtgtaggg      60
ctccaggcag gcggcgaagg ccatgacgtg cgctatgaag gtctgctcct gcacgccgtg     120
aaccaggtgc gcctgcgggc gcgcgcgaa caccgccacg tcctcgcctg cgtgggtctc      180
ttcgtccagg ggcactgctg actgctgccg atactcgggg ctcccgctct cgctctcggt     240
aacatccggc cgggcgccgt ccttgagcac atagcctgga ccgtttccgt ataggaggac     300
cgtgtaggcc ttcctgtccc gggccttgcc agcggccagc ccgatgaagg agctccctcg     360 caggggtag cctccgaagg agaagacgtg ggagtggtcg gcagtgacga ggctcagcgt      420
gtcctcctcg ctggtgagct ggcccgcct ctcaatggcg tcgtcgaaca tgatcgtctc      480
agtcagtgcc cggtaagccc tgctttcatg atgaccatgg tcgatgcgac caccctccac     540
gaagaggaag aagccgcggg ggtgtctgct cagcaggcgc agggcagcct ctgtcatctc      600
catcagggag gggtccagtg tggagtctcg gtggatctcg tatttcatgt ctccaggctc     660
aaagagaccc atgagatggg tcacagacgg gtccaggaa gcctgcatga gctcagtgcg      720
gttccacacg taccgggcac cctggcgttc gccgagccat tcctgcacca gattcttccc     780
gtccagcctg gtcccaccttt ggctgtagtc atctgggtac tcagggtctg ggttcccat     840 gcgaaacatg tactttcggc ctcca                                           865
```

<210> SEQ ID NO 63
<211> LENGTH: 437

<212> TYPE: DNA
<213> ORGANISM: Homo sapiens

<400> SEQUENCE: 63

```
ccccgggtgc gcggcgtcgg tggtgccggc gggggcgcc aggtcgcagg cggtgtaggg      60
ctccaggcag gcggcgaagg ccatgacgtg cgctatgaag gtctgctcct gcacgccgtg    120
aaccaggtgc gcctgcgggc cgcgcgcgaa caccgccacg tcctcgcctg cgtgggtctc    180
ttcgtccagg ggcactgctg actgctgccg atactcgggg ctcccgctct cgctctcggt    240
aacatccggc cgggcgccgt ccttgagcac atagcctgga ccgtttccgt ataggaggac    300
cgtgtaggcc ttcctgtccc gggccttgcc agcggccagc ccgatgaagg agctccctcg    360
caggggtag cctccgaagg agaagacgtg ggagtggtcg gcagtgacga ggctcagcgt    420
gtcctcctcg ctggtga                                                   437
```

<210> SEQ ID NO 64
<211> LENGTH: 428
<212> TYPE: DNA
<213> ORGANISM: Homo sapiens

<400> SEQUENCE: 64

```
gctggcccgc cctctcaatg gcgtcgtcga acatgatcgt ctcagtcagt gcccggtaag     60
ccctgctttc atgatgacca tggtcgatgc gaccaccctc cacgaagagg aagaagccgc    120
gggggtgtct gctcagcagg cgcagggcag cctctgtcat ctccatcagg gagggggtcca   180
gtgtggagtc tcggtggatc tcgtatttca tgtctccagg ctcaaagaga cccatgagat    240
gggtcacaga cgggtccagg gaagcctgca tgagctcagt gcggttccac acgtaccggg    300
caccctggcg ttcgccgagc cattcctgca ccagattctt cccgtccagc ctggtcccac    360
cttggctgta gtcatctggg tactcagggt ctggggttcc catgcgaaac atgtactttc    420
ggcctcca                                                             428
```

<210> SEQ ID NO 65
<211> LENGTH: 287
<212> TYPE: DNA
<213> ORGANISM: Homo sapiens

<400> SEQUENCE: 65

```
ccccgggtgc gcggcgtcgg tggtgccggc gggggcgcc aggtcgcagg cggtgtaggg      60
ctccaggcag gcggcgaagg ccatgacgtg cgctatgaag gtctgctcct gcacgccgtg    120
aaccaggtgc gcctgcgggc cgcgcgcgaa caccgccacg tcctcgcctg cgtgggtctc    180
ttcgtccagg ggcactgctg actgctgccg atactcgggg ctcccgctct cgctctcggt    240
aacatccggc cgggcgccgt ccttgagcac atagcctgga ccgtttc                  287
```

<210> SEQ ID NO 66
<211> LENGTH: 290
<212> TYPE: DNA
<213> ORGANISM: Homo sapiens

<400> SEQUENCE: 66

```
cgtataggag gaccgtgtag gccttcctgt cccgggcctt gccagcggcc agcccgatga     60
aggagctccc tcgcaggggg tagcctccga aggagaagac gtgggagtgg tcggcagtga    120
cgaggctcag cgtgtcctcc tcgctggtga gctggcccgc cctctcaatg gcgtcgtcga    180
acatgatcgt ctcagtcagt gcccggtaag ccctgctttc atgatgacca tggtcgatgc    240
```

```
gaccaccctc cacgaagagg aagaagccgc gggggtgtct gctcagcagg            290

<210> SEQ ID NO 67
<211> LENGTH: 288
<212> TYPE: DNA
<213> ORGANISM: Homo sapiens

<400> SEQUENCE: 67
cgcagggcag cctctgtcat ctccatcagg gaggggtcca gtgtggagtc tcggtggatc     60
tcgtatttca tgtctccagg ctcaaagaga cccatgagat gggtcacaga cgggtccagg    120
gaagcctgca tgagctcagt gcggttccac acgtaccggg caccctggcg ttcgccgagc    180
cattcctgca ccagattctt cccgtccagc ctggtcccac cttggctgta gtcatctggg    240
tactcagggt ctggggttcc catgcgaaac atgtactttc ggcctcca               288

<210> SEQ ID NO 68
<211> LENGTH: 84
<212> TYPE: DNA
<213> ORGANISM: Artificial Sequence
<220> FEATURE:
<223> OTHER INFORMATION: Synthetic Construct

<400> SEQUENCE: 68
gtaagtatca aggttacaag acaggtttaa ggagaccaat agaaactggg cttgtcgaga     60
cagagaagac tcttgcgttt ctga                                           84

<210> SEQ ID NO 69
<211> LENGTH: 49
<212> TYPE: DNA
<213> ORGANISM: Artificial Sequence
<220> FEATURE:
<223> OTHER INFORMATION: Synthetic Construct

<400> SEQUENCE: 69
taggcaccta ttggtcttac tgacatccac tttgcctttc tctccacag              49
```

COMPOSITIONS AND METHODS FOR TREATING SENSORINEURAL HEARING LOSS USING OTOFERLIN DUAL VECTOR SYSTEMS

SEQUENCE LISTING

The instant application contains a Sequence Listing which has been submitted electronically in ASCII format and is hereby incorporated by reference in its entirety. Said ASCII copy, created Aug. 4, 2021, is named 51471-003005_Sequence_Listing_08_04_21_ST25, and is 246,168 bytes in size.

FIELD OF THE INVENTION

Described herein are compositions and methods for the treatment of sensorineural hearing loss and auditory neuropathy, particularly forms of the disease that are associated with mutations in otoferlin (OTOF), by way of OTOF gene therapy. The disclosure provides dual vector systems that include a first nucleic acid vector that contains a polynucleotide encoding an N-terminal portion of an OTOF protein and a second nucleic acid vector that contains a polynucleotide encoding a C-terminal portion of an OTOF protein. These vectors can be used to increase the expression of or provide wild-type OTOF to a subject, such as a human subject suffering from sensorineural hearing loss.

BACKGROUND

Sensorineural hearing loss is a type of hearing loss caused by defects in the cells of the inner ear or the neural pathways that project from the inner ear to the brain. Although sensorineural hearing loss is often acquired, and can be caused by noise, infections, head trauma, ototoxic drugs, or aging, there are also congenital forms of sensorineural hearing loss associated with autosomal recessive mutations. One such form of autosomal recessive sensorineural hearing loss is associated with mutation of the otoferlin (OTOF) gene, which is implicated in prelingual nonsyndromic hearing loss. In recent years, efforts to treat hearing loss have increasingly focused on gene therapy as a possible solution; however, OTOF is too large to allow for treatment using standard gene therapy approaches. There is a need for new therapeutics to treat OTOF-related sensorineural hearing loss.

SUMMARY OF THE INVENTION

The present invention provides compositions and methods for treating sensorineural hearing loss or auditory neuropathy in a subject, such as a human subject. The compositions and methods of the disclosure pertain to dual vector systems for the delivery of a polynucleotide encoding an otoferlin (OTOF) protein to a subject having or at risk of developing sensorineural hearing loss or auditory neuropathy (e.g., a subject with a mutation in OTOF). For example, using the compositions and methods described herein, a first nucleic acid vector and a second nucleic acid vector that each encode a portion of a functional OTOF protein may be delivered to a subject by way of viral gene therapy. The compositions and methods described herein may also be used to increase expression of a WT OTOF protein in a cochlear hair cell (e.g., an inner hair cell).

In a first aspect, the invention provides a composition comprising: a first nucleic acid vector containing a promoter selected from the group consisting of a myosin 15 (Myo15) promoter, a vesicular glutamate transporter 3 (VGLUT3) promoter, and a fibroblast growth factor 8 (FGF8) promoter operably linked to a first coding polynucleotide that encodes an N-terminal portion of an otoferlin (OTOF) protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In another aspect, the invention provides a dual vector system comprising: a first nucleic acid vector containing a promoter selected from the group consisting of a myosin 15 (Myo15) promoter, a vesicular glutamate transporter 3 (VGLUT3) promoter, and a fibroblast growth factor 8 (FGF8) promoter operably linked to a first coding polynucleotide that encodes an N-terminal portion of an otoferlin (OTOF) protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In another aspect, the invention provides a composition comprising: a first nucleic acid vector containing a promoter selected from the group consisting of a CAG promoter, a cytomegalovirus (CMV) promoter, a truncated CMV-chicken β-actin promoter (smCBA promoter), a Myo15 promoter, a Myosin 7A (Myo7A) promoter, a Myosin 6 (Myo6) promoter, a POU Class 4 Homeobox 3 (POU4F3) promoter, an OTOF promoter, an FGF8 promoter, and a VGLUT3 promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In another aspect, the invention provides a dual vector system comprising: a first nucleic acid vector containing a promoter selected from the group consisting of a CAG promoter, a cytomegalovirus (CMV) promoter, a smCBA promoter, a Myo15 promoter, a Myosin 7A (Myo7A) promoter, a Myosin 6 (Myo6) promoter, a POU Class 4 Homeobox 3 (POU4F3) promoter, an OTOF promoter, an FGF8 promoter, and a VGLUT3 promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In some embodiments of any of the foregoing aspects, the first and second nucleic acid vectors are adeno-associated virus (AAV) vectors. In some embodiments of any of the foregoing aspects, the serotype of the AAV vectors is selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a smCBA promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter selected from the group consisting of a CAG promoter, a CMV promoter, a smCBA promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In some embodiments of any of the foregoing aspects, the first and second coding polynucleotides that encode the OTOF protein (e.g., the human OTOF protein) do not contain introns.

In some embodiments of any of the foregoing aspects, the OTOF protein is a mammalian OTOF protein.

In some embodiments of any of the foregoing aspects, the OTOF protein is a murine OTOF protein. In some embodiments of any of the foregoing aspects, the murine OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 6, SEQ ID NO: 7, SEQ ID NO: 8, or SEQ ID NO: 9. In some embodiments of any of the foregoing aspects, the OTOF protein comprises or consists of the sequence of SEQ ID NO: 6.

In some embodiments of any of the foregoing aspects, the OTOF protein is a human OTOF protein. In some embodiments of any of the foregoing aspects, the human OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 1, SEQ ID NO: 2, SEQ ID NO:3, SEQ ID NO: 4, or SEQ ID NO: 5. In some embodiments of any of the foregoing aspects, the OTOF protein comprises or consists of the sequence of SEQ ID NO: 1. In some embodiments of any of the foregoing aspects, the OTOF protein comprises or consists of the sequence of SEQ ID NO: 2. In some embodiments of any of the foregoing aspects, the OTOF protein comprises or consists of the sequence of SEQ ID NO: 3. In some embodiments of any of the foregoing aspects, the OTOF protein comprises or consists of the sequence of SEQ ID NO: 4. In some embodiments of any of the foregoing aspects, the OTOF protein comprises or consists of the sequence of SEQ ID NO: 5.

In some embodiments of any of the foregoing aspects, the serotype of the AAV vectors is AAV1. In some embodiments of any of the foregoing aspects, the serotype of the AAV vectors is AAV9. In some embodiments of any of the foregoing aspects, the serotype of the AAV vectors is AAV6. In some embodiments of any of the foregoing aspects, the serotype of the AAV vectors is Anc80. In some embodiments of any of the foregoing aspects, the serotype of the AAV vectors is Anc80L65. In some embodiments of any of the foregoing aspects, the serotype of the AAV vectors is DJ/9. In some embodiments of any of the foregoing aspects, the serotype of the AAV vectors is 7m8. In some embodiments of any of the foregoing aspects, the serotype of the AAV vectors is AAV2. In some embodiments of any of the foregoing aspects, the serotype of the AAV vectors is AAV2quad(Y-F). In some embodiments of any of the foregoing aspects, the serotype of the AAV vectors is PHP.B. In some embodiments of any of the foregoing aspects, the serotype of the AAV vectors is AAV8. In some embodiments of any of the foregoing aspects, the first and second nucleic acid vectors have the same serotype (e.g., both the first and second nucleic acid vector are AAV vectors having an AAV1 serotype or an AAV9 serotype). In some embodiments of any of the foregoing aspects, the first and second nucleic acid vectors have different serotypes (e.g., the first nucleic acid vector is an AAV having an AAV1 serotype, and the second nucleic acid vector is an AAV having an AAV9 serotype).

In some embodiments of any of the foregoing aspects, each of the first and second coding polynucleotides encode about half of the OTOF protein sequence.

In some embodiments of any of the foregoing aspects, wherein the first coding polynucleotide overlaps with the second coding polynucleotide by at least 1 kilobase (kb).

In some embodiments of any of the foregoing aspects, the region of overlap between the first and second coding polynucleotides is centered at an OTOF exon boundary. In some embodiments of any of the foregoing aspects, the first coding polynucleotide encodes an N-terminal portion of the OTOF protein containing the OTOF N-terminus to 500 kb 3' of the exon boundary at the center of the overlap region; and the second coding polynucleotide encodes a C-terminal portion of the OTOF protein containing 500 kb 5' of the exon boundary at the center of the overlap region to the OTOF C-terminus.

In some embodiments of any of the foregoing aspects, the exon boundary at the center of the overlap region is not within a portion of the first coding polynucleotide or second coding polynucleotide that encodes a C2 domain.

In some embodiments of any of the foregoing aspects, the promoter is a Myo15 promoter.

In some embodiments of any of the foregoing aspects, the promoter is a long promoter (e.g., a promoter that is longer than 1 kb, e.g., 1.1 kb, 1.25 kb, 1.5 kb, 1.75 kb, 2 kb, 2.5 kb, 3 kb or longer). In some embodiments, the long promoter is a Myo15 promoter that is longer than 1 kb (e.g., a Myo15 promoter comprising or consisting of a sequence with at least 85% sequence identity (e.g., 85%, 90%, 95%, 96%, 97%, 98%, 99%, or more, sequence identity) to the sequence of SEQ ID NO: 36).

In some embodiments of any of the foregoing aspects, the exon boundary is selected such that the first coding polynucleotide encodes the entire C2C domain and the second coding polynucleotide encodes the entire C2D domain. In some embodiments of any of the foregoing aspects, the first coding polynucleotide contains exons 1-21 of a polynucleotide encoding the OTOF protein and 500 kb 3' of the exon 21/22 boundary; and the second coding polynucleotide contains 500 kb 5' of the exon 21/22 boundary and exons 22-48 of a polynucleotide encoding the OTOF protein. In some embodiments of any of the foregoing aspects, the first nucleic acid vector and the second nucleic acid vector do not contain OTOF untranslated regions (UTRs).

In some embodiments of any of the foregoing aspects, the promoter is a short promoter (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter). In some embodiments, the short promoter is a CAG promoter. In some embodiments, the short promoter is a CMV promoter. In some embodiments, the short promoter is a smCBA promoter. In some embodiments, the short promoter is a Myo15 promoter that is 1 kb or shorter (e.g., a Myo15 promoter having a sequence with at least 85% sequence identity (e.g., 85%, 90%, 95%, 96%, 97%, 98%, 99%, or more, sequence identity) to any one of SEQ ID NOs: 38, 39, or 49-60).

In some embodiments of any of the foregoing aspects, the exon boundary is within a portion of the first coding polynucleotide and the second coding polynucleotide that encodes the C2D domain. In some embodiments of any of the foregoing aspects, the first coding polynucleotide contains exons 1-24 of a polynucleotide encoding the OTOF protein and 500 kb 3' of the exon 24/25 boundary; and the second coding polynucleotide contains 500 kb 5' of the exon 24/25 boundary and exons 25-48 of a polynucleotide encoding the OTOF protein. In some embodiments of any of the foregoing aspects, the first and second nucleic acid vectors include OTOF UTRs (e.g., full-length 3' and 5' UTRs).

In some embodiments of any of the foregoing aspects, the exon boundary is selected such that the first coding polynucleotide encodes the entire C2D domain and the second coding polynucleotide encodes the entire C2E domain. In some embodiments of any of the foregoing aspects, the first coding polynucleotide contains exons 1-28 of a polynucleotide encoding the OTOF protein and 500 kb 3' of the exon 28/29 boundary; and the second coding polynucleotide contains 500 kb 5' of the exon 28/29 boundary and exons 29-48 of a polynucleotide encoding the OTOF protein. In some embodiments of any of the foregoing aspects, the second nucleic acid vector contains a full-length OTOF 3' UTR.

In another aspect, the invention provides a composition comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a composition comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, a splice donor signal sequence positioned at the 3 end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a composition comprising: a first nucleic acid vector containing a promoter selected from the group consisting of a CAG promoter, a CMV promoter, a smCBA promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3' end of the splice acceptor signal sequence, and a poly(A) sequence at the 3 end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a CAG promoter, a CMV promoter, a smCBA promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3 end of the splice acceptor signal sequence, and a poly(A) sequence at the 3' end of the second coding polynucleotide; wherein the first coding polynucleotide and the second coding polynucleotide do not overlap, and wherein neither the first nor second nucleic acid vector encodes a full-length OTOF protein.

In some embodiments of any of the foregoing aspects, the first and second nucleic acid vectors are adeno-associated virus (AAV) vectors. In some embodiments of any of the foregoing aspects, the serotype of the AAV vectors is selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a smCBA promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter selected from the group consisting of a CAG promoter, a CMV promoter, a smCBA promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3 end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3' end of the splice acceptor signal sequence, and a poly(A) sequence at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3' end of the splice acceptor signal sequence, and a poly(A) sequence at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a smCBA promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, a splice donor signal sequence positioned at the 3 end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a CAG promoter, a CMV promoter, a smCBA promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3' end of the splice acceptor signal sequence, and a poly(A) sequence positioned at the 3 end of the second coding polynucleotide; wherein the first coding polynucleotide and the second coding polynucleotide do not overlap, and wherein neither the first nor second nucleic acid vector encodes a full-length OTOF protein.

In some embodiments of any of the foregoing aspects, the first and second nucleic acid vectors are AAV vectors. In some embodiments of any of the foregoing aspects, the serotype of the AAV vectors is selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a smCBA promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, a splice donor signal sequence positioned at the 3 end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3 end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter selected from the group consisting of a CAG promoter, a CMV promoter, a smCBA promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter operably linked to a first coding polynucleotide that encodes an N-terminal portion of a human OTOF protein, a splice donor signal sequence positioned at the 3 end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3 end of the splice acceptor signal sequence, and a poly(A) sequence positioned at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter operably linked to a first coding polynucleotide that encodes an N-terminal portion of a human OTOF protein, a splice donor signal sequence positioned at the 3 end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3 end of the splice acceptor signal sequence, and a poly(A) sequence positioned at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In some embodiments of any of the foregoing aspects, the first and second coding polynucleotides that encode the OTOF protein (e.g., the human OTOF protein) do not contain introns.

In some embodiments of any of the foregoing aspects, the OTOF protein is a mammalian OTOF protein.

In some embodiments of any of the foregoing aspects, the OTOF protein is a murine OTOF protein. In some embodiments of any of the foregoing aspects, the murine OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 6, SEQ ID NO: 7, SEQ ID NO: 8, or SEQ ID NO: 9. In some embodiments of any of the foregoing aspects, the murine OTOF protein comprises or consists of the sequence of SEQ ID NO: 6.

In some embodiments of any of the foregoing aspects, the OTOF protein is a human OTOF protein. In some embodiments of any of the foregoing aspects, the human OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 1, SEQ ID NO: 2, SEQ ID NO:3, SEQ ID NO: 4, or SEQ ID NO: 5. In some embodiments of any of the foregoing aspects, the human OTOF protein comprises or consists of the sequence of SEQ ID NO: 1. In some embodiments of any of the foregoing aspects, the human OTOF protein comprises or consists of the sequence of SEQ ID NO: 2. In some embodiments of any of the foregoing aspects, the human OTOF protein comprises or consists of the sequence of SEQ ID NO: 3. In some embodiments of any of the foregoing aspects, the human OTOF protein comprises or consists of the sequence of SEQ ID NO: 4. In some embodiments of any of the foregoing aspects, the human OTOF protein comprises or consists of the sequence of SEQ ID NO: 5.

In some embodiments of any of the foregoing aspects, the serotype of the AAV vectors is AAV1. In some embodiments of any of the foregoing aspects, the serotype of the AAV vectors is AAV9. In some embodiments of any of the foregoing aspects, the serotype of the AAV vectors is AAV6. In some embodiments of any of the foregoing aspects, the serotype of the AAV vectors is Anc80. In some embodiments of any of the foregoing aspects, the serotype of the AAV vectors is Anc80L65. In some embodiments of any of the foregoing aspects, the serotype of the AAV vectors is DJ/9. In some embodiments of any of the foregoing aspects, the serotype of the AAV vectors is 7m8. In some embodiments of any of the foregoing aspects, the serotype of the AAV vectors is AAV2. In some embodiments of any of the foregoing aspects, the serotype of the AAV vectors is AAV2quad(Y-F). In some embodiments of any of the foregoing aspects, the serotype of the AAV vectors is PHP.B. In some embodiments of any of the foregoing aspects, the serotype of the AAV vectors is AAV8. In some embodiments of any of the foregoing aspects, the first and second nucleic acid vectors have the same serotype (e.g., both the first and second nucleic acid vector are AAV vectors having an AAV1 serotype or an AAV9 serotype). In some embodiments of any of the foregoing aspects, the first and second nucleic acid vectors have different serotypes (e.g., the first nucleic acid vector is an AAV having an AAV1 serotype, and the second nucleic acid vector is an AAV having an AAV9 serotype).

In some embodiments, of any of the foregoing aspects, the first and second recombinogenic regions are the same. In some embodiments, of any of the foregoing aspects, the recombinogenic region is an AP gene fragment or an F1 phage AK gene. In some embodiments of any of the foregoing aspects, the recombinogenic region is an F1 phage AK gene. In some embodiments of any of the foregoing aspects, the F1 phage AK gene comprises or consists of the sequence of SEQ ID NO: 19. In some embodiments of any of the foregoing aspects, the recombinogenic region is an AP gene fragment. In some embodiments of any of the foregoing aspects, the AP gene fragment comprises or consists of the sequence of any one of SEQ ID NOs: 62-67.

In some embodiments of any of the foregoing aspects, the first nucleic acid vector further includes a degradation signal sequence positioned 3' of the recombinogenic region; and the second nucleic acid vector further includes a degradation signal sequence positioned between the recombinogenic region and the splice acceptor signal sequence. In some embodiments of any of the foregoing aspects, the degradation signal sequence comprises or consists of the sequence of SEQ ID NO: 22.

In some embodiments of any of the foregoing aspects, each of the first and second coding polynucleotides encode about half of the OTOF protein sequence.

In some embodiments of any of the foregoing aspects, the division between the first and second coding polynucleotides is at an OTOF exon boundary.

In some embodiments of any of the foregoing aspects, the OTOF exon boundary is not within a portion of the first coding polynucleotide or second coding polynucleotide that encodes a C2 domain.

In some embodiments of any of the foregoing aspects, the promoter is a short promoter (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter). In some embodiments, the short promoter is a CAG promoter. In some embodiments, the short promoter is a CMV promoter. In some embodiments, the short promoter is a smCBA promoter. In some embodiments, the short promoter is a Myo15 promoter that is 1 kb or shorter (e.g., a Myo15 promoter having a sequence with at least 85% sequence identity (e.g., 85%, 90%, 95%, 96%, 97%, 98%, 99%, or more, sequence identity) to any one of SEQ ID NOs: 38, 39, or 49-60).

In some embodiments of any of the foregoing aspects, the exon boundary is selected such that the first coding polynucleotide encodes the entire C2D domain and the second coding polynucleotide encodes the entire C2E domain. In some embodiments of any of the foregoing aspects, the first coding polynucleotide encodes exons 1-26 of a polynucleotide encoding the OTOF protein and the second coding polynucleotide encodes exons 27-48 of a polynucleotide encoding the OTOF protein. In some embodiments of any of the foregoing aspects, the first coding polynucleotide encodes exons 1-28 of a polynucleotide encoding the OTOF protein and the second coding polynucleotide encodes exons 29-48 of a polynucleotide encoding the OTOF protein. In some embodiments of any of the foregoing aspects, the first and second nucleic acid vectors contain OTOF UTRs (e.g., full length 3' and 5' UTRs).

In some embodiments of any of the foregoing aspects, the promoter is a Myo15 promoter.

In some embodiments of any of the foregoing aspects, the promoter is a long promoter (e.g., a promoter that is longer than 1 kb, e.g., 1.1 kb, 1.25 kb, 1.5 kb, 1.75 kb, 2 kb, 2.5 kb, 3 kb or longer). In some embodiments, the long promoter is a Myo15 promoter that is longer than 1 kb (e.g., a Myo15 promoter comprising or consisting of a sequence with at least 85% sequence identity (e.g., 85%, 90%, 95%, 96%, 97%, 98%, 99%, or more, sequence identity) to the sequence of SEQ ID NO: 36).

In some embodiments of any of the foregoing aspects, the OTOF exon boundary is not within a portion of the first coding polynucleotide or second coding polynucleotide that encodes a C2 domain.

In some embodiments of any of the foregoing aspects, the exon boundary is selected such that the first coding polynucleotide encodes the entire C2C domain and the second coding polynucleotide encodes the entire C2D domain. In some embodiments of any of the foregoing aspects, the first coding polynucleotide encodes exons 1-19 of a polynucleotide encoding the OTOF protein and the second coding polynucleotide encodes exons 20-48 of a polynucleotide encoding the OTOF protein. In some embodiments of any of the foregoing aspects, the first coding polynucleotide encodes exons 1-20 of a polynucleotide encoding the OTOF protein and the second coding polynucleotide encodes exons 21-48 of a polynucleotide encoding the OTOF protein. In some embodiments of any of the foregoing aspects, the first nucleic acid vector and the second nucleic acid vector do not contain OTOF UTRs.

In some embodiments of any of the foregoing aspects, the exon boundary is within a portion of the first coding polynucleotide and the second coding polynucleotide that encodes the C2D domain. In some embodiments of any of the foregoing aspects, the first coding polynucleotide encodes exons 1-25 of a polynucleotide encoding the OTOF protein and the second coding polynucleotide encodes exons 26-48 of a polynucleotide encoding the OTOF protein. In some embodiments of any of the foregoing aspects, the first coding polynucleotide encodes exons 1-24 of a polynucleotide encoding the OTOF protein and the second coding polynucleotide encodes exons 25-48 of a polynucleotide encoding the OTOF protein. In some embodiments of any of the foregoing aspects, the second nucleic acid vector contains a full-length OTOF 3' UTR.

In some embodiments of any of the foregoing aspects, the splice donor sequence comprises or consists of the sequence of SEQ ID NO: 20. In some embodiments of any of the foregoing aspects, the splice donor sequence comprises or consists of the sequence of SEQ ID NO: 68.

In some embodiments of any of the foregoing aspects, the splice acceptor sequence comprises or consists of the sequence of SEQ ID NO: 21. In some embodiments of any of the foregoing aspects, the splice acceptor sequence comprises or consists of the sequence of SEQ ID NO: 69.

In some embodiments, the first and second nucleic acid vectors contain inverted terminal repeats (ITRs). In some embodiments of any of the foregoing aspects, the ITRs are AAV2 ITRs.

In some embodiments of any of the foregoing aspects, the poly(A) sequence is a bovine growth hormone (bGH) poly (A) signal sequence.

In some embodiments of any of the foregoing aspects, the second nucleic acid vector contains a Woodchuck Hepatitis Virus Posttranscriptional Regulatory Element (WPRE). In some embodiments of any of the foregoing aspects, the WPRE comprises or consists of the sequence of SEQ ID NO: 23. In some embodiments of any of the foregoing aspects, the WPRE comprises or consists of the sequence of SEQ ID NO: 61.

In some embodiments of any of the foregoing aspects, the composition contains a pharmaceutically acceptable excipient.

In another aspect, the invention provides a kit containing a composition of the invention.

In another aspect, the invention provides a method of increasing OTOF expression in a subject in need thereof by administering to the subject a therapeutically effective amount of a composition of the invention.

In another aspect, the invention provides a method of treating a subject having or at risk of developing sensorineural hearing loss by administering to the subject a therapeutically effective amount of a composition of the invention.

In another aspect, the invention provides a method of treating a subject having or at risk of developing auditory neuropathy by administering to the subject a therapeutically effective amount of a composition of the invention.

In another aspect, the invention provides a method of increasing OTOF expression in a subject in need thereof by administering to the subject a therapeutically effective amount of a pair of nucleic acid vectors listed in Table 4.

In another aspect, the invention provides a method of treating a subject having or at risk of developing sensorineural hearing loss by administering to the subject a therapeutically effective amount of a pair of nucleic acid vectors listed in Table 4.

In another aspect, the invention provides a method of treating a subject having or at risk of developing auditory neuropathy by administering to the subject a therapeutically effective amount of a pair of nucleic acid vectors listed in Table 4.

In some embodiments of any of the foregoing aspects, the subject has a mutation in OTOF.

In some embodiments of any of the foregoing aspects, the subject has been identified as having a mutation in OTOF.

In some embodiments of any of the foregoing aspects, the method further includes the step of identifying the subject as having a mutation in OTOF prior to administering the composition or the pair of nucleic acid vectors.

In some embodiments of any of the foregoing aspects, the method further includes the step of evaluating the hearing of the subject prior to administering the composition or the pair of nucleic acid vectors.

In some embodiments of any of the foregoing aspects, the composition or the pair of nucleic acid vectors is administered locally to the ear. In some embodiments of any of the foregoing aspects, the nucleic acid vectors are administered concurrently. In some embodiments of any of the foregoing aspects, the nucleic acid vectors are administered sequentially.

In some embodiments of any of the foregoing aspects, the method increases OTOF expression in a cochlear hair cell. In some embodiments of any of the foregoing aspects, the cochlear hair cell is an inner hair cell.

In some embodiments of any of the foregoing aspects, the subject is a mammal. In some embodiments of any of the foregoing aspects, the subject is a human.

In some embodiments of any of the foregoing aspects, the method further includes the step of evaluating the hearing of the subject after administering the composition or the pair of nucleic acid vectors. In some embodiments of any of the foregoing aspects, the method further includes the step of evaluating OTOF expression after administering the composition or the pair of nucleic acid vectors.

In some embodiments of any of the foregoing aspects, the composition or the pair of nucleic acid vectors increases OTOF expression in a cell (e.g., a cochlear hair cell), improves hearing (e.g., as assessed by standard tests, such as audiometry, auditory brainstem response (ABR), electrocochleography (ECOG), and otoacoustic emissions), prevents or reduces hearing loss, delays the development of hearing loss, slows the progression of hearing loss, improves speech discrimination, or improves hair cell function.

In some embodiments of any of the foregoing aspects, the composition or the pair of nucleic acid vectors is administered in an amount sufficient to increase OTOF expression in a cochlear hair cell, prevent or reduce hearing loss, delay the development of hearing loss, slow the progression of hearing loss, improve hearing (e.g., as assessed by standard tests, such as audiometry, ABR, ECOG, and otoacoustic emissions), improve speech discrimination, or improve hair cell function.

In another aspect, the invention provides a method of increasing OTOF expression in a cell by introducing a composition of the invention into the cell.

In another aspect, the invention provides a method of increasing OTOF expression in a cell by introducing a pair of nucleic acid vectors listed in Table 4 into the cell.

In some embodiments of any of the foregoing aspects, the cell is a cochlear hair cell. In some embodiments of any of the foregoing aspects, the cell is an inner hair cell.

In some embodiments of any of the foregoing aspects, the cell is a mammalian cell. In some embodiments of any of the foregoing aspects, the cell is a human cell.

In some embodiments of any of the foregoing aspects, the OTOF protein encoded by the pair of nucleic acid vectors has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 1, SEQ ID NO: 2, SEQ ID NO:3, SEQ ID NO: 4, or SEQ ID NO: 5. In some embodiments of any of the foregoing aspects, the OTOF protein encoded by the pair of nucleic acid vectors comprises or consists of the sequence of SEQ ID NO: 1. In some embodiments of any of the foregoing aspects, the OTOF protein encoded by the pair of nucleic acid vectors comprises or consists of the sequence of SEQ ID NO: 2. In some embodiments of any of the foregoing aspects, the OTOF protein encoded by the pair of nucleic acid vectors comprises or consists of the sequence of SEQ ID NO: 3. In some embodiments of any of the foregoing aspects, the OTOF protein encoded by the pair of nucleic acid vectors comprises or consists of the sequence of SEQ ID NO: 4. In some embodiments of any of the foregoing aspects, the OTOF protein encoded by the pair of nucleic acid vectors comprises or consists of the sequence of SEQ ID NO: 5.

In some embodiments of any of the foregoing aspects, the nucleic acid vectors are AAV vectors. In some embodiments of any of the foregoing aspects, the serotype of the AAV vectors is selected from the group consisting of AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, or 7m8. In some embodiments of any of the foregoing aspects, the serotype of the AAV vectors is AAV1. In some embodiments of any of the foregoing aspects, the serotype of the AAV vectors is AAV9. In some embodiments of any of the foregoing aspects, the serotype of the AAV vectors is AAV6. In some embodiments of any of the foregoing aspects, the serotype of the AAV vectors is Anc80. In some embodiments of any of the foregoing aspects, the serotype of the AAV vectors is Anc80L65. In some embodiments of any of the foregoing aspects, the serotype of the AAV vectors is DJ/9. In some embodiments of any of the foregoing aspects, the serotype of the AAV vectors is 7m8. In some embodiments of any of the foregoing aspects, the serotype of the AAV vectors is AAV2. In some embodiments of any of the foregoing aspects, the serotype of the AAV vectors is AAV2quad(Y-F). In some embodiments of any of the foregoing aspects, the serotype of the AAV vectors is PHP.B. In some embodiments of any of the foregoing aspects, the serotype of the AAV vectors is AAV8. In some embodiments of any of the foregoing aspects, the first and second nucleic acid vectors have the same serotype (e.g., both the first and second nucleic acid vector are AAV vectors having an AAV1 serotype or an AAV9 serotype). In some embodiments of any of the foregoing aspects, the first and second nucleic acid vectors have different serotypes (e.g., the first nucleic acid vector is an AAV having an AAV1 serotype, and the second nucleic acid vector is an AAV having an AAV9 serotype).

In some embodiments of any of the foregoing aspects, the vectors contain AAV2 ITRs.

In some embodiments of any of the foregoing aspects, the second nucleic acid vector in the pair of nucleic acid vectors contains a WPRE. In some embodiments of any of the foregoing aspects, the WPRE comprises or consists of the sequence of SEQ ID NO: 23. In some embodiments of any of the foregoing aspects, the WPRE comprises or consists of the sequence of SEQ ID NO: 61.

In some embodiments of any of the foregoing aspects, the nucleic acid vectors are overlapping dual vectors.

In some embodiments of any of the foregoing aspects, the nucleic acid vectors are trans-splicing dual vectors.

In some embodiments of any of the foregoing aspects, the nucleic acid vectors are dual hybrid vectors.

In some embodiments of any of the foregoing aspects, the recombinogenic region in the dual hybrid vectors is an AP gene fragment or an F1 phage AK gene. In some embodiments of any of the foregoing aspects, the F1 phage AK gene comprises or consists of the sequence of SEQ ID NO: 19. In some embodiments of any of the foregoing aspects, the AP gene fragment comprises or consists of the sequence of any one of SEQ ID NOs: 62-67. In some embodiments of any of the foregoing aspects, the first nucleic acid vector in the pair of nucleic acid vectors further contains a degradation signal sequence positioned 3' of the recombinogenic region; and the second nucleic acid vector in the pair of nucleic acid vectors further contains a degradation signal sequence positioned between the recombinogenic region and the splice acceptor sequence. In some embodiments of any of the foregoing aspects, the degradation signal sequence comprises or consists of the sequence of SEQ ID NO: 22.

In some embodiments of any of the foregoing aspects, the splice donor sequence in the first nucleic acid vector comprises or consists of the sequence of SEQ ID NO: 20. In some embodiments of any of the foregoing aspects, the splice donor sequence comprises or consists of the sequence of SEQ ID NO: 68.

In some embodiments of any of the foregoing aspects, the splice acceptor sequence in the second nucleic acid vector comprises or consists of the sequence of SEQ ID NO: 21. In some embodiments of any of the foregoing aspects, the splice acceptor sequence comprises or consists of the sequence of SEQ ID NO: 69.

In some embodiments of any of the foregoing aspects, the Myo15 promoter comprises or consists of a first region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27, operably linked to a second region having at least 85% sequence identity (e.g., 85%, 90%, 95%, 96%, 97%, 98%, 99%, or more, sequence identity) to SEQ ID NO: 25 or a functional portion or derivative thereof including the sequence of SEQ ID NO: 31 and/or SEQ ID NO: 32, optionally containing a linker including one to one hundred nucleotides (e.g., 1-5, 1-10, 1-15, 1-20, 1-25, 1-30, 1-35, 1-40, 1-45, 1-50, 1-60, 1-70, 1-80, 1-90, 10-20, 10-30, 10-40, 10-50, 10-60, 10-70, 10-80, 10-90, 10-100, 20-30, 20-40, 20-50, 20-60, 20-70, 20-80, 20-90, or 20-100 nucleotides) between the first region and the second region. In some embodiments, the first region comprises or consists of the sequence of SEQ ID NO: 24. In some embodiments, the second region comprises or consists of the sequence of SEQ ID NO: 25.

In some embodiments of any of the foregoing aspects, the Myo15 promoter comprises or consists of the sequence of SEQ ID NO: 36. In some embodiments of any of the foregoing aspects, the Myo15 promoter comprises or consists of the sequence of SEQ ID NO: 38. In some embodiments of any of the foregoing aspects, the Myo15 promoter comprises or consists of the sequence of SEQ ID NO: 39. In some embodiments of any of the foregoing aspects, the Myo15 promoter comprises or consists of the sequence of SEQ ID NO: 53. In some embodiments of any of the foregoing aspects, the Myo15 promoter comprises or consists of the sequence of SEQ ID NO: 54. In some embodiments of any of the foregoing aspects, the Myo15 promoter comprises or consists of the sequence of SEQ ID NO: 59. In some embodiments of any of the foregoing aspects, the Myo15 promoter comprises or consists of the sequence of SEQ ID NO: 60.

In some embodiments of any of the foregoing aspects, the Myo15 promoter comprises or consists of a first region having at least 85% sequence identity (e.g., 85%, 90%, 95%, 96%, 97%, 98%, 99%, or more, sequence identity) to SEQ ID NO: 25 or a functional portion or derivative thereof including the sequence of SEQ ID NO: 31 and/or SEQ ID NO: 32, operably linked to a second region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27, optionally containing a linker including one to one hundred nucleotides (e.g., 1-5, 1-10, 1-15, 1-20, 1-25, 1-30, 1-35, 1-40, 1-45, 1-50, 1-60, 1-70, 1-80, 1-90, 10-20, 10-30, 10-40, 10-50, 10-60, 10-70, 10-80, 10-90, 10-100, 20-30, 20-40, 20-50, 20-60, 20-70, 20-80, 20-90, or 20-100 nucleotides) between the first region and the second region. In some embodiments, the first region comprises or consists of the sequence of SEQ ID NO: 25. In some embodiments, the second region comprises or consists of the sequence of SEQ ID NO: 24.

In some embodiments of any of the foregoing aspects, the Myo15 promoter comprises or consists of the sequence of SEQ ID NO: 37. In some embodiments of any of the foregoing aspects, the Myo15 promoter comprises or consists of the sequence of SEQ ID NO: 58.

In some embodiments of any of the foregoing aspects, the Myo15 promoter comprises or consists of a region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27. In some embodiments, the region comprises or consists of the sequence of SEQ ID NO: 24.

In some embodiments of any of the foregoing aspects, the Myo15 promoter comprises or consists of a region having at least 85% sequence identity (e.g., 85%, 90%, 95%, 96%, 97%, 98%, 99%, or more, sequence identity) to SEQ ID NO: 25 or a functional portion or derivative thereof including the sequence of SEQ ID NO: 31 and/or SEQ ID NO: 32. In some embodiments, the region comprises or consists of the sequence of SEQ ID NO: 25.

In some embodiments of any of the foregoing aspects, the functional portion of SEQ ID NO: 24 contains the sequence of SEQ ID NO: 26. In some embodiments of any of the foregoing aspects, the functional portion of SEQ ID NO: 24 contains the sequence of SEQ ID NO: 27. In some embodiments of any of the foregoing aspects, the functional portion of SEQ ID NO: 24 contains the sequence of SEQ ID NO: 26 and the sequence of SEQ ID NO: 27. In some embodiments of any of the foregoing aspects, the functional portion of SEQ ID NO: 24 contains the sequence of SEQ ID NO: 28. In some embodiments of any of the foregoing aspects, the functional portion of SEQ ID NO: 24 contains the sequence of SEQ ID NO: 29. In some embodiments of any of the foregoing aspects, the functional portion of SEQ ID NO: 24 contains the sequence of SEQ ID NO: 30. In some embodiments of any of the foregoing aspects, the functional portion of SEQ ID NO: 24 contains the sequence of SEQ ID NO: 50.

In some embodiments of any of the foregoing aspects, the functional portion of SEQ ID NO: 25 contains the sequence of SEQ ID NO: 31. In some embodiments of any of the foregoing aspects, the functional portion of SEQ ID NO: 25 contains the sequence of SEQ ID NO: 32. In some embodiments of any of the foregoing aspects, the functional portion of SEQ ID NO: 25 contains the sequence of SEQ ID NO: 51. In some embodiments of any of the foregoing aspects, the functional portion of SEQ ID NO: 25 contains the sequence of SEQ ID NO: 51. In some embodiments of any of the foregoing aspects, the functional portion of SEQ ID NO: 25 contains the sequence of SEQ ID NO: 31 and the sequence of SEQ ID NO: 32. In some embodiments of any of the foregoing aspects, the functional portion of SEQ ID NO: 25 contains the sequence of SEQ ID NO: 33. In some embodiments of any of the foregoing aspects, the functional portion of SEQ ID NO: 25 contains the sequence of SEQ ID NO: 34. In some embodiments of any of the foregoing aspects, the functional portion of SEQ ID NO: 25 contains the sequence of SEQ ID NO: 35. In some embodiments of any of the foregoing aspects, the functional portion of SEQ ID NO: 25 contains the sequence of SEQ ID NO: 55.

In some embodiments of any of the foregoing aspects, the Myo15 promoter has at least 85% sequence identity (e.g., 85%, 90%, 95%, 96%, 97%, 98%, 99%, or more, sequence identity) to the nucleic acid sequence of any one of SEQ ID NOs: 50-58. In some embodiments, the Myo15 promoter comprises or consists of the sequence of SEQ ID NO: 50. In some embodiments, the Myo15 promoter comprises or consists of the sequence of SEQ ID NO: 51. In some embodiments, the Myo15 promoter comprises or consists of the sequence of SEQ ID NO: 52. In some embodiments, the Myo15 promoter comprises or consists of the sequence of SEQ ID NO: 53. In some embodiments, the Myo15 promoter comprises or consists of the sequence of SEQ ID NO: 54. In some embodiments, the Myo15 promoter comprises or consists of the sequence of SEQ ID NO: 55. In some embodiments, the Myo15 promoter comprises or consists of the sequence of SEQ ID NO: 56. In some embodiments, the Myo15 promoter comprises or consists of the sequence of SEQ ID NO: 57. In some embodiments, the Myo15 promoter comprises or consists of the sequence of SEQ ID NO: 58.

In some embodiments of any of the foregoing aspects, the Myo15 promoter comprises or consists of a first region having at least 85% sequence identity (e.g., 85%, 90%, 95%, 96%, 97%, 98%, 99%, or more, sequence identity) to SEQ ID NO: 40 or a functional portion or derivative thereof including the sequence of SEQ ID NO: 42, joined (e.g., operably linked) to a second region having at least 85% sequence identity (e.g., 85%, 90%, 95%, 96%, 97%, 98%, 99%, or more, sequence identity) to SEQ ID NO: 41 or a functional portion or derivative thereof including the sequence of SEQ ID NO: 43 and/or SEQ ID NO: 44, optionally containing a linker including one to four hundred nucleotides (e.g., 1-5, 1-10, 1-15, 1-20, 1-25, 1-30, 1-35, 1-40, 1-45, 1-50, 1-60, 1-70, 1-80, 1-90, 1-100, 1-125, 1-150, 1-175, 1-200, 1-225, 1-250, 1-275, 1-300, 1-325, 1-350, 1-375, 1-400, 10-20, 10-30, 10-40, 10-50, 10-60, 10-70, 10-80, 10-90, 10-100, 20-30, 20-40, 20-50, 20-60, 20-70, 20-80, 20-90, 20-100, 30-100, 40-100, 50-100, 50-150, 50-200, 50-250, 50-300, 50-350, 50-400, 100-150, 100-200, 100-250, 100-300, 100-350, 100-400, 150-200, 150-250, 150-300, 150-350, 150-400, 200-250, 200-300, 200-350, 200-400, 250-300, 250-350, 250-400, 300-400, or 350-400 nucleotides) between the first region and the second region. In some embodiments, the first region comprises or consists of the sequence of SEQ ID NO: 40. In some embodiments, the second region comprises or consists of the sequence of SEQ ID NO: 41.

In some embodiments of any of the foregoing aspects, the Myo15 promoter comprises or consists of the sequence of SEQ ID NO: 48.

In some embodiments of any of the foregoing aspects, the Myo15 promoter comprises or consists of the sequence of SEQ ID NO: 49.

In some embodiments of any of the foregoing aspects, the Myo15 promoter comprises or consists of a first region having at least 85% sequence identity (e.g., 85%, 90%, 95%, 96%, 97%, 98%, 99%, or more, sequence identity) to SEQ ID NO: 41 or a functional portion or derivative thereof including the sequence of SEQ ID NO: 43 and/or SEQ ID NO: 44, joined (e.g., operably linked) to a second region having at least 85% sequence identity (e.g., 85%, 90%, 95%, 96%, 97%, 98%, 99%, or more, sequence identity) to SEQ ID NO: 40 or a functional portion or derivative thereof including the sequence of SEQ ID NO: 42, optionally containing a linker including one to four hundred nucleotides (e.g., 1-5, 1-10, 1-15, 1-20, 1-25, 1-30, 1-35, 1-40, 1-45, 1-50, 1-60, 1-70, 1-80, 1-90, 1-100, 1-125, 1-150, 1-175, 1-200, 1-225, 1-250, 1-275, 1-300, 1-325, 1-350, 1-375, 1-400, 10-20, 10-30, 10-40, 10-50, 10-60, 10-70, 10-80, 10-90, 10-100, 20-30, 20-40, 20-50, 20-60, 20-70, 20-80, 20-90, 20-100, 30-100, 40-100, 50-100, 50-150, 50-200, 50-250, 50-300, 50-350, 50-400, 100-150, 100-200, 100-250, 100-300, 100-350, 100-400, 150-200, 150-250, 150-300, 150-350, 150-400, 200-250, 200-300, 200-350, 200-400, 250-300, 250-350, 250-400, 300-400, or 350-400 nucleotides) between the first region and the second region. In some embodiments, the first region comprises or consists of the sequence of SEQ ID NO: 41. In some embodiments, the second region comprises or consists of the sequence of SEQ ID NO: 40.

In some embodiments of any of the foregoing aspects, the Myo15 promoter comprises or consists of a region having at least 85% sequence identity (e.g., 85%, 90%, 95%, 96%, 97%, 98%, 99%, or more, sequence identity) to SEQ ID NO: 40 or a functional portion or derivative thereof including the sequence of SEQ ID NO: 42. In some embodiments, the region comprises or consists of the sequence of SEQ ID NO: 40.

In some embodiments of any of the foregoing aspects, the Myo15 promoter comprises or consists of a region having at least 85% sequence identity (e.g., 85%, 90%, 95%, 96%, 97%, 98%, 99%, or more, sequence identity) to SEQ ID NO: 41 or a functional portion or derivative thereof including the sequence of SEQ ID NO: 43 and/or SEQ ID NO: 44. In some embodiments, the region comprises or consists of the sequence of SEQ ID NO: 41.

In some embodiments of any of the foregoing aspects, the functional portion of SEQ ID NO: 40 contains the sequence of SEQ ID NO: 42.

In some embodiments of any of the foregoing aspects, the functional portion of SEQ ID NO: 41 contains the sequence of SEQ ID NO: 43. In some embodiments of any of the foregoing aspects, the functional portion of SEQ ID NO: 41 contains the sequence of SEQ ID NO: 44. In some embodiments of any of the foregoing aspects, the functional portion of SEQ ID NO: 41 contains the sequence of SEQ ID NO: 43 and the sequence of SEQ ID NO: 44. In some embodiments of any of the foregoing aspects, the functional portion of SEQ ID NO: 41 contains the sequence of SEQ ID NO: 45. In some embodiments of any of the foregoing aspects, the functional portion of SEQ ID NO: 41 contains the sequence of SEQ ID NO: 46. In some embodiments of any of the foregoing aspects, the functional portion of SEQ ID NO: 41 contains the sequence of SEQ ID NO: 47.

In some embodiments of any of the foregoing aspects, the Myo15 promoter induces transgene expression when operably linked to a transgene and introduced into a hair cell.

Definitions

As used herein, the term "about" refers to a value that is within 10% above or below the value being described.

As used herein, "administration" refers to providing or giving a subject a therapeutic agent (e.g., a composition containing a first nucleic acid vector containing a polynucleotide that encodes an N-terminal portion of an otoferlin protein and a second nucleic acid vector containing a polynucleotide that encodes a C-terminal portion of an otoferlin protein), by any effective route. Exemplary routes of administration are described herein below.

As used herein, the term "cell type" refers to a group of cells sharing a phenotype that is statistically separable based on gene expression data. For instance, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, or muscle tissue) and/or those that are isolated from a common organ, tissue system, blood vessel, or other structure and/or region in an organism.

As used herein, the term "cochlear hair cell" refers to a group of specialized cells in the inner ear that are involved in sensing sound. There are two types of cochlear hair cells: inner hair cells and outer hair cells. Damage to cochlear hair cells and genetic mutations that disrupt cochlear hair cell function are implicated in hearing loss and deafness.

As used herein, the terms "conservative mutation," "conservative substitution," and "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in table 1 below.

TABLE 1

Representative physicochemical properties of naturally-occurring amino acids

| Amino Acid | 3 Letter Code | 1 Letter Code | Side-chain Polarity | Electrostatic character at physiological pH (7.4) | Steric Volume[†] |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | non-polar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

[†]based on volume in $Å^3$: 50-100 is small,
100-150 is intermediate,
150-200 is large, and
>200 is bulky From this table it is appreciated that the conservative amino acid families include (i) G, A, V, L and I; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the term "degradation signal sequence" refers to a sequence (e.g., a nucleotide sequence that can be translated into an amino acid sequence) that mediates the degradation of a polypeptide in which it is contained. Degradation signal sequences can be included in the nucleic acid vectors of the invention to reduce or prevent the expression of portions of otoferlin proteins that have not undergone recombination and/or splicing. An exemplary degradation signal sequence for use in the invention is GCCTGCAAGAACTGGTTCAGCAGCCTGAGC-CACTTCGTGATCCACCTG (SEQ ID NO: 22).

As used herein, the terms "effective amount," "therapeutically effective amount," and a "sufficient amount" of a composition, vector construct, or viral vector described herein refer to a quantity sufficient to, when administered to the subject in need thereof, including a mammal, for example a human, effect beneficial or desired results, including clinical results, and, as such, an "effective amount" or synonym thereto depends upon the context in which it is being applied. For example, in the context of treating sensorineural hearing loss, it is an amount of the composition, vector construct, or viral vector sufficient to achieve a treatment response as compared to the response obtained without administration of the composition, vector construct, or viral vector. The amount of a given composition described herein that will correspond to such an amount will vary depending upon various factors, such as the given agent, the pharmaceutical formulation, the route of administration, the type of disease or disorder, the identity of the subject (e.g. age, sex, weight) or host being treated, and the like, but can nevertheless be routinely determined by one skilled in the art. Also, as used herein, a "therapeutically effective amount" of a composition, vector construct, or viral vector of the present disclosure is an amount which results in a beneficial or desired result in a subject as compared to a control. Note that when a combination of active ingredients is administered, the effective amount of the combination may or may not include amounts of each ingredient that would have been effective if administered individually. As defined herein, a therapeutically effective amount of a composition, vector construct, viral vector or cell of the present disclosure may be readily determined by one of ordinary skill by routine methods known in the art.

Dosage regime may be adjusted to provide the optimum therapeutic response.

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell, e.g., a human cochlear hair cell).

As used herein, the term "express" refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell, e.g., a human cochlear hair cell). Exogenous materials include those that are provided from an external source to an organism or to cultured matter extracted there from.

As used herein, the term "hair cell-specific expression" refers to production of an RNA transcript or polypeptide primarily within hair cells (e.g., cochlear hair cells) as compared to other cell types of the inner ear (e.g., spiral ganglion neurons, glia, or other inner ear cell types). Hair cell-specific expression of a transgene can be confirmed by comparing transgene expression (e.g., RNA or protein expression) between various cell types of the inner ear (e.g., hair cells vs. non-hair cells) using any standard technique (e.g., quantitative RT PCR, immunohistochemistry, Western Blot analysis, or measurement of the fluorescence of a reporter (e.g., GFP) operably linked to a promoter). A hair cell-specific promoter induces expression (e.g., RNA or protein expression) of a transgene to which it is operably linked that is at least 50% greater (e.g., 50%, 75%, 100%, 125%, 150%, 175%, 200% greater or more) in hair cells (e.g., cochlear hair cells) compared to at least 3 (e.g., 3, 4, 5, 6, 7, 8, 9, 10, or more) of the following inner ear cell types: Border cells, inner phalangeal cells, inner pillar cells, outer pillar cells, first row Deiter cells, second row Deiter cells, third row Deiter cells, Hensen's cells, Claudius cells, inner sulcus cells, outer sulcus cells, spiral prominence cells, root cells, interdental cells, basal cells of the stria vascularis, intermediate cells of the stria vascularis, marginal cells of the stria vascularis, spiral ganglion neurons, Schwann cells.

As used herein, the terms "increasing" and "decreasing" refer to modulating resulting in, respectively, greater or lesser amounts, of function, expression, or activity of a metric relative to a reference. For example, subsequent to administration of a composition in a method described herein, the amount of a marker of a metric (e.g., OTOF expression) as described herein may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the marker prior to administration. Generally, the metric is measured subsequent to administration at a time that the administration has had the recited effect, e.g., at least one week, one month, 3 months, or 6 months, after a treatment regimen has begun.

As used herein, the term "intron" refers to a region within the coding region of a gene, the nucleotide sequence of which is not translated into the amino acid sequence of the corresponding protein. The term intron also refers to the corresponding region of the RNA transcribed from a gene. Introns are transcribed into pre-mRNA, but are removed during processing, and are not included in the mature mRNA.

As used herein, "locally" or "local administration" means administration at a particular site of the body intended for a local effect and not a systemic effect. Examples of local administration are epicutaneous, inhalational, intra-articular, intrathecal, intravaginal, intravitreal, intrauterine, intra-lesional administration, lymph node administration, intratumoral administration, administration to the inner ear, and administration to a mucous membrane of the subject, wherein the administration is intended to have a local and not a systemic effect.

As used herein, the term "operably linked" refers to a first molecule that can be joined to a second molecule, wherein the molecules are so arranged that the first molecule affects the function of the second molecule. The term "operably linked" includes the juxtaposition of two or more components (e.g., a promoter and another sequence element) such that both components function normally and allow for the possibility that at least one of the components can mediate a function that is exerted upon at least one of the other components. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. In additional embodiments, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

As used herein, the terms "otoferlin" and "OTOF" refer to the gene associated with nonsyndromic recessive deafness DNFB9. The terms "otoferlin" and "OTOF" also refer to variants of wild-type OTOF protein and nucleic acids encoding the same, such as variant proteins having at least 85% sequence identity (e.g., 85%, 86%, 87%, 88%, 89%, 90%, 91%, 92%, 93%, 94%, 95%, 96%, 97%, 98%, 99%, or 99.9% identity, or more) to the amino acid sequence of a wild-type OTOF protein (e.g., any one of SEQ ID NOs: 1-5) or polynucleotides having at least 85% sequence identity (e.g., 85%, 86%, 87%, 88%, 89%, 90%, 91%, 92%, 93%, 94%, 95%, 96%, 97%, 98%, 99%, or 99.9% identity, or more) to the nucleic acid sequence of a wild-type OTOF gene, provided that the OTOF analog encoded retains the therapeutic function of wild-type OTOF. As used herein, OTOF may refer to the protein localized to inner hair cells or to the gene encoding this protein, depending upon the context, as will be appreciated by one of skill in the art.

As used herein, the term "plasmid" refers to a to an extrachromosomal circular double stranded DNA molecule into which additional DNA segments may be ligated. A plasmid is a type of vector, a nucleic acid molecule capable of transporting another nucleic acid to which it has been linked. Certain plasmids are capable of autonomous replication in a host cell into which they are introduced (e.g., bacterial plasmids having a bacterial origin of replication and episomal mammalian plasmids). Other vectors (e.g., non-episomal mammalian vectors) can be integrated into the genome of a host cell upon introduction into the host cell, and thereby are replicated along with the host genome. Certain plasmids are capable of directing the expression of genes to which they are operably linked.

As used herein, the terms "nucleic acid" and "polynucleotide," used interchangeably herein, refer to a polymeric form of nucleosides in any length. Typically, a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds.

However, the term encompasses molecules containing nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e., the succession of letters used as abbreviations for bases) that biochemically characterizes a specific nucleic acid. A polynucleotide sequence presented herein is presented in a 5 to 3 direction unless otherwise indicated.

As used herein, the terms "complementarity" or "complementary" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

As used herein, the term "promoter" refers to a recognition site on DNA that is bound by an RNA polymerase. The polymerase drives transcription of the transgene. Exemplary promoters suitable for use with the compositions and methods described herein include ubiquitous promoters (e.g., the CAG promoter, cytomegalovirus (CMV) promoter, and a truncated form of the chimeric CMV-chicken β-actin promoter (CBA), in which the hybrid chicken β-actin/rabbit β-globin intron is greatly shortened to produce a smaller version of the promoter called smCBA), cochlear hair cell-specific promoters (e.g., the Myosin 15 (Myo15) promoter, the Myosin 7A (Myo7A) promoter, the Myosin 6 (Myo6) promoter, the POU Class 4 Homeobox 3 (POU4F3) promoter), and inner hair cell-specific promoters (e.g., the Fibroblast growth factor 8 (FGF8) promoter, the vesicular glutamate transporter 3 (VGLUT3) promoter, and the OTOF promoter).

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

$$100 \text{ multiplied by (the fraction } X/Y)$$

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

The term "derivative" as used herein refers to a nucleic acid, peptide, or protein or a variant or analog thereof comprising one or more mutations and/or chemical modifications as compared to a corresponding full-length wild-type nucleic acid, peptide, or protein. Non-limiting examples of chemical modifications involving nucleic acids include, for example, modifications to the base moiety, sugar moiety, phosphate moiety, phosphate-sugar backbone, or a combination thereof.

As used herein, the term "pharmaceutical composition" refers to a mixture containing a therapeutic agent, optionally in combination with one or more pharmaceutically acceptable excipients, diluents, and/or carriers, to be administered to a subject, such as a mammal, e.g., a human, in order to prevent, treat or control a particular disease or condition affecting or that may affect the subject.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio. Preferably, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "recombinogenic region" refers to a region of homology that mediates recombination between two different sequences.

As used herein, the term "regulatory sequence" includes promoters, enhancers and other expression control elements (e.g., polyadenylation signals) that control the transcription or translation of the polynucleotides that encode OTOF. Such regulatory sequences are described, for example, in Goeddel, Gene Expression Technology: Methods in Enzymology 185 (Academic Press, San Diego, Calif., 1990); incorporated herein by reference.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a subject.

As used herein, the term "transfection" refers to any of a wide variety of techniques commonly used for the introduction of exogenous DNA into a prokaryotic or eukaryotic host cell, e.g., electroporation, lipofection, calcium-phosphate precipitation, DEAE-dextran transfection, Nucleofection, squeeze-poration, sonoporation, optical transfection, Magnetofection, impalefection and the like.

As used herein, the terms "subject" and "patient" refer to an animal (e.g., a mammal, such as a human), veterinary animals (e.g., cats, dogs, cows, horses, sheep, pigs, etc.) and experimental animal models of diseases (e.g., mice, rats). A subject to be treated according to the methods described herein may be one who has been diagnosed with hearing loss (e.g., hearing loss associated with a mutation in OTOF), or one at risk of developing these conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the terms "transduction" and "transduce" refer to a method of introducing a vector construct or a part thereof into a cell. Wherein the vector construct is contained in a viral vector such as for example an AAV vector, transduction refers to viral infection of the cell and subsequent transfer and integration of the vector construct or part thereof into the cell genome.

As used herein, "treatment" and "treating" of a state, disorder or condition can include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "vector" includes a nucleic acid vector, e.g., a DNA vector, such as a plasmid, an RNA vector, virus or other suitable replicon (e.g., viral vector). A variety of vectors have been developed for the delivery of polynucleotides encoding exogenous proteins into a prokaryotic or eukaryotic cell. Examples of such expression vectors are disclosed in, e.g., WO94/11026; incorporated herein by reference as it pertains to vectors suitable for the expression of a gene of interest. Expression vectors suitable for use with the compositions and methods described herein contain a polynucleotide sequence as well as, e.g., additional sequence elements used for the expression of proteins and/or the integration of these polynucleotide sequences into the genome of a mammalian cell. Certain vectors that can be used for the expression of OTOF as described herein include vectors that contain regulatory sequences, such as promoter and enhancer regions, which direct gene transcription. Other useful vectors for expression of OTOF contain polynucleotide sequences that enhance the rate of translation of these genes or improve the stability or nuclear export of the mRNA that results from gene transcription. These sequence elements include, e.g., 5' and 3' untranslated regions and a polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

As used herein, the term "wild-type" refers to a genotype with the highest frequency for a particular gene in a given organism.

Figure 1A:
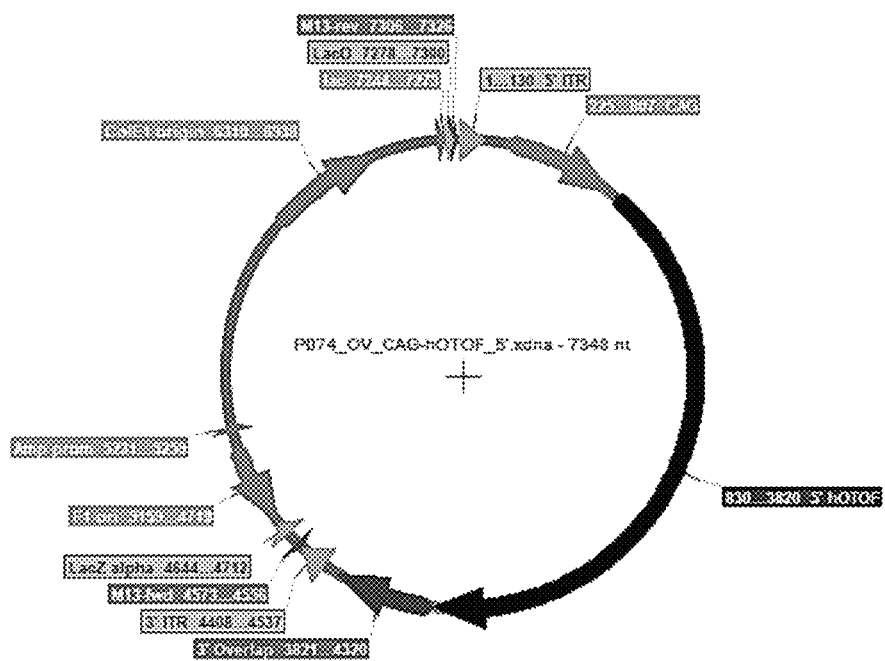
FIGS. 1A and 1B are maps of the 5' and 3' vectors in an overlapping dual vector system. The 5' vector contains AAV2 ITRs, and a CAG promoter operably linked to exons 1-24 of a polynucleotide encoding the human OTOF protein of SEQ ID NO: 1 and the 500 kb immediately 3' of the exon 24/25 boundary (FIG. 1A). The 3' vector contains AAV2 ITRs, the 500 kb immediately 5' of the exon 24/25 boundary and exons 25-48 of a polynucleotide encoding the human OTOF protein of SEQ ID NO: 1, and a WPRE sequence (SEQ ID NO: 23) (FIG. 1B).
Figure 1B:
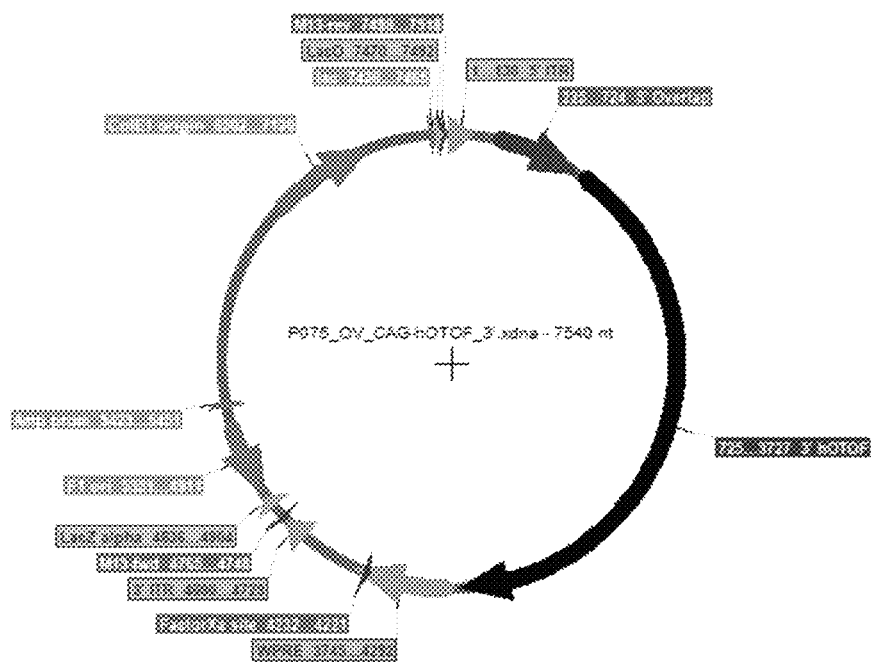
Figure 2A:
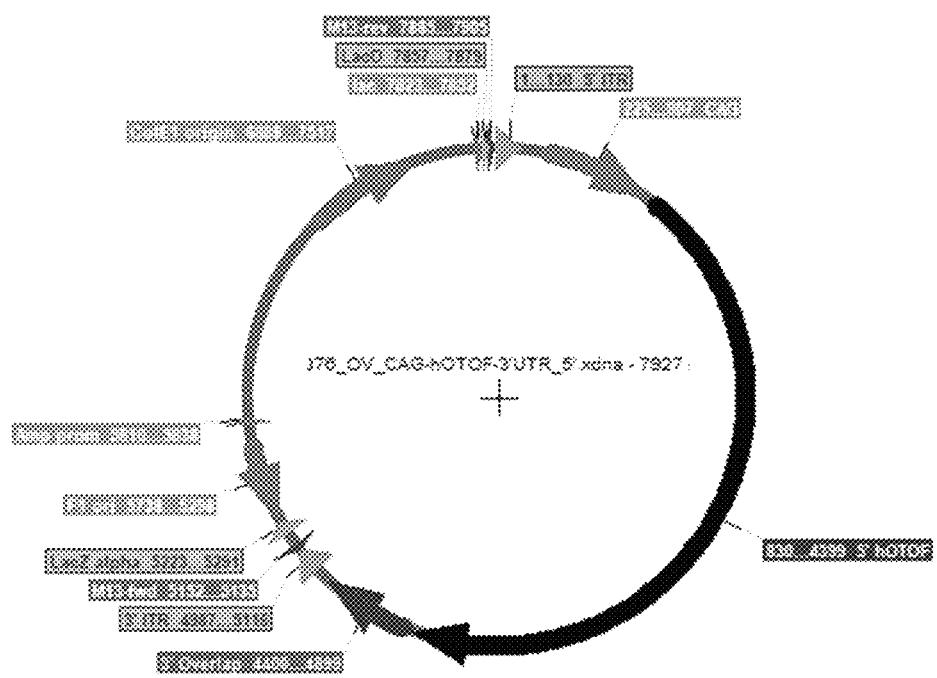
FIGS. 2A and 2B are maps of the 5' and 3' vectors in an overlapping dual vector system. The 5' vector contains AAV2 ITRs, and a CAG promoter operably linked to exons 1-28 of a polynucleotide encoding the human OTOF protein of SEQ ID NO: 1 and the 500 kb immediately 3' of the exon 28/29 boundary (FIG. 2A). The 3' vector contains AAV2 ITRs, the 500 kb immediately 5' of the exon 28/29 boundary and exons 29-48 of a polynucleotide encoding the human OTOF protein of SEQ ID NO: 1, the full-length human OTOF 3' UTR, and a WPRE sequence (SEQ ID NO: 23) (FIG. 2B).
Figure 2B:
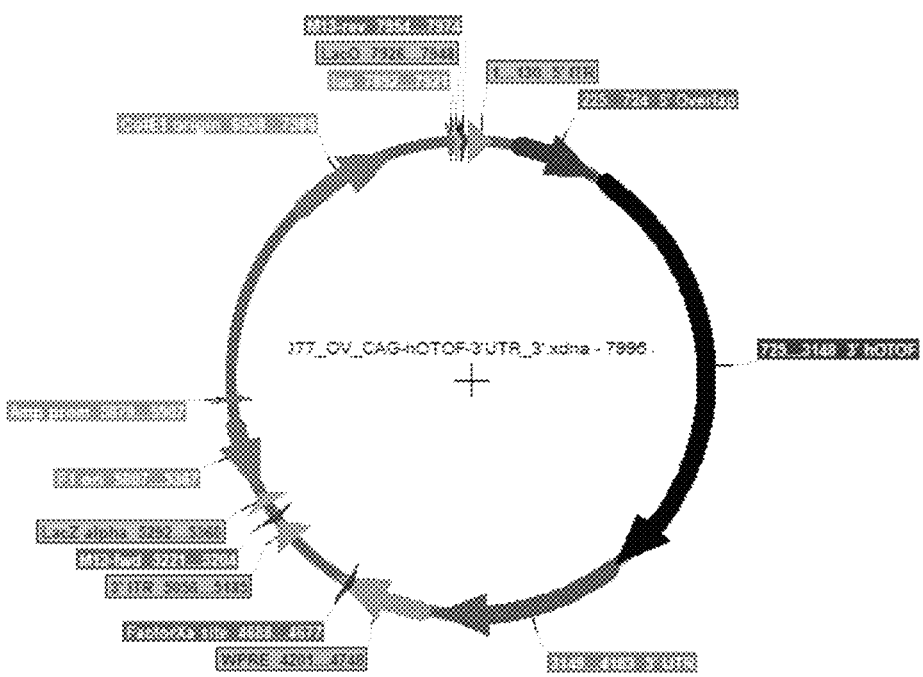
Figure 3A:
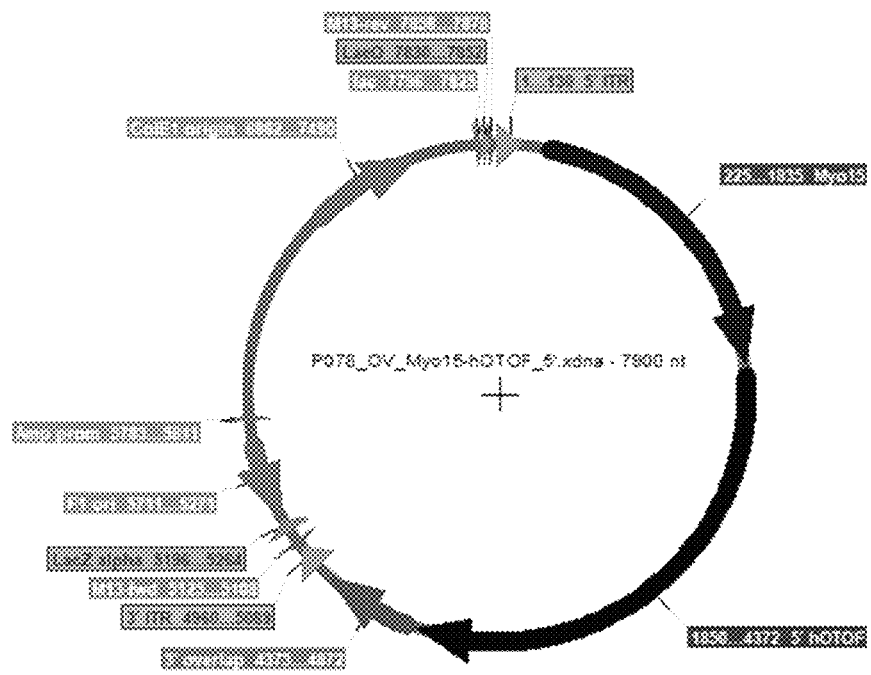
FIGS. 3A and 3B are maps of the 5' and 3' vectors in an overlapping dual vector system. The 5' vector contains AAV2 ITRs, and a Myo15 promoter (SEQ ID NO: 36) operably linked to exons 1-21 of a polynucleotide encoding the human OTOF protein of SEQ ID NO: 1 and the 500 kb immediately 3' of the exon 21/22 boundary (FIG. 3A). The 3' vector contains AAV2 ITRs, the 500 kb immediately 5' of the exon 21/22 boundary and exons 22-48 of a polynucleotide encoding the human OTOF protein of SEQ ID NO: 1, and a WPRE sequence (SEQ ID NO: 23) (FIG. 3B).
Figure 3B:
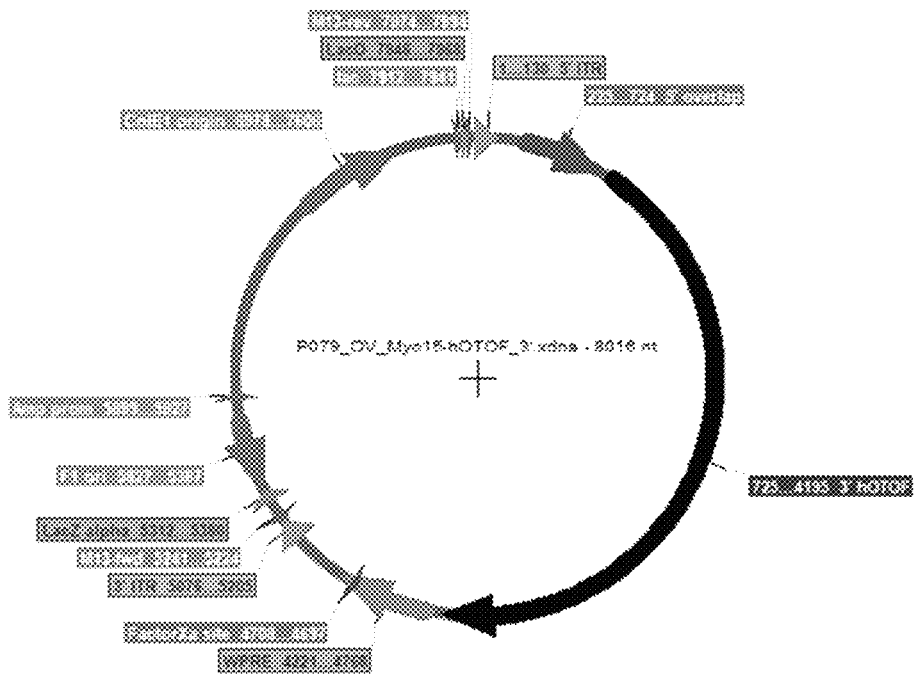
Figure 4A:
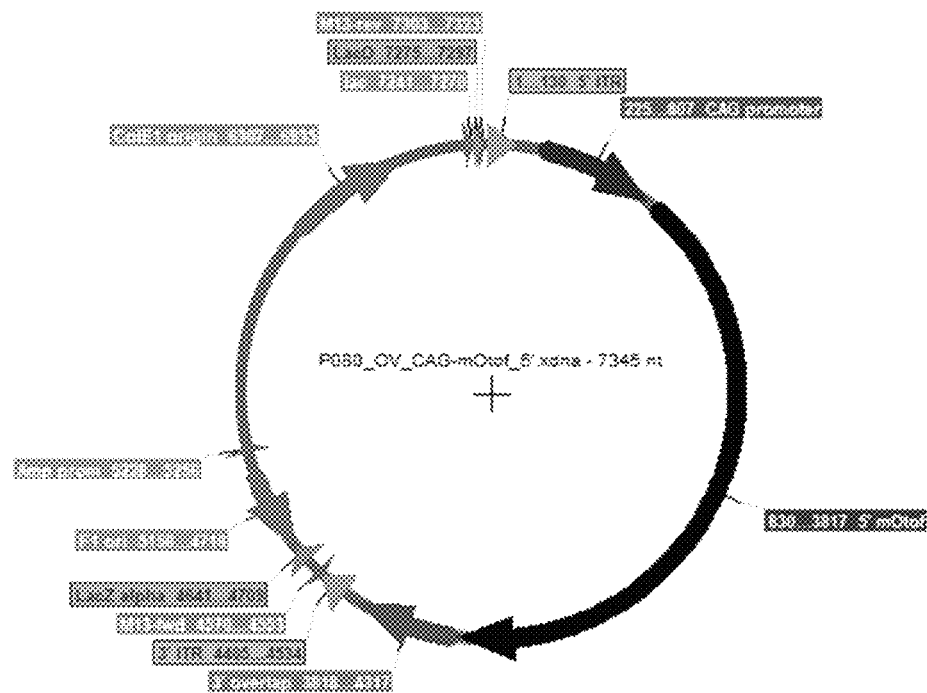
FIGS. 4A and 4B are maps of the 5' and 3' vectors in an overlapping dual vector system. The 5' vector contains AAV2 ITRs, and a CAG promoter operably linked to exons 1-24 of a polynucleotide encoding the mouse OTOF protein of SEQ ID NO: 6 and the 500 kb immediately 3' of the exon 24/25 boundary (FIG. 4A). The 3' vector contains AAV2 ITRs, the 500 kb immediately 5' of the exon 24/25 boundary and exons 25-48 of a polynucleotide encoding the mouse OTOF protein of SEQ ID NO: 6, and a WPRE sequence (SEQ ID NO: 23) (FIG. 4B).
Figure 4B:
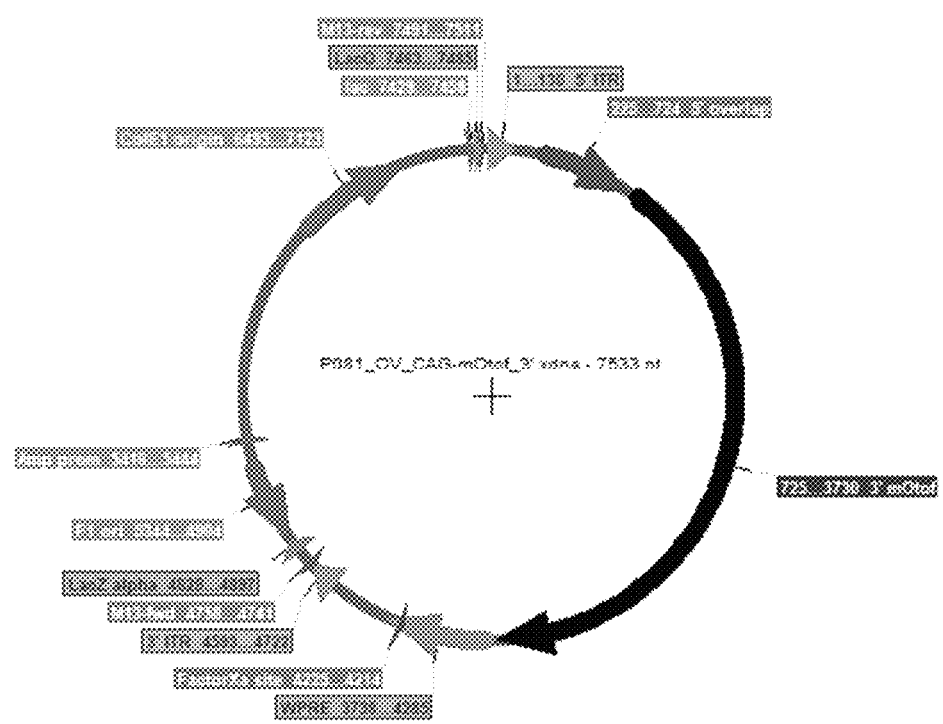
Figure 5A:
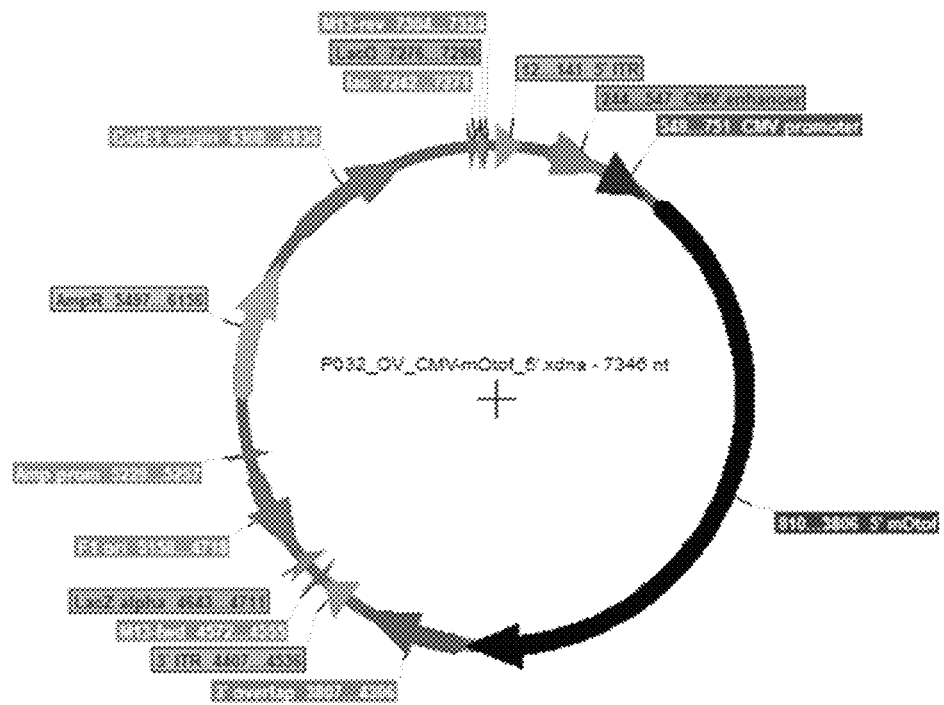
FIGS. 5A and 5B are maps of the 5' and 3' vectors in an overlapping dual vector system. The 5' vector contains AAV2 ITRs, a CMV enhancer, and a CMV promoter operably linked to exons 1-24 of a polynucleotide encoding the mouse OTOF protein of SEQ ID NO: 6 and the 500 kb immediately 3' of the exon 24/25 boundary (FIG. 5A). The 3' vector contains AAV2 ITRs, the 500 kb immediately 5' of the exon 24/25 boundary and exons 25-48 of a polynucleotide encoding the mouse OTOF protein of SEQ ID NO: 6, and a WPRE sequence (SEQ ID NO: 23) (FIG. 5B).
Figure 5B:
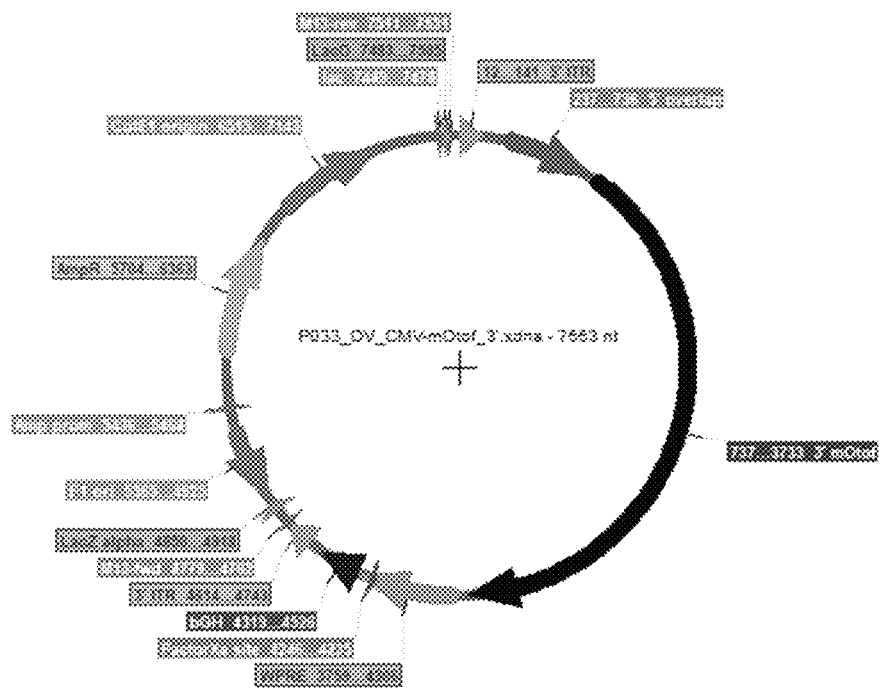
Figure 6A:
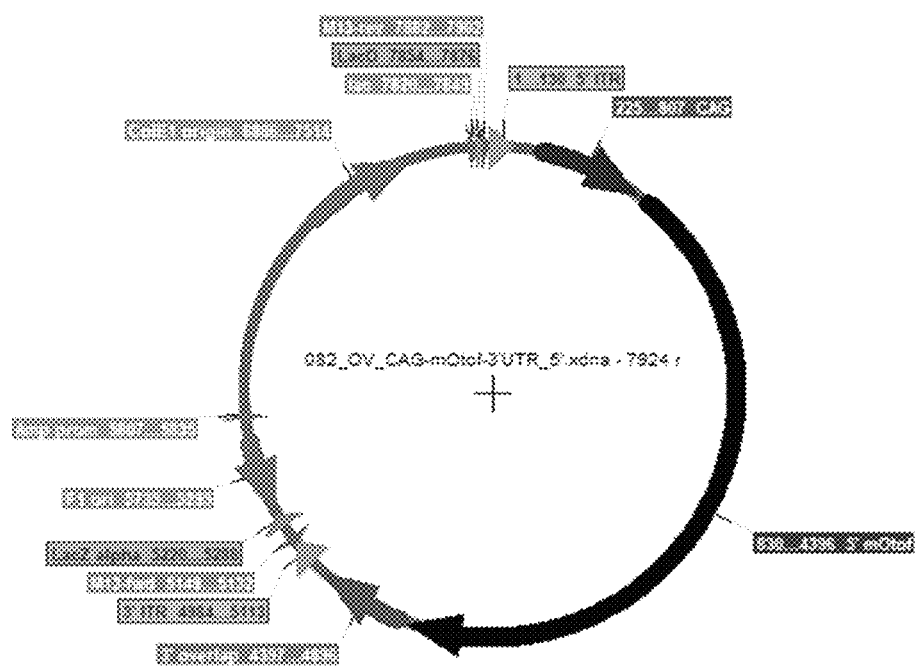
FIGS. 6A and 6B are maps of the 5' and 3' vectors in an overlapping dual vector system. The 5' vector contains AAV2 ITRs, and a CAG promoter operably linked to exons 1-28 of a polynucleotide encoding the mouse OTOF protein of SEQ ID NO: 6 and the 500 kb immediately 3' of the exon 28/29 boundary (FIG. 6A). The 3' vector contains AAV2 ITRs, the 500 kb immediately 5' of the exon 28/29 boundary and exons 29-48 of a polynucleotide encoding the mouse OTOF protein of SEQ ID NO: 6, the full-length mouse OTOF 3' UTR, and a WPRE sequence (SEQ ID NO: 23) (FIG. 6B).
Figure 6B:
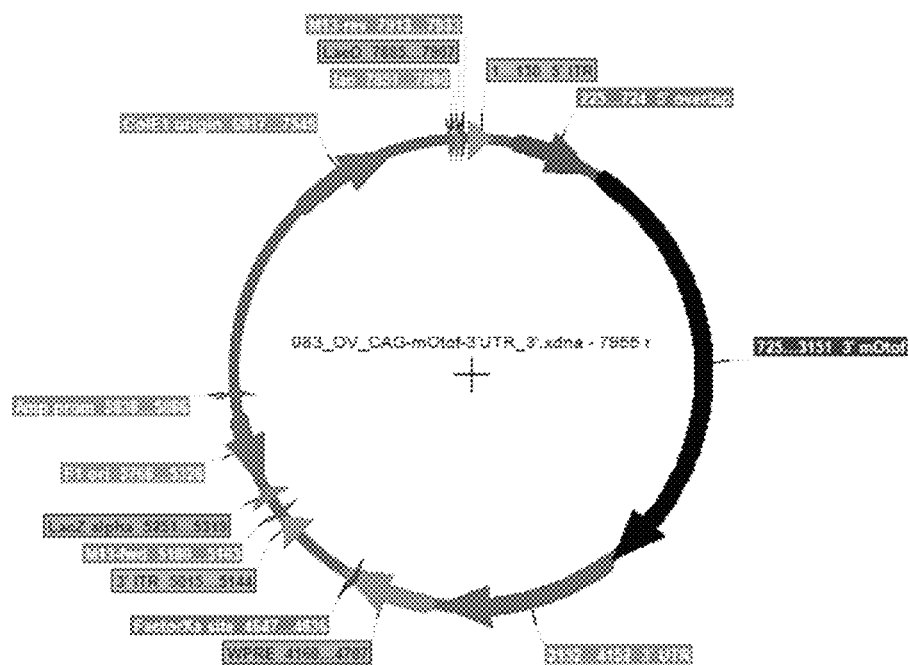
Figure 7A:
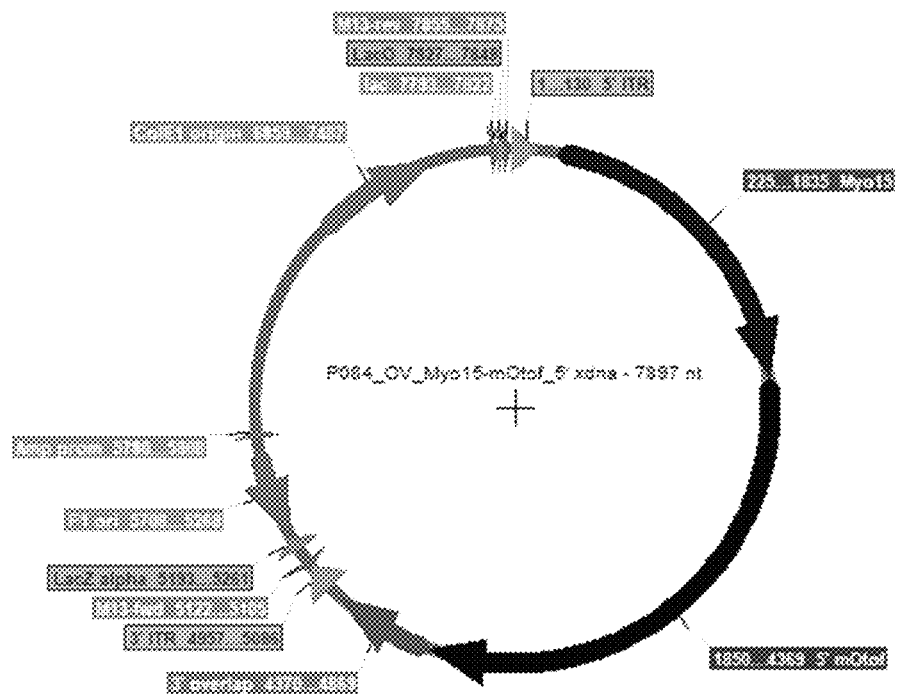
FIGS. 7A and 7B are maps of the 5' and 3' vectors in an overlapping dual vector system. The 5' vector contains AAV2 ITRs, and a Myo15 promoter (SEQ ID NO: 36) operably linked to exons 1-21 of a polynucleotide encoding the mouse OTOF protein of SEQ ID NO: 6 and the 500 kb immediately 3' of the exon 21/22 boundary (FIG. 7A). The 3' vector contains AAV2 ITRs, the 500 kb immediately 5' of the exon 21/22 boundary and exons 22-48 of a polynucleotide encoding the mouse OTOF protein of SEQ ID NO: 6, and a WPRE sequence (SEQ ID NO: 23) (FIG. 7B).
Figure 7B:
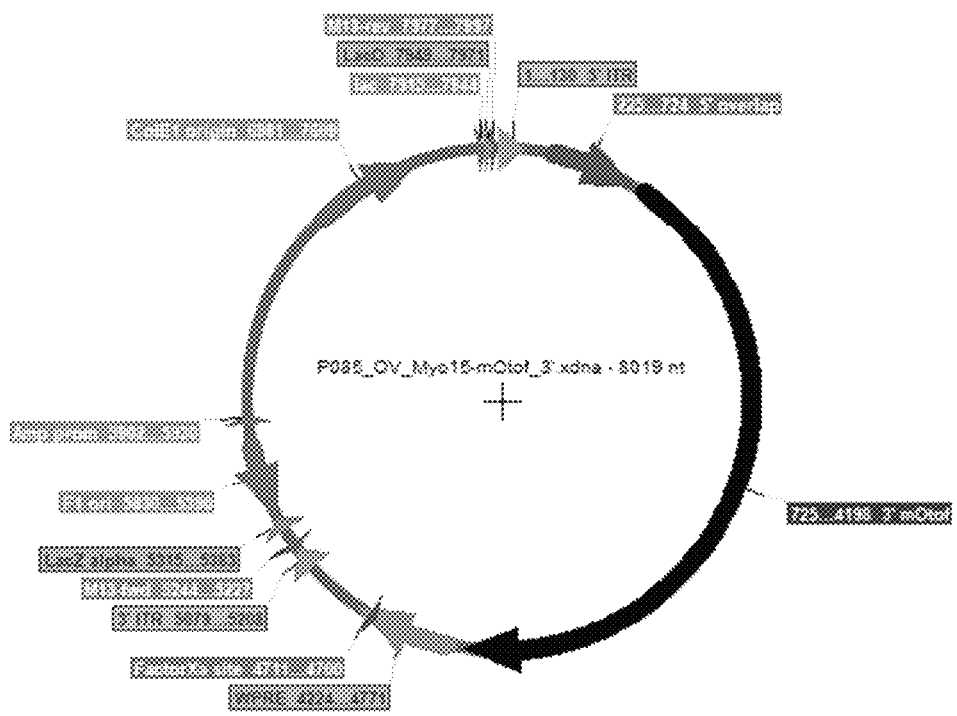
Figure 8A:
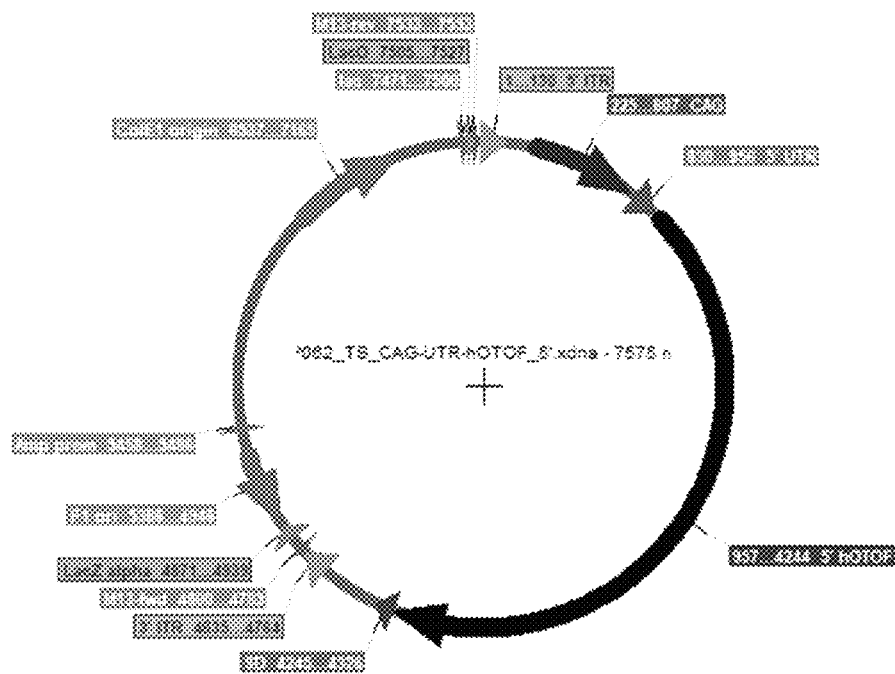
FIGS. 8A and 8B are maps of the 5' and 3' vectors in a trans-splicing dual vector system. The 5' vector contains AAV2 ITRs, a CAG promoter operably linked to the full-length human OTOF 5' UTR and exons 1-26 of a polynucleotide encoding the human OTOF protein of SEQ ID NO: 1, and a splice donor sequence (SD) (FIG. 8A). The 3' vector contains AAV2 ITRs, a splice acceptor sequence (SA), exons 27-48 of a polynucleotide encoding the human OTOF protein of SEQ ID NO: 1, the full-length human OTOF 3' UTR, and a WPRE sequence (SEQ ID NO: 23) (FIG. 8B).
Figure 8B:
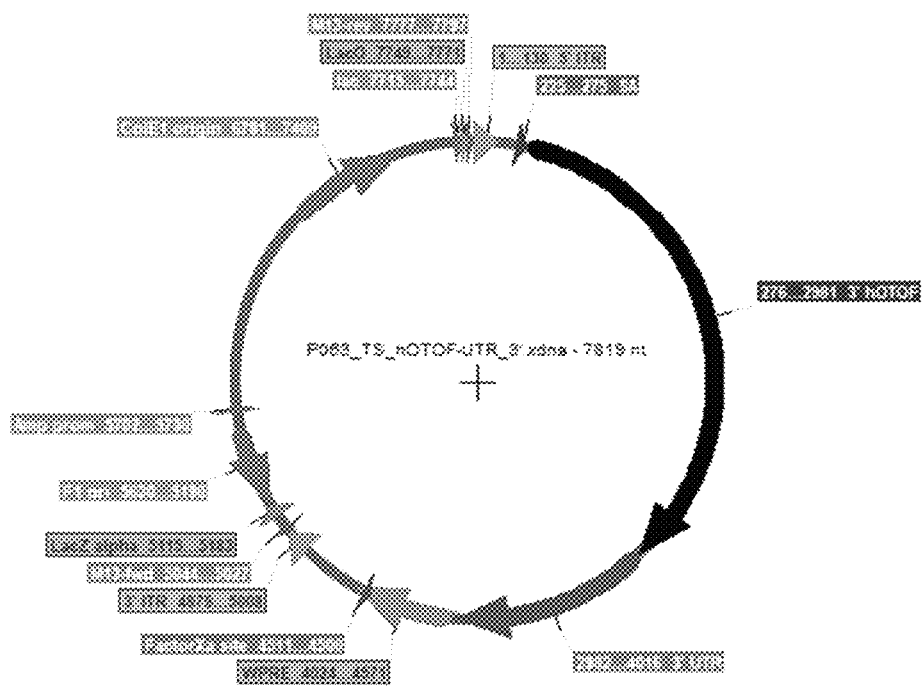
Figure 9A:
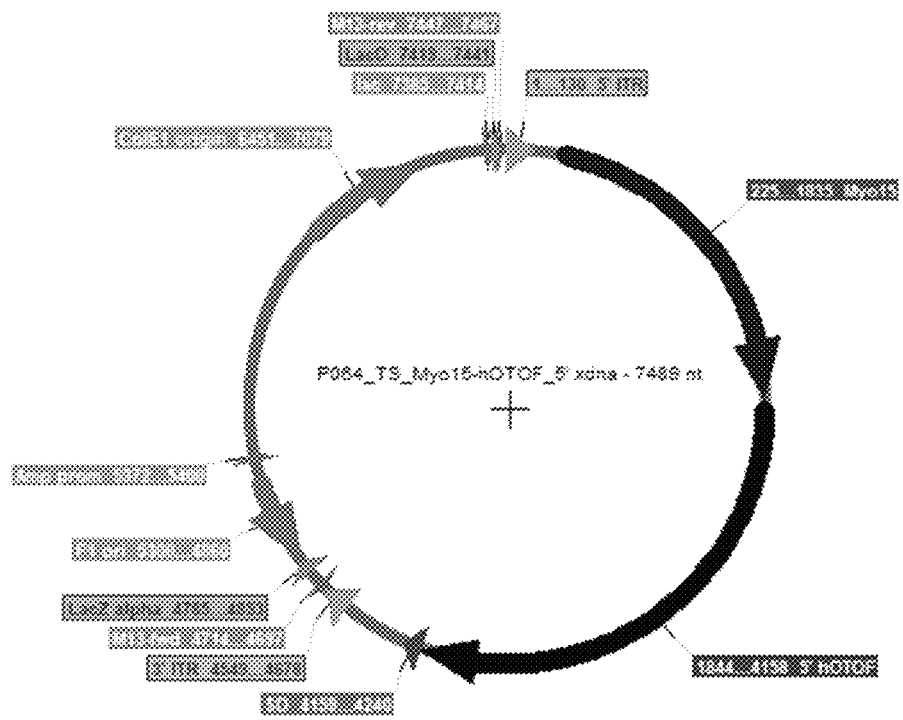
FIGS. 9A and 9B are maps of the 5' and 3' vectors in a trans-splicing dual vector system. The 5' vector contains AAV2 ITRs, a Myo15 promoter (SEQ ID NO: 36) operably linked to exons 1-19 of a polynucleotide encoding the human OTOF protein of SEQ ID NO: 1, and a splice donor sequence (SD) (FIG. 9A). The 3' vector contains AAV2 ITRs, a splice acceptor sequence (SA), exons 20-48 of a polynucleotide encoding the human OTOF protein of SEQ ID NO: 1, and a WPRE sequence (SEQ ID NO: 23) (FIG. 9B).
Figure 9B:
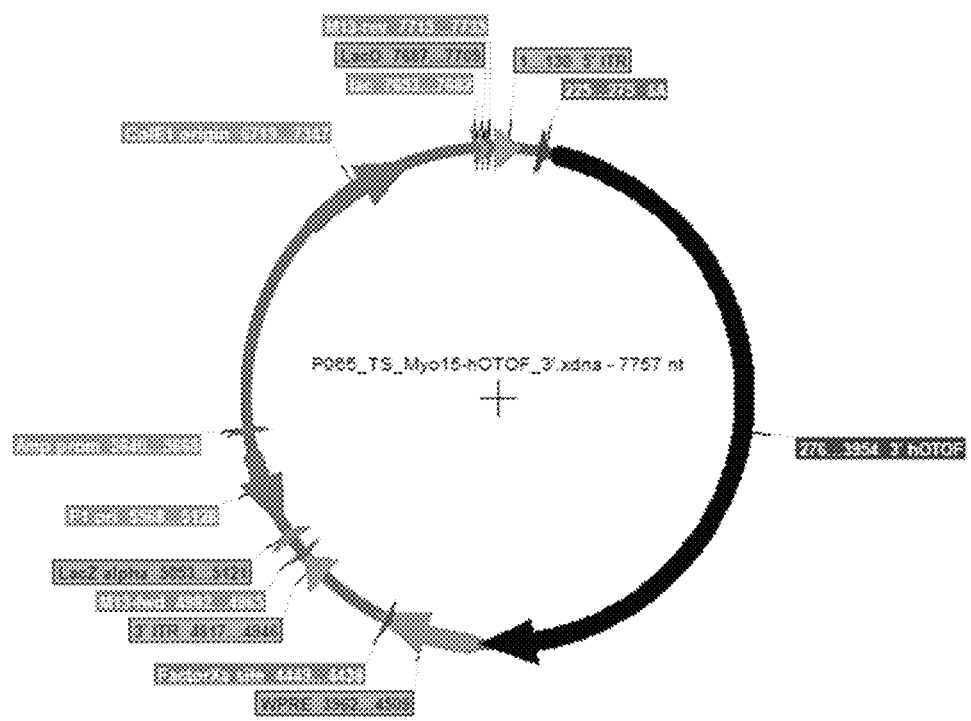
Figure 10A:
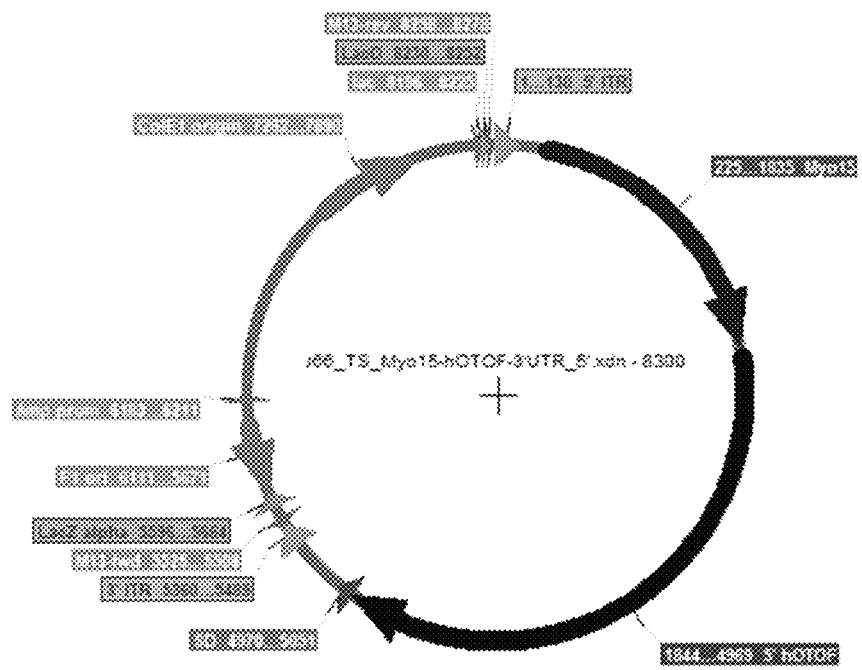
FIGS. 10A and 10B are maps of the 5' and 3' vectors in a trans-splicing dual vector system. The 5' vector contains AAV2 ITRs, a Myo15 promoter (SEQ ID NO: 36) operably linked to exons 1-25 of a polynucleotide encoding the human OTOF protein of SEQ ID NO: 1, and a splice donor sequence (SD) (FIG. 10A). The 3' vector contains AAV2 ITRs, a splice acceptor sequence (SA), exons 26-48 of a polynucleotide encoding the human OTOF protein of SEQ ID NO: 1, the full-length human OTOF 3' UTR, and a WPRE sequence (SEQ ID NO: 23) (FIG. 10B).
Figure 10B:
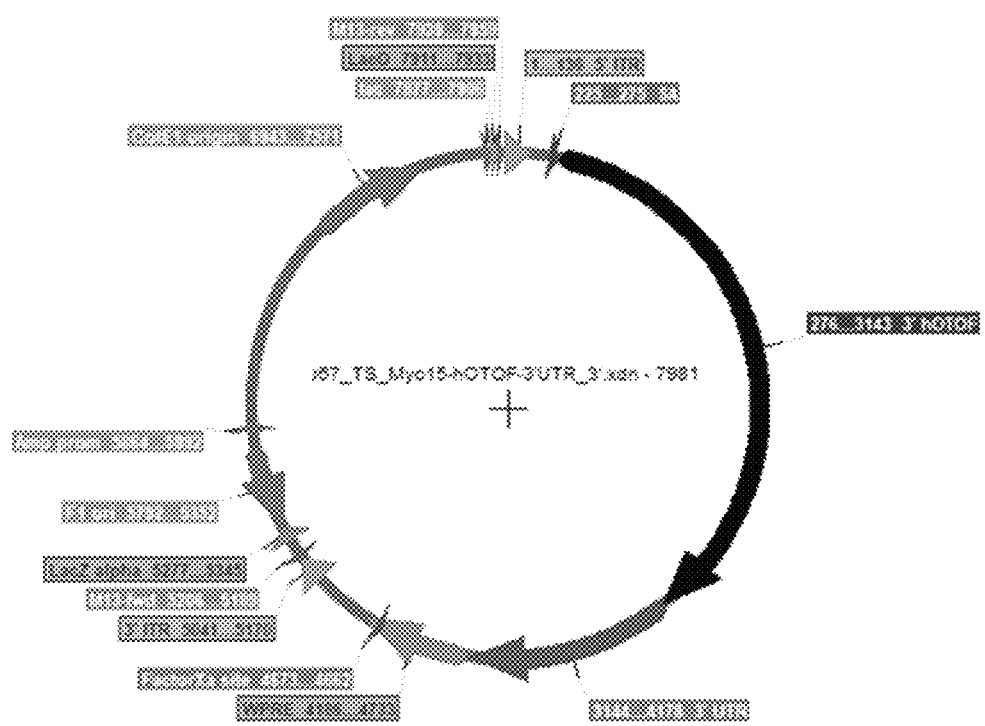
Figure 11A:
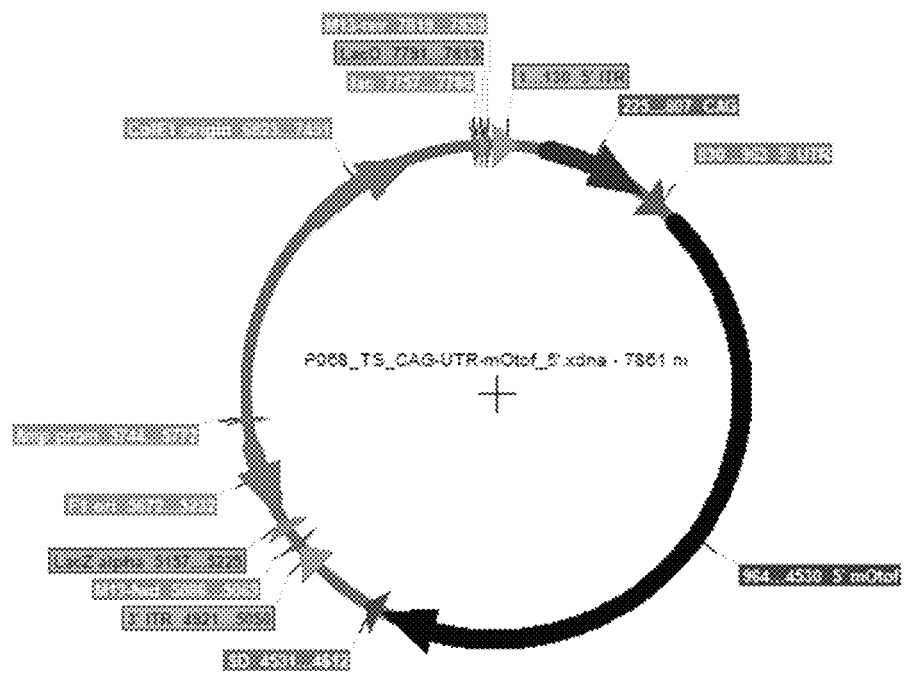
FIGS. 11A and 11B are maps of the 5' and 3' vectors in a trans-splicing dual vector system. The 5' vector contains AAV2 ITRs, a CAG promoter operably linked to the full-length mouse OTOF 5' UTR and exons 1-28 of a polynucleotide encoding the mouse OTOF protein of SEQ ID NO: 6, and a splice donor sequence (SD) (FIG. 11A). The 3' vector contains AAV2 ITRs, a splice acceptor sequence (SA), exons 29-48 of a polynucleotide encoding the mouse OTOF protein of SEQ ID NO: 6, the full-length mouse OTOF 3' UTR, and a WPRE sequence (SEQ ID NO: 23) (FIG. 11B).
Figure 11B:
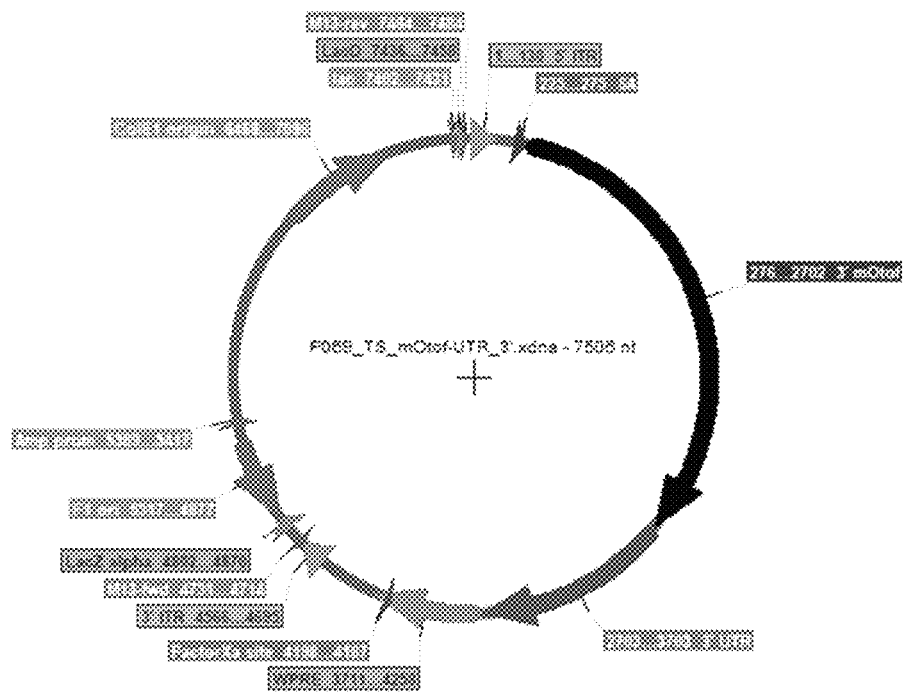
Figure 12A:
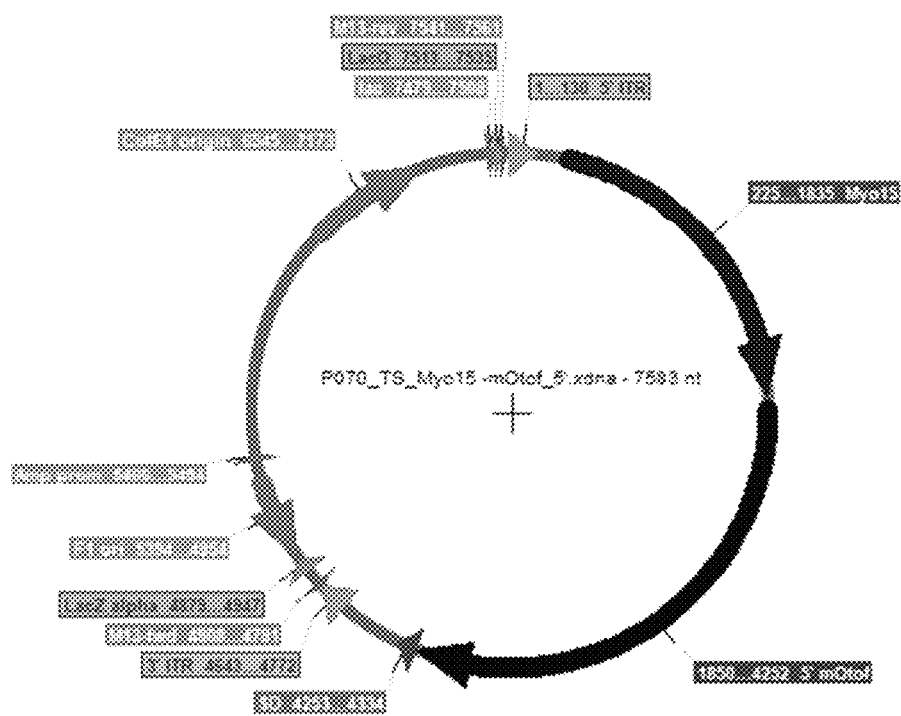
FIGS. 12A and 12B are maps of the 5' and 3' vectors in a trans-splicing dual vector system. The 5' vector contains AAV2 ITRs, a Myo15 promoter (SEQ ID NO: 36) operably linked to exons 1-20 of a polynucleotide encoding the mouse OTOF protein of SEQ ID NO: 6, and a splice donor sequence (SD) (FIG. 12A). The 3' vector contains AAV2 ITRs, a splice acceptor sequence (SA), exons 21-48 of a polynucleotide encoding the mouse OTOF protein of SEQ ID NO: 6, and a WPRE sequence (SEQ ID NO: 23) (FIG. 12B).
Figure 12B:
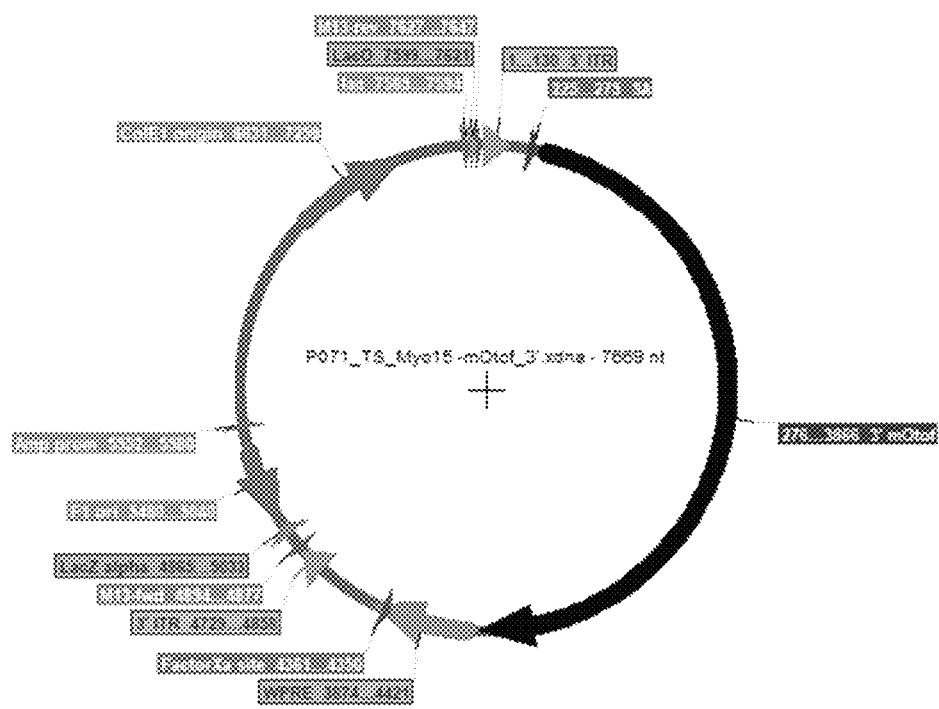
Figure 13A:
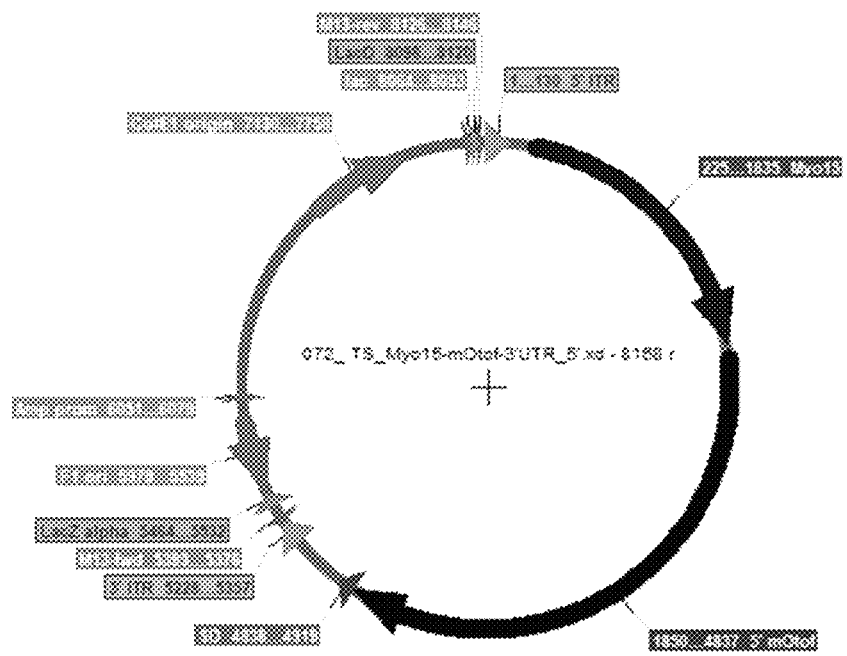
FIGS. 13A and 13B are maps of the 5' and 3' vectors in a trans-splicing dual vector system. The 5' vector contains AAV2 ITRs, a Myo15 promoter (SEQ ID NO: 36) operably linked to exons 1-24 of a polynucleotide encoding the mouse OTOF protein of SEQ ID NO: 6, and a splice donor sequence (SD) (FIG. 13A). The 3' vector contains AAV2 ITRs, a splice acceptor sequence (SA), exons 25-48 of a polynucleotide encoding the mouse OTOF protein of SEQ ID NO: 6, the full-length mouse OTOF 3' UTR, and a WPRE sequence (SEQ ID NO: 23) (FIG. 13B).
Figure 13B:
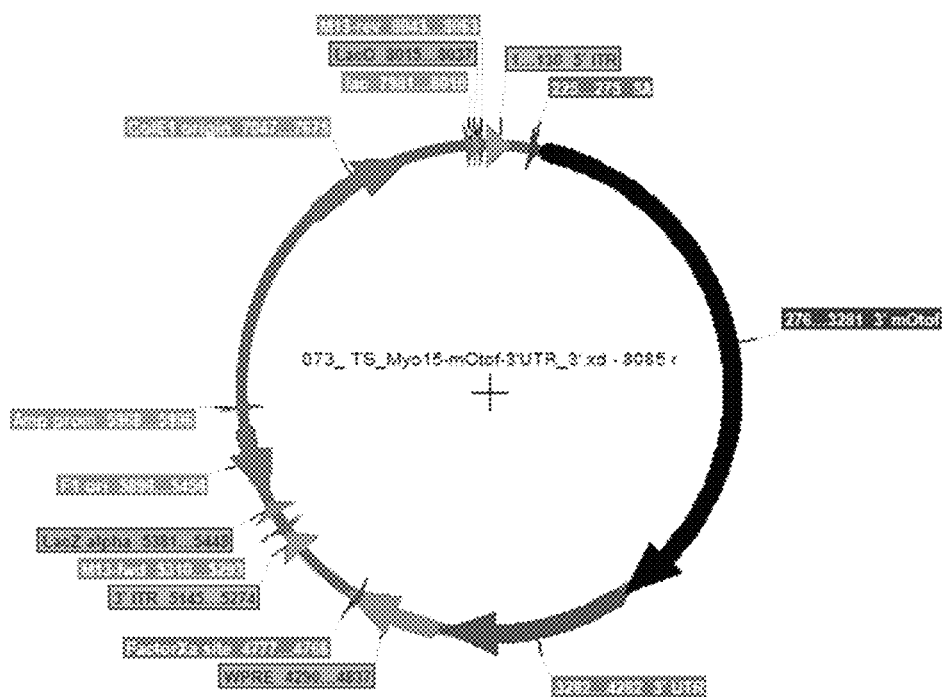
Figure 14A:
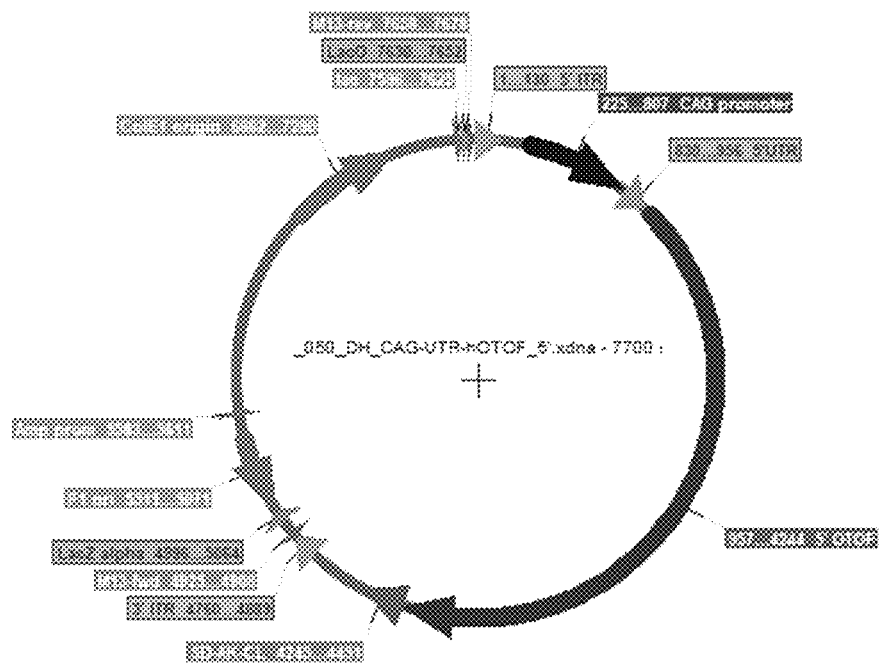
FIGS. 14A and 14B are maps of the 5' and 3' vectors in a dual hybrid vector system. The 5' vector contains AAV2 ITRs, a CAG promoter operably linked to the full-length human OTOF 5' UTR and exons 1-26 of a polynucleotide encoding the human OTOF protein of SEQ ID NO: 1, a splice donor sequence (SD), a recombinogenic region (AK), and a degradation signal sequence (CL1) (FIG. 14A). The 3' vector contains AAV2 ITRs, a recombinogenic region (AK), a degradation signal sequence (CL1), a splice acceptor sequence (SA), exons 27-48 of a polynucleotide encoding the human OTOF protein of SEQ ID NO: 1, the full-length human OTOF 3' UTR, and a WPRE sequence (SEQ ID NO: 23) (FIG. 14B).
Figure 14B:
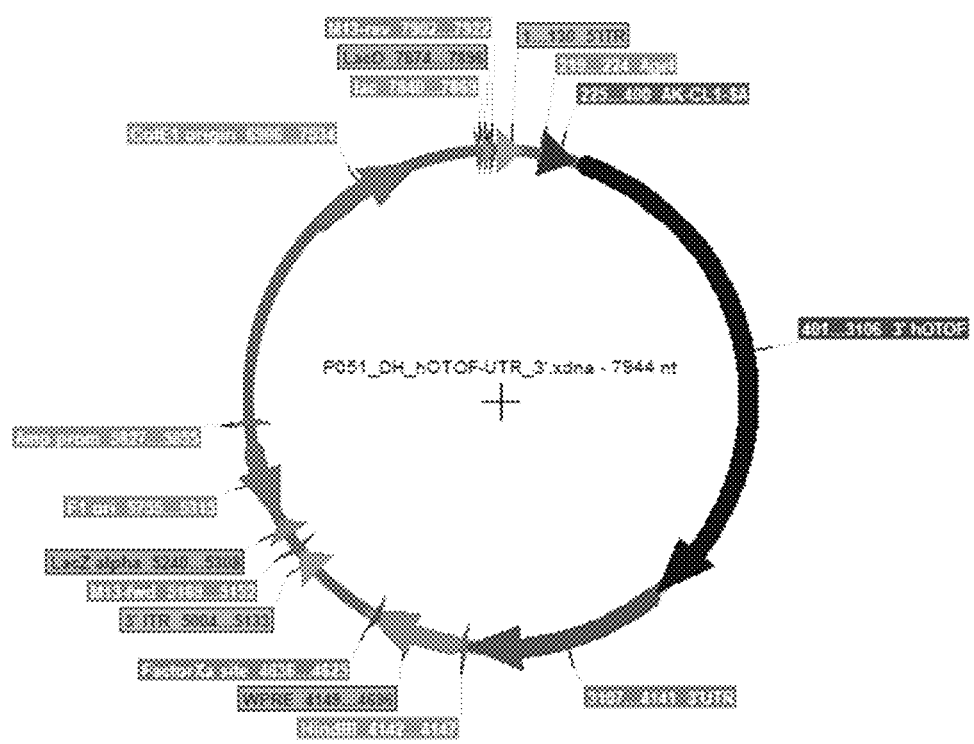
Figure 15A:
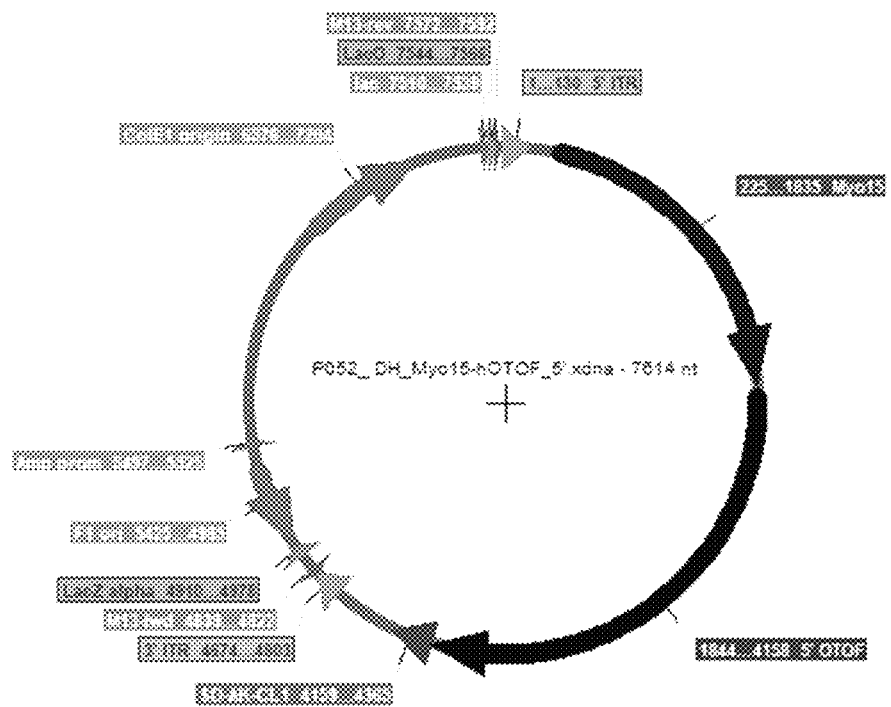
Figure 15B:
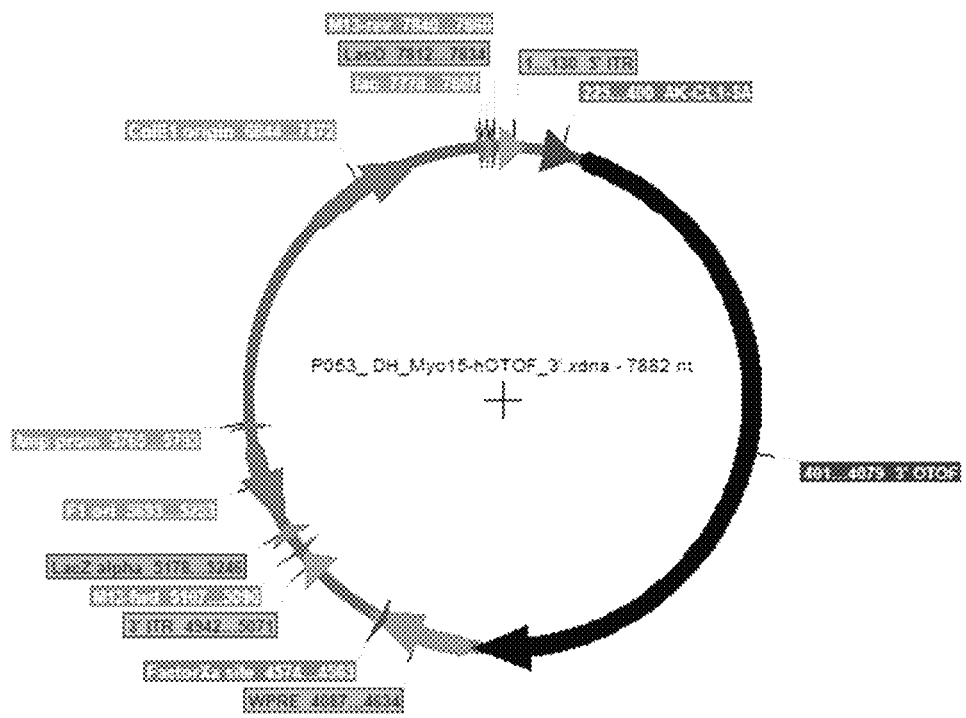

FIGS. 15A and 15B are maps of the 5' and 3' vectors in a dual hybrid vector system. The 5' vector contains AAV2 ITRs, a Myo15 promoter (SEQ ID NO: 36) operably linked to exons 1-19 of a polynucleotide encoding the human OTOF protein of SEQ ID NO: 1, a splice donor sequence (SD), a recombinogenic region (AK), and a degradation signal sequence (CL1) (FIG. 15A). The 3' vector contains AAV2 ITRs, a recombinogenic region (AK), a degradation signal sequence (CL1), a splice acceptor sequence (SA), exons 20-48 of a polynucleotide encoding the human OTOF protein of SEQ ID NO: 1, and a WPRE sequence (SEQ ID NO: 23) (FIG. 15B).

Figure 16A:
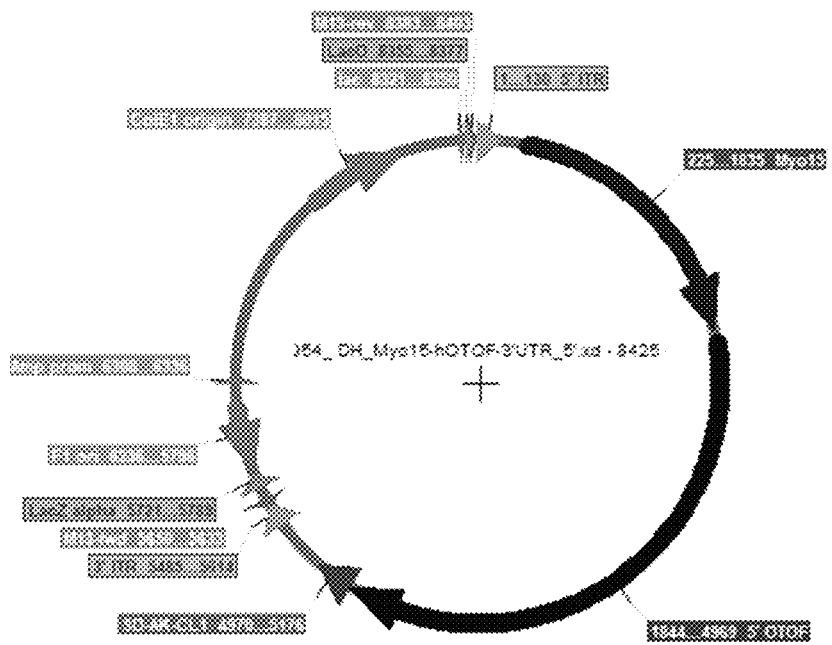
Figure 16B:
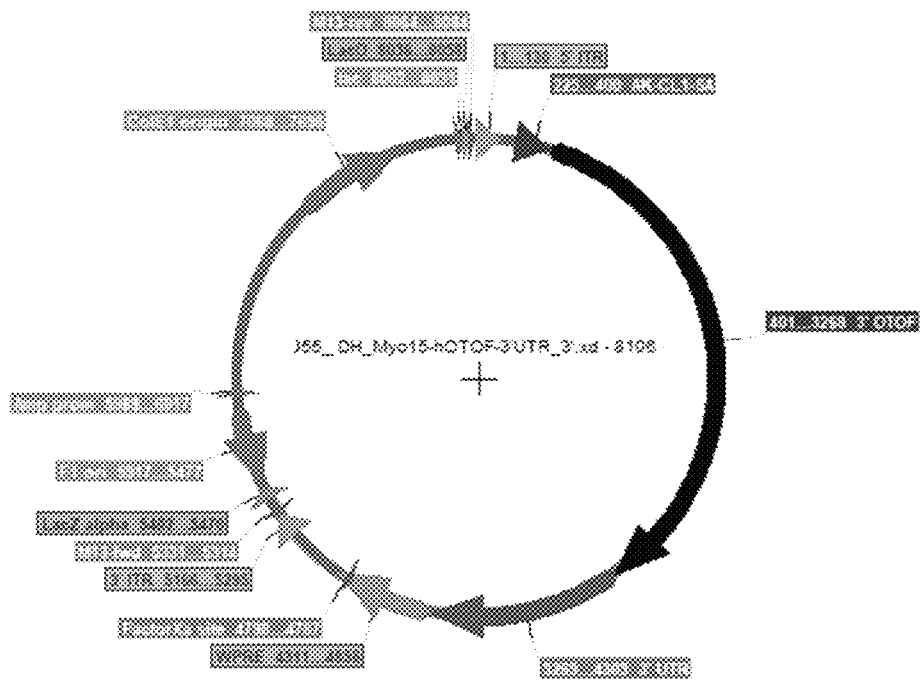

FIGS. 16A and 16B are maps of the 5' and 3' vectors in a dual hybrid vector system. The 5' vector contains AAV2 ITRs, a Myo15 promoter (SEQ ID NO: 36) operably linked to exons 1-25 of a polynucleotide encoding the human OTOF protein of SEQ ID NO: 1, a splice donor sequence (SD), a recombinogenic region (AK), and a degradation signal sequence (CL1) (FIG. 16A). The 3' vector contains AAV2 ITRs, a recombinogenic region (AK), a degradation signal sequence (CL1), a splice acceptor sequence (SA), exons 26-48 of a polynucleotide encoding the human OTOF protein of SEQ ID NO: 1, the full-length human OTOF 3' UTR, and a WPRE sequence (SEQ ID NO: 23) (FIG. 16B).

Figure 17A:
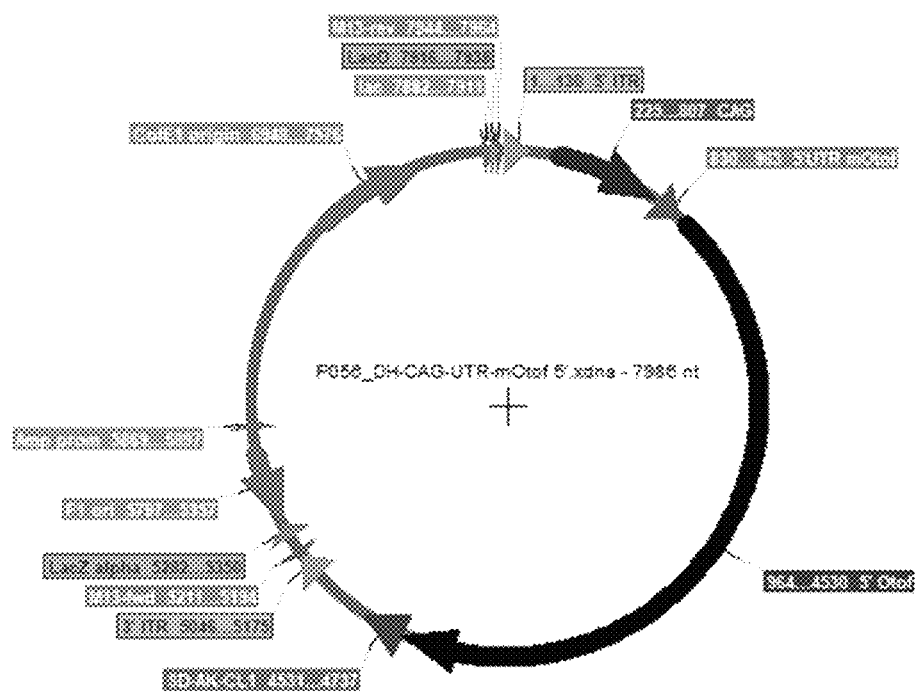
Figure 17B:
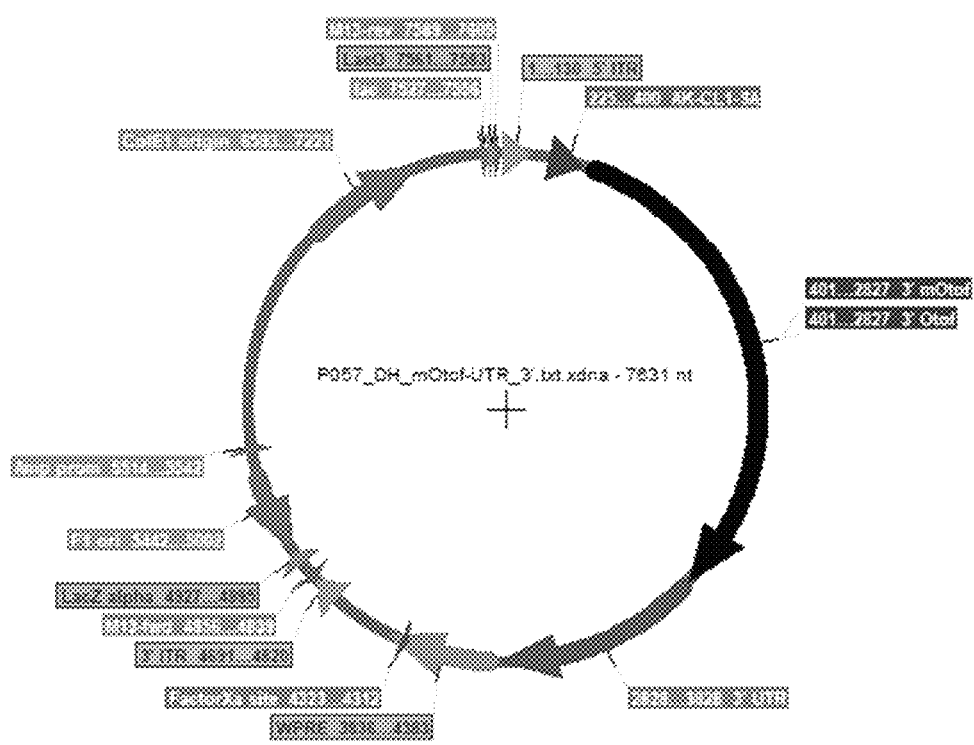

FIGS. 17A and 17B are maps of the 5' and 3' vectors in a dual hybrid vector system. The 5' vector contains AAV2 ITRs, a CAG promoter operably linked to the full-length mouse OTOF 5' UTR and exons 1-28 of a polynucleotide encoding the mouse OTOF protein of SEQ ID NO: 6, a splice donor sequence (SD), a recombinogenic region (AK), and a degradation signal sequence (CL1) (FIG. 17A). The 3' vector contains AAV2 ITRs, a recombinogenic region (AK), a degradation signal sequence (CL1), a splice acceptor sequence (SA), exons 29-48 of a polynucleotide encoding the mouse OTOF protein of SEQ ID NO: 6, the full-length mouse OTOF 3' UTR, and a WPRE sequence (SEQ ID NO: 23) (FIG. 17B).

Figure 18A:
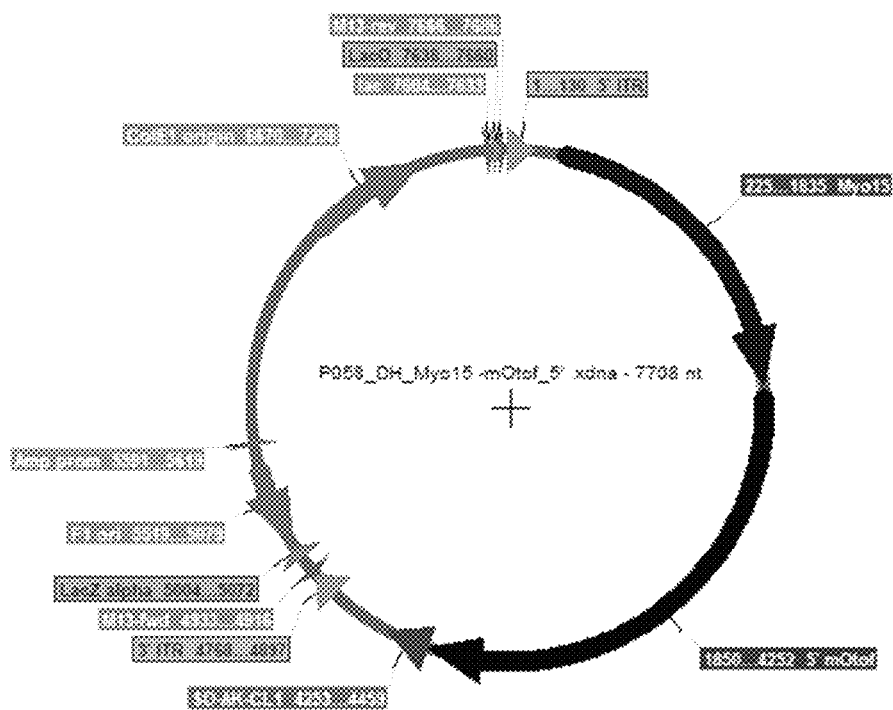
Figure 18B:
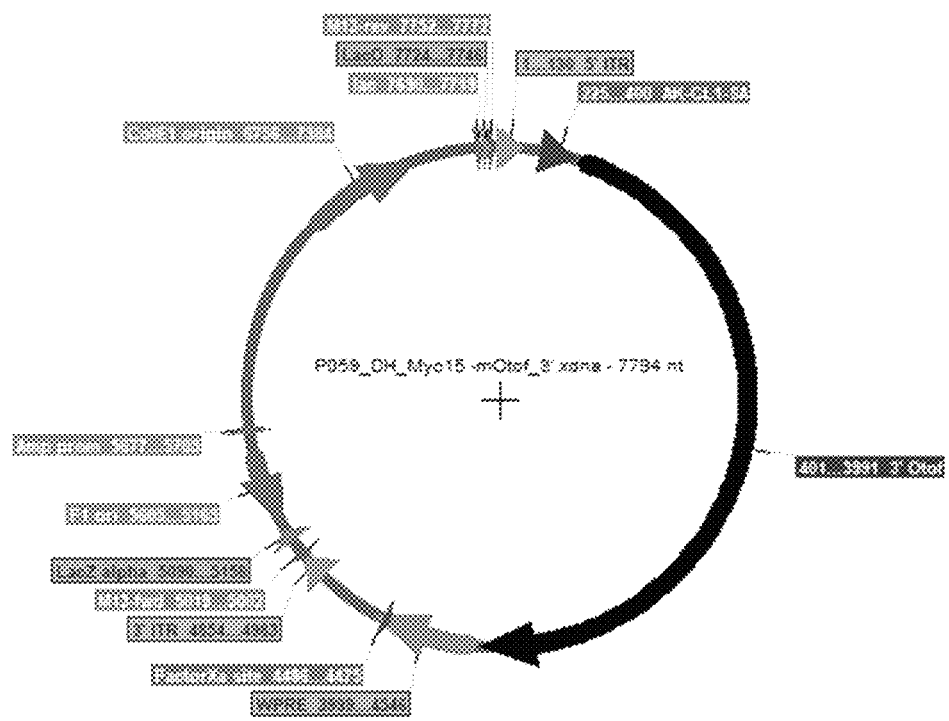

FIGS. 18A and 18B are maps of the 5' and 3' vectors in a dual hybrid vector system. The 5' vector contains AAV2 ITRs, a Myo15 promoter (SEQ ID NO: 36) operably linked to exons 1-20 of a polynucleotide encoding the mouse OTOF protein of SEQ ID NO: 6, a splice donor sequence (SD), a recombinogenic region (AK), and a degradation signal sequence (CL1) (FIG. 18A). The 3' vector contains AAV2 ITRs, a recombinogenic region (AK), a degradation signal sequence (CL1), a splice acceptor sequence (SA), exons 21-48 of a polynucleotide encoding the mouse OTOF protein of SEQ ID NO: 6, and a WPRE sequence (SEQ ID NO: 23) (FIG. 18B).

Figure 19A:
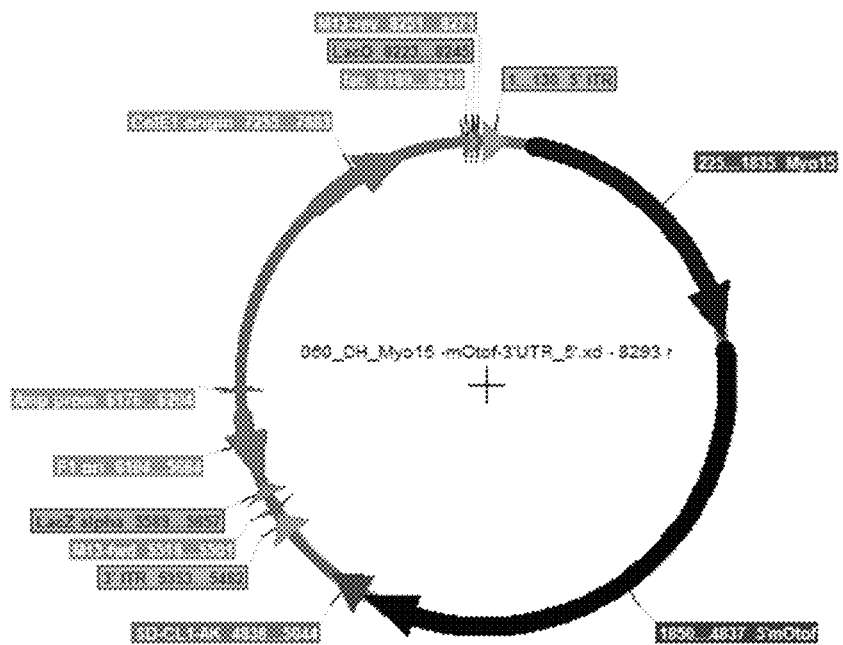
Figure 19B:
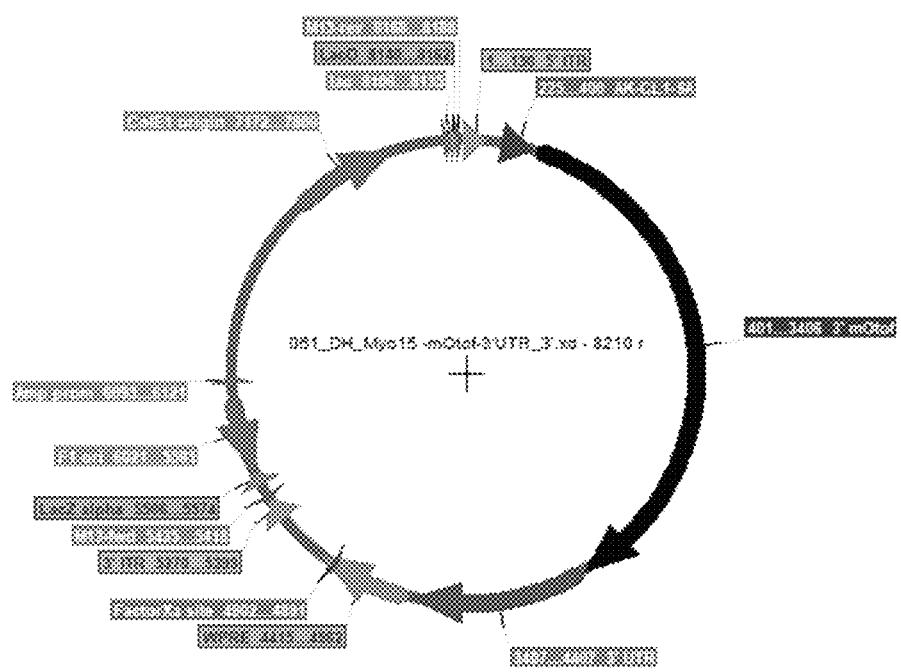

FIGS. 19A and 19B are maps of the 5' and 3' vectors in a dual hybrid vector system. The 5' vector contains AAV2 ITRs, a Myo15 promoter (SEQ ID NO: 36) operably linked to exons 1-24 of a polynucleotide encoding the mouse OTOF protein of SEQ ID NO: 6, a splice donor sequence (SD), a recombinogenic region (AK), and a degradation signal sequence (CL1) (FIG. 19A). The 3' vector contains AAV2 ITRs, a recombinogenic region (AK), a degradation signal sequence (CL1), a splice acceptor sequence (SA), exons 25-48 of a polynucleotide encoding the mouse OTOF protein of SEQ ID NO: 6, the full-length mouse OTOF 3' UTR, and a WPRE sequence (SEQ ID NO: 23) (FIG. 19B).

Figure 20A:
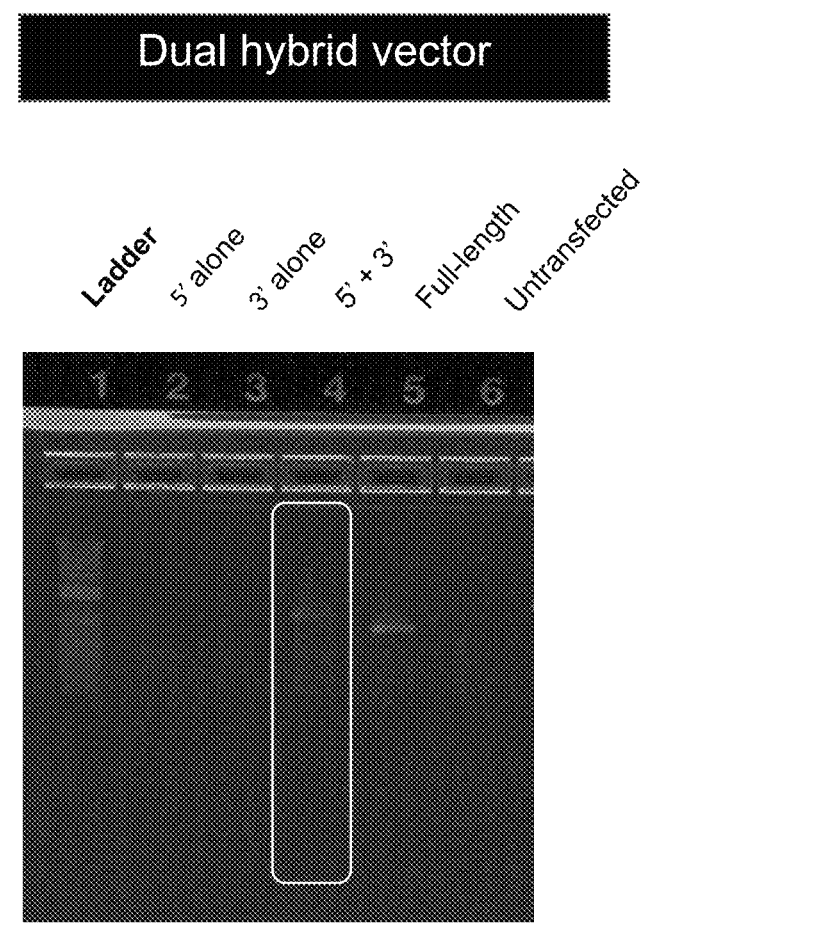
Figure 20A:
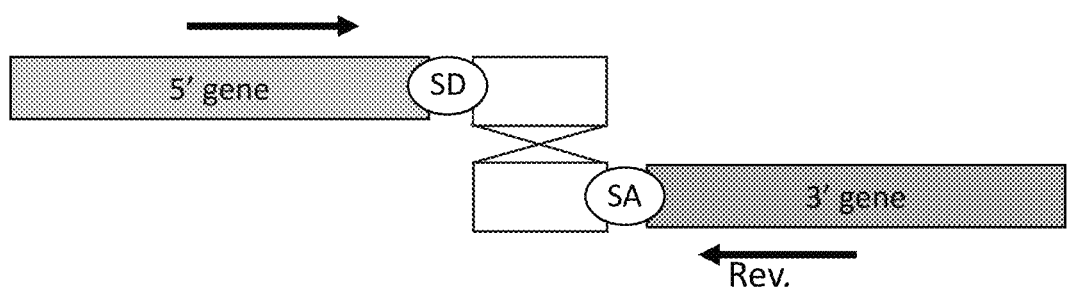
Figure 20B:
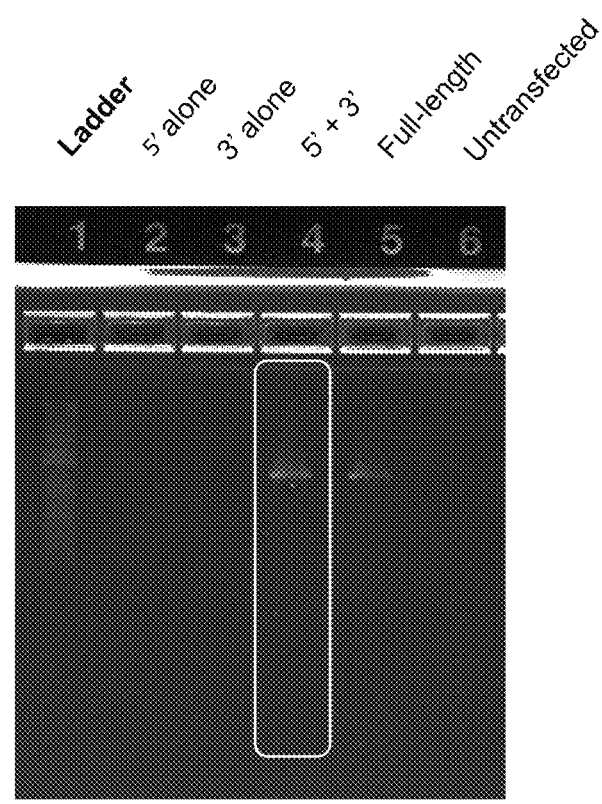
Figure 20B:
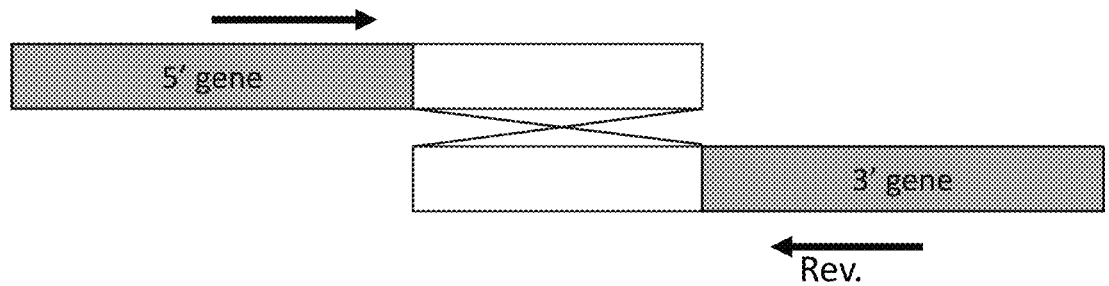

FIGS. 20A and 20B are images demonstrating that polynucleotides encoded by dual hybrid vectors (FIG. 20A) and overlapping vectors (FIG. 20B) undergo recombination in cell culture (top). Beneath each image is a schematic depicting the type of recombination that occurs in each dual vector system (bottom). Inner ear-derived House Ear Institute-Organ of Corti 1 (HEI-OC1) cells were transfected with plasmids containing either the 5' half of OTOF alone, the 3' half of OTOF alone, or both the 5' and 3' halves together. For the dual hybrid vector experiment, the 5' vector contained a Myo15 promoter (SEQ ID NO: 36) operably linked to exons 1-19 of a polynucleotide encoding the human OTOF protein of SEQ ID NO: 1, a splice donor sequence (SD), a recombinogenic region (AK), and a degradation signal sequence (CL1); and the 3' vector contained a recombinogenic region (AK), a degradation signal sequence (CL1), a splice acceptor sequence (SA), exons 20-48 of a polynucleotide encoding the human OTOF protein of SEQ ID NO: 1, and a WPRE sequence (SEQ ID NO: 23). For the overlapping dual vector experiment, the 5' vector contained a Myo15 promoter (SEQ ID NO: 36) operably linked to exons 1-21 of a polynucleotide encoding the human OTOF protein of SEQ ID NO: 1 and the 500 kb immediately 3' of the exon 21/22 boundary; and the 3' vector contained the 500 kb immediately 5' of the exon 21/22 boundary and exons 22-48 of a polynucleotide encoding the human OTOF protein of SEQ ID NO: 1, and a WPRE sequence (SEQ ID NO: 23). Full-length otoferlin was transfected as a positive control and untransfected cells were used a negative control. Genomic DNA was extracted from cells using a standard column from a gDNA isolation kit. PCR primers were designed to anneal outside of the region of splice sites or overlap and PCR was performed using standard molecular biology techniques. Amplicons were visualized using gel electrophoresis. The white box in the gel image indicates the lane in which 5' and 3' halves were transfected together and where a roughly 1 kb amplicon is seen, indicating recombination.

Figure 21A:
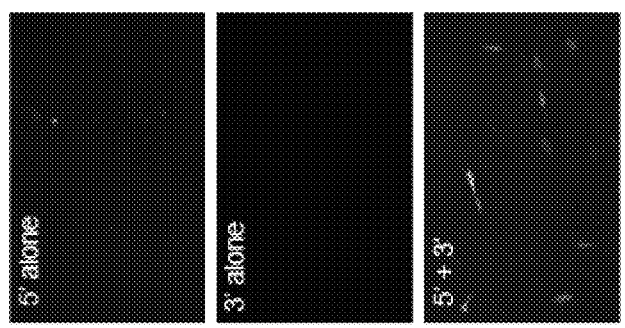
Figure 21A:
Figure 21B:
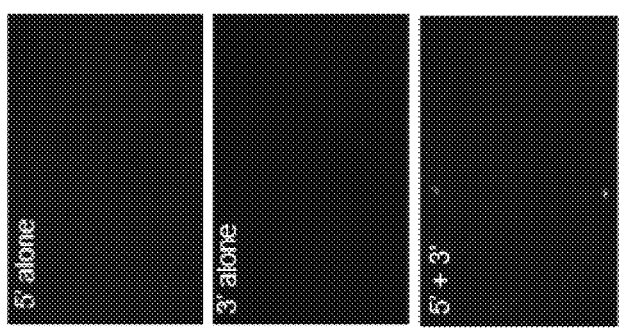
Figure 21B:
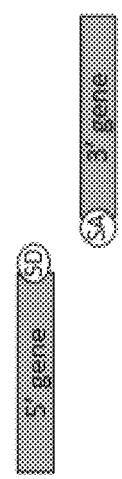
Figure 21C:
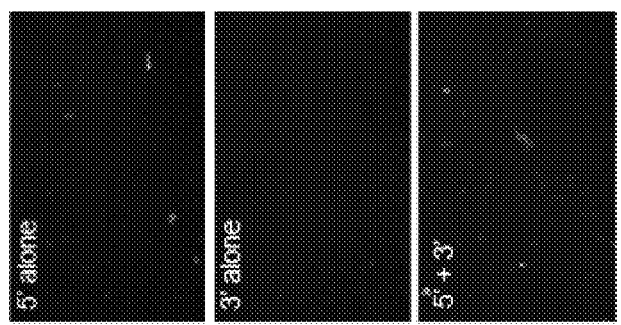
Figure 21C:
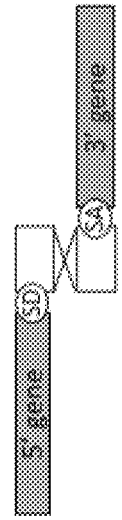

FIGS. 21A-21C are images demonstrating that polynucleotides encoded by dual hybrid vectors (FIG. 21A), trans-splicing vectors (FIG. 21B), and overlapping vectors (FIG. 21C) undergo recombination in cell culture and produce OTOF protein (top). Beneath each image is a schematic depicting the type of recombination that occurs in each dual vector system (bottom). Inner ear derived HEI-OC1 cells were transfected with plasmids containing either the 5' half of otoferlin alone, the 3' half of otoferlin alone, or both 5' and 3' halves together. For the dual hybrid vector experiment, the 5' vector contained a CAG promoter operably linked to the full-length human OTOF 5' UTR and exons 1-26 of a polynucleotide encoding the human OTOF protein of SEQ ID NO: 1, a splice donor sequence (SD), a recombinogenic region (AK), and a degradation signal sequence (CL1); and the 3' vector contained a recombinogenic region (AK), a degradation signal sequence (CL1), a splice acceptor sequence (SA), exons 27-48 of a polynucleotide encoding the human OTOF protein of SEQ ID NO: 1, the full-length human OTOF 3' UTR, and a WPRE sequence (SEQ ID NO: 23). For the trans-splicing dual vector experiment, the 5' vector contained a Myo15 promoter (SEQ ID NO: 36) operably linked to exons 1-24 of a polynucleotide encoding the mouse OTOF protein of SEQ ID NO: 6, and a splice donor sequence (SD); and the 3' vector contained a splice acceptor sequence (SA), exons 25-48 of a polynucleotide encoding the mouse OTOF protein of SEQ ID NO: 6, the full-length mouse OTOF 3' UTR, and a WPRE sequence (SEQ ID NO: 23). For the overlapping dual vector experiment, the 5' vector contained a CMV promoter operably linked to exons 1-24 of a polynucleotide encoding the mouse OTOF protein of SEQ ID NO: 6 and the 500 kb immediately 3' of the exon 24/25 boundary; and the 3' vector contained the 500 kb immediately 5' of the exon 24/25 boundary and exons 25-48 of a polynucleotide encoding the mouse OTOF protein of SEQ ID NO: 6, and a WPRE sequence (SEQ ID NO: 23). Cells were fixed in 4% PFA 48 hours post transfection and processed for immunohistochemistry. An antibody specific to OTOF protein labels some cells in the 5' alone transfected cells, no cells in the 3' alone transfected cells, and more cells than both previous conditions combined in the 5'+3' transfected cells.

Figure 22A:
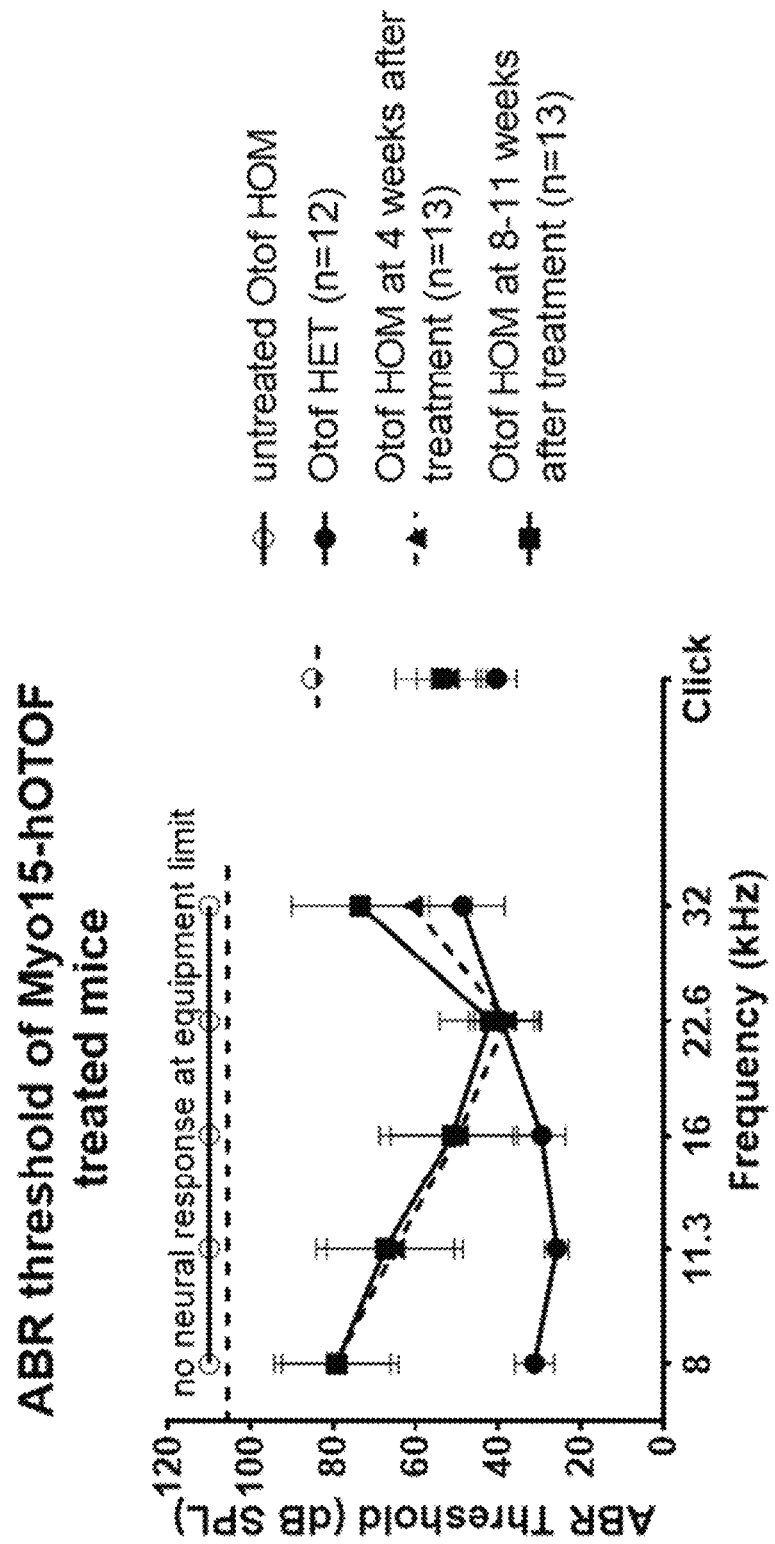
Figure 22B:
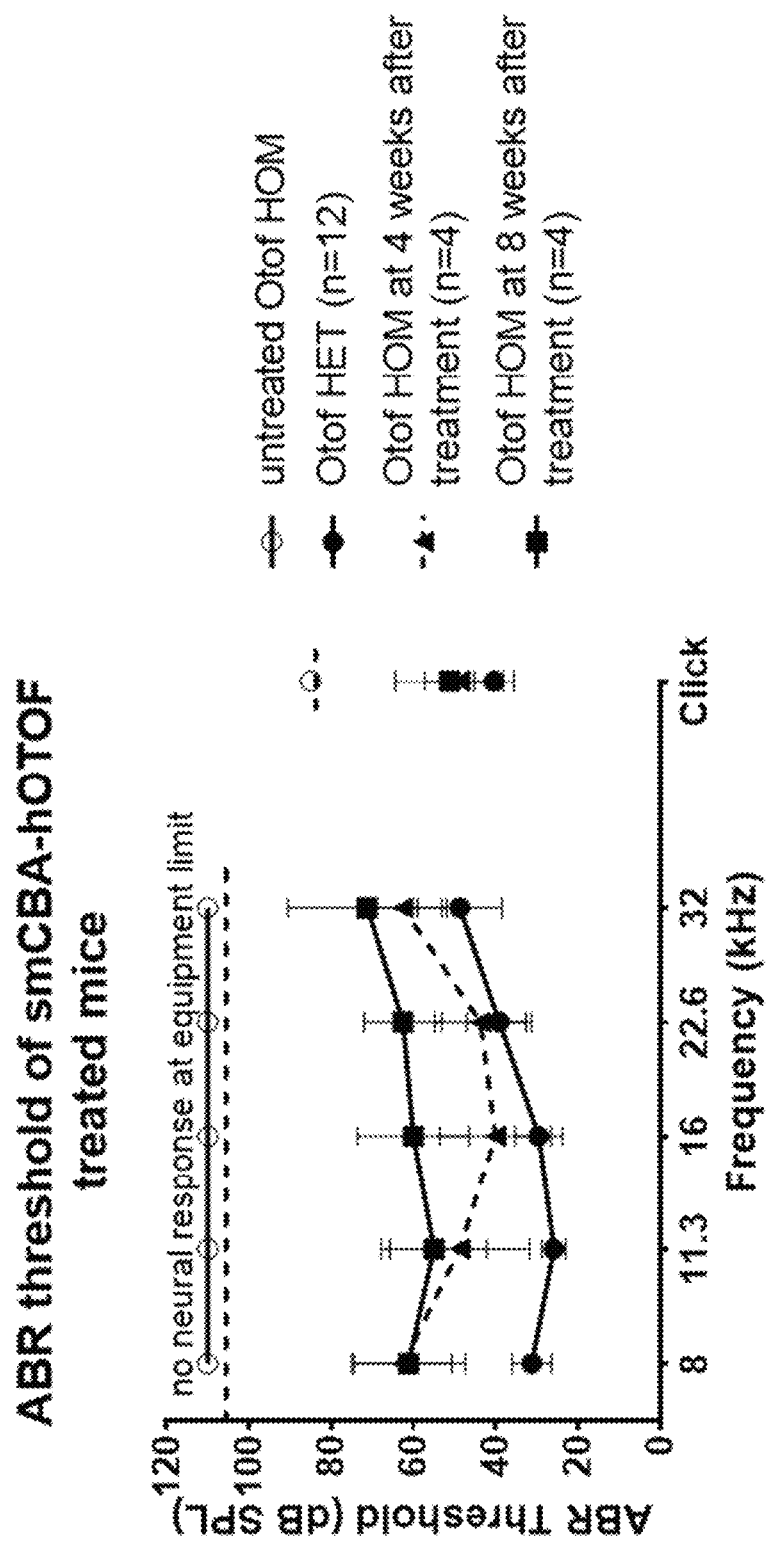
Figure 22C:
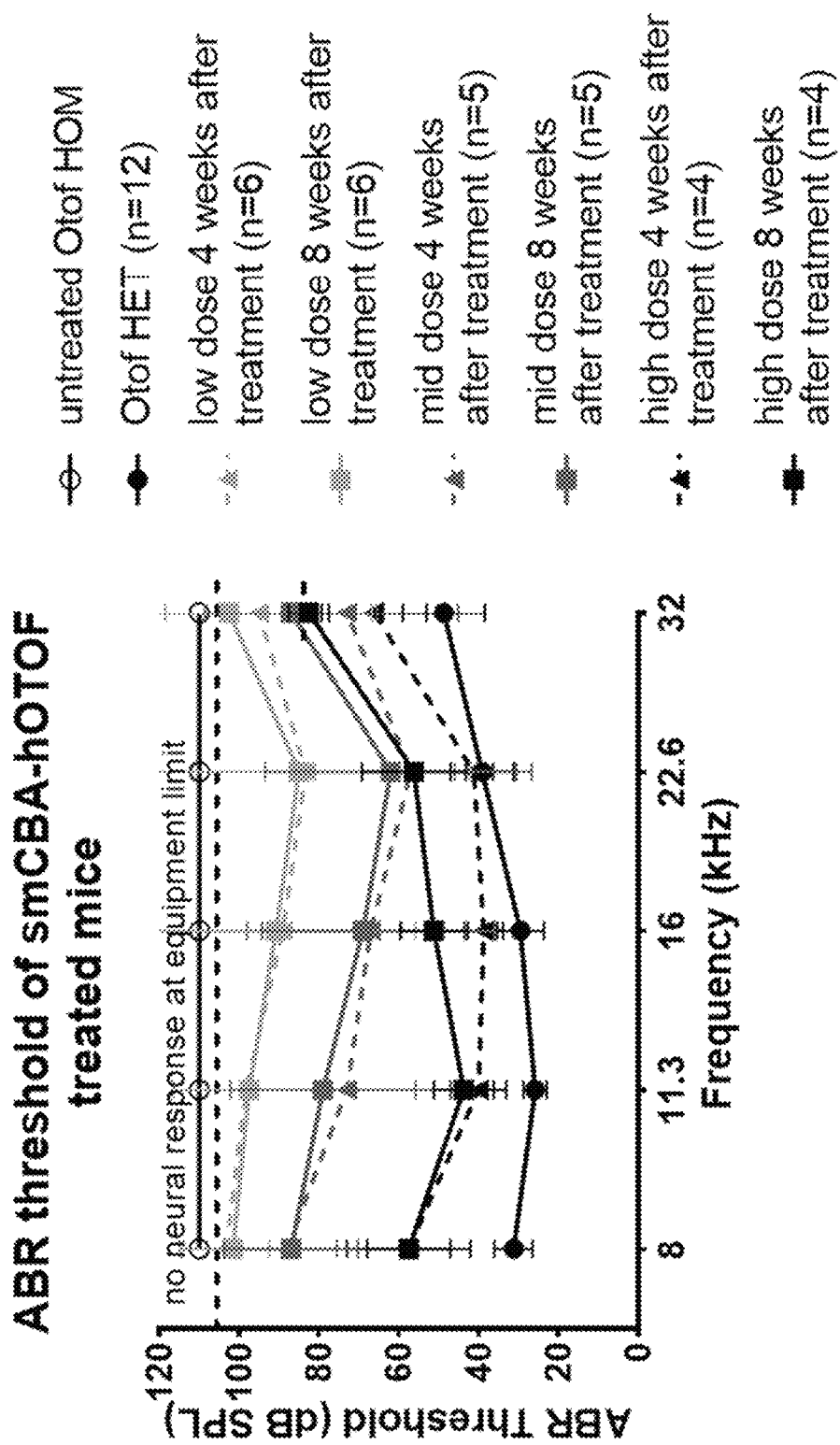

FIGS. 22A-22C are a series of graphs showing electrophysiological signatures of hearing function in mice treated with viral vectors expressing OTOF via dual hybrid vector systems. Homozygous OTOF-Q828X mice (a mouse model of human OTOF mutation p.Gln828Ter) were treated with an AAV1-Myo15 (SEQ ID NO: 38)-hOTOF (isoform 5, SEQ ID NO: 5) dual hybrid vector system by injection through the round window membrane and auditory brainstem response (ABR) thresholds were used to assess hearing function (FIG. 22A). Untreated animals (untreated Otof HOM) showed no detectable recovery in hearing function, whereas treated animals exhibited robust recovery, which was consistent from four weeks post-treatment (Otof HOM at 4 weeks after treatment) to eight weeks post-treatment (Otof HOM at 8-11 weeks after treatment). ABR thresholds from heterozygous mice (Otof HET) were also tested.

In another set of experiments, Homozygous OTOF-Q828X mice were treated with an AAV1-truncated chimeric CMV-chicken β-actin (smCBA)-hOTOF (isoform 5, SEQ ID NO: 5) dual hybrid vector system by injection through the round window membrane and ABR thresholds were used to assess hearing function as described above (FIG. 22B). Untreated animals showed no detectable recovery in hearing function, while treated animals exhibited a robust recovery at four weeks post-treatment (Otof HOM at 4 weeks after treatment). When the same mice were evaluated at eight weeks post-treatment (Otof HOM at 8 weeks after treatment), ABR thresholds increased, suggesting less durable recovery with the smCBA promoter. ABR thresholds from heterozygous mice were also tested.

In yet another set of experiments, homozygous OTOF-Q828X mice were treated with an AAV1-smCBA-hOTOF (isoform 5, SEQ ID NO: 5) dual hybrid vector system by injection through the round window membrane at low, medium (mid), and high doses and ABR thresholds were used to assess hearing function at four weeks and eight weeks post-treatment (FIG. 22C). A dose-dependent recovery in ABR thresholds was observed at both timepoints. When comparing the eight weeks versus the four weeks timepoints, recovery was steady for the low and mid doses, but decreased for the high dose animals. ABR thresholds for HET animals were also tested.

DETAILED DESCRIPTION

Described herein are compositions and methods for the treatment of sensorineural hearing loss or auditory neuropathy in a subject (such as a mammalian subject, for instance, a human) by administering a first nucleic acid vector containing a promoter and a polynucleotide encoding an N-terminal portion of an otoferlin (OTOF) protein (e.g., a wild-type (WT) OTOF protein) and a second nucleic acid vector containing a polynucleotide encoding a C-terminal portion of an OTOF protein and a polyadenylation (poly(A)) sequence. When introduced into a mammalian cell, such as a cochlear hair cell, the polynucleotides encoded by the two nucleic acid vectors can combine to form a nucleic acid molecule that encodes the full-length OTOF protein. The compositions and methods described herein can, therefore, be used to induce or increase expression of WT OTOF in cochlear hair cells of a subject who has an OTOF deficiency (e.g., low OTOF expression or an OTOF mutation that impairs OTOF expression or function).

Otofelin

OTOF is a 230 kDa membrane protein that contains at least six C2 domains implicated in calcium, phospholipid, and protein binding. It is encoded by a gene that contains 48 exons, and the full-length protein is made up of 1,997 amino acids. OTOF is located at ribbon synapses in inner hair cells, where it is believed to function as a calcium sensor in synaptic vesicle fusion, triggering the fusion of neurotransmitter-containing vesicles with the plasma membrane. It has also been implicated in vesicle replenishment and clathrin-mediated endocytosis, and has been shown to interact with Myosin VI, Rab8b, SNARE proteins, calcium channel Cav1.3, Ergic2, and AP-2. The mechanism by which OTOF mediates exocytosis and the physiological significance of its interactions with its binding partners remain to be determined.

Otoferlin-Associated Hearing Loss

OTOF was first identified by a study investigating the genetics of a non-syndromic form of deafness, autosomal recessive deafness-9 (DFNB9). Mutations in OTOF have since been found to cause sensorineural hearing loss in patients throughout the world, with many patients carrying OTOF mutations having auditory neuropathy, a disorder in which the inner ear detects sound, but is unable to properly transmit sound from the ear to the brain. These patients have an abnormal auditory brainstem response (ABR) and impaired speech discrimination with initially normal otoacoustic emissions. Patients carrying homozygous or compound heterozygous mutations often develop hearing loss in early childhood, and the severity of hearing impairment has been found to vary with the location and type of mutation in OTOF.

The compositions and methods described herein can be used to treat sensorineural hearing loss or auditory neuropathy by administering a first nucleic acid vector containing a polynucleotide encoding an N-terminal portion of an OTOF protein and a second nucleic acid vector containing a polynucleotide encoding a C-terminal portion of an OTOF protein. The full-length OTOF coding sequence is too large to include in the type of vector that is commonly used for gene therapy (e.g., an adeno-associated virus (AAV) vector, which is thought to have a packaging limit of 5 kb). The compositions and methods described herein overcome this problem by dividing the OTOF coding sequence between two different nucleic acid vectors that can recombine in a cell to reconstitute the full-length OTOF sequence. These compositions and methods can be used to treat subjects having one or more mutations in the OTOF gene, e.g., an OTOF mutation that reduces OTOF expression, reduces OTOF function, or is associated with hearing loss. When the first and second nucleic acid vectors are administered in a composition, the polynucleotides encoding the N-terminal and C-terminal portions of OTOF can combine within a cell (e.g., a human cell, e.g., a cochlear hair cell) to form a single nucleic acid molecule that contains the full-length OTOF coding sequence (e.g., through homologous recombination and/or splicing).

The nucleic acid vectors used in the compositions and methods described herein include nucleic acid sequences that encode wild-type OTOF, or a variant thereof, such as a nucleic acid sequences that, when combined, encode a protein having at least 85% sequence identity (e.g., 85%, 90%, 95%, 96%, 97, 98%, 99, or more, sequence identity) to the amino acid sequence of wild-type human or mouse OTOF. The polynucleotides used in the nucleic acid vectors described herein encode an N-terminal portion and a C-terminal portion of an OTOF amino acid sequence in Table 2 below (e.g., two portions that, when combined, encode a full-length OTOF amino acid sequence listed in Table 2, e.g., any one of SEQ ID NOs: 1-5).

According to the methods described herein, a subject can be administered a composition containing a first nucleic acid vector and a second nucleic acid vector that encode an N-terminal and C-terminal portion, respectively, of a nucleic acid sequence encoding the amino acid sequence of any one of SEQ ID NOs: 1-5, or a nucleic acid sequence encoding an amino acid sequence having at least 85% sequence identity (e.g., 85%, 90%, 95%, 96%, 97%, 98%, 99%, or more, sequence identity) to the amino acid sequence of any one of SEQ ID NOs: 1-5, or a nucleic acid sequence encoding an amino acid sequence that contains one or more conservative amino acid substitutions relative to any one of SEQ ID NOs: 1-5 (e.g., 1, 2, 3, 4, 5, 6, 7, 8, 9, or 10 or more conservative amino acid substitutions), provided that the OTOF analog encoded retains the therapeutic function of wild-type OTOF (e.g., the ability to regulate exocytosis at ribbon synapses).

TABLE 2

OTOF Sequences

| SEQ ID NO. | Sequence Name | Sequence |
|---|---|---|
| 1 | OTOF-201 protein (NP_919224.1), human otoferlin isoform a, 1997 aa | MALLIHLKTVSELRGRGDRIAKVTFRGQSFYSRVLENCEDVADFDE TFRWPVASSIDRNEMLEIQVFNYSKVFSNKLIGTFRMVLQKVVEES HVEVTDTLIDDNNAIIKTSLCVEVRYQATDGTVGSWDDGDFLGDES LQEEEKDSQETDGLLPGSRPSSRPPGEKSFRRAGRSVFSAMKLGK NRSHKEEPQRPDEPAVLEMEDLDHLAIRLGDGLDPDSVSLASVTAL TTNVSNKRSKPDIKMEPSAGRPMDYQVSITVIEARQLVGLNMDPVV CVEVGDDKKYTSMKESTNCPYYNEYFVFDPHVSPDVMFDKIIKISVI HSKNLLRSGTLVGSFKMDVGTVYSQPEHQFHHKWAILSDPDDISS GLKGYVKCDVAVVGKGDNIKTPHKANETDEDDIEGNLLLPEGVPPE RQWARFYVKIYRAEGLPRMNTSLMANVKKAFIGENKDLVDPYVQV FFAGQKGKTSVQKSSYEPLWNEQVVFTDLFPPLCKRMKVQIRDSD KVNDVAIGTHFIDLRKISNDGDKGFLPTLGPAWVNMYGSTRNYTLL DEHQDLNEGLGEGVSFRARLLLGLAVEIVDTSNPELTSSTEVQVEQ ATPISESCAGKMEEFFLFGAFLEASMIDRRNGDKPITFEVTIGNYGN EVDGLSRPQRPRPRKEPGDEEEVDLIQNASDDEAGDAGDLASVSS TPPMRPQVTDRNYFHLPYLERKPCIYIKSWWPDQRRRLYNANIMD HIADKLEEGLNDIQEMIKTEKSYPERRLRGVLEELSCGCCRFLSLAD KDQGHSSRTRLDRERLKSCMRELENMGQQARMLRAQVKRHTVRD KLRLCQNFLQKLRFLADEPQHSIPDIFIWMMSNNKRVAYARVPSKD LLFSIVEEETGKDCAKVKTLFLKLPGKRGFGSAGWTVQAKVELYLW LGLSKQRKEFLCGLPCGFQEVKAAQGLGLHAFPPVSLVYTKKQAF QLRAHMYQARSLFAADSSGLSDPFARVFFINQSQCTEVLNETLCPT WDQMLVFDNLELYGEAHELRDDPPIIVIEIYDQDSMGKADFMGRTF AKPLVKMADEAYCPPRFPPQLEYYQIYRGNATAGDLLAAFELLQIG PAGKADLPPINGPVDVDRGPIMPVPMGIRPVLSKYRVEVLFWGLRD LKRVNLAQVDRPRVDIECAGKGVQSSLIHNYKKNPNFNTLVKWFEV DLPENELLHPPLNIRVVDCRAFGRYTLVGSHAVSSLRRFIYRPPDRS APSWNTTVRLLRRCRVLCNGGSSSHSTGEVVVTMEPEVPIKKLET MVKLDATSEAVVKVDVAEEEKEKKKKKKGTAEEPEEEEPDESMLD WWSKYFASIDTMKEQLRQQEPSGIDLEEKEEVDNTEGLKGSMKGK EKARAAKEEKKKKTQSSGSGQGSEAPEKKKPKIDELKVYPKELESE FDNFEDWLHTFNLLRGKTGDDEDGSTEEERIVGRFKGSLCVYKVPL PEDVSREAGYDSTYGMFQGIPSNDPINVLVRVYVVRATDLHPADIN GKADPYIAIRLGKTDIRDKENYISKQLNPVFGKSFDIEASFPMESMLT VAVYDWDLVGTDDLIGETKIDLENRFYSKHRATCGIAQTYSTHGYNI WRDPMKPSQILTRLCKDGKVDGPHFGPPGRVKVANRVFTGPSEIE DENGQRKPTDEHVALLALRHWEDIPRAGCRLVPEHVETRPLLNPD KPGIEQGRLELWVDMFPMDMPAPGTPLDISPRKPKKYELRVIIWNT DEVVLEDDDFFTGEKSSDIFVRGWLKGQQEDKQDTDVHYHSLTGE GNFNWRYLFPFDYLAAEEKIVISKKESMFSWDETEYKIPARLTLQIW DADHFSADDFLGAIELDLNRFPRGAKTAKQCTMEMATGEVDVPLV SIFKQKRVKGWWPLLARNENDEFELTGKVEAELHLLTAEEAEKNPV GLARNEPDPLEKPNRPDTSFIWFLNPLKSARYFLWHTYRWLLLKLL LLLLLLLLLALFLYSVPGYLVKKILGA |
| 2 | OTOF-202 protein (NP_004793.2), human otoferlin isoform b, 1230 aa | MIKTEKSYPERRLRGVLEELSCGCCRFLSLADKDQGHSSRTRLDRE RLKSCMRELENMGQQARMLRAQVKRHTVRDKLRLCQNFLQKLRF LADEPQHSIPDIFIWMMSNNKRVAYARVPSKDLLFSIVEEETGKDCA KVKTLFLKLPGKRGFGSAGWTVQAKVELYLWLGLSKQRKEFLCGL PCGFQEVKAAQGLGLHAFPPVSLVYTKKQAFQLRAHMYQARSLFA ADSSGLSDPFARVFFINQSQCTEVLNETLCPTWDQMLVFDNLELYG EAHELRDDPPIIVIEIYDQDSMGKADFMGRTFAKPLVKMADEAYCPP RFPPQLEYYQIYRGNATAGDLLAAFELLQIGPAGKADLPPINGPVDV DRGPIMPVPMGIRPVLSKYRVEVLFWGLRDLKRVNLAQVDRPRVDI ECAGKGVQSSLIHNYKKNPNFNTLVKWFEVDLPENELLHPPLNIRV VDCRAFGRYTLVGSHAVSSLRRFIYRPPDRSAPSWNTTGEVVVTM EPEVPIKKLETMVKLDATSEAVVKVDVAEEEKEKKKKKKGTAEEPE |

TABLE 2-continued

OTOF Sequences

| SEQ ID NO. | Sequence Name | Sequence |
|---|---|---|
| | | EEEPDESMLDWWSKYFASIDTMKEQLRQQEPSGIDLEEKEEVDNT EGLKGSMKGKEKARAAKEEKKKKTQSSGSGQGSEAPEKKKPKIDE LKVYPKELESEFDNFEDWLHTFNLLRGKTGDDEDGSTEEERIVGRF KGSLCVYKVPLPEDVSREAGYDSTYGMFQGIPSNDPINVLVRVYVV RATDLHPADINGKADPYIAIRLGKTDIRDKENYISKQLNPVFGKSFDI EASFPMESMLTVAVYDWDLVGTDDLIGETKIDLENRFYSKHRATCG IAQTYSTHGYNIWRDPMKPSQILTRLCKDGKVDGPHFGPPGRVKVA NRVFTGPSEIEDENGQRKPTDEHVALLALRHWEDIPRAGCRLVPEH VETRPLLNPDKPGIEQGRLELWVDMFPMDMPAPGTPLDISPRKPKK YELRVIIWNTDEVVLEDDDFFTGEKSSDIFVRGWLKGQQEDKQDTD VHYHSLTGEGNFNWRYLFPFDYLAAEEKIVISKKESMFSWDETEYKI PARLTLQIWDADHFSADDFLGAIELDLNRFPRGAKTAKQCTMEMAT GEVDVPLVSIFKQKRVKGWWPLLARNENDEFELTGKVEAELHLLTA EEEAEKNPVGLARNEPDPLEKPNRPDTSFIWFLNPLKSARYFLWHTY RWLLLKLLLLLLLLLLLALFLYSVPGYLVKKILGA |
| 3 | OTOF-203 protein (NP_919304.1), human otoferlin isoform d, 1230 aa | MIKTEKSYPERRLRGVLEELSCGCCRFLSLADKDQGHSSRTRLDRE RLKSCMRELENMGQQARMLRAQVKRHTVRDKLRLCQNFLQKLRF LADEPQHSIPDIFIWMMSNNKRVAYARVPSKDLLFSIVEEETGKDCA KVKTLFLKLPGKRGFGSAGWTVQAKVELYLWLGLSKQRKEFLCGL PCGFQEVKAAQGLGLHAFPPVSLVYTKKQAFQLRAHMYQARSLFA ADSSGLSDPFARVFFINQSQCTEVLNETLCPTWDQMLVFDNLELYG EAHELRDDPPIIVIEIYDQDSMGKADFMGRTFAKPLVKMADEAYCPP RFPPQLEYYQIYRGNATAGDLLAAFELLQIGPAGKADLPPINGPVDV DRGPIMPVPMGIRPVLSKYRVEVLFWGLRDLKRVNLAQVDRPRVDI ECAGKGVQSSLIHNYKKNPNFNTLVKWFEVDLPENELLHPPLNIRV VDCRAFGRYTLVGSHAVSSLRRFIYRPPDRSAPSWNTTGEVVVTM EPEVPIKKLETMVKLDATSEAVVKVDVAEEEKEKKKKKKGTAEEPE EEEPDESMLDWWSKYFASIDTMKEQLRQQEPSGIDLEEKEEVDNT EGLKGSMKGKEKARAAKEEKKKKTQSSGSGQGSEAPEKKKPKIDE LKVYPKELESEFDNFEDWLHTFNLLRGKTGDDEDGSTEEERIVGRF KGSLCVYKVPLPEDVSREAGYDSTYGMFQGIPSNDPINVLVRVYVV RATDLHPADINGKADPYIAIRLGKTDIRDKENYISKQLNPVFGKSFDI EASFPMESMLTVAVYDWDLVGTDDLIGETKIDLENRFYSKHRATCG IAQTYSTHGYNIWRDPMKPSQILTRLCKDGKVDGPHFGPPGRVKVA NRVFTGPSEIEDENGQRKPTDEHVALLALRHWEDIPRAGCRLVPEH VETRPLLNPDKPGIEQGRLELWVDMFPMDMPAPGTPLDISPRKPKK YELRVIIWNTDEVVLEDDDFFTGEKSSDIFVRGWLKGQQEDKQDTD VHYHSLTGEGNFNWRYLFPFDYLAAEEKIVISKKESMFSWDETEYKI PARLTLQIWDADHFSADDFLGAIELDLNRFPRGAKTAKQCTMEMAT GEVDVPLVSIFKQKRVKGWWPLLARNENDEFELTGKVEAELHLLTA EEEAEKNPVGLARNEPDPLEKPNRPDTAFVWFLNPLKSIKYLICTRYK WLIIKIVLALLGLLMLGLFLYSLPGYMVKKLLGA |
| 4 | OTOF-208 protein (NP_919303.1), human otoferlin isoform c, 1307 aa | MMTDTQDGPSESSQIMRSLTPLINREEAFGEAGEAGLWPSITHTPD SQEEGLNDIQEMIKTEKSYPERRLRGVLEELSCGCCRFLSLADKDQ GHSSRTRLDRERLKSCMRELENMGQQARMLRAQVKRHTVRDKLR LCQNFLQKLRFLADEPQHSIPDIFIWMMSNNKRVAYARVPSKDLLFS IVEEETGKDCAKVKTLFLKLPGKRGFGSAGWTVQAKVELYLWLGLS KQRKEFLCGLPCGFQEVKAAQGLGLHAFPPVSLVYTKKQAFQLRA HMYQARSLFAADSSGLSDPFARVFFINQSQCTEVLNETLCPTWDQ MLVFDNLELYGEAHELRDDPPIIVIEIYDQDSMGKADFMGRTFAKPL VKMADEAYCPPRFPPQLEYYQIYRGNATAGDLLAAFELLQIGPAGK ADLPPINGPVDVDRGPIMPVPMGIRPVLSKYRVEVLFWGLRDLKRV NLAQVDRPRVDIECAGKGVQSSLIHNYKKNPNFNTLVKWFEVDLPE NELLHPPLNIRVVDCRAFGRYTLVGSHAVSSLRRFIYRPPDRSAPS WNTTVRLLRRCRVLCNGGSSSHSTGEVVVTMEPEVPIKKLETMVK LDATSEAVVKVDVAEEEKEKKKKKKGTAEEPEEEEPDESMLDWWS KYFASIDTMKEQLRQQEPSGIDLEEKEEVDNTEGLKGSMKGKEKAR AAKEEKKKKTQSSGSGQGSEAPEKKKPKIDELKVYPKELESEFDNF EDWLHTFNLLRGKTGDDEDGSTEEERIVGRFKGSLCVYKVPLPED VSREAGYDSTYGMFQGIPSNDPINVLVRVYVVRATDLHPADINGKA DPYIAIRLGKTDIRDKENYISKQLNPVFGKSFDIEASFPMESMLTVAV YDWDLVGTDDLIGETKIDLENRFYSKHRATCGIAQTYSTHGYNIWR DPMKPSQILTRLCKDGKVDGPHFGPPGRVKVANRVFTGPSEIEDE NGQRKPTDEHVALLALRHWEDIPRAGCRLVPEHVETRPLLNPDKP GIEQGRLELWVDMFPMDMPAPGTPLDISPRKPKKYELRVIIWNTDE VVLEDDDFFTGEKSSDIFVRGWLKGQQEDKQDTDVHYHSLTGEGN FNWRYLFPFDYLAAEEKIVISKKESMFSWDETEYKIPARLTLQIWDA DHFSADDFLGAIELDLNRFPRGAKTAKQCTMEMATGEVDVPLVSIF KQKRVKGWWPLLARNENDEFELTGKVEAELHLLTAEEEAEKNPVGL ARNEPDPLEKPNRPDTSFIWFLNPLKSARYFLWHTYRWLLLKLLLLL LLLLLLALFLYSVPGYLVKKILGA |

TABLE 2-continued

OTOF Sequences

| SEQ ID NO. | Sequence Name | Sequence |
|---|---|---|
| 5 | OTOF-205 protein (NP_001274418.1), human otoferlin isoform e, 1997 aa | MALLIHLKTVSELRGRGDRIAKVTFRGQSFYSRVLENCEDVADFDE<br>TFRWPVASSIDRNEMLEIQVFNYSKVFSNKLIGTFRMVLQKVVEES<br>HVEVTDTLIDDNNAIIKTSLCVEVRYQATDGTVGSWDDGDFLGDES<br>LQEEEKDSQETDGLLPGSRPSSRPPGEKSFRRAGRSVFSAMKLGK<br>NRSHKEEPQRPDEPAVLEMEDLDHLAIRLGDGLDPDSVSLASVTAL<br>TTNVSNKRSKPDIKMEPSAGRPMDYQVSITVIEARQLVGLNMDPVV<br>CVEVGDDKKYTSMKESTNCPYYNEYFVFDFHVSPDVMFDKIIKISVI<br>HSKNLLRSGTLVGSFKMDVGTVYSQPEHQFHHKWAILSDPDDISS<br>GLKGYVKCDVAVVGKGDNIKTPHKANETDEDDIEGNLLLPEGVPPE<br>RQWARFYVKIYRAEGLPRMNTSLMANVKKAFIGENKDLVDPYVQV<br>FFAGQKGKTSVQKSSYEPLWNEQVVFTDLFPPLCKRMKVQIRDSD<br>KVNDVAIGTHFIDLRKISNDGDKGFLPTLGPAWVNMYGSTRNYTLL<br>DEHQDLNEGLGEGVSFRARLLLGLAVEIVDTSNPELTSSTEVQVEQ<br>ATPISESCAGKMEEFFLFGAFLEASMIDRRNGDKPITFEVTIGNYGN<br>EVDGLSRPQRPRPRKEPGDEEEVDLIQNASDDEAGDAGDLASVSS<br>TPPMRPQVTDRNYFHLPYLERKPCIYIKSWWPDQRRRLYNANIMD<br>HIADKLEEGLNDIQEMIKTEKSYPERRLRGVLEELSCGCCRFLSLAD<br>KDQGHSSRTRLDRERLKSCMRELENMGQQARMLRAQVKRHTVRD<br>KLRLCQNFLQKLRFLADEPQHSIPDIFIWMMSNNKRVAYARVPSKD<br>LLFSIVEEETGKDCAKVKTLFLKLPGKRGFGSAGWTVQAKVELYLW<br>LGLSKQRKEFLCGLPCGFQEVKAAQGLGLHAFPPVSLVYTKKQAF<br>QLRAHMYQARSLFAADSSGLSDPFARVFFINQSQCTEVLNETLCPT<br>WDQMLVFDNLELYGEAHELRDDPPIIVIEIYDQDSMGKADFMGRTF<br>AKPLVKMADEAYCPPRFPPQLEYYQIYRGNATAGDLLAAFELLQIG<br>PAGKADLPPINGPVDVDRGPIMPVPMGIRPVLSKYRVEVLFWGLRD<br>LKRVNLAQVDRPRVDIECAGKGVQSSLIHNYKKNPNFNTLVKWFEV<br>DLPENELLHPPLNIRVVDCRAFGRYTLVGSHAVSSLRRFIYRPPDRS<br>APSWNTTVRLLRRCRVLCNGGSSSHSTGEVVVTMEPEVPIKKLET<br>MVKLDATSEAVVKDVAEEEKEKKKKKKGTAEEPEEEEPDESMLD<br>WWSKYFASIDTMKEQLRQQEPSGIDLEEKEEVDNTEGLKGSMKGK<br>EKARAAKEEKKKKTQSSGSGQGSEAPEKKKPKIDELKVYPKELESE<br>FDNFEDWLHTFNLLRGKTGDDEDGSTEEERIVGRFKGSLCVYKVPL<br>PEDVSREAGYDSTYGMFQGIPSNDPINVLVRVYVVRATDLHPADIN<br>GKADPYIAIRLGKTDIRDKENYISKQLNPVFGKSFDIEASFPMESMLT<br>VAVYDWDLVGTDDLIGETKIDLENRFYSKHRATCGIAQTYSTHGYNI<br>WRDPMKPSQILTRLCKDGKVDGPHFGPPGRVKVANRVFTGPSEIE<br>DENGQRKPTDEHVALLALRHWEDIPRAGCRLVPEHVETRPLLNPD<br>KPGIEQGRLELWVDMFPMDMPAPGTPLDISPRKPKKYELRVIIWNT<br>DEVVLEDDDFFTGEKSSDIFVRGWLKGQQEDKQDTDVHYHSLTGE<br>GNFNWRYLFPFDYLAAEEKIVISKKESMFSWDETEYKIPARLTLQIW<br>DADHFSADDFLGAIELDLNRFPRGAKTAKQCTMEATGEVDVPLV<br>SIFKQKRVKGWWPLLARNENDEFELTGKVEAELHLLTAEEAEKNPV<br>GLARNEPDPLEKPNRPDTAFVWFLNPLKSIKYLICTRYKWLIIKIVLAL<br>LGLLMLGLFLYSLPGYMVKKLLGA |
| 6 | mOTOF-201_1 protein (NP_114081.2), mouse otoferlin isoform 2, 1997 aa | MALIVHLKTVSELRGKGDRIAKVTFRGQSFYSRVLENCEGVADFDE<br>TFRWPVASSIDRNEVLEIQIFNYSKVFSNKLIGTFCMVLQKVVEENR<br>VEVTDTLMDDSNAIIKTSLSMEVRYQATDGTVGPWDDGDFLGDESL<br>QEEEKDSQETDGLLPGSRPSTRISGEKSFRRAGRSVFSAMKLGKR<br>SHKEEPQRQDEPAVLEMEDLDHLAIQLGDGLDPDSVSLASVTALTS<br>NVSNKRSKPDIKMEPSAGRPMDYQVSITVIEARQLVGLNMDPVVCV<br>EVGDDKKYTSMKESTNCPYYNEYFVFDFHVSPDVMFDKIIKISVIHS<br>KNLLRSGTLVGSFKMDVGTVYSQPEHQFHHKWAILSDPDDISAGLK<br>GYVKCDVAVVGKGDNIKTPHKANETDEDDIEGNLLLPEGVPPERQ<br>WARFYVKIYRAEGLPRMNTSLMANVKKAFIGENKDLVDPYVQVFFA<br>GQKGKTSVQKSSYEPLWNEQVVFTDLFPPLCKRMKVQIRDSDKVN<br>DVAIGTHFIDLRKISNDGDKGFLPTLGPAWVNMYGSTRNYTLLDEH<br>QDLNEGLGEGVSFRARLMLGLAVEILDTSNPELTSSTEVQVEQATP<br>VSESCTGRMEEFFLFGAFLEASMIDRKNGDKPITFEVTIGNYGNEV<br>DGMSRPLRPRPRKEPGDEEEVDLIQNSSDDEGDEAGDLASVSSTP<br>PMRPQITDRNYFHLPYLERKPCIYIKSWWPDQRRRLYNANIMDHIA<br>DKLEEGLNDVQEMIKTEKSYPERRLRGVLEELSCGCHRFLSLSDKD<br>QGRSSRTRLDRERLKSCMRELESMGQQAKSLRAQVKRHTVRDKL<br>RSCQNFLQKLRFLADEPQHSIPDVFIWMMSNNKRIAYARVPSKDLL<br>FSIVEEELGKDCAKVKTLFLKLPGKRGFGSAGWTVQAKLELYLWLG<br>LSKQRKDFLCGLPCGFEEVKAAQGLGLHSFPPISLVYTKKQAFQLR<br>AHMYQARSLFAADSSGLSDPFARVFFINQSQCTEVLNETLCPTWD<br>QMLVFDNLELYGEAHELRDDPPIIVIEIYDQDSMGKADFMGRTFAKP<br>LVKMADEAYCPPRFPPQLEYYQIYRGSATAGDLLAAFELLQIGPSG<br>KADLPPINGPVDMDRGPIMPVPVGIRPVLSKYRVEVLFWGLRDLK<br>VNLAQVDRPRVDIECAGKGVQSSLIHNYKKNPNFNTLVKWFEVDLP<br>ENELLHPPLNIRVVDCRAFGRYTLVGSHAVSSLRRFIYRPPDRSAP<br>NWNTTVRLLRGCHRLRNGGPSSRPTGEVVVSMEPEEPVKKLETM<br>VKLDATSDAVVKDVAEDEKERKKKKKKGPSEEPEEEEPDESMLD<br>WWSKYFASIDTMKEQLRQHETSGTDLEEKEEMESAEGLKGPMKS |

TABLE 2-continued

OTOF Sequences

| SEQ ID NO. | Sequence Name | Sequence |
|---|---|---|
| | | KEKSRAAKEEKKKKNQSPGPGQGSEAPEKKKAKIDELKVYPKELES EFDSFEDWLHTFNLLRGKTGDDEDGSTEEERIVGRFKGSLCVYKV PLPEDVSREAGYDPTYGMFQGIPSNDPINVLRIYVVRATDLHPADI NGKADPYIAIKLGKTDIRDKENYISKQLNPVFGKSFDIEASFPMESML TVAVYDWDLVGTDDLIGETKIDLENRFYSKHRATCGIAQTYSIHGYN IWRDPMKPSQILTRLCKEGKVDGPHFGPHGRVRVANRVFTGPSEIE DENGQRKPTDEHVALSALRHWEDIPRVGCRLVPEHVETRPLLNPD KPGIEQGRLELWVDMFPMDMPAPGTPLDISPRKPKKYELRVIVWNT DEVVLEDDDFFTGEKSSDIFVRGWLKGQQEDKQDTDVHYHSLTGE GNFNWRYLFPFDYLAAEEKIVMSKKESMFSWDETEYKIPARLTLQI WDADHFSADDFLGAIELDLNRFPRGAKTAKQCTMEMATGEVDVPL VSIFKQKRVKGWWPLLARNENDEFELTGKVEAELHLLTAEEAEKNP VGLARNEPDPLEKPNRPDTSFIWFLNPLKSARYFLWHTYRWLLLKF LLLFLLLLLFALFLYSLPGYLAKKILGA |
| 7 | mOTOF-201_2 protein (NP_001273350.1), mouse otoferlin isoform 3, 1977 aa | MALIVHLKTVSELRGKGDRIAKVTFRGQSFYSRVLENCEGVADFDE TFRWPVASSIDRNEVLEIQIFNYSKVFSNKLIGTFCMVLQKVVEENR VEVTDTLMDDSNAIIKTSLSMEVRYQATDGTVGPWDDGDFLGDESL QEEKDSQETDGLLPGSRPSTRISGEKSFRRAGRSVFSAMKLGKTR SHKEEPQRQDEPAVLEMEDLDHLAIQLGDGLDPDSVSLASVTALTS NVSNKRSKPDIKMEPSAGRPMDYQVSITVIEARQLVGLNMDPVVCV EVGDDKKYTSMKESTNCPYYNEYFVFDFHVSPDVMFDKIIKISVIHS KNLLRSGTLVGSFKMDVGTVYSQPEHQFHHKWAILSDPDDISAGLK GYVKCDVAVVGKGDNIKTPHKANETDEDDIEGNLLLPEGVPPERQ WARFYVKIYRAEGLPRMNTSLMANVKKAFIGENKDLVDPYVQVFFA GQKGKTSVQKSSYEPLWNEQVVFTDLFPPLCKRMKVQIRDSDKVN DVAIGTHFIDLRKISNDGDKGFLPTLGPAWVNMYGSTRNYTLLDEH QDLNEGLGEGVSFRARLMLGLAVEILDTSNPELTSSTEVQVEQATP VSESCTGRMEEFFLFGAFLEASMIDRKNGDKPITFEVTIGNYGNEV DGMSRPLRPRPRKEPGDEEEVDLIQNSSDDEGDEAGDLASVSSTP PMRPQITDRNYFHLPYLERKPCIYIKSWWPDQRRRLYNANIMDHIA DKLEEGLNDVQEMIKTEKSYPERRLRGVLEELSCGCHRFLSLSDKD QGRSSRTRLDRERLKSCMRELESMGQQAKSLRAQVKRHTVRDKL RSCQNFLQKLRFLADEPQHSIPDVFIWMMSNNKRIAYARVPSKDLL FSIVEEELGKDCAKVKTLFLKLPGKRGFGSAGWTVQAKLELYLWLG LSKQRKDFLCGLPCGFEEVKAAQGLGLHSFPPISLVYTKKQAFQLR AHMYQARSLFAADSSGLSDPFARVFFINQSQCTEVLNETLCPTWD QMLVFDNLELYGEAHELRDDPPIIVIEIYDQDSMGKADFMGRTFAKP LVKMADEAYCPPRFPPQLEYYQIYRGSATAGDLLAAFELLQIGPSG KADLPPINGPVDMDRGPIMPVPVGIRPVLSKYRVEVLFWGLRDLKR VNLAQVDRPRVDIECAGKGVQSSLIHNYKKNPNFNTLVKWFEVDLP ENELLHPPLNIRVVDCRAFGRYTLVGSHAVSSLRRFIYRPPDRSAP NWNTTGEVVVSMEPEEPVKKLETMVKLDATSDAVVKVDVAEDEKE RKKKKKKGPSEEPEEEEPDESMLDWWSKYFASIDTMKEQLRQHET SGTDLEEKEEMESAEGLKGPMKSKEKSRAAKEEKKKKNQSPGPG QGSEAPEKKKAKIDELKVYPKELESEFDSFEDWLHTFNLLRGKTGD DEDGSTEEERIVGRFKGSLCVYKVPLPEDVSREAGYDPTYGMFQGI PSNDPINVLRIYVVRATDLHPADINGKADPYIAIKLGKTDIRDKENYI SKQLNPVFGKSFDIEASFPMESMLTVAVYDWDLVGTDDLIGETKIDL ENRFYSKHRATCGIAQTYSIHGYNIWRDPMKPSQILTRLCKEGKVD GPHFGPHGRVRVANRVFTGPSEIEDENGQRKPTDEHVALSALRHW EDIPRVGCRLVPEHVETRPLLNPDKPGIEQGRLELWVDMFPMDMP APGTPLDISPRKPKKYELRVIVWNTDEVVLEDDDFFTGEKSSDIFVR GWLKGQQEDKQDTDVHYHSLTGEGNFNWRYLFPFDYLAAEEKIV MSKKESMFSWDETEYKIPARLTLQIWDADHFSADDFLGAIELDLNR FPRGAKTAKQCTMEMATGEVDVPLVSIFKQKRVKGWWPLLARNEN DEFELTGKVEAELHLLTAEEAEKNPVGLARNEPDPLEKPNRPDTSFI WFLNPLKSARYFLWHTYRWLLLKFLLLFLLLLLFALFLYSLPGYLAKK ILGA |
| 8 | mOTOF-202_1 protein (NP_001093865.1), mouse otoferlin isoform 1, 1992 aa | MALIVHLKTVSELRGKGDRIAKVTFRGQSFYSRVLENCEGVADFDE TFRWPVASSIDRNEVLEIQIFNYSKVFSNKLIGTFCMVLQKVVEENR VEVTDTLMDDSNAIIKTSLSMEVRYQATDGTVGPWDDGDFLGDESL QEEKDSQETDGLLPGSRPSTRISGEKSFRSKGREKTKGGRDGEHK AGRSVFSAMKLGKTRSHKEEPQRQDEPAVLEMEDLDHLAIQLGDG LDPDSVSLASVTALTSNVSNKRSKPDIKMEPSAGRPMDYQVSITVIE ARQLVGLNMDPVVCVEVGDDKKYTSMKESTNCPYYNEYFVFDFHV SPDVMFDKIIKISVIHSKNLLRSGTLVGSFKMDVGTVYSQPEHQFHH KWAILSDPDDISAGLKGYVKCDVAVVGKGDNIKTPHKANETDEDDIE GNLLLPEGVPPERQWARFYVKIYRAEGLPRMNTSLMANVKKAFIGE NKDLVDPYVQVFFAGQKGKTSVQKSSYEPLWNEQVVFTDLFPPLC KRMKVQIRDSDKVNDVAIGTHFIDLRKISNDGDKGFLPTLGPAWVN MYGSTRNYTLLDEHQDLNEGLGEGVSFRARLMLGLAVEILDTSNPE LTSSTEVQVEQATPVSESCTGRMEEFFLFGAFLEASMIDRKNGDKP ITFEVTIGNYGNEVDGMSRPLRPRPRKEPGDEEEVDLIQNSSDDEG |

TABLE 2-continued

OTOF Sequences

| SEQ ID NO. | Sequence Name | Sequence |
|---|---|---|
| | | DEAGDLASVSSTPPMRPQITDRNYFHLPYLERKPCIYIKSWWPDQR
RRLYNANIMDHIADKLEEGLNDVQEMIKTEKSYPERRLRGVLEELSC
GCHRFLSLSDKDQGRSSRTRLDRERLKSCMRELESMGQQAKSLR
AQVKRHTVRDKLRSCQNFLQKLRFLADEPQHSIPDVFIWMMSNNK
RIAYARVPSKDLLFSIVEEELGKDCAKVKTLFLKLPGKRGFGSAGWT
VQQAKLELYLWLGLSKQRKDFLCGLPCGFEEVKAAQGLGLHSFPPIS
LVYTKKQAFQLRAHMYQARSLFAADSSGLSDPFARVFFINQSQCTE
VLNETLCPTWDQMLVFDNLELYGEAHELRDDPPIIVIEIYDQDSMGK
ADFMGRTFAKPLVKMADEAYCPPRFPPQLEYYQIYRGSATAGDLLA
AFELLQIGPSGKADLPPINGPVDMDRGPIMPVPVGIRPVLSKYRVEV
LFWGLRDLKRVNLAQVDRPRVDIECAGKGVQSSLIHNYKKNPNFNT
LVKWFEVDLPENELLHPPLNIRVVDCRAFGRYTLVGSHAVSSLRRFI
YRPPDRSAPNWNTTGEVVVSMEPEEPVKKLETMVKLDATSDAVVK
VDVAEDEKERKKKKKKGPSEEPEEEEPDESMLDWWSKYFASIDTM
KEQLRQHETSGTDLEEKEEMESAEGLKGPMKSKEKSRAAKEEKKK
KNQSPGPGQGSEAPEKKKAKIDELKVYPKELESEFDSFEDWLHTF
NLLRGKTGDDEDGSTEEERIVGRFKGSLCVYKVPLPEDVSREAGY
DPTYGMFQGIPSNDPINVLVRIYVVRATDLHPADINGKADPYIAIKLG
KTDIRDKENYISKQLNPVFGKSFDIEASFPMESMLTVAVYDWDLVG
TDDLIGETKIDLENRFYSKHRATCGIAQTYSIHGYNIWRDPMKPSQIL
TRLCKEGKVDGPHFGPHGRVRVANRVFTGPSEIEDENGQRKPTDE
HVALSALRHWEDIPRVGCRLVPEHVETRPLLNPDKPGIEQGRLELW
VDMFPMDMPAPGTPLDISPRKPKKYELRVIVWNTDEVVLEDDDFFT
GEKSSDIFVRGWLKGQQEDKQDTDVHYHSLTGEGNFNWRYLFPF
DYLAAEEKIVMSKKESMFSWDETEYKIPARLTLQIWDADHFSADDF
LGAIELDLNRFPRGAKTAKQCTMEMATGEVDVPLVSIFKQKRVKGW
WPLLARNENDEFELTGKVEAELHLLTAEEAEKNPVGLARNEPDPLE
KPNRPDTAFVWFLNPLKSIKYLICTRYKWLIIKIVLALLGLLMLALFLY
SLPGYMVKKLLGA |
| 9 | mOTOF-202_2 protein (NP_001300696.1), mouse otoferlin isoform 4, 1977 aa | MALIVHLKTVSELRGKGDRIAKVTFRGQSFYSRVLENCEGVADFDE
TFRWPVASSIDRNEVLEIQIFNYSKVFSNKLIGTFCMVLQKVVEENR
VEVTDTLMDDSNAIIKTSLSMEVRYQATDGTVGPWDDGDFLGDESL
QEEKDSQETDGLLPGSRPSTRISGEKSFRRAGRSVFSAMKLGKTR
SHKEEPQRQDEPAVLEMEDLDHLAIQLGDGLDPDSVSLASVTALTS
NVSNKRSKPDIKMEPSAGRPMDYQVSITVIEARQLVGLNMDPVVCV
EVGDDKKYTSMKESTNCPYYNEYFVFDFHVSPDVMFDKIIKISVIHS
KNLLRSGTLVGSFKMDVGTVYSQPEHQFHHKWAILSDPDDISAGLK
GYVKCDVAVVGKGDNIKTPHKANETDEDDIEGNLLLPEGVPPERQ
WARFYVKIYRAEGLPRMNTSLMANVKKAFIGENKDLVDPYVQVFFA
GQKGKTSVQKSSYEPLWNEQVVFTDLFPPLCKRMKVQIRDSDKVN
DVAIGTHFIDLRKISNDGDKGFLPTLGPAWVNMYGSTRNYTLLDEH
QDLNEGLGEGVSFRARLMLGLAVEILDTSNPELTSSTEVQVEQATP
VSESCTGRMEEFFLFGAFLEASMIDRKNGDKPITFEVTIGNYGNEV
DGMSRPLRPRPRKEPGDEEEVDLIQNSSDDEGDEAGDLASVSSTP
PMRPQITDRNYFHLPYLERKPCIYIKSWWPDQRRRLYNANIMDHIA
DKLEEGLNDVQEMIKTEKSYPERRLRGVLEELSCGCHRFLSLSDKD
QGRSSRTRLDRERLKSCMRELESMGQQAKSLRAQVKRHTVRDKL
RSCQNFLQKLRFLADEPQHSIPDVFIWMMSNNKRIAYARVPSKDLL
FSIVEEELGKDCAKVKTLFLKLPGKRGFGSAGWTVQQAKLELYLWLG
LSKQRKDFLCGLPCGFEEVKAAQGLGLHSFPPISLVYTKKQAFQLR
AHMYQARSLFAADSSGLSDPFARVFFINQSQCTEVLNETLCPTWD
QMLVFDNLELYGEAHELRDDPPIIVIEIYDQDSMGKADFMGRTFAKP
LVKMADEAYCPPRFPPQLEYYQIYRGSATAGDLLAAFELLQIGPSG
KADLPPINGPVDMDRGPIMPVPVGIRPVLSKYRVEVLFWGLRDLKR
VNLAQVDRPRVDIECAGKGVQSSLIHNYKKNPNFNTLVKWFEVDLP
ENELLHPPLNIRVVDCRAFGRYTLVGSHAVSSLRRFIYRPPDRSAP
NWNTTGEVVVSMEPEEPVKKLETMVKLDATSDAVVKVDVAEDEKE
RKKKKKKGPSEEPEEEEPDESMLDWWSKYFASIDTMKEQLRQHET
SGTDLEEKEEMESAEGLKGPMKSKEKSRAAKEEKKKKNQSPGPG
QGSEAPEKKKAKIDELKVYPKELESEFDSFEDWLHTFNLLRGKTGD
DEDGSTEEERIVGRFKGSLCVYKVPLPEDVSREAGYDPTYGMFQGI
PSNDPINVLVRIYVVRATDLHPADINGKADPYIAIKLGKTDIRDKENYI
SKQLNPVFGKSFDIEASFPMESMLTVAVYDWDLVGTDDLIGETKIDL
ENRFYSKHRATCGIAQTYSIHGYNIWRDPMKPSQILTRLCKEGKVD
GPHFGPHGRVRVANRVFTGPSEIEDENGQRKPTDEHVALSALRHW
EDIPRVGCRLVPEHVETRPLLNPDKPGIEQGRLELWVDMFPMDMP
APGTPLDISPRKPKKYELRVIVWNTDEVVLEDDDFFTGEKSSDIFVR
GWLKGQQEDKQDTDVHYHSLTGEGNFNWRYLFPFDYLAAEEKIV
MSKKESMFSWDETEYKIPARLTLQIWDADHFSADDFLGAIELDLNR
FPRGAKTAKQCTMEMATGEVDVPLVSIFKQKRVKGWWPLLARNEN
DEFELTGKVEAELHLLTAEEAEKNPVGLARNEPDPLEKPNRPDTAF
VWFLNPLKSIKYLICTRYKWLIIKIVLALLGLLMLALFLYSLPGYMVKK
LLGA |

TABLE 2-continued

OTOF Sequences

| SEQ ID NO. | Sequence Name | Sequence |
|---|---|---|
| 10 | OTOF-201 transcript (NM_194248.1), human otoferlin transcript variant 1, 7156 bp, encodes the protein of SEQ ID NO: 1 | ATCGGAGGGGGTCGGGAGGAGGAGGAGGAGGCAGCGGCAG<br>AGAAGAGAGAGGCGTGTGAGCCGTGCTCCACCGGCTAGCTCCT<br>TCCCGCTGCTCCTGCCTGGCAGTGCCAGGCAGCCCACACCAGC<br>ATGGCCTTGCTCATCCACCTCAAGACAGTCTCGGAGCTGCGGG<br>GCAGGGGCGACCGGATCGCCAAAGTGACTTTCCGAGGGCAATC<br>CTTCTACTCTCGGGTCCTGGAGAACTGTGAGGATGTGGCTGACT<br>TTGATGAGACATTTCGGTGGCCGGTGGCCAGCAGCATCGACAG<br>AAATGAGATGCTGGAGATTCAGGTTTTCAACTACAGCAAAGTCTT<br>CAGCAACAAGCTCATCGGGACCTTCCGCATGGTGCTGCAGAAG<br>GTGGTAGAGGAGAGCCATGTGGAGGTGACTGACACGCTGATTG<br>ATGACAACAATGCTATCATCAAGACCAGCCTGTGCGTGGAGGTC<br>CGGTATCAGGCCACTGACGGCACAGTGGGCTCCTGGGACGATG<br>GGGACTTCCTGGGAGATGAGTCTCTTCAAGAGGAAGAGAAGGA<br>CAGCCAAGAGACGGATGGACTGCTCCCAGGCTCCCGGCCCAGC<br>TCCCGGCCCCCAGGAGAGAAGAGCTTCCGGAGAGCCGGGAGG<br>AGCGTGTTCTCCGCCATGAAGCTCGGCAAAAACCGGTCTCACAA<br>GGAGGAGCCCCAAAGACCAGATGAACCGGCGGTGCTGGAGAT<br>GGAAGACCTTGACCATCTGGCCATTCGGCTAGGAGATGGACTG<br>GATCCCGACTCGGTGTCTCTAGCCTCAGTCACAGCTCTCACCAC<br>TAATGTCTCCAACAAGCGATCTAAGCCAGACATTAAGATGGAGC<br>CAAGTGCTGGGCGGCCCATGGATTACCAGGTCAGCATCACGGT<br>GATCGAGGCCCGGCAGCTGGTGGGCTTGAACATGGACCCTGTG<br>GTGTGCGTGGAGGTGGGTGACGACAAGAAGTACACATCCATGA<br>AGGAGTCCACTAACTGCCCCTATTACAACGAGTACTTCGTCTTC<br>GACTTCCATGTCTCTCCGGATGTCATGTTTGACAAGATCATCAAG<br>ATTTCGGTGATTCACTCCAAGAACCTGCTGCGCAGTGGCACCCT<br>GGTGGGCTCCTTCAAAATGGACGTGGGAACCGTGTACTCGCAG<br>CCAGAGCACCAGTTCCATCACAAGTGGGCCATCCTGTCTGACCC<br>CGATGACATCTCCTCGGGGCTGAAGGGCTACGTGAAGTGTGAC<br>GTTGCCGTGGTGGGCAAAGGGGACAACATCAAGACGCCCCACA<br>AGGCCAATGAGACCGACGAAGATGACATTGAGGGGAACTTGCT<br>GCTCCCCGAGGGGGTGCCCCCCGAACGCCAGTGGGCCCGGTT<br>CTATGTGAAAATTTACCGAGCAGAGGGGCTGCCCCGTATGAACA<br>CAAGCCTCATGGCCAATGTAAAGAAGGCTTTCATCGGTGAAAAC<br>AAGGACCTCGTGGACCCCTACGTGCAAGTCTTCTTTGCTGGCCA<br>GAAGGGCAAGACTTCAGTCAGAAGAGCAGCTATGAGCCCCTG<br>TGGAATGAGCAGGTCGTCTTTACAGACCTCTTCCCCCCACTCTG<br>CAAACGCATGAAGGTGCAGATCCGAGACTCGGACAAGGTCAAC<br>GACGTGGCCATCGGCACCCACTTCATTGACCTGCGCAAGATTTC<br>TAATGACGGAGACAAAGGCTTCCTGCCCACACTGGGCCCAGCC<br>TGGGTGAACATGTACGGCTCCACACGTAACTACACGCTGCTGGA<br>TGAGCATCAGGACCTGAACGAGGGCCTGGGGGAGGGTGTGTC<br>CTTCCGGGCCCGGCTCCTGCTGGGCCTGGCTGTGGAGATCGTA<br>GACACCTCCAACCCTGAGCTCACCAGCTCCACAGAGGTGCAGG<br>TGGAGCAGGCCACGCCCATCTCGGAGAGCTGTGCAGGTAAAAT<br>GGAAGAATTCTTTCTCTTTGGAGCCTTCCTGGAGGCCTCAATGA<br>TCGACCGGAGAAACGGAGACAAGCCCATCACCTTTGAGGTCAC<br>CATAGGCAACTATGGGAACGAAGTTGATGGCCTGTCCCGGCCC<br>CAGCGGCCTCGGCCCCGGAAGGAGCCGGGGGATGAGGAAGAA<br>GTAGACCTGATTCAGAACGCAAGTGATGACGAGGCCGGTGATG<br>CCGGGGACCTGGCCTCAGTCTCCTCCACTCCACCAATGCGGCC<br>CCAGGTCACCGACAGGAACTACTTCCATCTGCCCTACCTGGAGC<br>GAAAGCCCTGCATCTACATCAAGAGCTGGTGGCCGGACCAGCG<br>CCGCCGCCTCTACAATGCCAACATCATGGACCACATTGCCGACA<br>AGCTGGAAGAAGGCCTGAACGACATACAGGAGATGATCAAAAC<br>GGAGAAGTCCTACCCTGAGCGTCGCCTGCGGGCGTCCTGGA<br>GGAGCTGAGCTGTGGCTGCTGCCGCTTCCTCTCCCTCGCTGAC<br>AAGGACCAGGGCCACTCATCCCGCACCAGGCTTGACCGGGAGC<br>GCCTCAAGTCCTGCATGAGGGAGCTGGAAAACATGGGGCAGCA<br>GGCCAGGATGCTGCGGGCCCAGGTGAAGCGGCACACGGTGCG<br>GGACAAGCTGAGGCTGTGCCAGAACTTCCTGCAGAAGCTGCGC<br>TTCCTGGCGGACGAGCCCCAGCACAGCATTCCCGACATCTTCAT<br>CTGGATGATGAGCAACAACAAGCGTGTCGCCTATGCCCGTGTG<br>CCCTCCAAGGACCTGCTCTTCTCCATCGTGGAGGAGGAGACTG<br>GCAAGGACTGCGCCAAGGTCAAGAGCTCTTCCTTAAGCTGCC<br>AGGGAAGCGGGGCTTCGGCTCGGCAGGCTGGACAGTGCAGGC<br>CAAGGTGGAGCTGTACCTGTGGCTGGGCCTCAGCAAACAGCGC<br>AAGGAGTTCCTGTGCGGCCTGCCCTGTGGCTTCCAGGAGGTCA<br>AGGCAGCCCAGGGCCTGGGCCTGCATGCCTTCCCACCCGTCAG<br>CCTGGTCTACACCAAGAAGCAGGCGTTCCAGCTCCGAGCGCAC<br>ATGTACCAGGCCCGCAGCCTCTTTGCCGCCGACAGCAGCGGAC<br>TCTCAGACCCCTTTGCCCGCGTCTTCTTCATCAATCAGAGTCAG<br>TGCACAGAGGTGCTGAATGAGACCCTGTGTCCCACCTGGGACC<br>AGATGCTGGTGTTCGACAACCTGGAGCTCTATGGTGAAGCTCAT<br>GAGCTGAGGGACGATCCGCCCATCATTGTCATTGAAATCTATGA |

TABLE 2-continued

OTOF Sequences

| SEQ ID NO. | Sequence Name | Sequence |
|---|---|---|
| | | CCAGGATTCCATGGGCAAAGCTGACTTCATGGGCCGGACCTTC<br>GCCAAACCCCTGGTGAAGATGGCAGACGAGGCGTACTGCCCAC<br>CCCGCTTCCCACCTCAGCTCGAGTACTACCAGATCTACCGTGGC<br>AACGCCACAGCTGGAGACCTGCTGGCGGCCTTCGAGCTGCTGC<br>AGATTGGACCAGCAGGGAAGGCTGACCTGCCCCCCATCAATGG<br>CCCGGTGGACGTGGACCGAGGTCCCATCATGCCCGTGCCCATG<br>GGCATCCGGCCCGTGCTCAGCAAGTACCGAGTGGAGGTGCTGT<br>TCTGGGGCCTACGGGACCTAAAGCGGGTGAACCTGGCCCAGGT<br>GGACCGGCCACGGGTGGACATCGAGTGTGCAGGGAAGGGGGT<br>GCAGTCGTCCCTGATCCACAATTATAAGAAGAACCCCAACTTCA<br>ACACCCTCGTCAAGTGGTTTGAAGTGGACCTCCCAGAGAACGA<br>GCTGCTGCACCCGCCCTTGAACATCCGTGTGGTGGACTGCCGG<br>GCCTTCGGTCGCTACACACTGGTGGGCTCCCATGCCGTCAGCT<br>CCCTGCGACGCTTCATCTACCGGCCCCCAGACCGCTCGGCCCC<br>CAGCTGGAACACCACGGTCAGGCTTCTCCGGCGCTGCCGTGTG<br>CTGTGCAATGGGGGCTCCTCCTCTCACTCCACAGGGGAGGTTG<br>TGGTGACTATGGAGCCAGAGGTACCCATCAAGAAACTGGAGAC<br>CATGGTGAAGCTGGACGCGACTTCTGAAGCTGTTGTCAAGGTG<br>GATGTGGCTGAGGAGGAGAAGGAGAAGAAGAAGAAGAAGAAGG<br>GCACTGCGGAGGAGCCAGAGGAGGAGGAGCCAGACGAGAGCA<br>TGCTGGACTGGTGGTCCAAGTACTTTGCCTCCATTGACACCATG<br>AAGGAGCAACTTCGACAACAAGAGCCCTCTGGAATTGACTTGGA<br>GGAGAAGGAGGAAGTGGACAATACCGAGGGCCTGAAGGGGTC<br>AATGAAGGGCAAGGAGAAGGCAAGGGCTGCCAAAGAGGAGAAG<br>AAGAAGAAAACTCAGAGCTCTGGCTCTGGCCAGGGGTCCGAGG<br>CCCCCGAGAAGAAGAAACCCAAGATTGATGAGCTTAAGGTATAC<br>CCCAAAGAGCTGGAGTCCGAGTTTGATAACTTTGAGGACTGGCT<br>GCACACTTTCAACTTGCTTCGGGGCAAGACCGGGGATGATGAG<br>GATGGCTCCACCGAGGAGGAGCGCATTGTGGGACGCTTCAAGG<br>GCTCCCTCTGCGTGTACAAAGTGCCACTCCCAGAGGACGTGTC<br>CCGGGAAGCCGGCTACGACTCCACCTACGGCATGTTCCAGGGC<br>ATCCCGAGCAATGACCCCATCAATGTGCTGGTCCGAGTCTATGT<br>GGTCCGGGCCACGGACCTGCACCCTGCTGACATCAACGGCAAA<br>GCTGACCCCTACATCGCCATCCGGCTAGGCAAGACTGACATCC<br>GCGACAAGGAGAACTACATCTCCAAGCAGCTCAACCCTGTCTTT<br>GGGAAGTCCTTTGACATCGAGGCCTCCTTCCCCATGGAATCCAT<br>GCTGACGGTGGCTGTGTATGACTGGGACCTGGTGGGCACTGAT<br>GACCTCATTGGGGAAACCAAGATCGACCTGGAGAACCGCTTCTA<br>CAGCAAGCACCGCGCCACCTGCGGCATCGCCCAGACCTACTCC<br>ACACATGGCTACAATATCTGGCGGGACCCCATGAAGCCCAGCC<br>AGATCCTGACCCGCCTCTGCAAAGACGGCAAAGTGGACGGCCC<br>CCACTTTGGGCCCCCTGGGAGAGTGAAGGTGGCCAACCGCGTC<br>TTCACTGGGCCCTCTGAGATTGAGGACGAGAACGGTCAGAGGA<br>AGCCCACAGACGAGCATGTGGCGCTGTTGGCCCTGAGGCACTG<br>GGAGGACATCCCCCGCGCAGGCTGCCGCCTGGTGCCAGAGCA<br>TGTGGAGACGAGGCCGCTGCTCAACCCCGACAAGCCGGGCATC<br>GAGCAGGGCCGCCTGGAGCTGTGGGTGGACATGTTCCCCATGG<br>ACATGCCAGCCCTGGGACGCCTCTGGACATCTCACCTCGGAA<br>GCCCAAGAAGTACGAGCTGCGGGTCATCATCTGGAACACAGAT<br>GAGGTGGTCTTGGAGGACGACGACTTCTTCACAGGGGAGAAGT<br>CCAGTGACATCTTCGTGAGGGGGTGGCTGAAGGGCCAGCAGGA<br>GGACAAGCAGGACACAGACGTCCACTACCACTCCCTCACTGGC<br>GAGGGCAACTTCAACTGGCGCTACCTGTTCCCCTTCGACTACCT<br>GGCGGCGGAGGAGAAGATCGTCATCTCCAAGAAGGAGTCCATG<br>TTCTCCTGGGACGAGACCGAGTACAAGATCCCCGCGCGGCTCA<br>CCCTGCAGATCTGGGATGCGGACCACTTCTCCGCTGACGACTT<br>CCTGGGGGCCATCGAGCTGGACCTGAACCGGTTCCCGCGGGG<br>CGCAAAGACAGCCAAGCAGTGCACCATGGAGATGGCCACCGGG<br>GAGGTGGACGTGCCCCTCGTGTCCATCTTCAAGCAAAAGCGCG<br>TCAAAGGCTGGTGGCCCCTCCTGGCCCGCAATGAGAACGATGA<br>GTTTGAGCTCACGGGCAAGGTGGAGGCTGAGCTGCATTTACTG<br>ACAGCAGAGGAGGCAGAGAAGAACCCAGTGGGCCTGGCCCGC<br>AATGAACCTGACCCCCTAGAGAAACCCAACCGGCCCGACACGA<br>GCTTCATCTGGTTCCTGAACCCTCTCAAGTCGGCTCGCTACTTC<br>TTGTGGCACACGTATCGCTGGCTGCTCCTCAAACTGTTGCTGCT<br>CCTGCTGCTGCTCCTCCTCCTCGCCCTGTTCCTCTACTCTGTGC<br>CTGGCTACCTGGTCAAGAAAATCCTCGGGGCCTGAGCCCAGTG<br>GCCTCCTGGCCGGCCCGACACGGCCTTCGTCTGGTTCCTCAAC<br>CCTCTCAAGTCCATCAAGTACCTCATCTGCACCCGGTACAAGTG<br>GCTCATCATCAAGATCGTGCTGGCGCTGTTGGGGCTGCTCATGT<br>TGGGGCTCTTCCTCTACAGCCTCCCTGGCTACATGGTCAAAAAG<br>CTCCTTGGGCATGAAGGCCGCCAGCTCCCGCCAGCCGCTCCC<br>CAGCCCTGCCGCATTTCCTTTCAGTGGCTTGGACTCTTTCCCAT<br>CTCCCCTGGGGAGCCTGAGGAGCCCAGCGTCCACTCTTCATGC<br>CTTGGGCCGAGCCTGCCTCCTGCTTGCGGGGGCCGCCTGTCCT |

TABLE 2-continued

OTOF Sequences

| SEQ ID NO. | Sequence Name | Sequence |
|---|---|---|
| | | CACTGCCCCAGGCTGCGGCTTGCCCAGTCCCGCCCCTCTGACC<br>CCTGCCTGTGGGCTGGGGAGCCTTGGATGGGTGGGGACCTG<br>GAATGGGTCTCTCTTGCCCCACCTGGCTGAGGCGCCACCCTTC<br>TTCAGGCCCAGGCTCCAGAGGAAGACTCCTGAAACCCTCCCCA<br>GGTCTTCCAAGTACAGGATTGAAGCTTTAGTGAAATTAACCAAG<br>GACCATGGGTCAGTGCCCAGGGCTTTAAAAAGAATGAACGAGC<br>AAAAGGTATCCCCGCCGTGACCCCTGCAGATAGCACCGGTCTTT<br>GATCCGCAGCAGGGGCCAGACCCTGCCCACAAGTCCCAGCGC<br>GGCTGCTTCTGCCACTGCTGGGCTCCACTTGGCTCCTCTCACTT<br>CCCAGGGGGTCGCCTGTCCTGCCTGTGGGTTTCCATGGCTTCC<br>CAGAGCTCCCTCTGCCCCAGCCAGCGCCTCCAGGCCCAGCTGA<br>GGAGCTGTGAGAAGCAGCAGAGGGGACTCCCCATCCCGGGCA<br>CACCCTGTCCTCCCACCCCTGCCCCCTTGCCCTTCCAGCCCTTT<br>CAGCTGCAGCTGGGAGCTGGCCCGTCAAGTGCTGCCCCTGCCT<br>GTGTCTGGGTTTCTGTTGGCTGTTTTTCTTTTCTTGAGTGGTGAT<br>TTTTCTCTAAATAAAAGAAGTCAAGCACTGAAAAAAAAAAAAAAA<br>A |
| 11 | OTOF-202 transcript (NM_004802.3), human otoferlin transcript variant 2, 4954 bp, encodes the protein of SEQ ID NO: 2 | CCGTGAGTTCTGCCCAGGCCCTGTGAGCTCACCAGAGCCACAG<br>ACTCACAGCCCAGAGGTGGCTTCTTCCTTCAGGAACTGAAGAAC<br>CCCCATGAACACCAACATCTCCAGGTTCTGAGAACAGAACCTGG<br>GAAATTGATGACTTCCTCATGATGACCGATACTCAGGATGGCCC<br>TAGCGAGAGCTCCCAGATCATGAGGAAGAAGGCCTGAACGACA<br>TACAGGAGATGATCAAAACGGAGAAGTCCTACCCTGAGCGTCG<br>CCTGCGGGGCGTCCTGGAGGAGCTGAGCTGTGGCTGCTGCCG<br>CTTCCTCTCCCTCGCTGACAAGGACCAGGGCCACTCATCCCGC<br>ACCAGGCTTGACCGGGAGCGCCTCAAGTCCTGCATGAGGGAGC<br>TGGAAAACATGGGGCAGCAGGCCAGGATGCTGCGGGCCCAGG<br>TGAAGCGGCACACGGTGCGGGACAAGCTGAGGCTGTGCCAGAA<br>CTTCCTGCAGAAGCTGCGCTTCCTGGCGGACGAGCCCCAGCAC<br>AGCATTCCCGACATCTTCATCTGGATGATGAGCAACAACAAGCG<br>TGTCGCCTATGCCCGTGTGCCCTCCAAGGACCTGCTCTTCTCCA<br>TCGTGGAGGAGGAGACTGGCAAGGACTGCGCCAAGGTCAAGAC<br>GCTCTTCCTTAAGCTGCCAGGGAAGCGGGGCTTCGGCTCGGCA<br>GGCTGGACAGTGCAGGCCAAGGTGGAGCTGTACCTGTGGCTGG<br>GCCTCAGCAAACAGCGCAAGGAGTTCCTGTGCGGCCTGCCCTG<br>TGGCTTCCAGGAGGTCAAGGCAGCCCAGGGCCTGGGCCTGCAT<br>GCCTTCCCACCCGTCAGCCTGGTCTACACCAAGAAGCAGGCGT<br>TCCAGCTCCGAGCGCACATGTACCAGGCCCGCAGCCTCTTTGC<br>CGCCGACAGCAGCGGACTCTCAGACCCCTTTGCCCGCGTCTTC<br>TTCATCAATCAGAGTCAGTGCACAGAGGTGCTGAATGAGACCCT<br>GTGTCCCACCTGGGACCAGATGCTGGTGTTCGACAACCTGGAG<br>CTCTATGGTGAAGCTCATGAGCTGAGGGACGATCCGCCCATCAT<br>TGTCATTGAAATCTATGACCAGGATTCCATGGGCAAAGCTGACT<br>TCATGGGCCGGACCTTCGCCAAACCCCTGGTGAAGATGGCAGA<br>CGAGGCGTACTGCCCACCCCGCTTCCCACCTCAGCTCGAGTAC<br>TACCAGATCTACCGTGGCAACGCCACAGCTGGAGACCTGCTGG<br>CGGCCTTCGAGCTGCTGCAGATTGGACCAGCAGGGAAGGCTGA<br>CCTGCCCCCCATCAATGGCCCGGTGGACGTGGACCGAGGTCCC<br>ATCATGCCCGTGCCCATGGGCATCCGGCCCGTGCTCAGCAAGT<br>ACCGAGTGGAGGTGCTGTTCTGGGGCCTACGGGACCTAAAGCG<br>GGTGAACCTGGCCCAGGTGGACCGGCCACGGGTGGACATCGA<br>GTGTGCAGGGAAGGGGGTGCAGTCGTCCCTGATCCACAATTAT<br>AAGAAGAACCCCAACTTCAACACCCTCGTCAAGTGGTTTGAAGT<br>GGACCTCCCAGAGAACGAGCTGCTGCACCCGCCCTTGAACATC<br>CGTGTGGTGGACTGCCGGGCCTTCGGTCGCTACACACTGGTGG<br>GCTCCCATGCCGTCAGCTCCCTGCGACGCTTCATCTACCGGCC<br>CCCAGACCGCTCGGCCCCCAGCTGGAACACCACGGGGAGGT<br>TGTGGTGACTATGGAGCCAGAGGTACCCATCAAGAAACTGGAG<br>ACCATGGTGAAGCTGGACGCGACTTCTGAAGCTGTTGTCAAGGT<br>GGATGTGGCTGAGGAGGAGAAGGAGAAGAAGAAGAAGAAGAAG<br>GGCACTGCGGAGGAGCCAGAGGAGGAGGAGCCAGACGAGAGC<br>ATGCTGGACTGGTGGTCCAAGTACTTTGCCTCCATTGACACCAT<br>GAAGGAGCAACTTCGACAACAAGAGCCCTCTGGAATTGACTTGG<br>AGGAGAAGGAGGAAGTGGACAATACCGAGGGCCTGAAGGGGT<br>CAATGAAGGGCAAGGAGAAGGCAAGGGCTGCCAAAGAGGAGAA<br>GAAGAAGAAAACTCAGAGCTCTGGCTCTGGCCAGGGGTCCGAG<br>GCCCCGAGAAGAAGAAACCCAAGATTGATGAGCTTAAGGTATA<br>CCCCAAAGAGCTGGAGTCCGAGTTTGATAACTTTGAGGACTGGC<br>TGCACACTTTCAACTTGCTTCGGGGCAAGACCGGGGATGATGA<br>GGATGGCTCCACCGAGGAGGAGCGCATTGTGGGACGCTTCAAG<br>GGCTCCCTCTGCGTGTACAAAGTGCCACTCCCAGAGGACGTGT<br>CCCGGGAAGCCGGCTACGACTCCACCTACGGCATGTTCCAGGG<br>CATCCCGAGCAATGACCCCATCAATGTGCTGGTCCGAGTCTATG<br>TGGTCCGGGCCACGGACCTGCACCCTGCTGACATCAACGGCAA |

TABLE 2-continued

OTOF Sequences

| SEQ ID NO. | Sequence Name | Sequence |
|---|---|---|
| | | AGCTGACCCCTACATCGCCATCCGGCTAGGCAAGACTGACATC CGCGACAAGGAGAACTACATCTCCAAGCAGCTCAACCCTGTCTT TGGGAAGTCCTTTGACATCGAGGCCTCCTTCCCCATGGAATCCA TGCTGACGGTGGCTGTGTATGACTGGGACCTGGTGGGCACTGA TGACCTCATTGGGGAAACCAAGATCGACCTGGAGAACCGCTTCT ACAGCAAGCACCGCGCCACCTGCGGCATCGCCCAGACCTACTC CACACATGGCTACAATATCTGGCGGGACCCCATGAAGCCCAGC CAGATCCTGACCCGCCTCTGCAAAGACGGCAAAGTGGACGGCC CCCACTTTGGGCCCCCTGGGAGAGTGAAGGTGGCCAACCGCGT CTTCACTGGGCCCTCTGAGATTGAGGACGAGAACGGTCAGAGG AAGCCCACAGACGAGCATGTGGCGCTGTTGGCCCTGAGGCACT GGGAGGACATCCCCCGCGCAGGCTGCCGCCTGGTGCCAGAGC ATGTGGAGACGAGGCCGCTGCTCAACCCCGACAAGCCGGGCAT CGAGCAGGGCCGCCTGGAGCTGTGGGTGGACATGTTCCCCATG GACATGCCAGCCCCTGGGACGCCTCTGGACATCTCACCTCGGA AGCCCAAGAAGTACGAGCTGCGGGTCATCATCTGGAACACAGA TGAGGTGGTCTTGGAGGACGACGACTTCTTCACAGGGGAGAAG TCCAGTGACATCTTCGTGAGGGGGTGGCTGAAGGGCCAGCAGG AGGACAAGCAGGACACAGACGTCCACTACCACTCCCTCACTGG CGAGGGCAACTTCAACTGGCGCTACCTGTTCCCCTTCGACTACC TGGCGGCGGAGGAGAAGATCGTCATCTCCAAGAAGGAGTCCAT GTTCTCCTGGGACGAGACCGAGTACAAGATCCCCGCGCGGCTC ACCCTGCAGATCTGGGATGCGGACCACTTCTCCGCTGACGACTT CCTGGGGGCCATCGAGCTGGACCTGAACCGGTTCCCGCGGGG CGCAAAGACAGCCAAGCAGTGCACCATGGAGATGGCCACCGGG GAGGTGGACGTGCCCCTCGTGTCCATCTTCAAGCAAAAGCGCG TCAAAGGCTGGTGGCCCCTCCTGGCCCGCAATGAGAACGATGA GTTTGAGCTCACGGGCAAGGTGGAGGCTGAGCTGCATTTACTG ACAGCAGAGGAGGCAGAGAAGAACCCAGTGGGCCTGGCCCGC AATGAACCTGACCCCCTAGAGAAACCCAACCGGCCCGACACGA GCTTCATCTGGTTCCTGAACCCTCTCAAGTCGGCTCGCTACTTC TTGTGGCACACGTATCGCTGGCTGCTCCTCAAACTGTTGCTGCT CCTGCTGCTGCTCCTCCTCCGCCCTGTTCCTCTACTCTGTGC CTGGCTACCTGGTCAAGAAAATCCTCGGGGCTGAGCCCAGTG GCCTCCTGGCCGGCCCGACACGGCCTTCGTCTGGTTCCTCAAC CCTCTCAAGTCCATCAAGTACCTCATCTGCACCCGGTACAAGTG GCTCATCATCAAGATCGTGCTGGCGCTGTTGGGGCTGCTCATGT TGGGGCTCTTCCTCTACAGCCTCCCTGGCTACATGGTCAAAAAG CTCCTTGGGGCATGAAGGCCGCCAGCTCCCGCCAGCCGCTCCC CAGCCCTGCCGCATTTCCTTTCAGTGGCTTGGACTCTTTCCCAT CTCCCCTGGGGAGCCTGAGGAGCCCAGCGTCCACTCTTCATGC CTTGGGCCGAGCCTGCCTCCTGCTTGCGGGGCCGCCTGTCCT CACTGCCCCAGGCTGCGGCTTGCCCAGTCCCGCCCCTCTGACC CCTGCCTGTGGGCTGGGGAGCCTTGGATGGGTGGGGACCTG GAATGGGTCTCTCTTGCCCCACCTGGCTGAGGCGCCACCCTTC TTCAGGCCCAGGCTCCAGAGGAAGACTCCTGAAACCCTCCCCA GGTCTTCCAAGTACAGGATTGAAGCTTTAGTGAAATTAACCAAG GACCATGGGTCAGTGCCCAGGGCTTTAAAAAGAATGAACGAGC AAAAGGTATCCCCGCCGTGACCCCTGCAGATAGCACCGGTCTTT GATCCGCAGCAGGGGCCAGACCCTGCCCACAAGTCCCAGCGC GGCTGCTTCTGCCACTGCTGGGCTCCACTTGGCTCCTCTCACTT CCCAGGGGGTCGCCTGTCCTGCCTGTGGGTTTCCATGGCTTCC CAGAGCTCCCTCTGCCCCAGCCAGCGCCTCCAGGCCCAGCTGA GGAGCTGTGAGAAGCAGCAGAGGGGACTCCCCATCCCGGGCA CACCCTGTCCTCCCACCCCTGCCCCCTTGCCCTTCCAGCCCTTT CAGCTGCAGCTGGGAGCTGGCCCGTCAAGTGCTGCCCCTGCCT GTGTCTGGGTTTCTGTTGGCTGTTTTTCTTTTCTTGAGTGGTGAT TTTTCTCTAAATAAAAGAAGTCAAGCACTGAAAAAAAAAAAAAA A |
| 12 | OTOF-203 transcript (NM_194323.2), human otoferlin transcript variant 4, 4756 bp, encodes the protein of SEQ ID NO: 3 | CCGTGAGTTCTGCCCAGGCCCTGTGAGCTCACCAGAGCCACAG ACTCACAGCCCAGAGGTGGCTTCTTCCTTCAGGAACTGAAGAAC CCCCATGAACACCAACATCTCCAGGTTCTGAGAACAGAACCTGG GAAATTGATGACTTCCTCATGATGACCGATACTCAGGATGGCCC TAGCGAGAGCTCCCAGATCATGAGGAAGAAGGCCTGAACGACA TACAGGAGATGATCAAAACGGAGAAGTCCTACCCTGAGCGTCG CCTGCGGGGCGTCCTGAGGAGCTGAGCTGTGGCTGCTGCCG CTTCCTCTCCCTCGCTGACAAGGACCAGGGCCACTCATCCCGC ACCAGGCTTGACCGGGAGCGCCTCAAGTCCTGCATGAGGGAGC TGGAAAAACATGGGGCAGCAGGCCAGGATGCTGCTGGGGCCCAGG TGAAGCGGCACACGGTGCGGGACAAGCTGAGGCTGTGCCAGAA CTTCCTGCAGAAGCTGCGCTTCCTGGCGGACGAGCCCCAGCAC AGCATTCCCGACATCTTCATCTGGATGATGAGCAACAACAAGCG TGTCGCCTATGCCCGTGTGCCCTCAAGGACCTGCTCTTCTCCA TCGTGGAGGAGGAGACTGGCAAGGACTGCGCCAAGGTCAAGAC |

TABLE 2-continued

OTOF Sequences

| SEQ ID NO. | Sequence Name | Sequence |
|---|---|---|
| | | GCTCTTCCTTAAGCTGCCAGGGAAGCGGGGCTTCGGCTCGGCA
GGCTGGACAGTGCAGGCCAAGGTGGAGCTGTACCTGTGGCTGG
GCCTCAGCAAACAGCGCAAGGAGTTCCTGTGCGGCCTGCCCTG
TGGCTTCCAGGAGGTCAAGGCAGCCCAGGGCCTGGGCCTGCAT
GCCTTCCCACCCGTCAGCCTGGTCTACACCAAGAAGCAGGCGT
TCCAGCTCCGAGCGCACATGTACCAGGCCCGCAGCCTCTTTGC
CGCCGACAGCAGCGGACTCTCAGACCCCTTTGCCCGCGTCTTC
TTCATCAATCAGAGTCAGTGCACAGAGGTGCTGAATGAGACCCT
GTGTCCCACCTGGGACCAGATGCTGGTGTTCGACAACCTGGAG
CTCTATGGTGAAGCTCATGAGCTGAGGGACGATCCGCCCATCAT
TGTCATTGAAATCTATGACCAGGATTCCATGGGCAAAGCTGACT
TCATGGGCCGGACCTTCGCCAAACCCCTGGTGAAGATGGCAGA
CGAGGCGTACTGCCCACCCCGCTTCCCACCTCAGCTCGAGTAC
TACCAGATCTACCGTGGCAACGCCACAGCTGGAGACCTGCTGG
CGGCCTTCGAGCTGCTGCAGATTGGACCAGCAGGGAAGGCTGA
CCTGCCCCCATCAATGGCCCGGTGGACGTGGACCGAGGTCCC
ATCATGCCCGTGCCCATGGGCATCCGGCCCGTGCTCAGCAAGT
ACCGAGTGGAGGTGCTGTTCTGGGGCCTACGGGACCTAAAGCG
GGTGAACCTGGCCCAGGTGGACCGGCCACGGGTGGACATCGA
GTGTGCAGGGAAGGGGGTGCAGTCGTCCCTGATCCACAATTAT
AAGAAGAACCCCAACTTCAACACCCTCGTCAAGTGGTTTGAAGT
GGACCTCCCAGAGAACGAGCTGCTGCACCCGCCCTTGAACATC
CGTGTGGTGGACTGCCGGGCCTTCGGTCGCTACACACTGGTGG
GCTCCCATGCCGTCAGCTCCCTGCGACGCTTCATCTACCGGCC
CCCAGACCGCTCGGCCCCCAGCTGGAACACCACGGGGGAGGT
TGTGGTGACTATGGAGCCAGAGGTACCCATCAAGAAACTGGAG
ACCATGGTGAAGCTGGACGCGACTTCTGAAGCTGTTGTCAAGGT
GGATGTGGCTGAGGAGGAGAAGGAGAAGAAGAAGAAGAAGAG
GGCACTGCGGAGGAGCCAGAGGAGGAGGAGCCAGACGAGAGC
ATGCTGGACTGGTGGTCCAAGTACTTTGCCTCCATTGACACCAT
GAAGGAGCAACTTCGACAACAAGAGCCCTCTGGAATTGACTTGG
AGGAGAAGGAGGAAGTGGACAATACCGAGGGCCTGAAGGGGT
CAATGAAGGGCAAGGAGAAGGCAAGGGCTGCCAAAGAGGAGAA
GAAGAAGAAAACTCAGAGCTCTGGCTCTGGCCAGGGGTCCGAG
GCCCCCGAGAAGAAGAAACCCAAGATTGATGAGCTTAAGGTATA
CCCCAAAGAGCTGGAGTCCGAGTTTGATAACTTTGAGGACTGGC
TGCACACTTTCAACTTGCTTCGGGGCAAGACCGGGGATGATGA
GGATGGCTCCACCGAGGAGGAGCGCATTGTGGGACGCTTCAAG
GGCTCCCTCTGCGTGTACAAAGTGCCACTCCCAGAGGACGTGT
CCCGGGAAGCCGGCTACGACTCCACCTACGGCATGTTCCAGGG
CATCCCGAGCAATGACCCCATCAATGTGCTGGTCCGAGTCTATG
TGGTCCGGGCCACGGACCTGCACCCTGCTGACATCAACGGCAA
AGCTGACCCCTACATCGCCATCCGGCTAGGCAAGACTGACATC
CGCGACAAGGAGAACTACATCTCCAAGCAGCTCAACCCTGTCTT
TGGGAAGTCCTTTGACATCGAGGCCTCCTTCCCCATGGAATCCA
TGCTGACGGTGGCTGTGTATGACTGGGACCTGGTGGGCACTGA
TGACCTCATTGGGAAACCAAGATCGACCTGGAGAACCGCTTCT
ACAGCAAGCACCGCGCCACCTGCGGCATCGCCCAGACCTACTC
CACACATGGCTACAATATCTGGCGGGACCCCATGAAGCCCAGC
CAGATCCTGACCCGCCTCTGCAAAGACGGCAAAGTGGACGGCC
CCCACTTTGGGCCCCCTGGGAGAGTGAAGGTGGCCAACCGCGT
CTTCACTGGGCCCTCTGAGATTGAGGACGAGAACGGTCAGAGG
AAGCCCACAGACGAGCATGTGGCGCTGTTGGCCCTGAGGCACT
GGGAGGACATCCCCCGCGCAGGCTGCCGCCTGGTGCCAGAGC
ATGTGGAGACGAGGCCGCTGCTCAACCCCGACAAGCCGGGCAT
CGAGCAGGGCCGCCTGGAGCTGTGGGTGGACATGTTCCCCATG
GACATGCCAGCCCCTGGGACGCCTCTGGACATCTCACCTCGGA
AGCCCAAGAAGTACGAGCTGCGGGTCATCATCTGGAACACAGA
TGAGGTGGTCTTGGAGGACGACGACTTCTTCACAGGGGAGAAG
TCCAGTGACATCTTCGTGAGGGGTGGCTGAAGGGCCAGCAGG
AGGACAAGCAGGACACAGACGTCCACTACCACTCCCTCACTGG
CGAGGGCAACTTCAACTGGCGCTACCTGTTCCCCTTCGACTACC
TGGCGGCGGAGGAGAAGATCGTCATCTCCAAGAAGGAGTCCAT
GTTCTCCTGGGACGAGACCGAGTACAAGATCCCCGCGCGGCTC
ACCCTGCAGATCTGGGATGCGGACCACTTCTCCGCTGACGACTT
CCTGGGGCCATCGAGCTGGACCTGAACCGGTTCCCGCGGGG
CGCAAAGACAGCCAAGCAGTGCACCATGGAGATGGCCACCGGG
GAGGTGGACGTGCCCCTCGTGTCCATCTTCAAGCAAAAGCGCG
TCAAAGGCTGGTGGCCCCTCCTGGCCCGCAATGAGAACGATGA
GTTTGAGCTCACGGGCAAGGTGGAGGCTGAGCTGCATTTACTG
ACAGCAGAGGAGGCAGAGAAGAACCCAGTGGGCCTGGCCCGC
AATGAACCTGACCCCCTAGAGAAACCCAACCGGCCCGACACGG
CCTTCGTCTGGTTCCTCAACCCTCTCAAGTCCATCAAGTACCTCA
TCTGCACCCGGTACAAGTGGCTCATCATCAAGATCGTGCTGGCG
CTGTTGGGGCTGCTCATGTTGGGGCTCTTCCTCTACAGCCTCCC |

TABLE 2-continued

OTOF Sequences

| SEQ ID NO. | Sequence Name | Sequence |
|---|---|---|
| | | TGGCTACATGGTCAAAAAGCTCCTTGGGGCATGAAGGCCGCCA
GCTCCCGCCAGCCGCTCCCCAGCCCTGCCGCATTTCCTTTCAG
TGGCTTGGACTCTTTCCCATCTCCCCTGGGGAGCCTGAGGAGC
CCAGCGTCCACTCTTCATGCCTTGGGCCGAGCCTGCCTCCTGC
TTGCGGGGGCCGCCTGTCCTCACTGCCCCAGGCTGCGGCTTGC
CCAGTCCCGCCCCTCTGACCCCTGCCTGTGGGCTGGGGAGCCT
TGGATGGGGTGGGGACCTGGAATGGGTCTCTCTTGCCCCACCT
GGCTGAGGCGCCACCCTTCTTCAGGCCCAGGCTCCAGAGGAAG
ACTCCTGAAACCCTCCCCAGGTCTTCCAAGTACAGGATTGAAGC
TTTAGTGAAATTAACCAAGGACCATGGGTCAGTGCCCAGGGCTT
TAAAAAGAATGAACGAGCAAAAGGTATCCCCGCCGTGACCCCTG
CAGATAGCACCGGTCTTTGATCCGCAGCAGGGGCCAGACCCTG
CCCACAAGTCCCAGCGCGGCTGCTTCTGCCACTGCTGGGCTCC
ACTTGGCTCCTCTCACTTCCCAGGGGGTCGCCTGTCCTGCCTGT
GGGTTTCCATGGCTTCCCAGAGCTCCCTCTGCCCCAGCCAGCG
CCTCCAGGCCCAGCTGAGGAGCTGTGAGAAGCAGCAGAGGGG
ACTCCCCATCCCGGGCACACCCTGTCCTCCCACCCCTGCCCCC
TTGCCCTTCCAGCCCTTTCAGCTGCAGCTGGGAGCTGGCCCGT
CAAGTGCTGCCCCTGCCTGTGTCTGGGTTTCTGTTGGCTGTTTT
TCTTTTCTTGAGTGGTGATTTTTCTCTAAATAAAAGAAGTCAAGC
ACTGAAAAAAAAAAAAAAAA |
| 13 | OTOF-208 transcript (NM_194322.2), human otoferlin transcript variant 3, 3924 bp, encodes the protein of SEQ ID NO: 4 | CCGTGAGTTCTGCCCAGGCCCTGTGAGCTCACCAGAGCCACAG
ACTCACAGCCCAGAGGTGGCTTCTTCCTTCAGGAACTGAAGAAC
CCCCATGAACACCAACATCTCCAGGTTCTGAGAACAGAACCTGG
GAAATTGATGACTTCCTCATGATGACCGATACTCAGGATGGCCC
TAGCGAGAGCTCCCAGATCATGAGGTCCCTCACTCCCCTGATCA
ACAGGGAGGAGGCATTTGGGGAGGCTGGGGAGGCGGGGCTGT
GGCCCAGCATCACCCACACTCCTGATTCACAGGAAGAAGGCCT
GAACGACATACAGGAGATGATCAAAACGGAGAAGTCCTACCCTG
AGCGTCGCCTGCGGGGCGTCCTGGAGGAGCTGAGCTGTGGCT
GCTGCCGCTTCCTCTCCCTCGCTGACAAGGACCAGGGCCACTC
ATCCCGCACCAGGCTTGACCGGGAGCGCCTCAAGTCCTGCATG
AGGGGAGCTGGAAAACATGGGGCAGCAGGCCAGGATGCTGCGG
GCCCAGGTGAAGCGGCACACGGTGCGGGACAAGCTGAGGCTG
TGCCAGAACTTCCTGCAGAAGCTGCGCTTCCTGGCGGACGAGC
CCCAGCACAGCATTCCCGACATCTTCATCTGGATGATGAGCAAT
AACAAGCGTGTCGCCTATGCCCGTGTGCCCTCCAAGGACCTGC
TCTTCTCCATCGTGGAGGAGGAGACTGGCAAGGACTGCGCCAA
GGTCAAGACGCTCTTCCTTAAGCTGCCAGGGAAGCGGGGCTTC
GGCTCGGCAGGCTGGACAGTGCAGGCCAAGGTGGAGCTGTAC
CTGTGGCTGGGCCTCAGCAAACAGCGCAAGGAGTTCCTGTGCG
GCCTGCCCTGTGGCTTCCAGGAGGTCAAGGCAGCCCAGGGCCT
GGGCCTGCATGCCTTCCACCCGTCAGCCTGGTCTACACCAAG
AAGCAGGCGTTCCAGCTCCGAGCGCACATGTACCAGGCCCGCA
GCCTCTTTGCCGCCGACAGCAGCGGACTCTCAGACCCCTTTGC
CCGCGTCTTCTTCATCAATCAGAGTCAGTGCACAGAGGTGCTGA
ATGAGACCCTGTGTCCCACCTGGGACCAGATGCTGGTGTTCGA
CAACCTGGAGCTCTATGGTGAAGCTCATGAGCTGAGGGACGAT
CCGCCCATCATTGTCATTGAAATCTATGACCAGGATTCCATGGG
CAAAGCTGACTTCATGGGCCGGACCTTCGCCAAACCCCTGGTG
AAGATGGCAGACGAGGCGTACTGCCCACCCCGCTTCCCACCTC
AGCTCGAGTACTACCAGATCTACCGTGGCAACGCCACAGCTGG
AGACCTGCTGGCGGCCTTCGAGCTGCTGCAGATTGGACCAGCA
GGGAAGGCTGACCTGCCCCCCATCAATGGCCCGGTGGACGTG
GACCGAGGTCCCATCATGCCCGTGCCCATGGGCATCCGGCCCG
TGCTCAGCAAGTACCGAGTGGAGGTGCTGTTCTGGGGCCTACG
GGACCTAAAGCGGGTGAACCTGGCCCAGGTGGACCGGCCACG
GGTGGACATCGAGTGTGCAGGGAAGGGGTGCAGTCGTCCCT
GATCCACAATTATAAGAAGAACCCCAACTTCAACACCCTCGTCAA
GTGGTTTGAAGTGGACCTCCCAGAGAACGAGCTGCTGCACCCG
CCCTTGAACATCCGTGTGGTGGACTGCCGGGCCTTCGGTCGCT
ACACACTGGTGGGCTCCCATGCCGTCAGCTCCCTGCGACGCTT
CATCTACCGGCCCCAGACCGCTCGGCCCCCAGCTGGAACACC
ACGGTCAGGCTTCTCCGGCGCTGCCGTGTGCTGTGCAATGGGG
GCTCCTCCTCTCACTCCACAGGGGAGGTTGTGGTGACTATGGA
GCCAGAGGTACCCATCAAGAAACTGGAGACCATGGTGAAGCTG
GACGCGACTTCTGAAGCTGTTGTCAAGGTGGATGTGGCTGAGG
AGGAGAAGGAGAAGAAGAAGAAGAAGAAGGGCACTGCGGAGG
AGCCAGAGGAGGAGGAGCCAGACGAGAGCATGCTGGACTGGT
GGTCCAAGTACTTTGCCTCCATTGACACCATGAAGGAGCAACTT
CGACAACAAGAGCCCTCTGGAATTGACTTGGAGGAGAAGGAGG
AAGTGGACAATACCGAGGGCCTGAAGGGGTCAATGAAGGGCAA
GGAGAAGGCAAGGGCTGCCAAAGAGGAGAAGAAGAAGAAAACT
CAGAGCTCTGGCTCTGGCCAGGGGTCCGAGGCCCCCGAGAAG |

TABLE 2-continued

OTOF Sequences

| SEQ ID NO. | Sequence Name | Sequence |
|---|---|---|
| | | AAGAAACCCAAGATTGATGAGCTTAAGGTATACCCCAAAGAGCT
GGGAGTCCGAGTTTGATAACTTTGAGGACTGGCTGCACACTTTCA
ACTTGCTTCGGGGCAAGACCGGGGATGATGAGGATGGCTCCAC
CGAGGAGGAGCGCATTGTGGGACGCTTCAAGGGCTCCCTCTGC
GTGTACAAAGTGCCACTCCCAGAGGACGTGTCCCGGGAAGCCG
GCTACGACTCCACCTACGGCATGTTCCAGGGCATCCCGAGCAA
TGACCCCATCAATGTGCTGGTCCGAGTCTATGTGGTCCGGGCC
ACGGACCTGCACCCTGCTGACATCAACGGCAAAGCTGACCCCT
ACATCGCCATCCGGCTAGGCAAGACTGACATCCGCGACAAGGA
GAACTACATCTCCAAGCAGCTCAACCCTGTCTTTGGGAAGTCCT
TTGACATCGAGGCCTCCTTCCCCATGGAATCCATGCTGACGGTG
GCTGTGTATGACTGGGACCTGGTGGGCACTGATGACCTCATTG
GGGAAACCAAGATCGACCTGGAGAACCGCTTCTACAGCAAGCA
CCGCGCCACCTGCGGCATCGCCCAGACCTACTCCACACATGGC
TACAATATCTGGCGGGACCCCATGAAGCCCAGCCAGATCCTGA
CCCGCCTCTGCAAAGACGGCAAAGTGGACGGCCCCCACTTTGG
GCCCCCTGGGAGAGTGAAGGTGGCCAACCGCGTCTTCACTGGG
CCCTCTGAGATTGAGGACGAGAACGGTCAGAGGAAGCCCACAG
ACGAGCATGTGGCGCTGTTGGCCCTGAGGCACTGGGAGGACAT
CCCCCGCGCAGGCTGCCGCCTGGTGCCAGAGCATGTGGAGAC
GAGGCCGCTGCTCAACCCCGACAAGCCGGGCATCGAGCAGGG
CCGCCTGGAGCTGTGGGTGGACATGTTCCCCATGGACATGCCA
GCCCCTGGGACGCCTCTGGACATCTCACCTCGGAAGCCCAAGA
AGTACGAGCTGCGGGTCATCATCTGGAACACAGATGAGGTGGT
CTTGGAGGACGACGACTTCTTCACAGGGGAGAAGTCCAGTGAC
ATCTTCGTGAGGGGGTGGCTGAAGGGCCAGCAGGAGGACAAG
CAGGACACAGACGTCCACTACCACTCCCTCACTGGCGAGGGCA
ACTTCAACTGGCGCTACCTGTTCCCCTTCGACTACCTGGCGGCG
GAGGAGAAGATCGTCATCTCCAAGAAGGAGTCCATGTTCTCCTG
GGACGAGACCGAGTACAAGATCCCCGCGCGGCTCACCCTGCAG
ATCTGGGATGCGGACCACTTCTCCGCTGACGACTTCCTGGGGG
CCATCGAGCTGGACCTGAACCGGTTCCCGCGGGCGCAAAGAC
AGCCAAGCAGTGCACCATGGAGATGGCCACCGGGGAGGTGGA
CGTGCCCCTCGTGTCCATCTTCAAGCAAAAGCGCGTCAAAGGCT
GGTGGCCCCTCCTGGCCCGCAATGAGAACGATGAGTTTGAGCT
CACGGGCAAGGTGGAGGCTGAGCTGCATTTACTGACAGCAGAG
GAGGCAGAGAAGAACCCAGTGGGCCTGGCCCGCAATGAACCTG
ACCCCCTAGAGAAACCCAACCGGCCCGACACGAGCTTCATCTG
GTTCCTGAACCCTCTCAAGTCGGCTCGCTACTTCTTGTGGCACA
CGTATCGCTGGCTGCTCCTCAAACTGTTGCTGCTCCTGCTGCTG
CTCCTCCTCCTCGCCCTGTTCCTCTACTCTGTGCCTGGCTACCT
GGTCAAGAAAATCCTCGGGGCCTGAGCCCAGTGGCCTCCTGGC
CGGCCCCGACACGGCCTTCGTCTGGTTCCTCAACCCTCTCAAGTC
CATCAAGTACCTCATCTGCACCCGGTACAAGTGGCTCATCATCA
AGATCGTGCTGGCGCTGTTGGGGCTGCTCATGTTGGGGCTCTT
CCTCTACAGCCTCCCTGGCTACATGGTCAAAAAGCTCCTTGGGG
CATGAAGGCCGCCAGCTCCCGCCAGCCGCTCCCCAGCCCTGCC
GCATTTCCTTTCAGTGGCTTGGACTCTTTCCCATCTCCCCTGGG
GAGCCTGAGGAGCCCAGCGTCCACTCTTCATGCCTTGGGCCGA
GCCTGCCTCCTGCTTGCGGGGGCCGCCTGTCCTCACTGCCCCA
GGCTGCGGCTTGCCCAGTCCCGCCCCTCTGACCCCTGCCTGTG
GGCTGGGGAGCCTTGGATGGGTGGGGACCTGGAATGGGTCT
CTCTTGCCCCACCTGGCTGAGGCGCCACCCTTCTTCAGGCCCA
GGCTCCAGAGGAAGACTCCTGAAACCCTCCCCAGGTCTTCCAA
GTACAGGATTGAAGCTTTAGTGAAATTAACCAAGGACCATGGGT
CAGTGCCCAGGGCTTTAAAAAGAATGAACGAGCAAAAGGTATCC
CCGCCGTGACCCCTGCAGATAGCACCGGTCTTTGATCCGCAGC
AGGGGCCAGACCCTGCCCACAAGTCCCAGCGCGGCTGCTTCTG
CCACTGCTGGGCTCCACTTGGCTCCTCTCACTTCCCAGGGGGT
CGCCTGTCCTGCCTGTGGGTTTCCATGGCTTCCCAGAGCTCCCT
CTGCCCCAGCCAGCGCCTCCAGGCCCAGCTGAGGAGCTGTGA
GAAGCAGCAGAGGGGACTCCCCATCCCGGGCACACCCTGTCCT
CCCACCCCTGCCCCCTTGCCCTTCCAGCCCTTTCAGCTGCAGCT
GGGAGCTGGCCCGTCAAGTGCTGCCCCTGCCTGTGTCTGGGTT
TCTGTTGGCTGTTTTTCTTTTCTTGAGTGGTGATTTTCTCTAAAT
AAAAGAAGTCAAGCACTGAAAAAAAAAAAAAAA |
| 14 | OTOF-205 transcript (NM_001287489.1), human otoferlin transcript variant 5, 6937 bp, encodes the protein of SEQ ID NO: 5 | ATCGGAGGGGGTCGGAGGAGGAGGAGGAGGCAGCGGCAG
AGAAGAGAGAGGCGTGTGAGCCGTGCTCCACCGGCTAGCTCCT
TCCCGCTGCTCCTGCCTGGCAGTGCCAGGCAGCCCACACCAGC
ATGGCCTTGCTCATCCACCTCAAGACAGTCTCGGAGCTGCGGG
GCAGGGGCGACCGGATCGCCAAAGTGACTTTCCGAGGGCAATC
CTTCTACTCTCGGGTCCTGGAGAACTGTGAGGATGTGGCTGACT
TTGATGAGACATTTCGTGGCCGGTGGCCAGCAGCATCGACAG
AAATGAGATGCTGGAGATTCAGGTTTTCAACTACAGCAAAGTCTT |

TABLE 2-continued

OTOF Sequences

| SEQ ID NO. | Sequence Name | Sequence |
|---|---|---|
| | | CAGCAACAAGCTCATCGGGACCTTCCGCATGGTGCTGCAGAAG
GTGGTAGAGGAGAGCCATGTGGAGGTGACTGACACGCTGATTG
ATGACAACAATGCTATCATCAAGACCAGCCTGTGCGTGGAGGTC
CGGTATCAGGCCACTGACGGCACAGTGGGCTCCTGGGACGATG
GGGACTTCCTGGGAGATGAGTCTCTTCAAGAGGAAGAGAAGGA
CAGCCAAGAGACGGATGGACTGCTCCCAGGCTCCCGGCCCAGC
TCCCGGCCCCCAGGAGAGAAGAGCTTCCGGAGAGCCGGGAGG
AGCGTGTTCTCCGCCATGAAGCTCGGCAAAAACCGGTCTCACAA
GGAGGAGCCCCAAAGACCAGATGAACCGGCGGTGCTGGAGAT
GGAAGACCTTGACCATCTGGCCATTCGGCTAGGAGATGGACTG
GATCCCGACTCGGTGTCTCTAGCCTCAGTCACAGCTCTCACCAC
TAATGTCTCCAACAAGCGATCTAAGCCAGACATTAAGATGGAGC
CAAGTGCTGGGCGGCCCATGGATTACCAGGTCAGCATCACGGT
GATCGAGGCCCGGCAGCTGGTGGGCTTGAACATGGACCCTGTG
GTGTGCGTGGAGGTGGGTGACGACAAGAAGTACACATCCATGA
AGGAGTCCACTAACTGCCCCTATTACAACGAGTACTTCGTCTTC
GACTTCCATGTCTCTCCGGATGTCATGTTTGACAAGATCATCAAG
ATTTCGGTGATTCACTCCAAGAACCTGCTGCGCAGTGGCACCCT
GGTGGGCTCCTTCAAAATGGACGTGGGAACCGTGTACTCGCAG
CCAGAGCACCAGTTCCATCACAAGTGGGCCATCCTGTCTGACCC
CGATGACATCTCCTCGGGGCTGAAGGGCTACGTGAAGTGTGAC
GTTGCCGTGGTGGGCAAAGGGGACAACATCAAGACGCCCCACA
AGGCCAATGAGACCGACGAAGATGACATTGAGGGGAACTTGCT
GCTCCCCGAGGGGGTGCCCCCCGAACGCCAGTGGGCCCGGTT
CTATGTGAAAATTTACCGAGCAGAGGGGCTGCCCCGTATGAACA
CAAGCCTCATGGCCAATGTAAAGAAGGCTTTCATCGGTGAAAAC
AAGGACCTCGTGGACCCCTACGTGCAAGTCTTCTTTGCTGGCCA
GAAGGGCAAGACTTCAGTGCAGAAGAGCAGCTATGAGCCCCTG
TGGAATGAGCAGGTCGTCTTTACAGACCTCTTCCCCCCCACTCTG
CAAACGCATGAAGGTGCAGATCCGAGACTCGGACAAGGTCAAC
GACGTGGCCATCGGCACCCACTTCATTGACCTGCGCAAGATTTC
TAATGACGGAGACAAAGGCTTCCTGCCCACACTGGGCCCAGCC
TGGGTGAACATGTACGGCTCCACACGTAACTACACGCTGCTGGA
TGAGCATCAGGACCTGAACGAGGGCCTGGGGGAGGGTGTGTC
CTTCCGGGCCCGGCTCCTGCTGGGCCTGGCTGTGGAGATCGTA
GACACCTCCAACCCTGAGCTCACCAGCTCCACAGAGGTGCAGG
TGGAGCAGGCCACGCCCATCTCGGAGAGCTGTGCAGGTAAAAT
GGAAGAATTCTTTTCTCTTTGGAGCCTTCCTGGAGGCCTCAATGA
TCGACCGGAGAAACGGAGACAAGCCCATCACCTTTGAGGTCAC
CATAGGCAACTATGGGAACGAAGTTGATGGCCTGTCCCGGCCC
CAGCGGCCTCGGCCCCGGAAGGAGCCGGGGGATGAGGAAGAA
GTAGACCTGATTCAGAACGCAAGTGATGACGAGGCCGGTGATG
CCGGGGACCTGGCCTCAGTCTCCTCCACTCCACCAATGCGGCC
CCAGGTCACCGACAGGAACTACTTCCATCTGCCCTACCTGGAGC
GAAAGCCCTGCATCTACATCAAGAGCTGGTGGCCGGACCAGCG
CCGCCGCCTCTACAATGCCAACATCATGGACCACATTGCCGACA
AGCTGGAAGAAGGCCTGAACGACATACAGGAGATGATCAAAAC
GGAGAAGTCCTACCCTGAGCGTCGCCTGCGGGCGTCCTGGA
GGAGCTGAGCTGTGGCTGCTGCCGCTTCCTCTCCCTCGCTGAC
AAGGACCAGGGCCACTCATCCCGCACCAGGCTTGACCGGGAGC
GCCTCAAGTCCTGCATGAGGGAGCTGGAAAACATGGGGCAGCA
GGCCAGGATGCTGCGGGCCCAGGTGAAGCGGCACACGGTGCG
GGACAAGCTGAGGCTGTGCCAGAACTTCCTGCAGAAGCTGCGC
TTCCTGGCGGACGAGCCCCAGCACAGCATTCCCGACATCTTCAT
CTGGATGATGAGCAACAACAAGCGTGTCGCCTATGCCCGTGTG
CCCTCCAAGGACCTGCTCTTCTCCATCGTGGAGGAGGAGACTG
GCAAGGACTGCGCCAAGGTCAAGACGCTCTTCCTTAAGCTGCC
AGGGAAGCGGGGCTTCGGCTCGGCAGGCTGGACAGTGCAGGC
CAAGGTGGAGCTGTACCTGTGGCTGGGCCTCAGCAAACAGCGC
AAGGAGTTCCTGTGCGGCCTGCCCTGTGGCTTCCAGGAGGTCA
AGGCAGCCCAGGGCCTGGGCCTGCATGCCTTCCCACCCGTCAG
CCTGGTCTACACCAAGAAGCAGGCGTTCCAGCTCCGAGCGCAC
ATGTACCAGGCCCGCAGCCTCTTTGCCGCCGACAGCAGCGGAC
TCTCAGACCCCTTTGCCCGCGTCTTCTTCATCAATCAGAGTCAG
TGCACAGAGGTGCTGAATGAGACCCTGTGTCCCACCTGGGACC
AGATGCTGGTGTTCGACAACCTGGAGCTCTATGGTGAAGCTCAT
GAGCTGAGGGACGATCCGCCCATCATTGTCATTGAAATCTATGA
CCAGGATTCCATGGGCAAAGCTGACTTCATGGGCCGGACCTTC
GCCAAACCCCTGGTGAAGATGGCAGACGAGGCGTACTGCCCAC
CCCGCTTCCCACCTCAGCTCGAGTACTACCAGATCTACCGTGGC
AACGCCACAGCTGGAGACCTGCTGGCGGCCTTCGAGCTGCTGC
AGATTGACCAGCAGGGAAGGCTGACCTGCCCCCATCAATGG
CCCGGTGGACGTGGACCGAGGTCCCATCATGCCCGTGCCCATG
GGCATCCGGCCCGTGCTCAGCAAGTACCGAGTGGAGGTGCTGT
TCTGGGGCCTACGGGACCTAAAGCGGGTGAACCTGGCCCAGGT |

TABLE 2-continued

OTOF Sequences

| SEQ ID NO. | Sequence Name | Sequence |
|---|---|---|
| | | GGACCGGCCACGGGTGGACATCGAGTGTGCAGGGAAGGGGGT
GCAGTCGTCCCTGATCCACAATTATAAGAAGAACCCCAACTTCA
ACACCCTCGTCAAGTGGTTTGAAGTGGACCTCCCAGAGAACGA
GCTGCTGCACCCGCCCTTGAACATCCGTGTGGTGGACTGCCGG
GCCTTCGGTCGCTACACACTGGTGGGCTCCCATGCCGTCAGCT
CCCTGCGACGCTTCATCTACCGGCCCCAGACCGCTCGGCCCC
CAGCTGGAACACCACGGTCAGGCTTCTCCGGCGCTGCCGTGTG
CTGTGCAATGGGGGCTCCTCCTCTCACTCCACAGGGGAGGTTG
TGGTGACTATGGAGCCAGAGGTACCCATCAAGAAACTGGAGAC
CATGGTGAAGCTGGACGCGACTTCTGAAGCTGTTTGTCAAGGTG
GATGTGGCTGAGGAGGAGAAGGAGAAGAAGAAGAAGAAGAAGG
GCACTGCGGAGGAGCCAGAGGAGGAGGAGCCAGACGAGAGCA
TGCTGGACTGGTGGTCCAAGTACTTTGCCTCCATTGACACCATG
AAGGAGCAACTTCGACAACAAGAGCCCTCTGGAATTGACTTGGA
GGAGAAGGAGGAAGTGGACAATACCGAGGGCCTGAAGGGGTC
AATGAAGGGCAAGGAGAAGGCAAGGGCTGCCAAAGAGGAGAAG
AAGAAGAAAACTCAGAGCTCTGGCTCTGGCCAGGGGTCCGAGG
CCCCCGAGAAGAAGAAACCCAAGATTGATGAGCTTAAGGTATAC
CCCAAAGAGCTGGAGTCCGAGTTTGATAACTTTGAGGACTGGCT
GCACACTTTCAACTTGCTTCGGGGCAAGACCGGGGATGATGAG
GATGGCTCCACCGAGGAGGAGCGCATTGTGGGACGCTTCAAGG
GCTCCCTCTGCGTGTACAAAGTGCCACTCCCAGAGGACGTGTC
CCGGGAAGCCGGCTACGACTCCACCTACGGCATGTTCCAGGGC
ATCCCGAGCAATGACCCCATCAATGTGCTGGTCCGAGTCTATGT
GGTCCGGGCCACGGACCTGCACCCTGCTGACATCAACGGCAAA
GCTGACCCCTACATCGCCATCCGGCTAGGCAAGACTGACATCC
GCGACAAGGAGAACTACATCTCCAAGCAGCTCAACCCTGTCTTT
GGGAAGTCCTTTGACATCGAGGCCTCCTTCCCCATGGAATCCAT
GCTGACGGTGGCTGTGTATGACTGGGACCTGGTGGGCACTGAT
GACCTCATTGGGGAAACCAAGATCGACCTGGAGAACCGCTTCTA
CAGCAAGCACCGCGCCACCTGCGGCATCGCCCAGACCTACTCC
ACACATGGCTACAATATCTGGCGGGACCCCATGAAGCCCAGCC
AGATCCTGACCCGCCTCTGCAAAGACGGCAAAGTGGACGGCCC
CCACTTTGGGCCCCCTGGGAGAGTGAAGGTGGCCAACCGCGTC
TTCACTGGGCCCTCTGAGATTGAGGACGAGAACGGTCAGAGGA
AGCCCACAGACGAGCATGTGGCGCTGTTGGCCCTGAGGCACTG
GGAGGACATCCCCCGCGCAGGCTGCCGCCTGGTGCCAGAGCA
TGTGGAGACGAGGCCGCTGCTCAACCCCGACAAGCCGGGCATC
GAGCAGGGCCGCCTGGAGCTGTGGGTGGACATGTTCCCCATGG
ACATGCCAGCCCTGGGACGCCTCTGGACATCTCCACCTCGGAA
GCCCAAGAAGTACGAGCTGCGGGTCATCATCTGGAACACAGAT
GAGGTGGTCTTGGAGGACGACGACTTCTTCACAGGGGAGAAGT
CCAGTGACATCTTCGTGAGGGGTGGCTGAAGGGCCAGCAGGA
GGACAAGCAGGACACAGACGTCCACTACCACTCCCTCACTGGC
GAGGGCAACTTCAACTGGCGCTACCTGTTCCCCTTCGACTACCT
GGCGGCGGAGGAGAAGATCGTCATCTCCAAGAAGGAGTCCATG
TTCTCCTGGGACGAGACCGAGTACAAGATCCCCGCGCGGCTCA
CCCTGCAGATCTGGGATGCGGACCACTTCTCCGCTGACGACTT
CCTGGGGGCCATCGAGCTGGACCTGAACCGGTTCCCGCGGGG
CGCAAAGACAGCCAAGCAGTGCACCATGGAGATGGCCACCGGG
GAGGTGGACGTGCCCCTCGTGTCCATCTTCAAGCAAAAGCGCG
TCAAAGGCTGGTGGCCCCTCCTGGCCCGCAATGAGAACGATGA
GTTTGAGCTCACGGGCAAGGTGGAGGCTGAGCTGCATTTACTG
ACAGCAGAGGAGGCAGAGAAGAACCCAGTGGGCCTGGCCCGC
AATGAACCTGACCCCCTAGAGAAACCCAACCGGCCCGACACGG
CCTTCGTCTGGTTCCTCAACCCTCTCAAGTCCATCAAGTACCTCA
TCTGCACCCGGTACAAGTGGCTCATCATCAAGATCGTGCTGGCG
CTGTTGGGGCTGCTCATGTTGGGGCTCTTCCTCTACAGCCTCCC
TGGCTACATGGTCAAAAAGCTCCTTGGGGCATGAAGGCCGCCA
GCTCCCGCCAGCCGCTCCCCAGCCCTGCCGCATTTCCTTTCAG
TGGCTTGGACTCTTTCCCATCTCCCTGGGGAGCCTGAGGAGC
CCAGCGTCCACTCTTCATGCCTTGGGCCGAGCCTGCCTCCTGC
TTGCGGGGGCCGCCTGTCCTCACTGCCCCAGGCTGCGGCTTGC
CCAGTCCCGCCCCTCTGACCCCTGCCTGTGGGCTGGGAGCCT
TGGATGGGTGGGACCTGGAATGGGTCTCTCTTGCCCCACCT
GGCTGAGGCGCCACCCTTCTTCAGGCCCAGGCTCCAGAGGAAG
ACTCCTGAAACCCTCCCCAGGTCTTCCAAGTACAGGATTGAAGC
TTTAGTGAAATTAACCAAGGACCATGGGTCAGTGCCCAGGGCTT
TAAAAAGAATGAACGAGCAAAAGGTATCCCCGCCGTGACCCCTG
CAGATAGCACCGGTCTTTGATCCGCAGCAGGGGCCAGACCCTG
CCCACAAGTCCCAGCGCGGCTGCTTCGCCACTGCTGGGCTCC
ACTTGGCTCCTCTCACTTCCCAGGGGGTCGCCTGTCCTGCCTGT
GGGTTTCCATGGCTTCCCAGAGCTCCCTCTGCCCCAGCCAGCG
CCTCCAGGCCCAGCTGAGGAGCTGTGAGAAGCAGCAGAGGGG
ACTCCCCATCCCGGGCACACCCTGTCCTCCCACCCCTGCCCCC |

TABLE 2-continued

OTOF Sequences

| SEQ ID NO. | Sequence Name | Sequence |
|---|---|---|
| | | TTGCCCTTCCAGCCCTTTCAGCTGCAGCTGGGAGCTGGCCCGT CAAGTGCTGCCCCTGCCTGTGTCTGGGTTTCTGTTGGCTGTTTT TCTTTTCTTGAGTGGTGATTTTTCTCTAAATAAAAGAAGTCAAGC ACTGAAAAAAAAAAAAAAAA |
| 15 | mOTOF-201_1 transcript (NM_031875.2), mouse otoferlin transcript variant 2, 7129 bp, encodes the protein of SEQ ID NO: 6 | TTGGTTGCCTTGGTCTCTGTGGGCAGCAGCAGGAGGAGGCGGC AGCAGCCAGAGAAGAGGGAGGCGTGTGAGCCACACTCCACCAG CGAGCTTCTTCCCGCTGCTCTGGAACTGCCCAGGCTCTCCCCA CCAGCATGGCCCTGATTGTTCACCTCAAGACTGTCTCAGAGCTC CGAGGCAAAGGTGACCGGATTGCCAAAGTCACTTTCCGAGGGC AGTCTTTCTACTCCCGGGTCCTGGAGAACTGCGAGGGTGTGGC TGACTTTGATGAGACGTTCCGGTGGCCAGTGGCCAGCAGCATC GACCGGAATGAAGTGTTGGAGATTCAGATTTTCAACTACAGCAA AGTCTTCAGCAACAAGCTGATAGGGACCTTCTGCATGGTGCTGC AGAAAGTGGTGGAGGAGAATCGGGTAGAGGTGACCGACACGCT GATGGATGACAGCAATGCTATCATCAAGACCAGCCTGAGCATGG AGGTCCGGTATCAGGCCACAGATGGCACTGTGGGCCCCTGGGA TGATGGAGACTTCCTGGGAGATGAATCCCTCCAGGAGGAGAAG GACAGCCAGGAGACAGATGGGCTGCTACCTGGTTCCCGACCCA GCACCCGGATATCTGGCGAGAAGAGCTTTCGCAGAGCGGGAG GAGTGTGTTCTCGGCCATGAAACTCGGCAAAACTCGGTCCCACA AAGAGGAGCCCCAAAGACAAGATGAGCCAGCAGTGCTGGAGAT GGAGGACCTGGACCACCTAGCCATTCAGCTGGGGGATGGGCTG GATCCTGACTCCGTGTCTCTAGCCTCGGTCACCGCTCTCACCAG CAATGTCTCCAACAAACGGTCTAAGCCAGATATTAAGATGGAGC CCAGTGCTGGAAGGCCCATGGATTACCAGGTCAGCATCACAGT GATTGAGGCTCGGCAGCTGGTGGGCTTGAACATGGACCCTGTG GTGTGTGTGGAGGTGGGTGATGACAAGAAATACACGTCAATGAA GGAGTCCACAAACTGCCCTTACTACAACGAGTACTTTGTCTTCG ACTTCCATGTCTCTCCTGATGTCATGTTTGACAAGATCATCAAGA TCTCGGTTATCCATTCTAAGAACCTGCTTCGGAGCGGCACCCTG GTGGGTTCCTTCAAAATGGATGTGGGGACTGTGTATTCCCAGCC TGAACACCAGTTCCATCACAAATGGGCCATCCTGTCAGACCCCG ATGCACATCTCTGCTGGGTTGAAGGGTTATGTAAAGTGTGATGTC GCTGTGGTGGGCAAGGGAGACAACATCAAGACACCCCACAAGG CCAACGAGACGGATGAGGACGACATTGAAGGGAACTTGCTGCT CCCCGAGGGCGTGCCCCCCGAACGGCAGTGGGCACGGTTCTA TGTGAAAATTTACCGAGCAGAGGGACTGCCCCGGATGAACACAA GCCTCATGGCCAACGTGAAGAAGGCGTTCATCGGTGAGAACAA GGACCTCGTCGACCCCTATGTGCAAGTCTTCTTTGCTGGACAAA AGGGCAAAACATCAGTGCAGAAGAGCAGCTATGAGCCGCTATG GAATGAGCAGGTCGTCTTCACAGACTTGTTCCCCCCACTCTGCA AACGCATGAAGGTGCAGATCCGGGACTCTGACAAGGTCAATGAT GTGGCCATCGGCACCCACTTCATCGACCTGCGCAAGATTTCCAA CGATGGGAGACAAAGGCTTCCTGCCTACCCTCGGTCCAGCCTGG GTGAACATGTACGGCTCCACGCGCAACTACACACTGCTGGACG AGCACCAGGACTTGAATGAAGGCCTGGGGGAGGGTGTGTCCTT CCGGGCCCGCCTCATGTTGGGACTAGCTGTGGAGATCCTGGAC ACCTCCAACCCAGAGCTCACCAGCTCCACGGAGGTGCAGGTGG AGCAGGCCACGCCTGTCTCGGAGAGCTGCACAGGGAGAATGGA AGAATTTTTTCTATTTGGAGCCTTCTTGGAAGCCTCAATGATTGA CCGGAAAAATGGGGACAAGCCAATTACCTTTGAGGTGACCATAG GAAACTACGGCAATGAAGTCGATGGTATGTCCCGGCCCCTGAG GCCTCGGCCCCGGAAAGAGCCTGGGGATGAAGAAGAGGTAGA CCTGATTCAGAACTCCAGTGACGATGAAGGTGACGAAGCCGGG GACCTGGCCTCGGTGTCCTCCACCCCACCTATGCGGCCCCAGA TCACGGACAGGAACTATTTCCACCTGCCCTACCTGGAGCGCAAG CCCTGCATCTATATCAAGAGCTGGTGGCCTGACCAGAGGCGGC GCCTCTACAATGCCAACATCATGGATACATTGCTGACAAGCTG GAAGAAGGCCTGAATGATGTACAGGAGATGATCAAAACGGAGAA GTCCTACCCGGAGCGCCGCCTGCGGGGTGTGCTAGAGGAACTC AGCTGTGGCTGCCACCGCTTCCTCTCCCTCTCGGACAAGGACC AGGGCCGCTCGTCCCGCACCAGGCTGGATCGAGAGCGTCTTAA GTCCTGTATGAGGGAGTTGGAGAGCATGGACAGCAGGCCAAG AGCCTGAGGGCTCAGGTGAAGCGGCACACTGTTCGGGACAAGC TGAGGTCATGCCAGAACTTTCTGCAGAAGCTACGCTTCCTGGCG GATGAGCCCCAGCACAGCATTCCTGATGTGTTCATTTGGATGAT GAGCAACAACAAACGTATCGCCTATGCCCGCGTGCCTTCCAAAG ACCTGCTCTTCTCCATCGTGGAGGAGGAACTGGGCAAGGACTG CGCCAAAGTCAAGACCCTCTTCCTGAAGCTGCCAGGGAAGAGG GGCTTCGGCTCGGCAGGCTGGACAGTACAGGCCAAGCTGGAG CTCTACCTGTGGCTGGGCCTCAGCAAGCAGCGAAAGGACTTCC TGTGTGGTCTGCCCTGTGGCTTCGAGGAGGTCAAGGCAGCCCA AGGCCTGGGCCTGCATTCCTTTCCGCCCATCAGCCTAGTCTACA CCAAGAAGCAAGCCTTCCAGCTCCGAGCACACATGTATCAGGC |

TABLE 2-continued

OTOF Sequences

| SEQ ID NO. | Sequence Name | Sequence |
|---|---|---|
| | | CCGAAGCCTCTTTGCTGCTGACAGCAGTGGGCTCTCTGATCCCT
TTGCCCGTGTCTTCTTCATCAACCAGAGCCAATGCACTGAGGTT
CTAAACGAGACACTGTGTCCCACCTGGGACCAGATGCTGGTATT
TGACAACCTGGAGCTGTACGGTGAAGCTCACGAGTTACGAGAT
GATCCCCCCATCATTGTCATTGAAATCTACGACCAGGACAGCAT
GGGCAAAGCCGACTTCATGGGCCGGACCTTCGCCAAGCCCCTG
GTGAAGATGGCAGATGAAGCATACTGCCCACCTCGCTTCCCGC
CGCAGCTTGAGTACTACCAGATCTACCGAGGCAGTGCCACTGC
CGGAGACCTACTGGCTGCCTTCGAGCTGCTGCAGATTGGGCCA
TCAGGGAAGGCTGACCTGCCACCCATCAATGCCCAGTGGACA
TGGACAGAGGGCCCATCATGCCTGTGCCCGTGGGAATCCGGCC
AGTGCTCAGCAAGTACCGAGTGGAGGTGCTGTTCTGGGGCCTG
AGGGACCTAAAGAGGGTGAACCTGGCCCAGGTGGACCGACCAC
GGGTGGACATCGAGTGTGCAGGAAGGGGGTACAATCCTCCCT
GATTCACAATTATAAGAAGAACCCCAACTTCAACACGCTGGTCAA
GTGGTTTGAAGTGGACCTCCCGGAGAATGAGCTCCTGCACCCA
CCCTTGAACATCCGAGTGGTAGATTGCCGGGCCTTTGGACGATA
CACCCTGGTGGGTTCCCACGCAGTCAGCTCACTGAGGCGCTTC
ATCTACCGACCTCCAGACCGCTCAGCCCCAACTGGAACACCA
CAGTCAGGCTGCTCCGGGGCTGCCACAGGCTGCGCAATGGGG
GCCCCTCTTCTCGCCCCACAGGGGAGGTTGTAGTAAGCATGGA
GCCTGAGGAGCCAGTTAAGAAGCTGGAGACCATGGTGAAACTG
GATGCGACTTCTGATGCTGTGGTCAAGGTGGATGTGGCTGAAG
ATGAGAAGGAAAGGAAGAAGAAGAAAAAGAAAGGCCCGTCAGA
GGAGCCAGAGGAGGAAGAGCCCGATGAGAGCATGCTGGATTG
GTGGTCCAAGTACTTCGCCTCCATCGACACAATGAAGGAGCAAC
TTCGACAACATGAGACCTCTGGAACTGACTTGGAAGAGAAG  GAA
GAGATGGAAAGCGCTGAGGGCCTGAAGGGACCAATGAAGAGCA
AGGAGAAGTCCAGAGCTGCAAAGGAGGAGAAAAAGAAGAAAAA
CCAGAGCCCTGGCCCTGGCCAGGGATCGGAGGCTCCTGAGAA
GAAGAAAGCCAAGATCGATGAGCTTAAGGTGTACCCCAAGGAG
CTGGAATCGGAGTTTGACAGCTTTGAGGACTGGCTGCACACCTT
CAACCTGTTGAGGGGCAAGACGGGAGATGATGAGGATGGCTCC
ACAGAGGAGGAGCGCATAGTAGGCCGATTCAAGGGCTCCCTCT
GTGTGTACAAAGTGCCACTCCCAGAAGATGTATCTCGAGAAGCT
GGCTATGATCCCACCTATGGAATGTTCCAGGGCATCCCAAGCAA
TGACCCCATCAATGTGCTGGTCCGAATCTATGTGGTCCGGGCCA
CAGACCTGCACCCGGCCGACATCAATGGCAAAGCTGACCCCTA
TATTGCCATCAAGTTAGGCAAGACCGACATCCGAGACAAGGAGA
ACTACATCTCCAAGCAGCTCAACCCTGTGTTTGGGAAGTCCTTT
GACATTGAGGCCTCCTTCCCCATGGAGTCCATGTTGACAGTGGC
CGTGTACGACTGGGATCGGTGGGCACTGATGACCTCATCGGA
GAAACCAAGATTGACCTGGAAAACCGCTTCTACAGCAAGCATCG
CGCCACCTGCGCATCGCACAGACCTATTCCATACATGGCTACA
ATATCTGGAGGGACCCCATGAAGCCCAGCCAGATCCTGACACG
CCTCTGTAAAGAGGGCAAAGTGGACGGCCCCCACTTTGGTCCC
CATGGGAGAGTGAGGGTTGCCAACCGTGTCTTCACGGGGCCTT
CAGAAATAGAGGATGAGAATGGTCAGAGGAAGCCCACAGATGA
GCACGTGGCACTGTCTGCTCTGAGCACACTGGGAGGACATCCCC
CGGGTGGGCTGCCGCCTTGTGCCGGAACACGTGGAGACCAGG
CCGCTGCTCAACCCTGACAAGCCAGGCATTGAGCAGGGCCGCC
TGGAGCTGTGGGTGGACATGTTCCCCATGGACATGCCAGCCCC
TGGGACACCTCTGGATATATCCCCAGGAAACCCAAGAAGTACG
AGCTGCGGGTCATCGTGTGGAACACAGACGAGGTGGTCCTGGA
AGACGATGATTTCTTCACGGGAGAGAAGTCCAGTGACATTTTTG
TGAGGGGTGGCTGAAGGGCCAGCAGGAGGACAAACAGGACA
CAGATGTCCACTATCACTCCCTCACGGGGGAGGGCAACTTCAAC
TGGAGATACCTCTTCCCCTTCGACTACCTAGCGGCCGAAGAGAA
GATCGTTATGTCCAAAAAGGAGTCTATGTTCTCCTGGGATGAGA
CGGAGTACAAGATCCCTGCGCGGCTCACCCTGCAGATCTGGGA
CGCTGACCACTTCTCGGCTGACGACTTCCTGGGGGCTATCGAG
CTGGACCTGAACCGGTTCCCGAGGGGCGCTAAGACAGCCAAGC
AGTGCACCATGGAGATGGCCACCGGGAGGTGGACGTACCCCT
GGTTTCCATCTTTAAACAGAAACGTGTCAAAGGCTGGTGGCCCC
TCCTGGCCCGCAATGAGAATGATGAGTTTGAGCTCACAGGCAAA
GTGGAGGCGGAGCTACACCTACTCACGGCAGAGGAGGCAGAG
AAGAACCCTGTGGGCCTGGCTCGCAATGAACCTGATCCCCTAG
AAAAACCCAATCGGCCGGACACAAGCTTCATCTGGTTCTTGAAC
CCTCTCAAGTCTGCCCGCTACTTCCTGTGGCATACCTACCGCTG
GCTACTCCTCAAATTCCTGCTGCTCTTCCTCCTGCTGCTGCTCTT
CGCCCTGTTTCTCTACTCTCTGCCTGGCTACCTGGCCAAGAAGA
TCCTTGGGGCCTGAGCCCTGCAGTCGCCTAGGCCTGCCGGCCT
GACACGGCATTCGTCTGGTTCCTGAACCCACTCAAATCTATCAA
GTACCTCATCTGCACCCGGTACAAGTGGCCTGATCATCAAGATCG
TGCTGGCGCTGCTGGGGCTGCTCATGCTGGCCCTCTTCCTTTAC |

TABLE 2-continued

OTOF Sequences

| SEQ ID NO. | Sequence Name | Sequence |
|---|---|---|
| | | AGCCTCCCAGGCTACATGGTCAAGAAGCTCCTAGGGGCCTGAA GTGTGCCCCACCCCAGCCCGCTCCAGCATCCCTCCAGGGGCTG CTGCGTATTTTGCCTTCCCTCACCTGGACTCTCTCCCAACTCCCT GAGGGAGCCCTCCCACGCCTGCCAGCCTTGAGCAAGACACCTGC TTGCTGGACTTCATCCCCACCCCACACCCAAACTGTTGCTTGCC TGATCTTGTCCCAGGCCTGCCTGGGGTTTGGGGCACAGTTGGC CTCCAAAACCAGATACCCTCTTGTCTAAAGTACCAGGTTCCTCTG CCCAACCCCAAGAGTGGTAGTGGCCCAACCCTCCCTGTGCTTTC CAAATCTTGTCTTAAGGCACCAGTGAAATTAACCAAGAAACGCG GAGCAATGCCCAAGGCTCTGATGAGTAGGAACACGTGGAAAGC ACCAGGAATGCCAGCAGAGGCGAGGCGGCACACCTCTCTGCAG AGCATCCAGGCCGAGCGGCGGGCAGCGGCCAGCTGCTTCTGC GCATGCTCTCCTCTTGGCTCTGCTTCTTTCTCACAGTCACAGTCA CTTCACAGCTTAGCCTTGGGCTTCCCATCACTTCCAGGGGTGCC TCTGCCTTGGCCAGTGTGTGTCAGCTAGTACACAAGCTCCAAGT GTGAATCAGGTGTACTGGCCGTCCTGAAGACTGACTGCCCTGTC CTTCCTGCCGACAGCCACACCCGAGTGTACACTTAAAGCGGTG CCCTTCTGCCTCTGTGGGCCTGCTGGCTGCTGTTCCTTTCTTGA GTGTGATTTTTTTTTCTCCCCTCAATAAAATAAATCAAACTCTG AGAC |
| 16 | mOTOF-201 2 transcript (NM_001286421.1), mouse otoferlin transcript variant 3, 7129 bp, encodes the protein of SEQ ID NO: 7 | TTGGTTGCCTTGGTCTCTGTGGGCAGCAGCAGGAGGAGGCGGC AGCAGCCAGAGAAGAGGGAGGCGTGTGAGCCACACTCCACCAG CGAGCTTCTTCCCGCTGCTCTGGAACTGCCCAGGCTCTCCCCA CCAGCATGGCCCTGATTGTTCACCTCAAGACTGTCTCAGAGCTC CGAGGCAAAGGTGACCGGATTGCCAAAGTCACTTTCCGAGGGC AGTCTTTCTACTCCCGGGTCCTGGAGAACTGCGAGGGTGTGGC TGACTTTGATGAGACGTTCCGGTGGCCAGTGGCCAGCAGCATC GACCGGAATGAAGTGTTGGAGATTCAGATTTTCAACTACAGCAA AGTCTTCAGCAACAAGCTGATAGGGACCTTCTGCATGGTGCTGC AGAAAGTGGTGGAGGAGAATCGGGTAGAGGTGACCGACACGCT GATGGATGACAGCAATGCTATCATCAAGACCAGCCTGAGCATGG AGGTCCGGTATCAGGCCACAGATGGCACTGTGGGCCCCTGGGA TGATGGAGACTTCCTGGGAGATGAATCCCTCCAGGAGGAGAAG GACAGCCAGGAGACAGATGGGCTGCTACCTGGTTCCCGACCCA GCACCCCGGATATCTGGCGAGAAGAGCTTTCGCAGAGCGGGAAG GAGTGTGTTCTCGGCCATGAAACTCGGCAAAACTCGGTCCCACA AAGAGGAGCCCCAAAGACAAGATGAGCCAGCAGTGCTGGAGAT GGAGGACCTGGACCACCTAGCCATTCAGCTGGGGATGGGCTG GATCCTGACTCCGTGTCTCTAGCCTCGGTCACCGCTCTCACCAG CAATGTCTCCAACAAACGGTCTAAGCCAGATATTAAGATGGAGC CCAGTGCTGGAAGGCCCATGGATTACCAGGTCAGCATCACAGT GATTGAGGCTCGGCAGCTGGTGGGCTTGAACATGGACCCTGTG GTGTGTGTGGAGGTGGGTGATGACAAGAAATACACGTCAATGAA GGAGTCCACAAACTGCCCTTACTACAACGAGTACTTTGTCTTCG ACTTCCATGTCTCTCCTGATGTCATGTTTGACAAGATCATCAAGA TCTCGGTTATCCATTCTAAGAACCTGCTTCGGAGCGGCACCCTG GTGGGTTCCTTCAAAATGGATGTGGGGACTGTGTATTCCCAGCC TGAACACCAGTTCCATCACAAATGGGCCATCCTGTCAGACCCCG ATGACATCTCTGCTGGGTTGAAGGGTTATGTAAAGTGTGATGTC GCTGTGGTGGGCAAGGGAGACAACATCAAGACACCCCACAAGG CCAACGAGACGGATGAGGACGACATTGAAGGGAACTTGCTGCT CCCCGAGGGCGTGCCCCCCGAACGGCAGTGGGCACGGTTCTA TGTGAAAATTTACCGAGCAGAGGGACTGCCCCGGATGAACACAA GCCTCATGGCCAACGTGAAGAAGGCGTTCATCGGTGAGAACAA GGACCTCGTCGACCCCTATGTGCAAGTCTTCTTTGCTGGACAAA AGGGCAAAACATCAGTGCAGAAGAGCAGCTATGAGCCGCTATG GAATGAGCAGGTCGTCTTCACAGACTTGTTCCCCCCACTCTGCA AACGCATGAAGGTGCAGATCCGGGACTCTGACAAGGTCAATGAT GTGGCCATCGGCACCCACTTCATCGACCTGCGCAAGATTTCCAA CGATGGAGACAAAGGCTTCCTGCCTACCCTCGGTCCAGCCTGG GTGAACATGTACGGCTCCACGCGCAACTACACACTGCTGGACG AGCACCAGGACTTGAATGAAGGCCTGGGGGAGGGTGTGTCCTT CCGGGCCCGCCTCATGTTGGGACTAGCTGTGGAGATCCTGGAC ACCTCCAACCCAGAGCTCACCAGCTCCACGGAGGTGCAGGTGG AGCAGGCCACGCCTGTCTCGGAGAGCTGCACAGGGAGAATGGA AGAATTTTTTCTATTTGGAGCCTTCTTGGAAGCCTCAATGATTGA CCGGAAAAATGGGGACAAGCCAATTACCTTTGAGGTGACCATAG GAAACTACGGCAATGAAGTCGATGGTATGTCCCGGCCCCTGAG GCCTCGGCCCCGGAAAGAGCCTGGGGATGAAGAAGAGGGTAGA CCTGATTCAGAACTCCAGTGACGATGAAGGTGACGAAGCCGGG GACCTGGCCTCGGTGTCCTCCACCCCACCTATGCGGCCCCAGA TCACGGACAGGAACTATTTCCACCTGCCCTACCTGGAGCGCAAG CCCTGCATCTATATATCAAGAGCTGGTGGCCTGACCAGAGGCGGC GCCTCTACAATGCCAACATCATGGATCACATTGCTGACAAGCTG |

TABLE 2-continued

OTOF Sequences

| SEQ ID NO. | Sequence Name | Sequence |
|---|---|---|
| | | GAAGAAGGCCTGAATGATGTACAGGAGATGATCAAAACGGAGAA
GTCCTACCCGGAGCGCCGCCTGCGGGGTGTGCTAGAGGAACTC
AGCTGTGGCTGCCACCGCTTCCTCTCCCTCTCGGACAAGGACC
AGGGCCGCTCGTCCCGCACCAGGCTGGATCGAGAGCGTCTTAA
GTCCTGTATGAGGGAGTTGGAGAGCATGGGACAGCAGGCCAAG
AGCCTGAGGGCTCAGGTGAAGCGGCACACTGTTCGGGACAAGC
TGAGGTCATGCCAGAACTTTCTGCAGAAGCTACGCTTCCTGGCG
GATGAGCCCCAGCACAGCATTCCTGATGTGTTCATTTGGATGAT
GAGCAACAACAAACGTATCGCCTATGCCCGCGTGCCTTCCAAAG
ACCTGCTCTTCTCCATCGTGGAGGAGGAACTGGGCAAGGACTG
CGCCAAAGTCAAGACCCTCTTCCTGAAGCTGCCAGGGAAGAGG
GGCTTCGGCTCGGCAGGCTGGACAGTACAGGCCAAGCTGGAG
CTCTACCTGTGGCTGGGCCTCAGCAAGCAGCGAAAGGACTTCC
TGTGTGGTCTGCCCTGTGGCTTCGAGGAGGTCAAGGCAGCCCA
AGGCCTGGGCCTGCATTCCTTTCCGCCCATCAGCCTAGTCTACA
CCAAGAAGCAAGCCTTCCAGCTCCGAGCACACATGTATCAGGC
CCGAAGCCTCTTTGCTGCTGACAGCAGTGGGCTCTCTGATCCCT
TTGCCCGTGTCTTCTTCATCAACCAGAGCCAATGCACTGAGGTT
CTAAACGAGACACTGTGTCCCACCTGGGACCAGATGCTGGTATT
TGACAACCTGGAGCTGTACGGTGAAGCTCACGAGTTACGAGAT
GATCCCCCCATCATTGTCATTGAAATCTACGACCAGGACAGCAT
GGGCAAAGCCGACTTCATGGGCCGGACCTTCGCCAAGCCCCTG
GTGAAGATGGCAGATGAAGCATACTGCCCACCTCGCTTCCCGC
CGCAGCTTGAGTACTACCAGATCTACCGAGGCAGTGCCACTGC
CGGAGACCTACTGGCTGCCTTCGAGCTGCTGCAGATTGGGCCA
TCAGGGAAGGCTGACCTGCCACCCATCAATGCCCAGTGGACA
TGGACAGAGGGCCCATCATGCCTGTGCCCGTGGGAATCCGGCC
AGTGCTCAGCAAGTACCGAGTGGAGGTGCTGTTCTGGGGCCTG
AGGGACCTAAAGAGGGTGAACCTGGCCCAGGTGGACCGACCAC
GGGTGGACATCGAGTGTGCAGGAAAGGGGGTACAATCCTCCCT
GATTCACAATTATAAGAAGAACCCCAACTTCAACACGCTGGTCAA
GTGGTTTGAAGTGGACCTCCCGGAGAATGAGCTCCTGCACCCA
CCCTTGAACATCCGAGTGGTAGATTGCCGGGCCTTTGGACGATA
CACCCTGGTGGGTTCCCACGCAGTCAGCTCACTGAGGCGCTTC
ATCTACCGACCTCCAGACCGCTCAGCCCCCAACTGGAACACCA
CAGGGGAGGTTGTAGTAAGCATGGAGCCTGAGGAGCCAGTTAA
GAAGCTGGAGACCATGGTGAAACTGGATGCGACTTCTGATGCT
GTGGTCAAGGTGGATGTGGCTGAAGATGAGAAGGAAAGGAAGA
AGAAGAAAAGAAAGGCCCGTCAGAGGAGCCAGAGGAGGAAGA
GCCCGATGAGAGCATGCTGGATTGGTGGTCCAAGTACTTCGCC
TCCATCGACACAATGAAGGAGCAACTTCGACAACATGAGACCTC
TGGAACTGACTTGGAAGAGAAGGAAGAGATGGAAAGCGCTGAG
GGCCTGAAGGGACCAATGAAGAGCAAGGAGAAGTCCAGAGCTG
CAAAGGAGGAGAAAAAGAAGAAAAACCAGAGCCCTGGCCCTGG
CCAGGGATCGGAGGCTCCTGAGAAGAAGAAAGCCAAGATCGAT
GAGCTTAAGGTGTACCCCAAGGAGCTGGAATCGGAGTTTGACA
GCTTTGAGGACTGGCTGCACACCTTCAACCTGTTGAGGGGCAA
GACGGGAGATGATGAGGATGGCTCCACAGAGGAGGAGCGCATA
GTAGGCCGATTCAAGGGCTCCCTCTGTGTGTACAAAGTGCCACT
CCCAGAAGATGTATCTCGAGAAGCTGGCTATGATCCCACCTATG
GAATGTTCCAGGGCATCCCAAGCAATGACCCCATCAATGTGCTG
GTCCGAATCTATGTGGTCCGGGCCACAGACCTGCACCCGGCCG
ACATCAATGGCAAAGCTGACCCCTATATTGCCATCAAGTTAGGC
AAGACCGACATCCGAGACAAGGAGAACTACATCTCCAAGCAGCT
CAACCCTGTGTTTGGGAAGTCCTTTGACATTGAGGCCTCCTTCC
CCATGGAGTCCATGTTGACAGTGGCCGTGTACGACTGGGATCT
GGTGGGCACTGATGACCTCATCGGAGAAACCAAGATTGACCTG
GAAAACCGCTTCTACAGCAAGCATCGCGCCACCTGCGGCATCG
CACAGACCTATTCCATACATGGCTACAATATCTGGAGGGACCCC
ATGAAGCCCAGCCAGATCCTGACACGCCTCTGTAAAGAGGGCA
AAGTGGACGCCCCCACTTTGGTCCCCATGGGAGAGTGAGGGT
TGCCAACCGTGTCTTCACGGGGCCTTCAGAAATAGAGGATGAGA
ATGGTCAGAGGAAGCCCACAGATGAGCACGTGGCACTGTCTGC
TCTGAGACACTGGGAGGACATCCCCCGGGTGGGCTGCCGCCTT
GTGCCGGAACACGTGGAGACCAGGCCGCTGCTCAACCCTGACA
AGCCAGGCATTGAGCAGGGCCGCCTGGAGCTGTGGGTGGACAT
GTTCCCCATGGACATGCCAGCCCCTGGGACACCTCTGGATATAT
CCCCCAGGAAACCCAAGAAGTACGAGCTGCGGGTCATCGTGTG
GAACACAGACGAGGTGGTCCTGGAAGACGATGATTTCTTCACG
GGAGAGAAGTCCAGTGACATTTTTGTGAGGGGGTGGCTGAAGG
GCCAGCAGGAGGACAAACAGGACACAGATGTCCACTATCACTC
CCTCACGGGGGAGGGCAACTTCAACTGGAGATACCTCTTCCCC
TTCGACTACCTAGCGGCCGAAGAGAAGATCGTTATGTCCAAAAA
GGAGTCTATGTTCTCCTGGGATGAGACGGAGTACAAGATCCCTG
CGCGGCTCACCCTGCAGATCTGGGACGCTGACCACTTCTCGGC |

TABLE 2-continued

OTOF Sequences

| SEQ ID NO. | Sequence Name | Sequence |
|---|---|---|
| | | TGACGACTTCCTGGGGGCTATCGAGCTGGACCTGAACCGGTTC<br>CCGAGGGGCGCTAAGACAGCCAAGCAGTGCACCATGGAGATGG<br>CCACCGGGGAGGTGGACGTACCCCTGGTTTCCATCTTTAAACAG<br>AAACGTGTCAAAGGCTGGTGGCCCCTCCTGGCCCGCAATGAGA<br>ATGATGAGTTTGAGCTCACAGGCAAAGTGGAGGCGGAGCTACA<br>CCTACTCACGGCAGAGGAGGCAGAGAAGAACCCTGTGGGCCTG<br>GCTCGCAATGAACCTGATCCCCTAGAAAAACCCAATCGGCCGGA<br>CACAAGCTTCATCTGGTTCTTGAACCCTCTCAAGTCTGCCCGCT<br>ACTTCCTGTGGCATACCTACCGCTGGCTACTCCTCAAATTCCTG<br>CTGCTCTTCCTCCTGCTGCTGCTCTTCGCCCTGTTTCTCTACTCT<br>CTGCCTGGCTACCTGGCCAAGAAGATCCTTGGGGCCTGAGCCC<br>TGCAGTCGCCTAGGCCTGCCGGCCTGACACGGCATTCGTCTGG<br>TTCCTGAACCCACTCAAATCTATCAAGTACCTCATCTGCACCCG<br>GTACAAGTGGCTGATCATCAAGATCGTGCTGGCGCTGCTGGGG<br>CTGCTCATGCTGGCCCTCTTCCTTTACAGCCTCCCAGGCTACAT<br>GGTCAAGAAGCTCCTAGGGGCCTGAAGTGTGCCCCACCCCAGC<br>CCGCTCCAGCATCCCTCCAGGGGCTGCTGCGTATTTTGCCTTCC<br>CTCACCTGGACTCTCTCCCAACTCCCTGAGGAGCCCTCCCACG<br>CCTGCCAGCCTTGAGCAAGACACCTGCTTGCTGGACTTCATCCC<br>CACCCCACACCCAAACTGTTGCTTGCCTGATCTTGTCCCAGGCC<br>TGCCTGGGGTTTGGGGCACAGTTGGCCTCCAAAACCAGATACC<br>CTCTTGTCTAAAGTACCAGGTTCCTCTGCCCAACCCCAAGAGTG<br>GTAGTGGCCCAACCCTCCCTGTGCTTTCCAAATCTTGTCTTAAG<br>GCACCAGTGAAATTAACCAAGAAACGCGGAGCAATGCCCAAGG<br>CTCTGATGAGTAGGAACACGTGGAAAGCACCAGGAATGCCAGC<br>AGAGGCGAGGCGGCACACCTCTCTGCAGAGCATCCAGGCCGA<br>GCGGCGGGCAGCGGCCAGCTGCTTCTGCGCATGCTCTCCTCTT<br>GGCTCTGCTTCTTTCTCACAGTCACAGTCACTTCACAGCTTAGC<br>CTTGGGCTTCCCATCACTTCCAGGGGTGCCTCTGCCTTGGCCA<br>GTGTGTGTCAGCTAGTACACAAGCTCCAAGTGTGAATCAGGTGT<br>ACTGGCCGTCCTGAAGACTGACTGCCCGTCCTTCCTGCCGACA<br>GCCACACCCGAGTGTACACTTAAAGCGGTGCCCTTCTGCCTCTG<br>TGGGCCTGCTGGCTGCTGTTCCTTTCTTGAGTGTGATTTTTTTTT<br>TCTCTCCCTCAATAAAATAAATCAAACTCTGAGAC |
| 17 | mOTOF-202_1 transcript (NM_001100395.1), mouse otoferlin transcript variant 1, 6881 bp, encodes the protein of SEQ ID NO: 8 | TTGGTTGCCTTGGTCTCTGTGGGCAGCAGCAGGAGGAGGCGGC<br>AGCAGCCAGAGAAGAGGGAGGCGTGTGAGCCACACTCCACCAG<br>CGAGCTTCTTCCCGCTGCTCTGGAACTGCCCAGGCTCTCCCCA<br>CCAGCATGGCCCTGATTGTTCACCTCAAGACTGTCTCAGAGCTC<br>CGAGGCAAAGGTGACCGGATTGCCAAAGTCACTTTCCGAGGGC<br>AGTCTTTCTACTCCCGGGTCCTGGAGAACTGCGAGGGTGTGGC<br>TGACTTTGATGAGACGTTCCGGTGGCCAGTGGCCAGCAGCATC<br>GACCGGAATGAAGTGTTGGAGATTCAGATTTTCAACTACAGCAA<br>AGTCTTCAGCAACAAGCTGATAGGGACCTTCTGCATGGTGCTGC<br>AGAAAGTGGTGGAGGAGAATCGGGTAGAGGTGACCGACACGCT<br>GATGGATGACAGCAATGCTATCATCAAGACCAGCCTGAGCATGG<br>AGGTCCGGTATCAGGCCACAGATGGCACTGTGGGCCCCTGGGA<br>TGATGGAGACTTCCTGGGAGATGAATCCCTCCAGGAGGAGAAG<br>GACAGCCAGGAGACAGATGGGCTGCTACCTGGTTCCCGACCCA<br>GCACCCGGATATCTGGCGAGAAGAGCTTTCGCAGCAAAGGCAG<br>AGAGAAGACCAAGGGAGGCAGAGATGGCGAGCACAAAGCGGG<br>AAGGAGTGTGTTCTCGGCCATGAAACTCGGCAAAACTCGGTCCC<br>ACAAAGAGGAGCCCCAAAGACAAGATGAGCCAGCAGTGCTGGA<br>GATGGAGGACCTGGACCACCTAGCCATTCAGCTGGGGGATGGG<br>CTGGATCCTGACTCCGTGTCTCTAGCCTCGGTCACCGCTCTCAC<br>CAGCAATGTCTCCAACAAACGGTCTAAGCCAGATATTAAGATGG<br>AGCCCAGTGCTGGAAGGCCCATGGATTACCAGGTCAGCATCAC<br>AGTGATTGAGGCTCGGCAGCTGGTGGGCTTGAACATGGACCCT<br>GTGGTGTGTGTGGAGGTGGGTGATGACAAGAAATACACGTCAAT<br>GAAGGAGTCCACAAACTGCCCTTACTACAACGAGTACTTTGTCT<br>TCGACTTCCATGTCTCCTGATGTCATGTTTGACAAGATCATCA<br>AGATCTCGGTTATCCATTCTAAGAACCTGCTTCGGAGCGGCACC<br>CTGGTGGGTTCCTTCAAAATGGATGTGGGGACTGTGTATTCCCA<br>GCCTGAACACCAGTTCCATCACAAATGGGCCATCCTGTCAGACC<br>CCGATGACATCTCTGCTGGGTTGAAGGGTTATGTAAAGTGTGAT<br>GTCGCTGTGGTGGGCAAGGGAGACAACATCAAGACACCCCACA<br>AGGCCAACGAGACGGATGAGGACGACATTGAAGGGAACTTGCT<br>GCTCCCCGAGGGCGTGCCCCCGAACGGCAGTGGGCACGGTT<br>CTATGTGAAAATTTACCGAGCAGAGGGACTGCCCCGGATGAACA<br>CAAGCCTCATGGCCAACGTGAAGAAGGCGTTCATCGGTCGGAGAA<br>CAAGGACCTCGTCGACCCCTATGTGCAAGTCTTCTTTGCTGGAC<br>AAAAGGGCAAAACATCAGTGCAGAAGAGCAGCTATGAGCCGCT<br>ATGGAATGAGCAGGTCGTCTTCACAGACTTGTTCCCCCCACTCT<br>GCAAACGCATGAAGGTGCAGATCCGGGACTCTGACAAGGTCAA<br>TGATGTGGCCATCGGCACCCACTTCATCGACCTGCGCAAGATTT |

TABLE 2-continued

OTOF Sequences

| SEQ ID NO. | Sequence Name | Sequence |
|---|---|---|
| | | CCAACGATGGAGACAAAGGCTTCCTGCCTACCCTCGGTCCAGC
CTGGGTGAACATGTACGGCTCCACGCGCAACTACACACTGCTG
GACGAGCACCAGGACTTGAATGAAGGCCTGGGGGAGGGTGTGT
CCTTCCGGGCCCGCCTCATGTTGGGACTAGCTGTGGAGATCCT
GGACACCTCCAACCCAGAGCTCACCAGCTCCACGGAGGTGCAG
GTGGAGCAGGCCACGCCTGTCTCGGAGAGCTGCACAGGGAGA
ATGGAAGAATTTTTTCTATTTGGAGCCTTCTTGGAAGCCTCAATG
ATTGACCGGAAAAATGGGGACAAGCCAATTACCTTTGAGGTGAC
CATAGGAAACTACGGCAATGAAGTCGATGGTATGTCCCGGCCC
CTGAGGCCTCGGCCCCGGAAAGAGCCTGGGGATGAAGAAGAG
GTAGACCTGATTCAGAACTCCAGTGACGATGAAGGTGACGAAGC
CGGGGACCTGGCCTCGGTGTCCTCCACCCCACCTATGCGGCCC
CAGATCACGGACAGGAACTATTTCCACCTGCCCTACCTGGAGCG
CAAGCCCTGCATCTATATCAAGAGCTGGTGGCCTGACCAGAGG
CGGCGCCTCTACAATGCCAACATCATGGATCACATTGCTGACAA
GCTGGAAGAAGGCCTGAATGATGTACAGGAGATGATCAAAACG
GAGAAGTCCTACCCGGAGCGCCGCCTGCGGGGTGTGCTAGAG
GAACTCAGCTGTGGCTGCCACCGCTTCCTCTCCCTCTCGGACAA
GGACCAGGGCCGCTCGTCCCGCACCAGGCTGGATCGAGAGCG
TCTTAAGTCCTGTATGAGGGAGTTGGAGAGCATGGGACAGCAG
GCCAAGAGCCTGAGGGCTCAGGTGAAGCGGCACACTGTTCGGG
ACAAGCTGAGGTCATGCCAGAACTTTCTGCAGAAGCTACGCTTC
CTGGCGGATGAGCCCCAGCACAGCATTCCTGATGTGTTCATTTG
GATGATGAGCAACAACAAACGTATCGCCTATGCCCGCGTGCCTT
CCAAAGACCTGCTCTTCTCCATCGTGGAGGAGGAACTGGGCAA
GGACTGCGCCAAAGTCAAGACCCTCTTCCTGAAGCTGCCAGGG
AAGAGGGGCTTCGGCTCGGCAGGCTGGACAGTACAGGCCAAG
CTGGAGCTCTACCTGTGGCTGGGCCTCAGCAAGCAGCGAAAGG
ACTTCCTGTGTGGTCTGCCCTGTGGCTTCGAGGAGGTCAAGGC
AGCCCAAGGCCTGGGCCTGCATTCCTTTCCGCCCATCAGCCTA
GTCTACACCAAGAAGCAAGCCTTCCAGCTCCGAGCACACATGTA
TCAGGCCCGAAGCCTCTTTGCTGCTGACAGCAGTGGGCTCTCT
GATCCCTTTGCCCGTGTCTTCTTCATCAACCAGAGCCAATGCAC
TGAGGTTCTAAACGAGACACTGTGTCCCACCTGGGACCAGATGC
TGGTATTTGACAACCTGGAGCTGTACGGTGAAGCTCACGAGTTA
CGAGATGATCCCCCCATCATTGTCATTGAAATCTACGACCAGGA
CAGCATGGGCAAAGCCGACTTCATGGGCCGGACCTTCGCCAAG
CCCCTGGTGAAGATGGCAGATGAAGCATACTGCCCACCTCGCTT
CCCGCCGCAGCTTGAGTACTACCAGATCTACCGAGGCAGTGCC
ACTGCCGGAGACCTACTGGCTGCCTTCGAGCTGCTGCAGATTG
GGCCATCAGGGAAGGCTGACCTGCCACCCATCAATGCCCAGT
GGACATGGACAGAGGGCCCATCATGCCTGTGCCCGTGGGAATC
CGGCCAGTGCTCAGCAAGTACCGAGTGGAGGTGCTGTTCTGGG
GCCTGAGGGACCTAAAGAGGGTGAACCTGGCCCAGGTGGACC
GACCACGGGTGGACATCGAGTGTGCAGGAAAGGGGGTACAATC
CTCCCTGATTCACAATTATAAGAAGAACCCCAACTTCAACACGCT
GGTCAAGTGGTTTGAAGTGGACCTCCCGGAGAATGAGCTCCTG
CACCCACCCTTGAACATCCGAGTGGTAGATTGCCGGGCCTTTG
GACGATACACCCTGGTGGGTTCCCACGCAGTCAGCTCACTGAG
GCGCTTCATCTACCGACCTCCAGACCGCTCAGCCCCCAACTGG
AACACCACAGGGGAGGTTGTAGTAAGCATGGAGCCTGAGGAGC
CAGTTAAGAAGCTGGAGACCATGGTGAAACTGGATGCGACTTCT
GATGCTGTGGTCAAGGTGGATGTGGCTGAAGATGAGAAGGAAA
GGAAGAAGAAGAAAAAGAAAGGCCCGTCAGAGGAGCCAGAGGA
GGAAGAGCCCGATGAGAGCATGCTGGATTGTGGTCCAAGTAC
TTCGCCTCCATCGACACAATGAAGGAGCAACTTCGACAACATGA
GACCTCTGGAACTGACTTGGAAGAGAAGGAAGAGATGGAAAGC
GCTGAGGGCCTGAAGGGACCAATGAAGAGCAAGGAGAAGTCCA
GAGCTGCAAAGGAGGAGAAAAAGAAGAAAAACCAGAGCCCTGG
CCCTGGCCAGGGATCGGAGGCTCCTGAGAAGAAGAAAGCCAAG
ATCGATGAGCTTAAGGTGTACCCCAAGGAGCTGGAATCGGAGTT
TGACAGCTTTGAGGACTGGCTGCACACCTTCAACCTGTTGAGGG
GCAAGACGGGAGATGATGAGGATGGCTCCACAGAGGAGGAGC
GCATAGTAGGCCGATTCAAGGGCTCCCTCTGTGTGTACAAAGTG
CCACTCCCAGAAGATGTATCTCGAGAAGCTGGCTATGATCCCAC
CTATGGAATGTTCCAGGGCATCCCAAGCAATGACCCCATCAATG
TGCTGGTCCGAATCTATGTGGTCCGGGCCACAGACCTGCACCC
GGCCGACATCAATGGCAAAGCTGACCCCTATATTGCCATCAAGT
TAGGCAAGACCGACATCCGAGACAAGGAGAACTACATCTCCAAG
CAGCTCAACCCTGTGTTTGGGAAGTCCTTTGACATTGAGGCCTC
CTTCCCCCATGGAGTCCATGTTGACAGTGGCCGTGTACGACTGG
GATCTGGTGGGCACTGATGACCTCATCGGAGAAACCAAGATTGA
CCTGGAAAACCGCTTCTACAGCAAGCATCGCGCCACCTGCGGC
ATCGCACAGACCTATTCCATACATGGCTACAATATCTGGAGGGA
CCCCATGAAGCCCAGCCAGATCCTGACACGCCTCTGTAAAGAG |

TABLE 2-continued

OTOF Sequences

| SEQ ID NO. | Sequence Name | Sequence |
|---|---|---|
| | | GGCAAAGTGGACGGCCCCCACTTTGGTCCCCATGGGAGAGTGA
GGGTTGCCAACCGTGTCTTCACGGGGCCTTCAGAAATAGAGGA
TGAGAATGGTCAGAGGAAGCCCACAGATGAGCACGTGGCACTG
TCTGCTCTGAGACACTGGGAGGACATCCCCCGGGTGGGCTGCC
GCCTTGTGCCGGAACACGTGGAGACCAGGCCGCTGCTCAACCC
TGACAAGCCAGGCATTGAGCAGGGCCGCCTGGAGCTGTGGGTG
GACATGTTCCCCATGGACATGCCAGCCCCTGGGACACCTCTGG
ATATATCCCCCAGGAAACCCAAGAAGTACGAGCTGCGGGTCATC
GTGTGGAACACAGACGAGGTGGTCCTGGAAGACGATGATTTCTT
CACGGGAGAGAAGTCCAGTGACATTTTTGTGAGGGGGTGGCTG
AAGGGCCAGCAGGAGGACAAACAGGACACAGATGTCCACTATC
ACTCCCTCACGGGGAGGGCAACTTCAACTGGAGATACCTCTTC
CCCTTCGACTACCTAGCGGCCGAAGAGAAGATCGTTATGTCCAA
AAAGGAGTCTATGTTCTCCTGGGATGAGACGGAGTACAAGATCC
CTGCGCGGCTCACCCTGCAGATCTGGGACGCTGACCACTTCTC
GGCTGACGACTTCCTGGGGGCTATCGAGCTGGACCTGAACCGG
TTCCCGAGGGGCGCTAAGACAGCCAAGCAGTGCACCATGGAGA
TGGCCACCGGGGAGGTGGACGTACCCCTGGTTTCCATCTTTAAA
CAGAAACGTGTCAAAGGCTGGTGGCCCCTCCTGGCCCGCAATG
AGAATGATGAGTTTGAGCTCACAGGCAAAGTGGAGGCGGAGCT
ACACCTACTCACGGCAGAGGAGGCAGAGAAGAACCCTGTGGGC
CTGGCTCGCAATGAACCTGATCCCCTAGAAAAACCCAACCGGCC
TGACACGGCATTCGTCTGGTTCCTGAACCCACTCAAATCTATCA
AGTACCTCATCTGCACCCGGTACAAGTGGCTGATCATCAAGATC
GTGCTGGCGCTGCTGGGGCTGCTCATGCTGGCCCTCTTCCTTT
ACAGCCTCCCAGGCTACATGGTCAAGAAGCTCCTAGGGGCCTG
AAGTGTGCCCCACCCCAGCCCGCTCCAGCATCCCTCCAGGGGC
TGCTGCGTATTTTGCCTTCCCTCACCTGGACTCTCTCCCAACTC
CCTGAGGAGCCCTCCCACGCCTGCCAGCCTTGAGCAAGACACC
TGCTTGCTGGACTTCATCCCCACCCCACACCCAAACTGTTGCTT
GCCTGATCTTGTCCCAGGCCTGCCTGGGGTTTGGGGCACAGTT
GGCCTCCAAAACCAGATACCCTCTTGTCTAAAGTACCAGGTTCC
TCTGCCCAACCCCAAGAGTGGTAGTGGCCCAACCCTCCCTGTG
CTTTCCAAATCTTGTCTTAAGGCACCAGTGAAATTAACCAAGAAA
CGCGGAGCAATGCCCAAGGCTCTGATGAGTAGGAACACGTGGA
AAGCACCAGGAATGCCAGCAGAGGCGAGGCGGCACACCTCTCT
GCAGAGCATCCAGGCCGAGCGGCGGGCAGCGGCCAGCTGCTT
CTGCGCATGCTCTCCTCTTGGCTCTGCTTCTTTCTCACAGTCACA
GTCACTTCACAGCTTAGCCTTGGGCTTCCCATCACTTCCAGGGG
TGCCTCTGCCTTGGCCAGTGTGTGTCAGCTAGTACACAAGCT
CCAAGTGTGAATCAGGTGTACTGGCCGTCCTGAAGACTGACTGC
CCTGTCCTTCCTGCCGACAGCCACACCCGAGTGTACACTTAAAG
CGGTGCCCTTCTGCCTCTGTGGGCCTGCTGGCTGCTGTTCCTTT
CTTGAGTGTGATTTTTTTTTCTCCCCTCAATAAAATAAATCAAA
CTCTGAGAC |
| 18 | mOTOF-202_2 transcript (NM_001313767.1), mouse otoferlin transcript variant 4, 6881 bp, encodes the protein of SEQ ID NO: 9 | TTGGTTGCCTTGGTCTCTGTGGGCAGCAGCAGGAGGAGGCGGC
AGCAGCCAGAGAAGAGGGAGGCGTGTGAGCCACACTCCACCAG
CGAGCTTCTTCCCGCTGCTCTGGAACTGCCCAGGCTCTCCCCA
CCAGCATGGCCCTGATTGTTCACCTCAAGACTGTCTCAGAGCTC
CGAGGCAAAGGTGACCGGATTGCCAAAGTCACTTTCCGAGGGC
AGTCTTTCTACTCCCGGGTCCTGGAGAACTGCGAGGGTGTGGC
TGACTTTGATGAGACGTTCCGGTGGCCAGTGGCCAGCAGCATC
GACCGGAATGAAGTGTTGGAGATTCAGATTTTCAACTACAGCAA
AGTCTTCAGCAACAAGCTGATAGGGACCTTCTGCATGGTGCTGC
AGAAAGTGGTGGAGGAGAATCGGGTAGAGGTGACCGACACGCT
GATGGATGACAGCAATGCTATCATCAAGACCAGCCTGAGCATGG
AGGTCCGGTATCAGGCCACAGATGGCACTGTGGGCCCCTGGGA
TGATGGAGACTTCCTGGGAGATGAATCCCTCCAGGAGGAGAAG
GACAGCCAGGAGACAGATGGGCTGCTACCTGGTTCCCGACCCA
GCACCCGGATATCTGGCGAGAAGAGCTTTCGCAGAGCGGGAAG
GAGTGTGTTCTCGGCCATGAAACTCGGCAAAACTCGGTCCCACA
AAGAGGAGCCCCAAAGACAAGATGAGCCAGCAGTGCTGGAGAT
GGAGGACCTGGACCACCTAGCCATTCAGCTGGGGGATGGGCTG
GATCCTGACTCCGTGTCTCTAGCCTCGGTCACCGCTCTCACCAG
CAATGTCTCCAACAAACGGTCTAAGCCAGATATTAAGATGGAGC
CCAGTGCTGGAAGGCCCATGGATTACCAGGTCAGCATCACAGT
GATTGAGGCTCGGCAGCTGGTGGGCTTGAACATGGACCCTGTG
GTGTGTGTGGAGGTGGGTGATGACAAGAAATACAGGTCAATGAA
GGAGTCCACAAACTGCCCTTACTACAACGAGTACTTTGTCTTCG
ACTTCCATGTCTCTCCTGATGTCATGTTTGACAAGATCATCAAGA
TCTCGGTTATCCATTCTAAGAACCTGCTTCGGAGCGGCACCCTG
GTGGGTTCCTTCAAAATGGATGTGGGACTGTGTATTCCCAGCC
TGAACACCAGTTCCATCACAAATGGGCCATCCTGTCAGACCCCG
ATGACATCTCTGCTGGGTTGAAGGGTTATGTAAAGTGTGATGTC |

TABLE 2-continued

OTOF Sequences

| SEQ ID NO. | Sequence Name | Sequence |
|---|---|---|
| | | GCTGTGGTGGGCAAGGGAGACAACATCAAGACACCCCACAAGG |
| | | CCAACGAGACGGATGAGGACGACATTGAAGGGAACTTGCTGCT |
| | | CCCCGAGGGCGTGCCCCCCGAACGGCAGTGGGCACGGTTCTA |
| | | TGTGAAAATTTACCGAGCAGAGGGACTGCCCCGGATGAACACAA |
| | | GCCTCATGGCCAACGTGAAGAAGGCGTTCATCGGTGAGAACAA |
| | | GGACCTCGTCGACCCCTATGTGCAAGTCTTCTTTGCTGGACAAA |
| | | AGGGCAAAACATCAGTGCAGAAGAGCAGCTATGAGCCGCTATG |
| | | GAATGAGCAGGTCGTCTTCACAGACTTGTTCCCCCCACTCTGCA |
| | | AACGCATGAAGGTGCAGATCCGGGACTCTGACAAGGTCAATGAT |
| | | GTGGCCATCGGCACCCACTTCATCGACCTGCGCAAGATTTCCAA |
| | | CGATGGAGACAAAGGCTTCCTGCCTACCCTCGGTCCAGCCTGG |
| | | GTGAACATGTACGGCTCCACGCGCAACTACACACTGCTGGACG |
| | | AGCACCAGGACTTGAATGAAGGCCTGGGGGAGGGTGTGTCCTT |
| | | CCGGGCCCGCCTCATGTTGGGACTAGCTGTGGAGATCCTGGAC |
| | | ACCTCCAACCCAGAGCTCACCAGCTCCACGGAGGTGCAGGTGG |
| | | AGCAGGCCACGCCTGTCTCGGAGAGCTGCACAGGGAGAATGGA |
| | | AGAATTTTTCTATTTGGAGCCTTCTTGGAAGCCTCAATGATTGA |
| | | CCGGAAAAATGGGGACAAGCCAATTACCTTTGAGGTGACCATAG |
| | | GAAACTACGGCAATGAAGTCGATGGTATGTCCCGGCCCCTGAG |
| | | GCCTCGGCCCCGGAAAGAGCCTGGGGATGAAGAAGAGGTAGA |
| | | CCTGATTCAGAACTCCAGTGACGATGAAGGTGACGAAGCCGGG |
| | | GACCTGGCCTCGGTGTCCTCCACCCCACCTATGCGGCCCCAGA |
| | | TCACGGACAGGAACTATTTCCACCTGCCCTACCTGGAGCGCAAG |
| | | CCCTGCATCTATATCAAGAGCTGGTGGCCTGACCAGAGGCGGC |
| | | GCCTCTACAATGCCAACATCATGGATCACATTGCTGACAAGCTG |
| | | GAAGAAGGCCTGAATGATGTACAGGAGATGATCAAAACGGAGAA |
| | | GTCCTACCCGGAGCGCCGCCTGCGGGGTGTGCTAGAGGAACTC |
| | | AGCTGTGGCTGCCACCGCTTCCTCTCCCTCTCGGACAAGGACC |
| | | AGGGCCGCTCGTCCCGCACCAGGCTGGATCGAGAGCGTCTTAA |
| | | GTCCTGTATGAGGGAGTTGGAGAGCATGGGACAGCAGGCCAAG |
| | | AGCCTGAGGGCTCAGGTGAAGCGGCACACTGTTCGGGACAAGC |
| | | TGAGGTCATGCCAGAACTTTCTGCAGAAGCTACGCTTCCTGGCG |
| | | GATGAGCCCCAGCACAGCATTCCTGATGTGTTCATTTGGATGAT |
| | | GAGCAACAACAAACGTATCGCCTATGCCCGCGTGCCTTCCAAAG |
| | | ACCTGCTCTTCTCCATCGTGGAGGAGGAACTGGGCAAGGACTG |
| | | CGCCAAAGTCAAGACCCTCTTCCTGAAGCTGCCAGGGAAGAGG |
| | | GGCTTCGGCTCGGCAGGCTGGACAGTACAGGCCAAGCTGGAG |
| | | CTCTACCTGTGGCTGGGCCTCAGCAAGCAGCGAAAGGACTTCC |
| | | TGTGTGGTCTGCCCTGTGGCTTCGAGGAGGTCAAGGCAGCCCA |
| | | AGGCCTGGGCCTGCATTCCTTTCCGCCCATCAGCCTAGTCTACA |
| | | CCAAGAAGCAAGCCTTCCAGCTCCGAGCACACATGTATCAGGC |
| | | CCGAAGCCTCTTTGCTGCTGACAGCAGTGGGCTCTCTGATCCCT |
| | | TTGCCCGTGTCTTCTTCATCAACCAGAGCCAATGCACTGAGGTT |
| | | CTAAACGAGACACTGTGTCCCACCTGGGACCAGATGCTGGTATT |
| | | TGACAACCTGGAGCTGTACGGTGAAGCTCACGAGTTACGAGAT |
| | | GATCCCCCCATCATTGTCATTGAAATCTACGACCAGGACAGCAT |
| | | GGGCAAAGCCGACTTCATGGGCCGGACCTTCGCCAAGCCCCTG |
| | | GTGAAGATGGCAGATGAAGCATACTGCCCACCTCGCTTCCCGC |
| | | CGCAGCTTGAGTACTACCAGATCTACCGAGGCAGTGCCACTGC |
| | | CGGAGACCTACTGGCTGCCTTCGAGCTGCTGCAGATTGGGCCA |
| | | TCAGGGAAGGCTGACCTGCCACCCATCAATGCCCAGTGGACA |
| | | TGGACAGAGGGCCCATCATGCCTGTGCCCGTGGGAATCCGGCC |
| | | AGTGCTCAGCAAGTACCGAGTGGAGGTGCTGTTCTGGGGCCTG |
| | | AGGGACCTAAAGAGGGTGAACCTGGCCCAGGTGGACCGACCAC |
| | | GGGTGGACATCGAGTGTGCAGGAAAGGGGGTACAATCCTCCCT |
| | | GATTCACAATTATAAGAAGAACCCCAACTTCAACACGCTGGTCAA |
| | | GTGGTTTGAAGTGGACCTCCCGGAGAATGAGCTCCTGCACCCA |
| | | CCCTTGAACATCCGAGTGGTAGATTGCCGGGCCTTTGGACGATA |
| | | CACCCTGGTGGGTTCCCACGCAGTCAGCTCACTGAGGCGCTTC |
| | | ATCTACCGACCTCCAGACCGCTCAGCCCCAACTGGAACACCA |
| | | CAGGGGAGGTTGTAGTAAGCATGGAGCCTGAGGAGCCAGTTAA |
| | | GAAGCTGGAGACCATGGTGAAACTGGATGCGACTTCTGATGCT |
| | | GTGGTCAAGGTGGATGTGGCTGAAGATGAGAAGGAAAGGAAGA |
| | | AGAAGAAAAGAAAGGCCCGTCAGAGGAGCCAGAGGAGGAAGA |
| | | GCCCGATGAGAGCATGCTGGATTGGTGGTCCAAGTACTTCGCC |
| | | TCCATCGACACAATGAAGGAGCAACTTCGACAACATGAGACCTC |
| | | TGGAACTGACTTGGAAGAGAAGGAAGAGATGGAAAGCGCTGAG |
| | | GGCCTGAAGGGACCAATGAAGAGCAAGGAGAAGTCCAGAGCTG |
| | | CAAAGGAGGAGAAAAAGAAGAAAAACCAGAGCCCTGGCCCTGG |
| | | CCAGGGATCGGAGGCTCCTGAGAAGAAAAGCCAAGATCGAT |
| | | GAGCTTAAGGTGTACCCCAAGGAGCTGGAATCGGAGTTTGACA |
| | | GCTTTGAGGACTGGCTGCACACCTTCAACCTGTTGAGGGGCAA |
| | | GACGGGAGATGATGAGGATGGCTCCACAGAGGAGGAGCGCATA |
| | | GTAGGCCGATTCAAGGGCTCCCTCTGTGTGTACAAAGTGCCACT |
| | | CCCAGAAGATGTATCTCGAGAAGCTGGCTATGATCCCACCTATG |

TABLE 2-continued

OTOF Sequences

| SEQ ID NO. | Sequence Name | Sequence |
|---|---|---|
| | | GAATGTTCCAGGGCATCCCAAGCAATGACCCCATCAATGTGCTG
GTCCGAATCTATGTGGTCCGGGCCACAGACCTGCACCCGGCCG
ACATCAATGGCAAAGCTGACCCCTATATTGCCATCAAGTTAGGC
AAGACCGACATCCGAGACAAGGAGAACTACATCTCCAAGCAGCT
CAACCCTGTGTTTGGGAAGTCCTTTGACATTGAGGCCTCCTTCC
CCATGGAGTCCATGTTGACAGTGGCCGTGTACGACTGGGATCT
GGTGGGCACTGATGACCTCATCGGAGAAACCAAGATTGACCTG
GAAAACCGCTTCTACAGCAAGCATCGCGCCACCTGCGGCATCG
CACAGACCTATTCCATACATGGCTACAATATCTGGAGGGACCCC
ATGAAGCCCAGCCAGATCCTGACACGCCTCTGTAAAGAGGGCA
AAGTGGACGGCCCCCACTTTGGTCCCCATGGGAGAGTGAGGGT
TGCCAACCGTGTCTTCACGGGGCCTTCAGAAATAGAGGATGAGA
ATGGTCAGAGGAAGCCCACAGATGAGCACGTGGCACTGTCTGC
TCTGAGACACTGGGAGGACATCCCCCGGGTGGGCTGCCGCCTT
GTGCCGGAACACGTGGAGACCAGGCCGCTGCTCAACCCTGACA
AGCCAGGCATTGAGCAGGGCCGCCTGGAGCTGTGGGTGGACAT
GTTCCCCATGGACATGCCAGCCCCTGGGACACCTCTGGATATAT
CCCCCAGGAAACCCAAGAAGTACGAGCTGCGGGTCATCGTGTG
GAACACAGACGAGGTGGTCCTGGAAGACGATGATTTCTTCACG
GGAGAGAAGTCCAGTGACATTTTTGTGAGGGGGTGGCTGAAGG
GCCAGCAGGAGGACAAACAGGACACAGATGTCCACTATCACTC
CCTCACGGGGAGGGCAACTTCAACTGGAGATACCTCTTCCCC
TTCGACTACCTAGCGGCCGAAGAGAAGATCGTTATGTCCAAAAA
GGAGTCTATGTTCTCCTGGGATGAGACGGAGTACAAGATCCCTG
CGCGGCTCACCCTGCAGATCTGGGACGCTGACCACTTCTCGGC
TGACGACTTCCTGGGGGCTATCGAGCTGGACCTGAACCGGTTC
CCGAGGGGCGCTAAGACAGCCAAGCAGTGCACCATGGAGATGG
CCACCGGGGAGGTGGACGTACCCCTGGTTTCCATCTTTAAACAG
AAACGTGTCAAAGGCTGGTGGCCCCTCCTGGCCCGCAATGAGA
ATGATGAGTTTGAGCTCACAGGCAAAGTGGAGGCGGAGCTACA
CCTACTCACGGCAGAGGAGGCAGAGAAGAACCCTGTGGGCCTG
GCTCGCAATGAACCTGATCCCCTAGAAAAACCCAACCGGCCTGA
CACGGCATTCGTCTGGTTCCTGAACCCACTCAAATCTATCAAGT
ACCTCATCTGCACCCGGTACAAGTGGCTGATCATCAAGATCGTG
CTGGCGCTGCTGGGGCTGCTCATGCTGGCCCTCTTCCTTTACA
GCCTCCCAGGCTACATGGTCAAGAAGCTCCTAGGGGCCTGAAG
TGTGCCCCACCCCAGCCCGCTCCAGCATCCCTCCAGGGGCTGC
TGCGTATTTTGCCTTCCCTCACCTGGACTCTCTCCCAACTCCCT
GAGGAGCCCTCCCACGCCTGCCAGCCTTGAGCAAGACACCTGC
TTGCTGGACTTCATCCCCACCCCACACCCAAACTGTTGCTTGCC
TGATCTTGTCCCAGGCCTGCCTGGGGTTTGGGGCACAGTTGGC
CTCCAAAACCAGATACCCTCTTGTCTAAAGTACCAGGTTCCTCTG
CCCAACCCCAAGAGTGGTAGTGGCCCAACCCTCCCTGTGCTTTC
CAAATCTTGTCTTAAGGCACCAGTGAAATTAACCAAGAAACGCG
GAGCAATGCCCAAGGCTCTGATGAGTAGGAACACGTGGAAAGC
ACCAGGAATGCCAGCAGAGGCGAGGCGGCACACCTCTCTGCAG
AGCATCCAGGCCGAGCGGCGGGCAGCGGCCAGCTGCTTCTGC
GCATGCTCTCCTCTTGGCTCTGCTTCTTTCTCACAGTCACAGTCA
CTTCACAGCTTAGCCTTGGGCTTCCCATCACTTCCAGGGGTGCC
TCTGCCTTGGCCAGTGTGTGTCAGCTAGTACACAAGCTCCAAGT
GTGAATCAGGTGTACTGGCCGTCCTGAAGACTGACTGCCCTGTC
CTTCCTGCCGACAGCCACACCCGAGTGTACACTTAAAGCGGTG
CCCTTCTGCCTCTGTGGGCCTGCTGGCTGCTGTTCCTTTCTTGA
GTGTGATTTTTTTTTTCTCTCCCTCAATAAAATAAATCAAACTCTG
AGAC |

Expression of OTOF in Mammalian Cells

Mutations in OTOF have been linked to sensorineural hearing loss and auditory neuropathy. The compositions and methods described herein increase the expression of WT OTOF protein by administering a first nucleic acid vector that contains a polynucleotide encoding an N-terminal portion of an OTOF protein and a second nucleic acid vector that contains a polynucleotide encoding a C-terminal portion of an OTOF protein. In order to utilize nucleic acid vectors for therapeutic application in the treatment of sensorineural hearing loss and auditory neuropathy, they can be directed to the interior of the cell, and, in particular, to specific cell types. A wide array of methods has been established for the delivery of proteins to mammalian cells and for the stable expression of genes encoding proteins in mammalian cells.

Polynucleotides Encoding OTOF

One platform that can be used to achieve therapeutically effective intracellular concentrations of OTOF in mammalian cells is via the stable expression of the gene encoding OTOF (e.g., by integration into the nuclear or mitochondrial genome of a mammalian cell, or by episomal concatemer formation in the nucleus of a mammalian cell). The gene is a polynucleotide that encodes the primary amino acid sequence of the corresponding protein. In order to introduce exogenous genes into a mammalian cell, genes can be incorporated into a vector. Vectors can be introduced into a cell by a variety of methods, including transformation, transfection, transduction, direct uptake, projectile bombardment, and by encapsulation of the vector in a liposome. Examples of suitable methods of transfecting or transforming cells include calcium phosphate precipitation, electroporation, microinjection, infection, lipofection and direct uptake. Such methods are described in more detail, for example, in Green, et al., Molecular Cloning: A Laboratory Manual, Fourth Edition (Cold Spring Harbor University Press, New York 2014); and Ausubel, et al., Current Protocols in Molecular Biology (John Wiley & Sons, New York 2015), the disclosures of each of which are incorporated herein by reference.

OTOF can also be introduced into a mammalian cell by targeting vectors containing portions of a gene encoding an OTOF protein to cell membrane phospholipids. For example, vectors can be targeted to the phospholipids on the extracellular surface of the cell membrane by linking the vector molecule to a VSV-G protein, a viral protein with affinity for all cell membrane phospholipids. Such a construct can be produced using methods well known to those of skill in the field.

Recognition and binding of the polynucleotide encoding an OTOF protein by mammalian RNA polymerase is important for gene expression. As such, one may include sequence elements within the polynucleotide that exhibit a high affinity for transcription factors that recruit RNA polymerase and promote the assembly of the transcription complex at the transcription initiation site. Such sequence elements include, e.g., a mammalian promoter, the sequence of which can be recognized and bound by specific transcription initiation factors and ultimately RNA polymerase.

Polynucleotides suitable for use in the compositions and methods described herein also include those that encode an OTOF protein downstream of a mammalian promoter (e.g., a polynucleotide that encodes an N-terminal portion of an OTOF protein downstream of a mammalian promoter). Promoters that are useful for the expression of an OTOF protein in mammalian cells include constitutive promoters, cochlear hair cell-specific promoters, and inner hair cell-specific promoters. Constitutive promoters include the CAG promoter, the cytomegalovirus (CMV) promoter, the smCBA promoter, the EF1α promoter, and the PGK promoter. Cochlear hair cell-specific promoters include the Myosin 15 (Myo15) promoter, the Myosin 7A (Myo7A) promoter, the Myosin 6 (Myo6) promoter, the POU4F3 promoter, the Atonal BHLH Transcription Factor 1 (ATOH1) promoter, the LIM Homeobox 3 (LHX3) promoter, the α9 acetylcholine receptor (α9AChR) promoter, and the α10 acetylcholine receptor (α10AChR) promoter. Inner hair cell-specific promoters include the FGF8 promoter, the VGLUT3 promoter, and the OTOF promoter. Alternatively, promoters derived from viral genomes can also be used for the stable expression of these agents in mammalian cells. Examples of functional viral promoters that can be used to promote mammalian expression of these agents include adenovirus late promoter, vaccinia virus 7.5K promoter, SV40 promoter, tk promoter of HSV, mouse mammary tumor virus (MMTV) promoter, LTR promoter of HIV, promoter of moloney virus, Epstein barr virus (EBV) promoter, and the Rous sarcoma virus (RSV) promoter.

Murine Myosin 15 Promoters

In some embodiments, the Myo15 promoter for use in the compositions and methods described herein includes nucleic acid sequences from regions of the murine Myo15 locus that are capable of expressing a transgene specifically in hair cells, or variants thereof, such as a nucleic acid sequences that have at least 85% sequence identity (e.g., 85%, 90%, 95%, 96%, 97%, 98%, 99%, or more, sequence identity) to regions of the murine Myo15 locus that are capable of expressing a transgene specifically in hair cells. These regions include nucleic acid sequences immediately preceding the murine Myo15 translation start site and an upstream regulatory element that is located over 5 kb from the murine Myo15 translation start site. The Myo15 promoter for use in the compositions and methods described herein can optionally include a linker operably linking the regions of the murine Myo15 locus that are capable of expressing a transgene specifically in hair cells, or the regions of the murine Myo15 locus can be joined directly without an intervening linker.

In some embodiments, the Myo15 promoter for use in the compositions and methods described herein contains a first region (an upstream regulatory element) having at least 85% sequence identity (e.g., 85%, 90%, 95%, 96%, 97%, 98%, 99%, or more, sequence identity) to a region containing the first non-coding exon of the murine Myo15 gene (nucleic acids from −6755 to −7209 with respect to the murine Myo15 translation start site, the sequence of which is set forth in SEQ ID NO: 24) or a functional portion or derivative thereof joined (e.g., operably linked) to a second region having at least 85% sequence identity (e.g., 85%, 90%, 95%, 96%, 97%, 98%, 99%, or more, sequence identity) to the nucleic acid sequence immediately preceding the murine Myo15 translation start site (nucleic acids from −1 to −1157 with respect to the murine Myo15 translation start site, the sequence of which is set forth in SEQ ID NO: 25) or a functional portion or derivative thereof. The functional portion of SEQ ID NO: 24 may have the sequence of nucleic acids from −7166 to −7091 with respect to the murine Myo15 translation start site (set forth in SEQ ID NO: 26) and/or the sequence of nucleic acids from −7077 to −6983 with respect to the murine Myo15 translation start site (set forth in SEQ ID NO: 27). The first region may contain the nucleic acid sequence of SEQ ID NO: 26 fused to the nucleic acid sequence of SEQ ID NO: 27 with no intervening nucleic acids, as set forth in SEQ ID NO: 28, or the first region may contain the nucleic acid sequence of SEQ ID NO: 27 fused to the nucleic acid sequence of SEQ ID NO: 26 with no intervening nucleic acids, as set forth in SEQ ID NO: 29. Alternatively, the first region may contain the sequences of SEQ ID NO: 26 and SEQ ID NO: 27 joined by the endogenous intervening nucleic acid sequence (e.g., the first region may have or include the sequence of nucleic acids from −7166 to −6983 with respect to the murine Myo15 translation start site, as set forth in SEQ ID NO: 30 and SEQ ID NO: 50) or a nucleic acid linker. In a murine Myo15 promoter in which the first region contains both SEQ ID NO: 26 and SEQ ID NO: 27, the two sequences can be included in any order (e.g., SEQ ID NO: 26 may be joined to (e.g., precede) SEQ ID NO: 27, or SEQ ID NO: 27 may be joined to (e.g., precede) SEQ ID NO: 26). The functional portion of SEQ ID NO: 25 may have the sequence of nucleic acids from −590 to −509 with respect to the murine Myo15 translation start site (set forth in SEQ ID NO: 31) and/or the sequence of nucleic acids from −266 to −161 with respect to the murine Myo15 translation start site (set forth in SEQ ID NO: 32). In some embodiments, the sequence containing SEQ ID NO: 31 has the sequence of SEQ ID NO: 51. In some embodiments, the sequence containing SEQ ID NO: 32 has the sequence of SEQ ID NO: 52. The second region may contain the nucleic acid sequence of SEQ ID NO: 31 fused to the nucleic acid sequence of SEQ ID NO: 32 with no intervening nucleic acids, as set forth in SEQ ID NO: 33, or the second region may contain the nucleic acid sequence of SEQ ID NO: 32 fused to the nucleic acid sequence of SEQ ID NO: 31 with no intervening nucleic acids, as set forth in SEQ ID NO: 34. The second region may contain the nucleic acid sequence of SEQ ID NO: 51 fused to the nucleic acid sequence of SEQ ID NO: 52 with no intervening nucleic acids, as set forth in SEQ ID NO: 55, or the second region may contain the nucleic acid sequence of SEQ ID NO: 52 fused to the nucleic acid sequence of SEQ ID NO: 51 with no intervening nucleic acids. Alternatively, the second region may contain the sequences of SEQ ID NO: 31 and SEQ ID NO: 32 joined by the endogenous intervening nucleic acid sequence (e.g., the second region may have the sequence of nucleic acids from −590 to −161 with respect to the murine Myo15 translation start site, as set forth in SEQ ID NO: 35) or a nucleic acid linker. In a murine Myo15 promoter in which the second region contains both SEQ ID NO: 31 and SEQ ID NO: 32, the two sequences can be included in any order (e.g., SEQ ID NO: 31 may be joined to (e.g., precede) SEQ ID NO: 32, or SEQ ID NO: 32 may be joined to (e.g., precede) SEQ ID NO: 31).

The first region and the second region of the murine Myo15 promoter can be joined directly or can be joined by a nucleic acid linker. For example, the murine Myo15 promoter can contain the sequence of SEQ ID NO: 24 or a functional portion or derivative thereof (e.g., any one or more of SEQ ID NOs: 26-30 and 50, e.g., SEQ ID NOs 26 and 27) fused to the sequence of SEQ ID NO: 25 or a functional portion or derivative thereof (e.g., any one or more of SEQ ID NOs: 31-35, 51, 52, and 55, e.g., SEQ ID NOs 31 and 32) with no intervening nucleic acids. For example, the nucleic acid sequence of the murine Myo15 promoter that results from direct fusion of SEQ ID NO: 24 to SEQ ID NO: 25 is set forth in SEQ ID NO: 36. Alternatively, a linker can be used to join the sequence of SEQ ID NO: 24 or a functional portion or derivative thereof (e.g., any one or more of SEQ ID NOs: 26-30 and 50, e.g., SEQ ID NOs 26 and 27) to the sequence of SEQ ID NO: 25 or a functional portion or derivative thereof (e.g., any one or more of SEQ ID NOs: 31-35, 51, 52, and 55, e.g., SEQ ID NOs 31 and 32). Exemplary Myo15 promoters containing functional portions of both SEQ ID NO: 24 and SEQ ID NO: 25 are provided in SEQ ID NOs: 38, 39, 53, 54, 59, and 60.

The length of a nucleic acid linker for use in a murine Myo15 promoter described herein can be about 5 kb or less (e.g., about 5 kb, 4.5, kb, 4, kb, 3.5 kb, 3 kb, 2.5 kb, 2 kb, 1.5 kb, 1 kb, 900 bp, 800 bp, 700 bp, 600 bp, 500 bp, 450 bp, 400 bp, 350 bp, 300 bp, 250 bp, 200 bp, 150 bp, 100 bp, 90 bp, 80 bp, 70 bp, 60 bp, 50 bp, 40 bp, 30 bp, 25 bp, 20 bp, 15, bp, 10 bp, 5 bp, 4 bp, 3 bp, 2 bp, or less). Nucleic acid linkers that can be used in the murine Myo15 promoter described herein do not disrupt the ability of the murine Myo15 promoter of the invention to induce transgene expression in hair cells.

In some embodiments, the sequence of SEQ ID NO: 24 or a functional portion or derivative thereof (e.g., any one or more of SEQ ID NOs: 26-30 and 50, e.g., SEQ ID NOs 26 and 27) is joined (e.g., operably linked) to the sequence of SEQ ID NO: 25 or a functional portion or derivative thereof (e.g., any one or more of SEQ ID NOs: 31-35, 51, 52, and 55, e.g., SEQ ID NOs 31 and 32), and, in some embodiments, the order of the regions is reversed (e.g., the sequence of SEQ ID NO: 25 or a functional portion or derivative thereof (e.g., any one or more of SEQ ID NOs: 31-35, 51, 52, and 55, e.g., SEQ ID NOs 31 and 32) is joined (e.g., operably linked) to the sequence of SEQ ID NO: 24 or a functional portion or derivative thereof (e.g., any one or more of SEQ ID NOs: 26-30 and 50, e.g., SEQ ID NOs 26 and 27)). For example, the nucleic acid sequence of a murine Myo15 promoter that results from direct fusion of SEQ ID NO: 25 to SEQ ID NO: 24 is set forth in SEQ ID NO: 37. An example of a murine Myo15 promoter in which a functional portion or derivative of SEQ ID NO: 25 precedes a functional portion or derivative of SEQ ID NO: 24 is provided in SEQ ID NO: 58. Regardless of order, the sequence of SEQ ID NO: 24 or a functional portion or derivative thereof and the sequence of SEQ ID NO: 25 or a functional portion or derivative thereof can be joined by direct fusion or a nucleic acid linker, as described above.

In some embodiments, the murine Myo15 promoter for use in the compositions and methods described herein contains a region having at least 85% sequence identity (e.g., 85%, 90%, 95%, 96%, 97%, 98%, 99%, or more, sequence identity) to a region containing the first non-coding exon of the murine Myo15 gene (nucleic acids from −6755 to −7209 with respect to the murine Myo15 translation start site, the sequence of which is set forth in SEQ ID NO: 24) or a functional portion or derivative thereof. The functional portion of SEQ ID NO: 24 may have the sequence of nucleic acids from −7166 to −7091 with respect to the murine Myo15 translation start site (set forth in SEQ ID NO: 26) and/or the sequence of nucleic acids from −7077 to −6983 with respect to the murine Myo15 translation start site (set forth in SEQ ID NO: 27). The murine Myo15 promoter may contain the nucleic acid sequence of SEQ ID NO: 26 fused to the nucleic acid sequence of SEQ ID NO: 27 with no intervening nucleic acids, as set forth in SEQ ID NO: 28, or the murine Myo15 promoter may contain the nucleic acid sequence of SEQ ID NO: 27 fused to the nucleic acid sequence of SEQ ID NO: 26 with no intervening nucleic acids, as set forth in SEQ ID NO: 29. Alternatively, the murine Myo15 promoter may contain the sequences of SEQ ID NO: 26 and SEQ ID NO: 27 joined by the endogenous intervening nucleic acid sequence (e.g., the first region may have or include the sequence of nucleic acids from −7166 to −6983 with respect to the murine Myo15 translation start site, as set forth in SEQ ID NO: 30 and SEQ ID NO: 50) or a nucleic acid linker. In a murine Myo15 promoter that contains both SEQ ID NO: 26 and SEQ ID NO: 27, the two sequences can be included in any order (e.g., SEQ ID NO: 26 may be joined to (e.g., precede) SEQ ID NO: 27, or SEQ ID NO: 27 may be joined to (e.g., precede) SEQ ID NO: 26).

In some embodiments, the murine Myo15 promoter for use in the compositions and methods described herein contains a region having at least 85% sequence identity (e.g., 85%, 90%, 95%, 96%, 97%, 98%, 99%, or more, sequence identity) to the nucleic acid sequence immediately upstream of the murine Myo15 translation start site (nucleic acids from −1 to −1157 with respect to the murine Myo15 translation start site, the sequence of which is set forth in SEQ ID NO: 25) or a functional portion or derivative thereof. The functional portion of SEQ ID NO: 25 may have the sequence of nucleic acids from −590 to −509 with respect to the murine Myo15 translation start site (set forth in SEQ ID NO: 31) and/or the sequence of nucleic acids from −266 to −161 with respect to the murine Myo15 translation start site (set forth in SEQ ID NO: 32). In some embodiments, the sequence containing SEQ ID NO: 31 has the sequence of SEQ ID NO: 51. In some embodiments, the sequence containing SEQ ID NO: 32 has the sequence of SEQ ID NO: 52. The murine Myo15 promoter may contain the nucleic acid sequence of SEQ ID NO: 31 fused to the nucleic acid sequence of SEQ ID NO: 32 with no intervening nucleic acids, as set forth in SEQ ID NO: 33, or the murine Myo15 promoter may contain the nucleic acid sequence of SEQ ID NO: 32 fused to the nucleic acid sequence of SEQ ID NO: 31 with no intervening nucleic acids, as set forth in SEQ ID NO: 34. The murine Myo15 promoter may contain the nucleic acid sequence of SEQ ID NO: 51 fused to the nucleic acid sequence of SEQ ID NO: 52 with no intervening nucleic acids, as set forth in SEQ ID NO: 55, or the murine Myo15 promoter may contain the nucleic acid sequence of SEQ ID NO: 52 fused to the nucleic acid sequence of SEQ ID NO: 51 with no intervening nucleic acids. Alternatively, the murine Myo15 promoter may contain the sequences of SEQ ID NO: 31 and SEQ ID NO: 32 joined by the endogenous intervening nucleic acid sequence (e.g., the second region may have the sequence of nucleic acids from −590 to −161 with respect to the murine Myo15 translation start site, as set forth in SEQ ID NO: 35) or a nucleic acid linker. In a murine Myo15 promoter that contains both SEQ ID NO: 31 and SEQ ID NO: 32, the two sequences can be included in any order (e.g., SEQ ID NO: 31 may be joined to (e.g., precede) SEQ ID NO: 32, or SEQ ID NO: 32 may be joined to (e.g., precede) SEQ ID NO: 31).

In some embodiments, the murine Myo15 promoter for use in the compositions and methods described herein contains a functional portion or derivative of a region having at least 85% sequence identity (e.g., 85%, 90%, 95%, 96%, 97%, 98%, 99%, or more, sequence identity) to a region containing the first non-coding exon of the Myo15 gene (nucleic acids from −6755 to −7209 with respect to the murine Myo15 translation start site, the sequence of which is set forth in SEQ ID NO: 24) flanked on both sides by a functional portion or derivative of a region having at least 85% sequence identity (e.g., 85%, 90%, 95%, 96%, 97%, 98%, 99%, or more, sequence identity) to the nucleic acid sequence immediately upstream of the murine Myo15 translation start site (nucleic acids from −1 to −1157 with respect to the murine Myo15 translation start site, the sequence of which is set forth in SEQ ID NO: 25). For example, a functional portion or derivative of SEQ ID NO: 25, such as SEQ ID NO: 31 or 51 may be directly fused or joined by a nucleic acid linker to a portion of SEQ ID NO: 24, such as any one of SEQ ID NOs: 26-30 and 50, which is directly fused or joined by a nucleic acid linker to a different functional portion of SEQ ID NO: 25, such as SEQ ID NO: 32 or 52. In other embodiments, a functional portion or derivative of SEQ ID NO: 25, such as SEQ ID NO: 32 or 52 may be directly fused or joined by a nucleic acid linker to a portion of SEQ ID NO: 24, such as any one of SEQ ID NOs: 26-30 and 50, which is directly fused or joined by a nucleic acid linker to a different functional portion of SEQ ID NO: 25, such as SEQ ID NO: 31 or 51. For example, polynucleotides having at least 85% sequence identity (e.g., 85%, 90%, 95%, 96%, 97%, 98%, 99%, or more, sequence identity) to the nucleic acid sequence of SEQ ID NOs: 51, 50, and 52 can be fused to produce a polynucleotide having at least 85% sequence identity (e.g., 85%, 90%, 95%, 96%, 97%, 98%, 99%, or more, sequence identity) to the nucleic acid sequence of SEQ ID NO: 56. In some embodiments, polynucleotides having at least 85% sequence identity (e.g., 85%, 90%, 95%, 96%, 97%, 98%, 99%, or more, sequence identity) to the nucleic acid sequence of SEQ ID NOs: 52, 50, and 51 can be fused to produce a polynucleotide having at least 85% sequence identity (e.g., 85%, 90%, 95%, 96%, 97%, 98%, 99%, or more, sequence identity) to the nucleic acid sequence of SEQ ID NO: 57.

Human Myosin 15 Promoters

In some embodiments, the Myo15 promoter for use in the compositions and methods described herein includes nucleic acid sequences from regions of the human Myo15 locus that are capable of expressing a transgene specifically in hair cells, or variants thereof, such as a nucleic acid sequences that have at least 85% sequence identity (e.g., 85%, 90%, 95%, 96%, 97%, 98%, 99%, or more, sequence identity) to regions of the human Myo15 locus that are capable of expressing a transgene specifically in hair cells. The Myo15 promoter for use in the compositions and methods described herein can optionally include a linker operably linking the regions of the human Myo15 locus that are capable of expressing a transgene specifically in hair cells, or the regions of the human Myo15 locus can be joined directly without an intervening linker.

In some embodiments, the Myo15 promoter for use in the compositions and methods described herein contains a first region having at least 85% sequence identity (e.g., 85%, 90%, 95%, 96%, 97%, 98%, 99%, or more, sequence identity) to the sequence set forth in SEQ ID NO: 40 or a functional portion or derivative thereof joined (e.g., operably linked) to a second region having at least 85% sequence identity (e.g., 85%, 90%, 95%, 96%, 97%, 98%, 99%, or more, sequence identity) to the sequence set forth in SEQ ID NO: 41 or a functional portion or derivative thereof. The functional portion of SEQ ID NO: 40 may have the sequence set forth in SEQ ID NO: 42. The functional portion of SEQ ID NO: 41 may have the sequence set forth in SEQ ID NO: 43 and/or the sequence set forth in SEQ ID NO: 44. The second region may contain the nucleic acid sequence of SEQ ID NO: 43 fused to the nucleic acid sequence of SEQ ID NO: 44 with no intervening nucleic acids, as set forth in SEQ ID NO: 45, or the second region may contain the nucleic acid sequence of SEQ ID NO: 44 fused to the nucleic acid sequence of SEQ ID NO: 43 with no intervening nucleic acids, as set forth in SEQ ID NO: 46. Alternatively, the second region may contain the sequences of SEQ ID NO: 43 and SEQ ID NO: 44 joined by the endogenous intervening nucleic acid sequence (as set forth in SEQ ID NO: 47) or a nucleic acid linker. In a human Myo15 promoter in which the second region contains both SEQ ID NO: 43 and SEQ ID NO: 44, the two sequences can be included in any order (e.g., SEQ ID NO: 43 may be joined to (e.g., precede) SEQ ID NO: 44, or SEQ ID NO: 44 may be joined to (e.g., precede) SEQ ID NO: 43).

The first region and the second region of the human Myo15 promoter can be joined directly or can be joined by a nucleic acid linker. For example, the human Myo15 promoter can contain the sequence of SEQ ID NO: 40 or a functional portion or derivative thereof (e.g., SEQ ID NO: 42) fused to the sequence of SEQ ID NO: 41 or a functional portion or derivative thereof (e.g., any one or more of SEQ ID NOs: 43-47, e.g., SEQ ID NOs: 43 and/or 44) with no intervening nucleic acids. Alternatively, a linker can be used to join the sequence of SEQ ID NO: 40 or a functional portion or derivative thereof (e.g., SEQ ID NO: 42) to the sequence of SEQ ID NO: 41 or a functional portion or derivative thereof (e.g., any one or more of SEQ ID NOs: 43-47, e.g., SEQ ID NOs: 43 and/or 44). Exemplary human Myo15 promoters containing functional portions of both SEQ ID NO: 40 and SEQ ID NO: 41 are provided in SEQ ID NOs: 48 and 49.

In some embodiments, the sequence of SEQ ID NO: 40 or a functional portion or derivative thereof (e.g., SEQ ID NO: 42) is joined (e.g., operably linked) to the sequence of SEQ ID NO: 41 or a functional portion or derivative thereof (e.g., any one or more of SEQ ID NOs: 43-47, e.g., SEQ ID NOs: 43 and 44), and, in some embodiments, the order of the regions is reversed (e.g., the sequence of SEQ ID NO: 41 or a functional portion or derivative thereof (e.g., any one or more of SEQ ID NOs: 43-47, e.g., SEQ ID NOs: 43 and/or 44) is joined (e.g., operably linked) to the sequence of SEQ ID NO: 40 or a functional portion or derivative thereof (e.g., SEQ ID NO: 42). Regardless of order, the sequence of SEQ ID NO: 40 or a functional portion or derivative thereof and the sequence of SEQ ID NO: 41 or a functional portion or derivative thereof can be joined by direct fusion or a nucleic acid linker, as described above.

In some embodiments, the human Myo15 promoter for use in the compositions and methods described herein contains a region having at least 85% sequence identity (e.g., 85%, 90%, 95%, 96%, 97%, 98%, 99%, or more, sequence identity) to a region containing the sequence set forth in SEQ ID NO: 40 or a functional portion or derivative thereof. The functional portion of SEQ ID NO: 40 may have the sequence of nucleic acids set forth in SEQ ID NO: 42.

In some embodiments, the human Myo15 promoter for use in the compositions and methods described herein contains a region having at least 85% sequence identity (e.g., 85%, 90%, 95%, 96%, 97%, 98%, 99%, or more, sequence identity) to the sequence set forth in SEQ ID NO: 41 or a functional portion or derivative thereof. The functional portion of SEQ ID NO: 41 may have the sequence set forth in SEQ ID NO: 43 and/or the sequence set forth in SEQ ID NO: 44. The human Myo15 promoter may contain the nucleic acid sequence of SEQ ID NO: 43 fused to the nucleic acid sequence of SEQ ID NO: 44 with no intervening nucleic acids, as set forth in SEQ ID NO: 45, or the human Myo15 promoter may contain the nucleic acid sequence of SEQ ID NO: 44 fused to the nucleic acid sequence of SEQ ID NO: 43 with no intervening nucleic acids, as set forth in SEQ ID NO: 46. Alternatively, the human Myo15 promoter may contain the sequences of SEQ ID NO: 43 and SEQ ID NO: 44 joined by the endogenous intervening nucleic acid sequence (e.g., as set forth in SEQ ID NO: 47) or a nucleic acid linker. In a human Myo15 promoter that contains both SEQ ID NO: 43 and SEQ ID NO: 44, the two sequences can be included in any order (e.g., SEQ ID NO: 43 may be joined to (e.g., precede) SEQ ID NO: 44, or SEQ ID NO: 44 may be joined to (e.g., precede) SEQ ID NO: 43).

The length of a nucleic acid linker for use in a human Myo15 promoter described herein can be about 5 kb or less (e.g., about 5 kb, 4.5, kb, 4, kb, 3.5 kb, 3 kb, 2.5 kb, 2 kb, 1.5 kb, 1 kb, 900 bp, 800 bp, 700 bp, 600 bp, 500 bp, 450 bp, 400 bp, 350 bp, 300 bp, 250 bp, 200 bp, 150 bp, 100 bp, 90 bp, 80 bp, 70 bp, 60 bp, 50 bp, 40 bp, 30 bp, 25 bp, 20 bp, 15, bp, 10 bp, 5 bp, 4 bp, 3 bp, 2 bp, or less). Nucleic acid linkers that can be used in the human Myo15 promoters described herein do not disrupt the ability of the human Myo15 promoter of the invention to induce transgene expression in hair cells.

The foregoing Myo15 promoter sequences are summarized in Table 3, below.

TABLE 3

Exemplary nucleotide sequences for use in the Myo15 promoter described herein

| SEQ ID NO. | Description of nucleic acid sequence | Nucleic Acid Sequence |
| --- | --- | --- |
| 24 | Region containing non-coding exon 1 of Myo15 (-6755 to -7209) | CTGCAGCTCAGCCTACTACTTGCTTTCCAGGCTGTTCCTAGT<br>TCCCATGTCAGCTGCTTGTGCTTTCCAGAGACAAAACAGGAA<br>TAATAGATGTCATTAAATATACATTGGGCCCCAGGCGGTCAAT<br>GTGGCAGCCTGAGCCTCCTTTCCATCTCTGTGGAGGCAGAC<br>ATAGGACCCCCAACAAACAGCATGCAGGTTGGGAGCCAGCC<br>ACAGGACCCAGGTAAGGGGCCCTGGGTCCTTAAGCTTCTGC<br>CACTGGCTCCGGCATTGCAGAGAGAAGAGAAGGGGCGGCA<br>GAGCTGAACCTTAGCCTTGCCTTCCTGGGTACCCTTCTGAGC<br>CTCACTGTCTTCTGTGAGATGGGCAAAGTGCGGGTGTGACTC<br>CTTGGCAACGGTGTTACACCAGGGCAGGTAAAGTTGTAGTTA<br>TTTGTGGGGTACACCAGGACTGTTAAAGGTGTAACTAT |
| 25 | Region immediately preceding the translation start site of Myo15 (-1 to -1157) | GGTCTCACCCAGCATTTTCACTTCTAATAAGTTCAAATGTGAT<br>ACGGCACCTTTCTAAAAATTAGTTTTCAGGGAAATAGGGTTCA<br>AAACTGGTAGTGGTAGGGTCCATTCTCACGACCCCCAGGCCT<br>GCTAACCCTGACCAAGCTACCTATTACTTACCCTCCTCTTTCT<br>CCTCCTCCTCTTTCTCCTTCTCCTGCTTCCCCTCTTCCTTCTC<br>CCTCCCTTCCTCTCCCTCCTCCCCCTCCTTGGCTGTGATCAG<br>ATCCAGAGCCTGAATGAGCCTCCTGACCCCACACCCCCACTA<br>GCATGGGCCTGCAAGTGCCCAGAAGTCCCTCCTGCCTCCTA<br>AACTGCCCAGCCGATCCATTAGCTCTTCCTTCTTCCCAGTGA<br>AAGAAGCAGGCACAGCCTGTCCCTCCCGTTCTACAGAAAGG<br>AAGCTACAGCACAGGGAGGGCCAAAGGCCTTCCTGGGACTA<br>GACAGTTGATCAACAGCAGGACTGGAGAGCTGGGCTCCATTT<br>TTGTTCCTTGGTGCCCTGCCCCTCCCCATGACCTGCAGAGAC<br>ATTCAGCCTGCCAGGCTTTATGAGGTGGGAGCTGGGCTCTC<br>CCTGATGTATTATTCAGCTCCCTGGAGTTGGCCAGCTCCTGT<br>TACACTGGCCACAGCCCTGGGCATCCGCTTCTCACTTCTAGT<br>TTCCCCTCCAAGGTAATGTGGTGGGTCATGATCATTCTATCCT<br>GGCTTCAGGGACCTGACTCCACTTTGGGGCCATTCGAGGGG<br>TCTAGGGTAGATGATGTCCCCCTGTGGGGATTAATGTCCTGC<br>TCTGTAAAACTGAGCTAGCTGAGATCCAGGAGGGCTTGGCCA<br>GAGACAGCAAGTTGTTGCCATGGTGACTTTAAAGCCAGGTTG<br>CTGCCCCAGCACAGGCCTCCCAGTCTACCCTCACTAGAAAAC<br>AACACCCAGGCACTTTCCACCACCTCTCAAAGGTGAAACCCA<br>AGGCTGGTCTAGAGAATGAATTATGGATCCTCGCTGTCCGTG<br>CCACCCAGCTAGTCCCAGCGGCTCAGACACTGAGGAGAGAC<br>TGTAGGTTCAGCTACAAGCAAAAAGACCTAGCTGGTCTCCAA<br>GCAGTGTCTCCAAGTCCCTGAACCTGTGACACCTGCCCCAG<br>GCATCATCAGGCACAGAGGGCCACC |
| 26 | Portion of SEQ ID NO: 24 (-7166 to -7091) | CCCATGTCAGCTGCTTGTGCTTTCCAGAGACAAAACAGGAAT<br>AATAGATGTCATTAAATATACATTGGGCCCCAGG |

TABLE 3-continued

Exemplary nucleotide sequences for use in the Myo15 promoter described herein

| SEQ ID NO. | Description of nucleic acid sequence | Nucleic Acid Sequence |
|---|---|---|
| 27 | Portion of SEQ ID NO: 24 (-7077 to -6983) | AGCCTGAGCCTCCTTTCCATCTCTGTGGAGGCAGACATAGGA CCCCCAACAAACAGCATGCAGGTTGGGAGCCAGCCACAGGA CCCAGGTAAGGG |
| 28 | Portion of SEQ ID NO: 24 (SEQ ID NO: 26 fused to SEQ ID NO: 27) | CCCATGTCAGCTGCTTGTGCTTTCCAGAGACAAAACAGGAAT AATAGATGTCATTAAATATACATTGGGCCCCAGGAGCCTGAG CCTCCTTTCCATCTCTGTGGAGGCAGACATAGGACCCCCAAC AAACAGCATGCAGGTTGGGAGCCAGCCACAGGACCCAGGTA AGGG |
| 29 | Portion of SEQ ID NO: 24 (SEQ ID NO: 27 fused to SEQ ID NO: 26) | AGCCTGAGCCTCCTTTCCATCTCTGTGGAGGCAGACATAGGA CCCCCAACAAACAGCATGCAGGTTGGGAGCCAGCCACAGGA CCCAGGTAAGGGCCCATGTCAGCTGCTTGTGCTTTCCAGAGA CAAAACAGGAATAATAGATGTCATTAAATATACATTGGGCCCC AGG |
| 30 | Portion of SEQ ID NO: 24 (-7166 to -6983) | CCCATGTCAGCTGCTTGTGCTTTCCAGAGACAAAACAGGAAT AATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGG |
| 31 | Portion of SEQ ID NO: 25 (-590 to -509) | TGAGGTGGGAGCTGGGCTCTCCCTGATGTATTATTCAGCTCC CTGGAGTTGGCCAGCTCCTGTTACACTGGCCACAGCCCTG |
| 32 | Portion of SEQ ID NO: 25 (-266 to -161) | CACAGGCCTCCCAGTCTACCCTCACTAGAAAACAACACCCAG GCACTTTCCACCACCTCTCAAAGGTGAAACCCAAGGCTGGTC TAGAGAATGAATTATGGATCCT |
| 33 | Portion of SEQ ID NO: 25 (SEQ ID NO: 31 fused to SEQ ID NO: 32) | TGAGGTGGGAGCTGGGCTCTCCCTGATGTATTATTCAGCTCC CTGGAGTTGGCCAGCTCCTGTTACACTGGCCACAGCCCTGC ACAGGCCTCCCAGTCTACCCTCACTAGAAAACAACACCCAGG CACTTTCCACCACCTCTCAAAGGTGAAACCCAAGGCTGGTCT AGAGAATGAATTATGGATCCT |
| 34 | Portion of SEQ ID NO: 25 (SEQ ID NO: 32 fused to SEQ ID NO: 31) | CACAGGCCTCCCAGTCTACCCTCACTAGAAAACAACACCCAG GCACTTTCCACCACCTCTCAAAGGTGAAACCCAAGGCTGGTC TAGAGAATGAATTATGGATCCTTGAGGTGGGAGCTGGGCTCT CCCTGATGTATTATTCAGCTCCCTGGAGTTGGCCAGCTCCTG TTACACTGGCCACAGCCCTG |
| 35 | Portion of SEQ ID NO: 25 (-590 to -161) | TGAGGTGGGAGCTGGGCTCTCCCTGATGTATTATTCAGCTCC CTGGAGTTGGCCAGCTCCTGTTACACTGGCCACAGCCCTGG GCATCCGCTTCTCACTTCTAGTTTCCCCTCCAAGGTAATGTG GTGGGTCATGATCATTCTATCCTGGCTTCAGGGACCTGACTC CACTTTGGGGCCATTCGAGGGGTCTAGGGTAGATGATGTCC CCCTGTGGGGATTAATGTCCTGCTCTGTAAAACTGAGCTAGC TGAGATCCAGGAGGGCTTGGCCAGAGACAGCAAGTTGTTGC CATGGTGACTTTAAAGCCAGGTTGCTGCCCCAGCACAGGCCT CCCAGTCTACCCTCACTAGAAAACAACACCCAGGCACTTTCC ACCACCTCTCAAAGGTGAAACCCAAGGCTGGTCTAGAGAATG AATTATGGATCCT |
| 36 | SEQ ID NO: 24 fused to SEQ ID NO: 25 | CTGCAGCTCAGCCTACTACTTGCTTTCCAGGCTGTTCCTAGT TCCCATGTCAGCTGCTTGTGCTTTCCAGAGACAAAACAGGAA TAATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTAAGCTTCTGC CACTGGCTCCGGCATTGCAGAGAGAAGAGAAGGGGCGGCA GAGCTGAACCTTAGCCTTGCCTTCCTGGGTACCCTTCTGAGC CTCACTGTCTTCTGTGAGATGGGCAAAGTGCGGGTGTGACTC CTTGGCAACGGTGTTACACCAGGGCAGGTAAAGTTGTAGTTA TTTGTGGGGTACACCAGGACTGTTAAAGGTGTAACTATGGTC TCACCCAGCATTTTCACTTCTAATAAGTTCAAATGTGATACGG CACCTTTCTAAAAATTAGTTTTCAGGGAAATAGGGTTCAAAAC TGGTAGTGGTAGGGTCCATTCTCACGACCCCCAGGCCTGCT AACCCTGACCAAGCTACCTATTACTTACCCTCCTCTTTCTCCT CCTCCTCTTTCTCCTTCTCCTGCTTCCCCTCTTCCTTCTCCCT CCCTTCCTCTCCCTCCTCCCCCTCCTTGGCTGTGATCAGATC CAGAGCCTGAATGAGCCTCCTGACCCCACACCCCCACTAGC ATGGGCCTGCAAGTGCCCAGAAGTCCCTCCTGCCTCCTAAAC TGCCCAGCCGATCCATTAGCTCTTCCTTCTTCCCAGTGAAAG AAGCAGGCACAGCCTGTCCCTCCCGTTCTACAGAAAGGAAG |

TABLE 3-continued

Exemplary nucleotide sequences for use in the Myo15 promoter described herein

| SEQ ID NO. | Description of nucleic acid sequence | Nucleic Acid Sequence |
| --- | --- | --- |
| | | CTACAGCACAGGGAGGGCCAAAGGCCTTCCTGGGACTAGAC<br>AGTTGATCAACAGCAGGACTGGAGAGCTGGGCTCCATTTTTG<br>TTCCTTGGTGCCCTGCCCCTCCCCATGACCTGCAGAGACATT<br>CAGCCTGCCAGGCTTTATGAGGTGGGAGCTGGGCTCTCCCT<br>GATGTATTATTCAGCTCCCTGGAGTTGGCCAGCTCCTGTTAC<br>ACTGGCCACAGCCCTGGGCATCCGCTTCTCACTTCTAGTTTC<br>CCCTCCAAGGTAATGTGGTGGGTCATGATCATTCTATCCTGG<br>CTTCAGGGACCTGACTCCACTTTGGGGCCATTCGAGGGGTC<br>TAGGGTAGATGATGTCCCCCTGTGGGGATTAATGTCCTGCTC<br>TGTAAAACTGAGCTAGCTGAGATCCAGGAGGGCTTGGCCAG<br>AGACAGCAAGTTGTTGCCATGGTGACTTTAAAGCCAGGTTGC<br>TGCCCCAGCACAGGCCTCCCAGTCTACCCTCACTAGAAAACA<br>ACACCCAGGCACTTTCCACCACCTCTCAAAGGTGAAACCCAA<br>GGCTGGTCTAGAGAATGAATTATGGATCCTCGCTGTCCGTGC<br>CACCCAGCTAGTCCCAGCGGCTCAGACACTGAGGAGAGACT<br>GTAGGTTCAGCTACAAGCAAAAAGACCTAGCTGGTCTCCAAG<br>CAGTGTCTCCAAGTCCCTGAACCTGTGACACCTGCCCCAGG<br>CATCATCAGGCACAGAGGGCCACC |
| 37 | SEQ ID NO: 25 fused to SEQ ID NO: 24 | GGTCTCACCCAGCATTTTCACTTCTAATAAGTTCAAATGTGAT<br>ACGGCACCTTTCTAAAAATTAGTTTTCAGGGAAATAGGGTTCA<br>AAACTGGTAGTGGTAGGGTCCATTCTCACGACCCCCAGGCCT<br>GCTAACCCTGACCAAGCTACCTATTACTTACCCTCCTCTTTCT<br>CCTCCTCCTCTTTCTCCTTCTCCTGCTTCCCCTCTTCCTTCTC<br>CCTCCCTTCCTCTCCCTCCTCCCCCTCCTTGGCTGTGATCAG<br>ATCCAGAGCCTGAATGAGCCTCCTGACCCCACACCCCCACTA<br>GCATGGGCCTGCAAGTGCCCAGAAGTCCCTCCTGCCTCCTA<br>AACTGCCCAGCCGATCCATTAGCTCTTCCTTCTTCCCAGTGA<br>AAGAAGCAGGCACAGCCTGTCCCTCCCGTTCTACAGAAAGG<br>AAGCTACAGCACAGGGAGGGCCAAAGGCCTTCCTGGGACTA<br>GACAGTTGATCAACAGCAGGACTGGAGAGCTGGGCTCCATTT<br>TTGTTCCTTGGTGCCCTGCCCCTCCCCATGACCTGCAGAGAC<br>ATTCAGCCTGCCAGGCTTTATGAGGTGGGAGCTGGGCTCTC<br>CCTGATGTATTATTCAGCTCCCTGGAGTTGGCCAGCTCCTGT<br>TACACTGGCCACAGCCCTGGGCATCCGCTTCTCACTTCTAGT<br>TTCCCCTCCAAGGTAATGTGGTGGGTCATGATCATTCTATCCT<br>GGCTTCAGGGACCTGACTCCACTTTGGGGCCATTCGAGGGG<br>TCTAGGGTAGATGATGTCCCCCTGTGGGGATTAATGTCCTGC<br>TCTGTAAAACTGAGCTAGCTGAGATCCAGGAGGGCTTGGCCA<br>GAGACAGCAAGTTGTTGCCATGGTGACTTTAAAGCCAGGTTG<br>CTGCCCCAGCACAGGCCTCCCAGTCTACCCTCACTAGAAAC<br>AACACCCAGGCACTTTCCACCACCTCTCAAAGGTGAAACCCA<br>AGGCTGGTCTAGAGAATGAATTATGGATCCTCGCTGTCCGTG<br>CCACCCAGCTAGTCCCAGCGGCTCAGACACTGAGGAGAGAC<br>TGTAGGTTCAGCTACAAGCAAAAAGACCTAGCTGGTCTCCAA<br>GCAGTGTCTCCAAGTCCCTGAACCTGTGACACCTGCCCCAG<br>GCATCATCAGGCACAGAGGGCCACCCTGCAGCTCAGCCTAC<br>TACTTGCTTTCCAGGCTGTTCCTAGTTCCCATGTCAGCTGCTT<br>GTGCTTTCCAGAGACAAAACAGGAATAATAGATGTCATTAAAT<br>ATACATTGGGCCCCAGGCGGTCAATGTGGCAGCCTGAGCCT<br>CCTTTCCATCTCTGTGGAGGCAGACATAGGACCCCCAACAAA<br>CAGCATGCAGGTTGGGAGCCAGCCACAGGACCCAGGTAAGG<br>GGCCCTGGGTCCTTAAGCTTCTGCCACTGGCTCCGGCATTG<br>CAGAGAGAAGAGAAGGGGCGGCAGAGCTGAACCTTAGCCTT<br>GCCTTCCTGGGTACCCTTCTGAGCCTCACTGTCTTCTGTGAG<br>ATGGGCAAAGTGCGGGTGTGACTCCTTGGCAACGGTGTTAC<br>ACCAGGGCAGGTAAAGTTGTAGTTATTTGTGGGGTACACCAG<br>GACTGTTAAAGGTGTAACTAT |
| 38 | Portion of SEQ ID NO: 24 that contains SEQ ID NO: 26 and SEQ ID NO: 27 fused to portion of SEQ ID NO: 25 that contains SEQ ID NO: 31 and SEQ ID NO: 32 | CTGCAGCTCAGCCTACTACTTGCTTTCCAGGCTGTTCCTAGT<br>TCCCATGTCAGCTGCTTGTGCTTTCCAGAGACAAAACAGGAA<br>TAATAGATGTCATTAAATATACATTGGGCCCCAGGCGGTCAAT<br>GTGGCAGCCTGAGCCTCCTTTCCATCTCTGTGGAGGCAGAC<br>ATAGGACCCCCAACAAACAGCATGCAGGTTGGGAGCCAGCC<br>ACAGGACCCAGGTAAGGGGCCCTGGGTCCTTAAGCTTCTGC<br>CACTGGCTCCGGCATTGCAGAGAGAAGAGAAGGGGCGGCA<br>GACTGGAGAGCTGGGCTCCATTTTTGTTCCTTGGTGCCCTGC<br>CCCTCCCCATGACCTGCAGAGACATTCAGCCTGCCAGGCTTT<br>ATGAGGTGGGAGCTGGGCTCTCCCTGATGTATTATTCAGCTC<br>CCTGGAGTTGGCCAGCTCCTGTTACACTGGCCACAGCCCTG<br>GGCATCCGCTTCTCACTTCTAGTTTCCCCTCCAAGGTAATGT<br>GGTGGGTCATGATCATTCTATCCTGGCTTCAGGGACCTGACT<br>CCACTTTGGGGCCATTCGAGGGGTCTAGGGTAGATGATGTC<br>CCCCTGTGGGGATTAATGTCCTGCTCTGTAAAACTGAGCTAG<br>CTGAGATCCAGGAGGGCTTGGCCAGAGACAGCAAGTTGTTG |

TABLE 3-continued

Exemplary nucleotide sequences for use in the Myo15 promoter described herein

| SEQ ID NO. | Description of nucleic acid sequence | Nucleic Acid Sequence |
|---|---|---|
| | | CCATGGTGACTTTAAAGCCAGGTTGCTGCCCCAGCACAGGC<br>CTCCCAGTCTACCCTCACTAGAAAACAACACCCAGGCACTTT<br>CCACCACCTCTCAAAGGTGAAACCCAAGGCTGGTCTAGAGAA<br>TGAATTATGGATCCTCGCTGTCCGTGCCACCCAGCTAGTCCC<br>AGCGGCTCAGACACTGAGGAGAGACTGTAGGTTCAGCTACA<br>AGCAAAAAGACCTAGCTGGTCTCCAAGCAGTGTCTCCAAGTC<br>CCTGAACCTGTGACACCTGCCCCAGGCATCATCAGGCACAG<br>AGGGCCACC |
| 39 | Portion of SEQ ID NO: 24 that contains SEQ ID NO: 26 and SEQ ID NO: 27 fused to portion of SEQ ID NO: 25 that contains SEQ ID NO: 31 and SEQ ID NO: 32 | CTGCAGCTCAGCCTACTACTTGCTTTCCAGGCTGTTCCTAGT<br>TCCCATGTCAGCTGCTTGTGCTTTCCAGAGACAAAACAGGAA<br>TAATAGATGTCATTAAATATACATTGGGCCCCAGGCGGTCAAT<br>GTGGCAGCCTGAGCCTCCTTTCCATCTCTGTGGAGGCAGAC<br>ATAGGACCCCCAACAAACAGCATGCAGGTTGGGAGCCAGCC<br>ACAGGACCCAGGTAAGGGGCCCTGGGTCCTTTTTATGAGGT<br>GGGAGCTGGGCTCTCCCTGATGTATTATTCAGCTCCCTGGAG<br>TTGGCCAGCTCCTGTTACACTGGCCACAGCCCTGGGCATCC<br>GCTGCCATGGTGACTTTAAAGCCAGGTTGCTGCCCCAGCACA<br>GGCCTCCCAGTCTACCCTCACTAGAAAACAACACCCAGGCAC<br>TTTCCACCACCTCTCAAAGGTGAAACCCAAGGCTGGTCTAGA<br>GAATGAATTATGGATCCTCGCTGTCCGTGCCACCCAGCTAGT<br>CCCAGCGGCTCAGACACTG |
| 40 | Region 1 of the human Myo15 promoter | GTATGCCTTTTGAGATGGATGCAGCAGGTTCTGTGAGGCTGC<br>CAGGAGGGGTAGAGTTCCCGGGGGCCTCGGGCCCCGCTGG<br>AGTGTGGAGCAGGCCCATGCTCAGCTCTCCAGGCTGTTCGT<br>GGCTCCCTGTCAGCTGCTCACTCCTTTCCAGAGACAAAACA<br>GGAATAATAGACATCATTAAATATACATAGGGCCCCAGGCGG<br>TCGGCGTGGTGGGCTGGGCCTCCCTTCC |
| 41 | Region 2 of human Myo15 promoter | TGCCCTGCCTTCTGAGCCGGCAGCCTGGCTCCCCACCCCAT<br>GTATTATTCAGCTCCTGAGAGCCAGCCAGCTCCTGTTACACT<br>GACCGCAGCCCAGCACCTGCTCTGCCCATTCCCCTCCTCCC<br>TTGCCTAGGACCTAGAGGGTTCAAAGTTCTCCTCCAAGATGA<br>CTTGGTGGGCTTTGGCCATCCCACCCTAGGCCCCACTTCTG<br>GCCCAGTGCAGGTGTGCTGGTGATTTAGGGCAGGTGGCATT<br>CCATCTCTGTGGCTCAATGTCTTCCTCTGTGAAGCCGAAGTG<br>ACCCAAGGGCTCCCTTCATGGGGTTGAGCCAGCTGTGGCCC<br>AGGGGAGGGCCTAACCAGGATGAGCACTGATGTTGCCATGAC<br>GACTCCGAGGCCAGAATGTCTCCCCCAGCACAGGCCTCATA<br>GGCAGGCTTCCCCATCCTGGTAAACAACACCCACACACTTTC<br>TACTACTGCTCTAGGGTGAAACCCAAGGCGCTCTAGAGGAGA<br>TGAATTATGGATCCGCCCTCCCGGAATCCTGGCTCGGCCCTC<br>CCCACGCCACCCAGGGCCAGTCGGGTCTGCTCACAGCCCGA<br>GGAGGCCGCGTGTCCAGCCGCGGGCAAGAGACAGAGCAGG<br>TCCCTGTGTCTCCAAGTCCCTGAGCCCGTGACACCGGCCCC<br>AGGCCCTGTAGAGAGCAGGCAGCCACC |
| 42 | Portion of SEQ ID NO: 40 | CCCCTGTCAGCTGCTCACTCCTTTCCAGAGACAAAACAGGAA<br>TAATAGACATCATTAAATATACATAGGGCCCCAGG |
| 43 | Portion of SEQ ID NO: 41 | TGAGCCGGCAGCCTGGCTCCCCACCCCATGTATTATTCAGCT<br>CCTGAGAGCCAGCCAGCTCCTGTTACACTGACCGCAGCCC |
| 44 | Portion of SEQ ID NO: 41 | CACAGGCCTCATAGGCAGGCTTCCCCATCCTGGTAAACAACA<br>CCCACACACTTTCTACTACTGCTCTAGGGTGAAACCCAAGGC<br>GCTCTAGAGGAGATGAATTATGGATCC |
| 45 | Portion of SEQ ID NO: 41 (SEQ ID NO: 43 fused to SEQ ID NO: 44) | TGAGCCGGCAGCCTGGCTCCCCACCCCATGTATTATTCAGCT<br>CCTGAGAGCCAGCCAGCTCCTGTTACACTGACCGCAGCCC<br>ACAGGCCTCATAGGCAGGCTTCCCCATCCTGGTAAACAACAC<br>CCACACACTTTCTACTACTGCTCTAGGGTGAAACCCAAGGCG<br>CTCTAGAGGAGATGAATTATGGATCC |
| 46 | Portion of SEQ ID NO: 41 (SEQ ID NO: 44 fused to SEQ ID NO: 43) | CACAGGCCTCATAGGCAGGCTTCCCCATCCTGGTAAACAACA<br>CCCACACACTTTCTACTACTGCTCTAGGGTGAAACCCAAGGC<br>GCTCTAGAGGAGATGAATTATGGATCCTGAGCCGGCAGCCT<br>GGCTCCCCACCCCATGTATTATTCAGCTCCTGAGAGCCAGCC<br>AGCTCCTGTTACACTGACCGCAGCCC |
| 47 | Portion of SEQ ID NO: 41 (contiguous sequence including SEQ ID NO: 43 and SEQ ID NO: 44) | TGAGCCGGCAGCCTGGCTCCCCACCCCATGTATTATTCAGCT<br>CCTGAGAGCCAGCCAGCTCCTGTTACACTGACCGCAGCCCA<br>GCACCTGCTCTGCCCATTCCCCTCCTCCCTTGCCTAGGACCT<br>AGAGGGTTCAAAGTTCTCCTCCAAGATGACTTGGTGGCTTT<br>GGCCATCCCACCCTAGGCCCCACTTCTGGCCCAGTGCAGGT |

TABLE 3-continued

Exemplary nucleotide sequences for use in the Myo15 promoter described herein

| SEQ ID NO. | Description of nucleic acid sequence | Nucleic Acid Sequence |
|---|---|---|
| | | GTGCTGGTGATTTAGGGCAGGTGGCATTCCATCTCTGTGGCT<br>CAATGTCTTCCTCTGTGAAGCCGAAGTGACCCAAGGGCTCCC<br>TTCATGGGGTTGAGCCAGCTGTGGCCCAGGGAGGGCCTAAC<br>CAGGATGAGCACTGATGTTGCCATGACGACTCCGAGGCCAG<br>AATGTCTCCCCCAGCACAGGCCTCATAGGCAGGCTTCCCCAT<br>CCTGGTAAACAACACCCACACACTTTCTACTACTGCTCTAGG<br>GTGAAACCCAAGGCGCTCTAGAGGAGATGAATTATGGATCC |
| 48 | Polynucleotide containing SEQ ID NO: 40 and SEQ ID NO: 41 | GTATGCCTTTTGAGATGGATGCAGCAGGTTCTGTGAGGCTGC<br>CAGGAGGGGTAGAGTTCCCGGGGGCCTCGGGCCCCGCTGG<br>AGTGTGGAGCAGGCCCATGCTCAGCTCTCCAGGCTGTTCGT<br>GGCTCCCCTGTCAGCTGCTCACTCCTTTCCAGAGACAAAACA<br>GGAATAATAGACATCATTAAATATACATAGGGCCCCAGGCGG<br>TCGGCGTGGTGGGCTGGGCCTCCCTTCCCCATAACACTGAG<br>CTGCTCTGCTGGGCCAACCGTGCTCCTGGGCCAGCCAGAGG<br>ACCCCCATGAGGCGGCATGCAGGCGGGGAGCAGGCCACAG<br>AACGCAGGTAAGGAGACCTTAGCCTAGAGTCCTTGGGGTCT<br>GTCACTGGCCACCCTCGCATCCCAGGCTGCAGGAAACTGAG<br>GCCCAGAGAGGACAAGGACTTTCCTGGACCCACACAGCCAG<br>TCAGTGACAGAGCCTAGGGTCTGAGCCAGGCCTGACCCAAC<br>CTCCATTTCTGCCTCTCTACCCCTGCCCCCGCCCCAACACAC<br>ACACACACACAAGTGGAGTTCCACTGAAACGCCCCTCCTTGC<br>CCTGCCTTCTGAGCCGGCAGCCTGGCTCCCCACCCCATGTA<br>TTATTCAGCTCCTGAGAGCCAGCCAGCTCCTGTTACACTGAC<br>CGCAGCCCAGCACCTGCTCTGCCCATTCCCCTCCTCCCTTGC<br>CTAGGACCTAGAGGGTTCAAAGTTCTCCTCCAAGATGACTTG<br>GTGGGCTTTGGCCATCCCACCCTAGGCCCCACTTCTGGCCC<br>AGTGCAGGTGTGCTGGTGATTTAGGGCAGGTGGCATTCCAT<br>CTCTGTGGCTCAATGTCTTCCTCTGTGAAGCCGAAGTGACCC<br>AAGGGCTCCCTTCATGGGGTTGAGCCAGCTGTGGCCCAGGG<br>AGGGCCTAACCAGGATGAGCACTGATGTTGCCATGACGACT<br>CCGAGGCCAGAATGTCTCCCCCAGCACAGGCCTCATAGGCA<br>GGCTTCCCCATCCTGGTAAACAACACCCACACACTTTCTACT<br>ACTGCTCTAGGGTGAAACCCAAGGCGCTCTAGAGGAGATGA<br>ATTATGGATCCGCCCTCCCGGAATCCTGGCTCGGCCCTCCC<br>CACGCCACCCAGGGCCAGTCGGGTCTGCTCACAGCCCGAG<br>GAGGCCGCGTGTCCAGCCGCGGGCAAGAGACAGAGCAGGT<br>CCCTGTGTCTCCAAGTCCCTGAGCCCGTGACACCGGCCCCA<br>GGCCCTGTAGAGAGCAGGCAGCCACC |
| 49 | Polynucleotide containing SEQ ID NO: 42, SEQ ID NO: 43, and SEQ ID NO: 44 | GCAGGCCCATGCTCAGCTCTCCAGGCTGTTCGTGGCTCCCC<br>TGTCAGCTGCTCACTCCTTTCCAGAGACAAAACAGGAATAAT<br>AGACATCATTAAATATACATAGGGCCCCAGGCGGTCGGCGTG<br>GTGGGCTGGGCCTCCCTTCCCCATAACACTGAGCTGCTCTG<br>CTGGGCCAACCGTGCTCCTGGGCCAGCCAGAGGACCCCCAT<br>GAGGCGGCATGCAGGCGGGGAGCAGGCCACAGAACGCAGG<br>TAAGGAGACCTTGCCTTCTGAGCCGGCAGCCTGGCTCCCCA<br>CCCCATGTATTATTCAGCTCCTGAGAGCCAGCCAGCTCCTGT<br>TACACTGACCGCAGCCCAGCACCTGCTCTGCCCATTCCCCTC<br>CTCCCTTGCCTAGGACCTAGAGGGTTCAAAGTTCTCCTCCAA<br>GATGACTTGGTGGGCTTTGGCCATCGGGCCTAACCAGGATG<br>AGCACTGATGTTGCCATGACGACTCCGAGGCCAGAATGTCTC<br>CCCCAGCACAGGCCTCATAGGCAGGCTTCCCCATCCTGGTA<br>AACAACACCCACACACTTTCTACTACTGCTCTAGGGTGAAAC<br>CCAAGGCGCTCTAGAGGAGATGAATTATGGATCCGCCCTCC<br>CGGAATCCTGGCTCGGCCCTCCCCACGC |
| 50 | Portion of SEQ ID NO: 24 that contains SEQ ID NO: 26 and SEQ ID NO: 27 | CTGCAGCTCAGCCTACTACTTGCTTTCCAGGCTGTTCCTAGT<br>TCCCATGTCAGCTGCTTGTGCTTTCCAGAGACAAAACAGGAA<br>TAATAGATGTCATTAAATATACATTGGGCCCCAGGCGGTCAAT<br>GTGGCAGCCTGAGCCTCCTTTCCATCTCTGTGGAGGCAGAC<br>ATAGGACCCCCAACAAACAGCATGCAGGTTGGGAGCCAGCC<br>ACAGGACCCAGGTAAGGGGCCCTGGGTCCTT |
| 51 | Portion of SEQ ID NO: 25 that contains SEQ ID NO: 31 | TTTATGAGGTGGGAGCTGGGCTCTCCCTGATGTATTATTCAG<br>CTCCCTGGAGTTGGCCAGCTCCTGTTACACTGGCCACAGCC<br>CTGGGCATCCGC |
| 52 | Portion of SEQ ID NO: 25 that contains SEQ ID NO: 32 | TGCCATGGTGACTTTAAAGCCAGGTTGCTGCCCCAGCACAG<br>GCCTCCCAGTCTACCCTCACTAGAAAACAACACCCAGGCACT<br>TTCCACCACCTCTCAAAGGTGAAACCCAAGGCTGGTCTAGAG<br>AATGAATTATGGATCCTCGCTGTCCGTGCCACCCAGCTAGTC<br>CCAGCGGCTCAGACACTG |

TABLE 3-continued

Exemplary nucleotide sequences for use in the Myo15 promoter described herein

| SEQ ID NO. | Description of nucleic acid sequence | Nucleic Acid Sequence |
|---|---|---|
| 53 | SEQ ID NO: 50 fused to SEQ ID NO: 51 | CTGCAGCTCAGCCTACTACTTGCTTTCCAGGCTGTTCCTAGT TCCCATGTCAGCTGCTTGTGCTTTCCAGAGACAAAACAGGAA TAATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTTTTATGAGGT GGGAGCTGGGCTCTCCCTGATGTATTATTCAGCTCCCTGGAG TTGGCCAGCTCCTGTTACACTGGCCACAGCCCTGGGCATCC GC |
| 54 | SEQ ID NO: 50 fused to SEQ ID NO: 52 | CTGCAGCTCAGCCTACTACTTGCTTTCCAGGCTGTTCCTAGT TCCCATGTCAGCTGCTTGTGCTTTCCAGAGACAAAACAGGAA TAATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTTGCCATGGTG ACTTTAAAGCCAGGTTGCTGCCCCAGCACAGGCCTCCCAGTC TACCCTCACTAGAAAACAACACCCAGGCACTTTCCACCACCT CTCAAAGGTGAAACCCAAGGCTGGTCTAGAGAATGAATTATG GATCCTCGCTGTCCGTGCCACCCAGCTAGTCCCAGCGGCTC AGACACTG |
| 55 | SEQ ID NO: 51 fused to SEQ ID NO: 52 | TTTATGAGGTGGGAGCTGGGCTCTCCCTGATGTATTATTCAG CTCCCTGGAGTTGGCCAGCTCCTGTTACACTGGCCACAGCC CTGGGCATCCGCTGCCATGGTGACTTTAAAGCCAGGTTGCTG CCCCAGCACAGGCCTCCCAGTCTACCCTCACTAGAAAACAAC ACCCAGGCACTTTCCACCACCTCTCAAAGGTGAAACCCAAGG CTGGTCTAGAGAATGAATTATGGATCCTCGCTGTCCGTGCCA CCCAGCTAGTCCCAGCGGCTCAGACACTG |
| 56 | SEQ ID NO: 51 fused to SEQ ID NO: 50, which is fused to SEQ ID NO: 52 | TTTATGAGGTGGGAGCTGGGCTCTCCCTGATGTATTATTCAG CTCCCTGGAGTTGGCCAGCTCCTGTTACACTGGCCACAGCC CTGGGCATCCGCCTGCAGCTCAGCCTACTACTTGCTTTCCAG GCTGTTCCTAGTTCCCATGTCAGCTGCTTGTGCTTTCCAGAG ACAAAACAGGAATAATAGATGTCATTAAATATACATTGGGCCC CAGGCGGTCAATGTGGCAGCCTGAGCCTCCTTTCCATCTCTG TGGAGGCAGACATAGGACCCCCAACAAACAGCATGCAGGTT GGGAGCCAGCCACAGGACCCAGGTAAGGGGCCCTGGGTCC TTTGCCATGGTGACTTTAAAGCCAGGTTGCTGCCCCAGCACA GGCCTCCCAGTCTACCCTCACTAGAAAACAACACCCAGGCAC TTTCCACCACCTCTCAAAGGTGAAACCCAAGGCTGGTCTAGA GAATGAATTATGGATCCTCGCTGTCCGTGCCACCCAGCTAGT CCCAGCGGCTCAGACACTG |
| 57 | SEQ ID NO: 52 fused to SEQ ID NO: 50, which is fused to SEQ ID NO: 51 | TGCCATGGTGACTTTAAAGCCAGGTTGCTGCCCCAGCACAG GCCTCCCAGTCTACCCTCACTAGAAAACAACACCCAGGCACT TTCCACCACCTCTCAAAGGTGAAACCCAAGGCTGGTCTAGAG AATGAATTATGGATCCTCGCTGTCCGTGCCACCCAGCTAGTC CCAGCGGCTCAGACACTGCTGCAGCTCAGCCTACTACTTGCT TTCCAGGCTGTTCCTAGTTCCCATGTCAGCTGCTTGTGCTTTC CAGAGACAAAACAGGAATAATAGATGTCATTAAATATACATTG GGCCCCAGGCGGTCAATGTGGCAGCCTGAGCCTCCTTTCCA TCTCTGTGGAGGCAGACATAGGACCCCCAACAAACAGCATG CAGGTTGGGAGCCAGCCACAGGACCCAGGTAAGGGGCCCT GGGTCCTTTTTATGAGGTGGGAGCTGGGCTCTCCCTGATGTA TTATTCAGCTCCCTGGAGTTGGCCAGCTCCTGTTACACTGGC CACAGCCCTGGGCATCCGC |
| 58 | SEQ ID NO: 51 fused to SEQ ID NO: 52, which is fused to SEQ ID NO: 50 | TTTATGAGGTGGGAGCTGGGCTCTCCCTGATGTATTATTCAG CTCCCTGGAGTTGGCCAGCTCCTGTTACACTGGCCACAGCC CTGGGCATCCGCTGCCATGGTGACTTTAAAGCCAGGTTGCTG CCCCAGCACAGGCCTCCCAGTCTACCCTCACTAGAAAACAAC ACCCAGGCACTTTCCACCACCTCTCAAAGGTGAAACCCAAGG CTGGTCTAGAGAATGAATTATGGATCCTCGCTGTCCGTGCCA CCCAGCTAGTCCCAGCGGCTCAGACACTGCTGCAGCTCAGC CTACTACTTGCTTTCCAGGCTGTTCCTAGTTCCCATGTCAGCT GCTTGTGCTTTCCAGAGACAAAACAGGAATAATAGATGTCATT AAATATACATTGGGCCCCAGGCGGTCAATGTGGCAGCCTGA GCCTCCTTTCCATCTCTGTGGAGGCAGACATAGGACCCCCAA CAAACAGCATGCAGGTTGGGAGCCAGCCACAGGACCCAGGT AAGGGGCCCTGGGTCCTT |
| 59 | Portion of SEQ ID NO: 24 that contains SEQ ID NO: 26 and SEQ ID | TGCAGCTCAGCCTACTACTTGCTTTCCAGGCTGTTCCTAGTT CCCATGTCAGCTGCTTGTGCTTTCCAGAGACAAAACAGGAAT AATAGATGTCATTAAATATACATTGGGCCCCAGGCGGTCAAT |

TABLE 3-continued

Exemplary nucleotide sequences for use in the Myo15 promoter described herein

| SEQ ID NO. | Description of nucleic acid sequence | Nucleic Acid Sequence |
|---|---|---|
|  | NO: 27 fused to portion of SEQ ID NO: 25 that contains SEQ ID NO: 31 and SEQ ID NO: 32 | GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTAAGCTTCTGC CACTGGCTCCGGCATTGCAGAGAGAAGAGAAGGGGCGGCA GACTGGAGAGCTGGGCTCCATTTTTGTTCCTTGGTGCCCTGC CCCTCCCCATGACCTGCAGAGACATTCAGCCTGCCAGGCTTT ATGAGGTGGGAGCTGGGCTCTCCCTGATGTATTATTCAGCTC CCTGGAGTTGGCCAGCTCCTGTTACACTGGCCACAGCCCTG GGCATCCGCTTCTCACTTCTAGTTTCCCCTCCAAGGTAATGT GGTGGGTCATGATCATTCTATCCTGGCTTCAGGGACCTGACT CCACTTTGGGGCCATTCGAGGGGTCTAGGGTAGATGATGTC CCCCTGTGGGGATTAATGTCCTGCTCTGTAAAACTGAGCTAG CTGAGATCCAGGAGGGCTTGGCCAGAGACAGCAAGTTGTTG CCATGGTGACTTTAAAGCCAGGTTGCTGCCCCAGCACAGGC CTCCCAGTCTACCCTCACTAGAAAACAACACCCAGGCACTTT CCACCACCTCTCAAAGGTGAAACCCAAGGCTGGTCTAGAGAA TGAATTATGGATCCTCGCTGTCCGTGCCACCCAGCTAGTCCC AGCGGCTCAGACACTGAGGAGAGACTGTAGGTTCAGCTACA AGCAAAAAGACCTAGCTGGTCTCCAAGCAGTGTCTCCAAGTC CCTGAACCTGTGACACCTGCCCCAGGCATCATCAGGCACAG AGGGCCACC |
| 60 | Portion of SEQ ID NO: 24 that contains SEQ ID NO: 26 and SEQ ID NO: 27 fused to portion of SEQ ID NO: 25 that contains SEQ ID NO: 31 and SEQ ID NO: 32 | TGCAGCTCAGCCTACTACTTGCTTTCCAGGCTGTTCCTAGTT CCCATGTCAGCTGCTTGTGCTTTCCAGAGACAAAACAGGAAT AATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTTTATGAGGT GGGAGCTGGGCTCTCCCTGATGTATTATTCAGCTCCCTGGAG TTGGCCAGCTCCTGTTACACTGGCCACAGCCCTGGGCATCC GCTGCCATGGTGACTTTAAAGCCAGGTTGCTGCCCCAGCACA GGCCTCCCAGTCTACCCTCACTAGAAAACAACACCCAGGCAC TTTCCACCACCTCTCAAAGGTGAAACCCAAGGCTGGTCTAGA GAATGAATTATGGATCCTCGCTGTCCGTGCCACCCAGCTAGT CCCAGCGGCTCAGACACTG |

Additional Myo15 promoters useful in conjunction with the compositions and methods described herein include nucleic acid molecules that have at least 85% sequence identity (e.g., 85%, 90%, 95%, 96%, 97%, 98%, 99%, or more, sequence identity) to the nucleic acid sequences set forth in Table 3, as well as functional portions or derivatives of the nucleic acid sequences set forth in Table 3. The Myo15 promoters listed in Table 3 are characterized in U.S. Provisional Application Nos. 62/663,679, 62/802,874, 62/928,311, and 62/965,773 and International Application No. PCT/US2019/029336, which are incorporated herein by reference.

Once a polynucleotide encoding OTOF has been incorporated into the nuclear DNA of a mammalian cell or stabilized in an episomal monomer or concatemer, the transcription of this polynucleotide can be induced by methods known in the art. For example, expression can be induced by exposing the mammalian cell to an external chemical reagent, such as an agent that modulates the binding of a transcription factor and/or RNA polymerase to the mammalian promoter and thus regulates gene expression. The chemical reagent can serve to facilitate the binding of RNA polymerase and/or transcription factors to the mammalian promoter, e.g., by removing a repressor protein that has bound the promoter. Alternatively, the chemical reagent can serve to enhance the affinity of the mammalian promoter for RNA polymerase and/or transcription factors such that the rate of transcription of the gene located downstream of the promoter is increased in the presence of the chemical reagent. Examples of chemical reagents that potentiate polynucleotide transcription by the above mechanisms include tetracycline and doxycycline. These reagents are commercially available (Life Technologies, Carlsbad, Calif.) and can be administered to a mammalian cell in order to promote gene expression according to established protocols.

Other DNA sequence elements that may be included in the nucleic acid vectors for use in the compositions and methods described herein include enhancer sequences. Enhancers represent another class of regulatory elements that induce a conformational change in the polynucleotide containing the gene of interest such that the DNA adopts a three-dimensional orientation that is favorable for binding of transcription factors and RNA polymerase at the transcription initiation site. Thus, polynucleotides for use in the compositions and methods described herein include those that encode an OTOF protein and additionally include a mammalian enhancer sequence. Many enhancer sequences are now known from mammalian genes, and examples include enhancers from the genes that encode mammalian globin, elastase, albumin, α-fetoprotein, and insulin. Enhancers for use in the compositions and methods described herein also include those that are derived from the genetic material of a virus capable of infecting a eukaryotic cell. Examples include the SV40 enhancer on the late side of the replication origin (bp 100-270), the cytomegalovirus early promoter enhancer, the polyoma enhancer on the late side of the replication origin, and adenovirus enhancers. Additional enhancer sequences that induce activation of eukaryotic gene transcription are disclosed in Yaniv, et al., Nature 297:17 (1982). An enhancer may be spliced into a vector containing a polynucleotide encoding an OTOF protein, for example, at a position 5' or 3' to this gene. In a preferred orientation, the enhancer is positioned at the 5' side of the promoter, which in turn is located 5' relative to the polynucleotide encoding an OTOF protein.

The nucleic acid vectors described herein may include a Woodchuck Posttranscriptional Regulatory Element (WPRE). The WPRE acts at the mRNA level, by promoting nuclear export of transcripts and/or by increasing the efficiency of polyadenylation of the nascent transcript, thus increasing the total amount of mRNA in the cell. The addition of the WPRE to a vector can result in a substantial improvement in the level of transgene expression from several different promoters, both in vitro and in vivo. The WPRE can be located in the second nucleic acid vector between the polynucleotide encoding a C-terminal portion of an OTOF protein and the poly(A) sequence. In the compositions and methods described herein, the WPRE can have the sequence:

(SEQ ID NO: 23)
GATCCAATCAACCTCTGGATTACAAAATTTGTGAAAGATTGACTGGTATTC

TTAACTATGTTGCTCCTTTTACGCTATGTGGATACGCTGCTTTAATGCCTT

TGTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAAC

GTGGCGTGGTGTGCACTGTGTTTGCTGACGCAACCCCCACTGGTTGGGGCA

TTGCCACCACCTGTCAGCTCCTTTCCGGGACTTTCGCTTTCCCCCTCCCTA

TTGCCACGGCGGAACTCATCGCCGCCTGCCTTGCCCGCTGCTGGACAGGGG

CTCGGCTGTTGGGCACTGACAATTCCGTGGTGTTGTCGGGGAAATCATCGT

CCTTTCCTTGGCTGCTCGCCTGTGTTGCCACCTGGATTCTGCGCGGGACGT

CCTTCTGCTACGTCCCTTCGGCCCTCAATCCAGCGGACCTTCCTTCCCGCG

GCCTGCTGCCGGCTCTGCGGCCTCTTCCGCGTCTTCGA.

The WPRE can also have the sequence:

(SEQ ID NO: 61)
AATCAACCTCTGGATTACAAAATTTGTGAAAGATTGACTGGTATTCTTAAC

TATGTTGCTCCTTTTACGCTATGTGGATACGCTGCTTTAATGCCTTTGTAT

CATGCTATTGCTTCCCGTATGGCTTTCATTTTCTCCTCCTTGTATAAATCC

TGGTTAGTTCTTGCCACGGCGGAACTCATCGCCGCCTGCCTTGCCCGCTGC

TGGACAGGGGCTCGGCTGTTGGGCACTGACAATTCCGTGGTGTTTATTTGT

GAAATTTGTGATGCTATTGCTTTATTTGTAACCATCTAGCTTTATTTGTGA

AATTTGTGATGCTATTGCTTTATTTGTAACCATTATAAGCTGCAATAAACA

AGTTAACAACAACAATTGCATTCATTTTATGTTTCAGGTTCAGGGGGAGAT

GTGGGAGGTTTTTTAAA.

In some embodiments, the nucleic acid vectors for use in the compositions and methods described herein include a reporter sequence, which can be useful in verifying OTOF gene expression, for example, in specific cells and tissues (e.g., in cochlear hair cells). Reporter sequences that may be provided in a transgene include DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA), and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer.

Overlapping Dual Vectors

One approach for expressing large proteins in mammalian cells involves the use of overlapping dual vectors. This approach is based on the use of two nucleic acid vectors, each of which contains a portion of a polynucleotide that encodes a protein of interest and has a defined region of sequence overlap with the other polynucleotide. Homologous recombination can occur at the region of overlap and lead to the formation of a single nucleic acid molecule that encodes the full-length protein of interest.

Overlapping dual vectors for use in the methods and compositions described herein contain at least one kilobase (kb) of overlapping sequence (e.g., 1 kb, 1.5 kb, 2 kb, 2.5 kb, 3 kb or more of overlapping sequence). The nucleic acid vectors are designed such that the overlapping region is centered at an OTOF exon boundary, with an equal amount of overlap on either side of the boundary. The boundaries are chosen based on the size of the promoter and the locations of the portions of the polynucleotide that encode OTOF C2 domains. Overlapping regions are centered on exon boundaries that occur outside of the portion of the polynucleotide that encodes the C2C domain (e.g., after the portion of the polynucleotide that encodes the C2C domain). Exon boundaries within the portion of the polynucleotide that encodes the C2D domain can be selected as the center of the overlapping region, or exon boundaries located after the portion of the polynucleotide that encodes the C2D domain and before the portion of the polynucleotide that encodes the C2E domain can serve as the center of an overlapping region. The nucleic acid vectors for use in the methods and compositions described herein are also designed such that approximately half of the OTOF gene is contained within each vector (e.g., each vector contains a polynucleotide that encodes approximately half of the OTOF protein).

One exemplary overlapping dual vector system includes a first nucleic acid vector containing a CAG promoter operably linked to exons 1-28 and the 500 kb immediately 3' of the exon 28/29 boundary of a polynucleotide encoding an OTOF protein (e.g., human OTOF, e.g., SEQ ID NO: 1 or SEQ ID NO: 5, or mouse OTOF, e.g., SEQ ID NO: 6); and a second nucleic acid vector containing the 500 kb immediately 5' of the exon 28/29 boundary and exons 29-48 of a polynucleotide encoding an OTOF protein (e.g., human OTOF, e.g., SEQ ID NO: 1 or SEQ ID NO: 5, or mouse OTOF, e.g., SEQ ID NO: 6) and a poly(A) sequence (e.g., a bovine growth hormone (bGH) poly(A) signal sequence). In this overlapping dual vector system, the overlapping sequence is centered at the exon 28/29 boundary, which is after the portion of the polynucleotide that encodes the C2D domain. Another exemplary overlapping dual vector system includes a first nucleic acid vector containing a CAG promoter operably linked to exons 1-24 and the 500 kb immediately 3' of the exon 24/25 boundary of a polynucleotide encoding an OTOF protein (e.g., human OTOF, e.g., SEQ ID NO: 1 or SEQ ID NO: 5, or mouse OTOF, e.g., SEQ ID NO: 6); and a second nucleic acid vector containing the 500 kb immediately 5' of the exon 24/25 boundary and exons 25-48 of a polynucleotide encoding an OTOF protein (e.g., human OTOF, e.g., SEQ ID NO: 1 or SEQ ID NO: 5, or mouse OTOF, e.g., SEQ ID NO: 6) and a poly(A) sequence (e.g., a bGH poly(A) signal sequence). In this overlapping dual vector system, the overlapping sequence is centered at the exon 24/25 boundary, which is within the portion of the polynucleotide that encodes the C2D domain. The two exon boundaries described above can be used with any promoter that is a similar size to the CAG promoter (e.g., the CMV promoter or smCBA promoter), such as promoters that are 1 kb or shorter (e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter). For example, in either of the foregoing dual vector systems, the CMV promoter or the smCBA promoter, can be used in the place of the CAG promoter. A Myo15 promoter having a sequence that is 1 kb or shorter (e.g., a Myo15 promoter described hereinabove, e.g., a Myo15 promoter having the sequence of any one of SEQ ID NOs: 38, 39, or 49-60) can also be used in place of the CAG promoter. Alternatively, a different exon boundary can be chosen that is within or after the portion of the polynucleotide that encodes the C2D domain and before the portion of the polynucleotide that encodes the C2E domain. The nucleic acid vectors containing promoters of this size can optionally contain OTOF UTRs. For example, in the foregoing overlapping dual vector system in which the overlapping region is centered at the exon 28/29 boundary of OTOF, the second nucleic acid vector can contain the full length OTOF 3' UTR (e.g., the 1035 bp human OTOF 3' UTR in dual vector systems encoding human OTOF, or the 1001 bp mouse OTOF 3' UTR in dual vector systems encoding mouse OTOF). In the foregoing overlapping dual vector system in which the overlapping region is centered at the exon 24/25 boundary of OTOF, neither the first nor the second nucleic acid vector contains an OTOF UTR.

In some embodiments, the first nucleic acid vector in the overlapping dual vector system contains a long promoter (e.g., a promoter that is longer than 1 kb, e.g., 1.1 kb, 1.25 kb, 1.5 kb, 1.75 kb, 2 kb, 2.5 kb, 3 kb or longer). In such overlapping dual vector systems, the overlapping region is centered at an exon boundary that is located after the portion of the polynucleotide that encodes the C2C domain and before the portion of the polynucleotide that encodes the C2D domain. For example, an overlapping dual vector system for use in the methods and compositions described herein includes a first nucleic acid vector containing a Myo15 promoter that is longer than 1 kb (e.g., SEQ ID NO: 36) operably linked exons 1-21 and the 500 kb immediately 3' of the exon 21/22 boundary of a polynucleotide encoding an OTOF protein (e.g., human OTOF, e.g., SEQ ID NO: 1 or SEQ ID NO: 5); and a second nucleic acid vector containing the 500 kb immediately 5' of the exon 21/22 boundary and exons 22-48 of a polynucleotide encoding an OTOF protein (e.g., human OTOF, e.g., SEQ ID NO: 1 or SEQ ID NO: 5) and a poly(A) sequence (e.g., a bGH poly(A) signal sequence). In this overlapping dual vector system, neither the first nor the second nucleic acid vector includes an OTOF UTR. A short promoter (e.g., a CMV promoter, CAG promoter, smCBA promoter, or a Myo15 promoter having a sequence that is 1 kb or shorter, e.g., a Myo15 promoter having the sequence of any one of SEQ ID NOs: 38, 39, or 49-60) can also be used in this dual vector system (e.g., a dual vector system in which the overlapping region is centered at the exon 21/22 boundary). If a short promoter is used, additional elements, such as a 5' OTOF UTR, can be included in the first vector (e.g., the vector containing exons 1-21 and the 500 kb immediately 3' of the exon 21/22 boundary of a polynucleotide encoding an OTOF protein).

Trans-Splicing Dual Vectors

A second approach for expressing large proteins in mammalian cells involves the use of trans-splicing dual vectors. In this approach, two nucleic acid vectors are used that contain distinct nucleic acid sequences, and the polynucleotide encoding the N-terminal portion of the protein of interest and the polynucleotide encoding the C-terminal portion of the protein of interest do not overlap. Instead, the first nucleic acid vector includes a splice donor sequence 3' of the polynucleotide encoding the N-terminal portion of the protein of interest, and the second nucleic acid vector includes a splice acceptor sequence 5' of the polynucleotide encoding the C-terminal portion of the protein of interest. When the first and second nucleic acids are present in the same cell, their ITRs can concatemerize, forming a single nucleic acid structure in which the concatemerized ITRs are positioned between the splice donor and splice acceptor. Trans-splicing then occurs during transcription, producing a nucleic acid molecule in which the polynucleotides encoding the N-terminal and C-terminal portions of the protein of interest are contiguous, thereby forming the full-length coding sequence.

Trans-splicing dual vectors for use in the methods and compositions described herein are designed such that approximately half of the OTOF gene is contained within each vector (e.g., each vector contains a polynucleotide that encodes approximately half of the OTOF protein). The determination of how to split the polynucleotide sequence between the two nucleic acid vectors is made based on the size of the promoter and the locations of the portions of the polynucleotide that encode the OTOF C2 domains. When a short promoter is used in the trans-splicing dual vector system (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter), such as a CAG promoter, a CMV promoter, a smCBA promoter, or a Myo15 promoter having a sequence that is 1 kb or shorter (e.g., a Myo15 promoter described hereinabove, e.g., a Myo15 promoter having the sequence of any one of SEQ ID NOs: 38, 39, or 49-60) the OTOF polynucleotide sequence is divided between the two nucleic acid vectors at an exon boundary that occurs after the portion of the polynucleotide that encodes the C2D domain and before the portion of the polynucleotide that encodes the C2E domain, for example, the exon 26/27 boundary. The nucleic acid vectors containing promoters of this size can optionally contain OTOF UTRs (e.g., both the 5' and 3' OTOF UTRs, e.g., full-length UTRs). When a long promoter is used in the trans-splicing dual vector system (e.g., a promoter that is longer than 1 kb, e.g., 1.1 kb, 1.25 kb, 1.5 kb, 1.75 kb, 2 kb, 2.5 kb, 3 kb or longer), such as a Myo15 promoter that is longer than 1 kb (e.g., SEQ ID NO: 36), the OTOF polynucleotide sequence will be divided between the two nucleic acid vectors at an exon boundary that occurs after the portion of the polynucleotide that encodes the C2C domain, and either before the portion of the polynucleotide that encodes the C2D domain, such as the exon 19/20 boundary, or within the portion of the polynucleotide that encodes the C2D domain, such as the exon 25/26 boundary. A short promoter (e.g., a CMV promoter, smCBA promoter, CAG promoter, or a Myo15 promoter having a sequence that is 1 kb or shorter, e.g., a Myo15 promoter having the sequence of any one of SEQ ID NOs: 38, 39, or 49-60) can also be used in the dual vector systems designed for large promoters, in which case additional elements (e.g., OTOF UTR sequences) may be included in the first vector (e.g., the vector containing the portion of the polynucleotide the encodes the C2C domain).

One exemplary trans-splicing dual vector system that uses a short promoter includes a first nucleic acid vector containing a CAG promoter operably linked to exons 1-26 of a polynucleotide encoding an OTOF protein (e.g., human OTOF, e.g., SEQ ID NO: 1 or SEQ ID NO: 5) and a splice donor sequence 3' of the polynucleotide sequence; and a second nucleic acid vector containing a splice acceptor sequence 5' of exons 27-48 of a polynucleotide encoding an OTOF protein (e.g., human OTOF, e.g., SEQ ID NO: 1 or SEQ ID NO: 5) and a poly(A) sequence (e.g., a bGH poly(A) signal sequence). An alternative trans-splicing dual vector system includes a first nucleic acid vector containing a CAG promoter operably linked to exons 1-28 of a polynucleotide encoding an OTOF protein (e.g., mouse OTOF, e.g., SEQ ID NO: 6) and a splice donor sequence 3' of the polynucleotide sequence; and a second nucleic acid vector containing a splice acceptor sequence 5' of exons 29-48 of a polynucleotide encoding an OTOF protein (e.g., mouse OTOF, e.g., SEQ ID NO: 6) and a poly(A) sequence (e.g., a bGH poly(A) signal sequence). The CMV promoter, smCBA promoter, or a Myo15 promoter having a sequence that is 1 kb or shorter (e.g., a Myo15 promoter described hereinabove, e.g., a Myo15 promoter having the sequence of any one of SEQ ID NOs: 38, 39, or 49-60) can be used in place of the CAG promoter either of the foregoing dual vector systems. These nucleic acid vectors can also contain full length 5' and 3' OTOF UTRs in the first and second nucleic acid vectors, respectively (e.g., the first nucleic acid vector can contain the 5' human OTOF UTR (127 bp) in dual vector systems encoding human OTOF, or the 5' mouse UTR (134 bp) in dual vector systems encoding mouse OTOF; and the second nucleic acid vector can contain the 3' human OTOF UTR (1035 bp) in dual vector systems encoding human OTOF, or the 3' mouse OTOF UTR (1001 bp) in dual vector systems encoding mouse OTOF).

An exemplary trans-splicing dual vector system that uses a long promoter includes a first nucleic acid vector containing a Myo15 promoter that is longer than 1 kb (e.g., SEQ ID NO: 36) operably linked to exons 1-19 of a polynucleotide encoding an OTOF protein (e.g., human OTOF, e.g., SEQ ID NO: 1 or SEQ ID NO: 5) and a splice donor sequence 3' of the polynucleotide sequence; and a second nucleic acid vector containing a splice acceptor sequence 5' of exons 20-48 of a polynucleotide encoding an OTOF protein (e.g., human OTOF, e.g., SEQ ID NO: 1 or SEQ ID NO: 5) and a poly(A) sequence (e.g., a bGH poly(A) signal sequence). Alternatively, the trans-splicing dual vector system can include a first nucleic acid vector containing a Myo15 promoter that is longer than 1 kb (e.g., SEQ ID NO: 36) operably linked to exons 1-20 of a polynucleotide encoding an OTOF protein (e.g., mouse OTOF, e.g., SEQ ID NO: 6) and a splice donor sequence 3' of the polynucleotide sequence; and a second nucleic acid vector containing a splice acceptor sequence 5' of exons 21-48 of a polynucleotide encoding an OTOF protein (e.g., mouse OTOF, e.g., SEQ ID NO: 6) and a poly(A) sequence (e.g., a bGH poly(A) signal sequence). Neither the first nor the second nucleic acid vector in either of the foregoing Myo15 promoter trans-splicing dual vector systems contains an OTOF UTR. A short promoter (e.g., a CMV promoter, smCBA promoter, CAG promoter, or a Myo15 promoter having a sequence that is 1 kb or shorter, e.g., a Myo15 promoter having the sequence of any one of SEQ ID NOs: 38, 39, or 49-60) can also be used in the foregoing dual vector systems designed for large promoters. If these dual vector systems contain a short promoter, they may also include a 5' OTOF UTR in the first vector.

To accommodate an OTOF UTR, the OTOF coding sequence can be divided in a different position. For example, in a trans-splicing dual vector system in which the first nucleic acid vector contains a Myo15 promoter that is longer than 1 kb (e.g., SEQ ID NO: 36) operably linked to exons 1-25 of a polynucleotide encoding an OTOF protein (e.g., human OTOF, e.g., SEQ ID NO: 1 or SEQ ID NO: 5) and a splice donor sequence 3' of the polynucleotide sequence; and the second nucleic acid vector contains a splice acceptor sequence 5' of exons 26-48 of a polynucleotide encoding an OTOF protein (e.g., human OTOF, e.g., SEQ ID NO: 1 or SEQ ID NO: 5) and a poly(A) sequence (e.g., a bGH poly(A) signal sequence), the second nucleic acid can also contain a full length OTOF 3' UTR (e.g., the 1035 bp human OTOF 3' UTR). For mouse OTOF, the trans-splicing dual vector system can contain a 3' UTR if the first nucleic acid vector contains a Myo15 promoter that is longer than 1 kb (e.g., SEQ ID NO: 36) operably linked to exons 1-24 of a polynucleotide encoding an OTOF protein (e.g., mouse OTOF, e.g., SEQ ID NO: 6) and a splice donor sequence 3' of the polynucleotide sequence; and the second nucleic acid vector contains a splice acceptor sequence 5' of exons 25-48 of a polynucleotide encoding an OTOF protein (e.g., mouse OTOF, e.g., SEQ ID NO: 6) and a poly(A) sequence (e.g., a bGH poly(A) signal sequence). In this dual vector system, the second nucleic acid can also contain a full length OTOF 3' UTR (e.g., the 1001 bp mouse OTOF 3' UTR). A short promoter (e.g., a CMV promoter, smCBA promoter, CAG promoter, or a Myo15 promoter having a sequence that is 1 kb or shorter, e.g., a Myo15 promoter having the sequence of any one of SEQ ID NOs: 38, 39, or 49-60) can also be used in the foregoing dual vector systems designed for large promoters. If these dual vector systems contain a short promoter, they may also include a 5' OTOF UTR in the first vector.

Dual Hybrid Vectors

A third approach for expressing large proteins in mammalian cells involves the use of dual hybrid vectors. This approach combines elements of the overlapping dual vector strategy and the trans-splicing strategy in that it features both an overlapping region at which homologous recombination can occur and splice donor and splice acceptor sequences. In dual hybrid vector systems, the overlapping region is a recombinogenic region that is contained in both the first and second nucleic acid vectors, rather than a portion of the polynucleotide sequence encoding the protein of interest—the polynucleotide encoding the N-terminal portion of the protein of interest and the polynucleotide encoding the C-terminal portion of the protein of interest do not overlap in this approach. The recombinogenic region is 3' of the splice donor sequence in the first nucleic acid vector and 5' of the splice acceptor sequence in the second nucleic acid sequence. The first and second nucleic acid sequences can then join to form a single sequence based on one of two mechanisms: 1) recombination at the overlapping region, or 2) concatemerization of the ITRs. The remaining recombinogenic region(s) and/or the concatemerized ITRs can be removed by splicing, leading to the formation of a contiguous polynucleotide sequence that encodes the full-length protein of interest.

Recombinogenic regions that can be used in the compositions and methods described herein include the F1 phage AK gene having a sequence of: GGGATTTTGCCGATTTCGGCCTATTGGTTAA AAAATGAGCTGATTTAACAAAAATTTAACGCGAATTTTAACAAAAT (SEQ ID NO: 19) and alkaline phosphatase (AP) gene fragments as described in U.S. Pat. No. 8,236,557, which are incorporated herein by reference. In some embodiments, the AP gene fragment has the sequence of:

(SEQ ID NO: 62)
CCCCGGGTGCGCGGCGTCGGTGGTGCCGGCGGGGGGCGCCAGGTCGCAGGC

GGTGTAGGGCTCCAGGCAGGCGGCGAAGGCCATGACGTGCGCTATGAAGGT

CTGCTCCTGCACGCCGTGAACCAGGTGCGCCTGCGGGCCGCGCGCGAACAC

CGCCACGTCCTCGCCTGCGTGGGTCTCTTCGTCCAGGGGCACTGCTGACTG

CTGCCGATACTCGGGGCTCCCGCTCTCGCTCTCGGTAACATCCGGCCGGGC

GCCGTCCTTGAGCACATAGCCTGGACCGTTTCCGTATAGGAGGACCGTGTA

GGCCTTCCTGTCCCGGGCCTTGCCAGCGGCCAGCCCGATGAAGGAGCTCCC

TCGCAGGGGTAGCCTCCGAAGGAGAAGACGTGGGAGTGGTCGGCAGTGAC

GAGGCTCAGCGTGTCCTCCTCGCTGGTGAGCTGGCCCGCCCTCTCAATGGC

GTCGTCGAACATGATCGTCTCAGTCAGTGCCCGGTAAGCCCTGCTTTCATG

ATGACCATGGTCGATGCGACCACCCTCCACGAAGAGGAAGAAGCCGCGGGG

GTGTCTGCTCAGCAGGCGCAGGGCAGCCTCTGTCATCTCCATCAGGGAGGG

GTCCAGTGTGGAGTCTCGGTGGATCTCGTATTTCATGTCTCCAGGCTCAAA

GAGACCCATGAGATGGGTCACAGACGGGTCCAGGGAAGCCTGCATGAGCTC

AGTGCGGTTCCACACGTACCGGGCACCCTGGCGTTCGCCGAGCCATTCCTG

CACCAGATTCTTCCCGTCCAGCCTGGTCCCACCTTGGCTGTAGTCATCTGG

GTACTCAGGGTCTGGGGTTCCCATGCGAAACATGTACTTTCGGCCTCCA.

In some embodiments, the AP gene fragment has the sequence of:

(SEQ ID NO: 63)
CCCCGGGTGCGCGGCGTCGGTGGTGCCGGCGGGGGGCGCCAGGTCGCAGGC

GGTGTAGGGCTCCAGGCAGGCGGCGAAGGCCATGACGTGCGCTATGAAGGT

CTGCTCCTGCACGCCGTGAACCAGGTGCGCCTGCGGGCCGCGCGCGAACAC

CGCCACGTCCTCGCCTGCGTGGGTCTCTTCGTCCAGGGGCACTGCTGACTG

CTGCCGATACTCGGGGCTCCCGCTCTCGCTCTCGGTAACATCCGGCCGGGC

GCCGTCCTTGAGCACATAGCCTGGACCGTTTCCGTATAGGAGGACCGTGTA

GGCCTTCCTGTCCCGGGCCTTGCCAGCGGCCAGCCCGATGAAGGAGCTCCC

TCGCAGGGGTAGCCTCCGAAGGAGAAGACGTGGGAGTGGTCGGCAGTGAC

GAGGCTCAGCGTGTCCTCCTCG CTGGTGA.

In some embodiments, the AP gene fragment has the sequence of:

(SEQ ID NO: 64)
GCTGGCCCGCCCTCTCAATGGCGTCGTCGAACATGATCGTCTCAGTCAGTG

CCCGGTAAGCCCTGCTTTCATGATGACCATGGTCGATGCGACCACCCTCCA

CGAAGAGGAAGAAGCCGCGGGGGTGTCTGCTCAGCAGGCGCAGGGCAGCCT

CTGTCATCTCCATCAGGGAGGGGTCCAGTGTGGAGTCTCGGTGGATCTCGT

ATTTCATGTCTCCAGGCTCAAAGAGACCCATGAGATGGGTCACAGACGGGT

CCAGGGAAGCCTGCATGAGCTCAGTGCGGTTCCACACGTACCGGGCACCCT

GGCGTTCGCCGAGCCATTCCTGCACCAGATTCTTCCCGTCCAGCCTGGTCC

CACCTTGGCTGTAGTCATCTGGGTACTCAGGGTCTGGGGTTCCCATGCGAA

ACATGTACTTTCGGCCTCCA.

In some embodiments, the AP gene fragment has the sequence of:

(SEQ ID NO: 65)
CCCCGGGTGCGCGGCGTCGGTGGTGCCGGCGGGGGGCGCCAGGTCGCAGGC

GGTGTAGGGCTCCAGGCAGGCGGCGAAGGCCATGACGTGCGCTATGAAGGT

CTGCTCCTGCACGCCGTGAACCAGGTGCGCCTGCGGGCCGCGCGCGAACAC

CGCCACGTCCTCGCCTGCGTGGGTCTCTTCGTCCAGGGGCACTGCTGACTG

CTGCCGATACTCGGGGCTCCCGCTCTCGCTCTCGGTAACATCCGGCCGGGC

GCCGTCCTTGAGCACATAGCCTGGACCGTTTC

In some embodiments, the AP gene fragment has the sequence of:

(SEQ ID NO: 66)
CGTATAGGAGGACCGTGTAGGCCTTCCTGTCCCGGGCCTTGCCAGCGGCCA

GCCCGATGAAGGAGCTCCCTCGCAGGGGGTAGCCTCCGAAGGAGAAGACGT

GGGAGTGGTCGGCAGTGACGAGGCTCAGCGTGTCCTCCTCGCTGGTGAGCT

GGCCCGCCCTCTCAATGGCGTCGTCGAACATGATCGTCTCAGTCAGTGCCC

GGTAAGCCCTGCTTTCATGATGACCATGGTCGATGCGACCACCCTCCACGA

AGAGGAAGAAGCCGCGGGGGTGTCTGCTCAGCAGG.

In some embodiments, the AP gene fragment has the sequence of:

(SEQ ID NO: 67)
CGCAGGGCAGCCTCTGTCATCTCCATCAGGGAGGGGTCCAGTGTGGAGTCT

CGGTGGATCTCGTATTTCATGTCTCCAGGCTCAAAGAGACCCATGAGATGG

GTCACAGACGGGTCCAGGGAAGCCTGCATGAGCTCAGTGCGGTTCCACACG

TACCGGGCACCCTGGCGTTCGCCGAGCCATTCCTGCACCAGATTCTTCCCG

TCCAGCCTGGTCCCACCTTGGCTGTAGTCATCTGGGTACTCAGGGTCTGGG

GTTCCCATGCGAAACATGTACTTTCGGCCTCCA.

An exemplary splice donor sequence for use in the methods and compositions described herein (e.g., in trans-splicing and dual hybrid approaches) has the sequence: GTAAGTATCAAGGTTACAAGAC AGGTTTAAGGAGACCAATAGAAACTGGGCTTGTCGAGACAGAGAAGACTCTTGCGTTTCT (SEQ ID NO: 20). An exemplary splice acceptor sequence for use in the methods and compositions described herein (e.g., in trans-splicing and dual hybrid approaches) has the sequence: GATAGGCACCTATTGG TCTTACTGACATCCACTTTGCCTTTCTCTCCACAG (SEQ ID NO: 21). The splice donor sequence GTAAGTATCAAGGTTACAAGACAGGTTTAAGGA- GACCAATAGAAACTGGGCTTGTCGAGACAGAAGACTCTTGCGTTTCTGA (SEQ ID NO: 68) and the splice acceptor sequence TAGGCACCTATTGGTCTTACTGACATCCACTTTGCCTTTCTCTCCACAG (SEQ ID NO: 69) can also be used in the methods and compositions described herein. Additional examples of splice donor and splice acceptor sequences are known in the art.

Dual hybrid vectors for use in the methods and compositions described herein are designed such that approximately half of the OTOF gene is contained within each vector (e.g., each vector contains a polynucleotide that encodes approximately half of the OTOF protein). The determination of how to split the polynucleotide sequence between the two nucleic acid vectors is made based on the size of the promoter and the locations of the portions of the polynucleotide that encode the OTOF C2 domains. When a short promoter is used in the dual hybrid vector system (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter), such as CAG, CMV, smCBA, or a Myo15 promoter having a sequence that is 1 kb or shorter (e.g., a Myo15 promoter described hereinabove, e.g., a Myo15 promoter having the sequence of any one of SEQ ID NOs: 38, 39, or 49-60), the OTOF polynucleotide sequence is divided between the two nucleic acid vectors at an exon boundary that occurs after the portion of the polynucleotide that encodes the C2D domain and before the portion of the polynucleotide that encodes C2E domain, for example, the exon 26/27 boundary. The nucleic acid vectors containing promoters of this size can optionally contain OTOF UTRs (e.g., full-length 5' and 3' UTRs). When a long promoter is used in the dual hybrid vector system (e.g., a promoter that is longer than 1 kb, e.g., 1.1 kb, 1.25 kb, 1.5 kb, 1.75 kb, 2 kb, 2.5 kb, 3 kb or longer), such as a Myo15 promoter that is longer than 1 kb (e.g., SEQ ID NO: 36), the OTOF polynucleotide sequence will be divided between the two nucleic acid vectors at an exon boundary that occurs after the portion of the polynucleotide that encodes the C2C domain, and either before the portion of the polynucleotide that encodes the C2D domain, such as the exon 19/20 boundary, or within the portion of the polynucleotide that encodes the C2D domain, such as the exon 25/26 boundary. A short promoter (e.g., a CMV promoter, CAG promoter, smCBA promoter, or a Myo15 promoter having a sequence that is 1 kb or shorter, e.g., a Myo15 promoter having the sequence of any one of SEQ ID NOs: 38, 39, or 49-60) can also be used in the dual vector systems designed for large promoters, in which case additional elements (e.g., OTOF UTR sequences) may be included in the first vector (e.g., the vector containing the portion of the polynucleotide the encodes the C2C domain).

One exemplary dual hybrid vector system that uses a short promoter includes a first nucleic acid vector containing a CAG promoter operably linked to exons 1-26 of a polynucleotide encoding an OTOF protein (e.g., human OTOF, e.g., SEQ ID NO: 1 or SEQ ID NO: 5), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 27-48 of a polynucleotide encoding an OTOF protein (e.g., human OTOF, e.g., SEQ ID NO: 1 or SEQ ID NO: 5), and a poly(A) sequence (e.g., a bGH poly(A) signal sequence). The first and second nucleic acid vectors can also contain the full length 5' and 3' OTOF UTRs, respectively (e.g., the 127 bp human OTOF 5' UTR can be included in the first nucleic acid vector, and the 1035 bp human OTOF 3' UTR can be included in the second nucleic acid vector). Another exemplary dual hybrid vector system that uses a short promoter includes a first nucleic acid vector containing a CAG promoter operably linked to exons 1-28 of a polynucleotide encoding an OTOF protein (e.g., mouse OTOF, e.g., SEQ ID NO: 6), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 29-48 of a polynucleotide encoding an OTOF protein (e.g., mouse OTOF, e.g., SEQ ID NO: 6), and a poly(A) sequence (e.g., a bGH poly(A) signal sequence). The first and second nucleic acid vectors can also contain the full length 5' and 3' OTOF UTRs, respectively (e.g., the 134 bp mouse OTOF 5' UTR can be included in the first nucleic acid vector, and the 1001 bp mouse OTOF 3' UTR can be included in the second nucleic acid vector). The CMV promoter, smCBA promoter, or a Myo15 promoter having a sequence that is 1 kb or shorter (e.g., a Myo15 promoter described hereinabove, e.g., a Myo15 promoter having the sequence of any one of SEQ ID NOs: 38, 39, or 49-60) can be used in place of the CAG promoter either of the foregoing dual vector systems.

An exemplary dual hybrid vector system that uses a long promoter includes a first nucleic acid vector containing a Myo15 promoter that is longer than 1 kb (e.g., SEQ ID NO: 36) operably linked to exons 1-19 of a polynucleotide encoding an OTOF protein (e.g., human OTOF, e.g., SEQ ID NO: 1 or SEQ ID NO: 5), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 20-48 of a polynucleotide encoding an OTOF protein (e.g., human OTOF, e.g., SEQ ID NO: 1 or SEQ ID NO: 5), and a poly(A) sequence (e.g., a bGH poly(A) signal sequence). Another exemplary dual hybrid vector system that uses a long promoter includes a first nucleic acid vector containing a Myo15 promoter that is longer than 1 kb (e.g., SEQ ID NO: 36) operably linked to exons 1-20 of a polynucleotide encoding an OTOF protein (e.g., mouse OTOF, e.g., SEQ ID NO: 6), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 21-48 of a polynucleotide encoding an OTOF protein (e.g., mouse OTOF, e.g., SEQ ID NO: 6), and a poly(A) sequence (e.g., a bGH poly(A) signal sequence). Neither the first nor the second nucleic acid vector in either of the foregoing Myo15 promoter dual hybrid vector systems contains an OTOF UTR. A short promoter (e.g., a CMV promoter, smCBA promoter, CAG promoter, or a Myo15 promoter having a sequence that is 1 kb or shorter, e.g., a Myo15 promoter having the sequence of any one of SEQ ID NOs: 38, 39, or 49-60) can also be used in the foregoing dual vector systems designed for large promoters. If these dual vector systems contain a short promoter, they may also include a 5' OTOF UTR in the first vector.

To accommodate an OTOF UTR, the OTOF coding sequence can be divided in a different position. For example, in a dual hybrid vector system in which the first nucleic acid vector contains a Myo15 promoter that is longer than 1 kb (e.g., SEQ ID NO: 36) operably linked to exons 1-25 of a polynucleotide encoding an OTOF protein (e.g., human OTOF, e.g., SEQ ID NO: 1 or SEQ ID NO: 5), a splice donor sequence 3' of the polynucleotide sequence, and a recombinogenic region 3' of the splice donor sequence; and the second nucleic acid vector contains a recombinogenic region, a splice acceptor sequence 3' of the recombinogenic region, a polynucleotide 3' of the splice acceptor sequence that contains exons 26-48 of a polynucleotide encoding an OTOF protein (e.g., human OTOF, e.g., SEQ ID NO: 1 or SEQ ID NO: 5), and a poly(A) sequence (e.g., a bGH poly(A) signal sequence), the second nucleic acid can also contain a full-length OTOF 3' UTR (e.g., the 1035 bp human OTOF UTR). For mouse OTOF, the dual hybrid vector system can contain a 3' UTR if the first nucleic acid vector contains a Myo15 promoter that is longer than 1 kb (e.g., SEQ ID NO: 36) operably linked to exons 1-24 of a polynucleotide encoding an OTOF protein (e.g., mouse OTOF, e.g., SEQ ID NO: 6), a splice donor sequence 3' of the polynucleotide sequence, and a recombinogenic region 3' of the splice donor sequence; and the second nucleic acid vector contains a recombinogenic region, a splice acceptor sequence 3' of the recombinogenic region, a polynucleotide 3' of the splice acceptor sequence that contains exons 25-48 of a polynucleotide encoding an OTOF protein (e.g., human OTOF, e.g., SEQ ID NO: 1 or SEQ ID NO: 5), and a poly(A) sequence (e.g., a bGH poly(A) signal sequence). In this dual hybrid vector system, the second nucleic acid can also contain a full-length OTOF 3' UTR (e.g., the 1001 bp mouse OTOF UTR). A short promoter (e.g., a CMV promoter, smCBA promoter, CAG promoter, or a Myo15 promoter having a sequence that is 1 kb or shorter, e.g., a Myo15 promoter having the sequence of any one of SEQ ID NOs: 38, 39, or 49-60) can also be used in the foregoing dual vector systems designed for large promoters. If these dual vector systems contain a short promoter, they may also include a 5' OTOF UTR in the first vector.

The dual hybrid vectors used in the methods and compositions described herein can optionally include a degradation signal sequence in both the first and second nucleic acid vectors. The degradation signal sequence can be included to prevent or reduce the expression of portions of the OTOF protein from polynucleotides that failed to recombine and/or undergo splicing. The degradation signal sequence is positioned 3' of the recombinogenic region in the first nucleic acid vector, and is positioned between the recombinogenic region and the splice acceptor in the second nucleic acid vector. A degradation signal sequence that can be used in the compositions and methods described herein has the sequence of:

(SEQ ID NO: 22)
GCCTGCAAGAACTGGTTCAGCAGCCTGAGCCACTTCGTGATCCACCTG.

Exemplary pairs of overlapping, trans-splicing, and dual hybrid vectors are described in Table 4 below.

TABLE 4

Exemplary pairs of overlapping, trans-splicing, and hybrid dual vectors for use in the methods and compositions described herein

| Vector Pair Number | Vector Type | Vector Pair |
|---|---|---|
| 1 | Overlapping | First nucleic acid vector contains: CAG promoter operably linked to exons 1-24 and the 500 kb 3' of the exon 24/25 boundary of a polynucleotide encoding a human OTOF protein<br>Second nucleic acid vector contains: the 500 kb 5' of the exon 24/25 boundary and exons 25-48 of a polynucleotide encoding a human OTOF protein and a bGH poly(A) sequence |
| 2 | Overlapping | First nucleic acid vector contains: CAG promoter operably linked to exons 1-28 and the 500 kb 3' of the exon 28/29 boundary of a polynucleotide encoding a human OTOF protein<br>Second nucleic acid vector contains: the 500 kb 5' of the exon 28/29 boundary and exons 29-48 of a polynucleotide encoding a human OTOF protein and a bGH poly(A) sequence |
| 3 | Overlapping | First nucleic acid vector contains: Myo15 promoter operably linked to exons 1-21 and the 500 kb 3' of the exon 21/22 boundary of a polynucleotide encoding a human OTOF protein<br>Second nucleic acid vector contains: the 500 kb 5' of the exon 21/22 boundary and exons 22-48 of a polynucleotide encoding a human OTOF protein and a bGH poly(A) sequence |
| 4 | Trans-splicing | First nucleic acid vector contains: CAG promoter operably linked to exons 1-26 of a polynucleotide encoding a human OTOF protein and a splice donor sequence 3' of the polynucleotide<br>Second nucleic acid vector contains: a splice acceptor sequence 5' of exons 27-48 of a polynucleotide encoding a human OTOF protein and a bGH poly(A) sequence |
| 5 | Trans-splicing | First nucleic acid vector contains: Myo15 promoter operably linked to exons 1-19 of a polynucleotide encoding a human OTOF protein and a splice donor sequence 3' of the polynucleotide<br>Second nucleic acid vector contains: a splice acceptor sequence 5' of exons 20-48 of a polynucleotide encoding a human OTOF protein and a bGH poly(A) sequence |
| 6 | Trans-splicing | First nucleic acid vector contains: Myo15 promoter operably linked to exons 1-25 of a polynucleotide encoding a human OTOF protein and a splice donor sequence 3' of the polynucleotide<br>Second nucleic acid vector contains: a splice acceptor sequence 5' of exons 26-48 of a polynucleotide encoding a human OTOF protein and a bGH poly(A) sequence |

TABLE 4-continued

Exemplary pairs of overlapping, trans-splicing, and hybrid dual vectors for use in the methods and compositions described herein

| Vector Pair Number | Vector Type | Vector Pair |
|---|---|---|
| 7 | Hybrid | First nucleic acid vector contains: CAG promoter operably linked to exons 1-26 of a polynucleotide encoding a human OTOF protein, a splice donor sequence 3' of the polynucleotide, and a recombinogenic region 3' of the splice donor sequence<br>Second nucleic acid vector contains: a recombinogenic region, a splice acceptor sequence 3' of the recombinogenic region, exons 27-48 of a polynucleotide encoding a human OTOF protein 3' of the splice acceptor sequence, and a bGH poly(A) sequence |
| 8 | Hybrid | First nucleic acid vector contains: Myo15 promoter operably linked to exons 1-19 of a polynucleotide encoding a human OTOF protein, a splice donor sequence 3' of the polynucleotide, and a recombinogenic region 3' of the splice donor sequence<br>Second nucleic acid vector contains: a recombinogenic region, a splice acceptor sequence 3' of the recombinogenic region, exons 20-48 of a polynucleotide encoding a human OTOF protein 3' of the splice acceptor sequence, and a bGH poly(A) sequence |
| 9 | Hybrid | First nucleic acid vector contains: Myo15 promoter operably linked to exons 1-25 of a polynucleotide encoding a human OTOF protein, a splice donor sequence 3' of the polynucleotide, and a recombinogenic region 3' of the splice donor sequence<br>Second nucleic acid vector contains: a recombinogenic region, a splice acceptor sequence 3' of the recombinogenic region, exons 26-48 of a polynucleotide encoding a human OTOF protein 3' of the splice acceptor sequence, and a bGH poly(A) sequence |

Vectors for the Expression of OTOF

In addition to achieving high rates of transcription and translation, stable expression of an exogenous gene in a mammalian cell can be achieved by integration of the polynucleotide containing the gene into the nuclear genome of the mammalian cell. A variety of vectors for the delivery and integration of polynucleotides encoding exogenous proteins into the nuclear DNA of a mammalian cell have been developed. Examples of expression vectors are disclosed in, e.g., WO 1994/011026 and are incorporated herein by reference. Expression vectors for use in the compositions and methods described herein contain a polynucleotide sequence that encodes a portion of OTOF, as well as, e.g., additional sequence elements used for the expression of these agents and/or the integration of these polynucleotide sequences into the genome of a mammalian cell. Certain vectors that can be used for the expression of OTOF include plasmids that contain regulatory sequences, such as promoter and enhancer regions, which direct gene transcription. Other useful vectors for expression of OTOF contain polynucleotide sequences that enhance the rate of translation of these genes or improve the stability or nuclear export of the mRNA that results from gene transcription. These sequence elements include, e.g., 5' and 3' untranslated regions and a polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

AAV Vectors for Nucleic Acid Delivery

In some embodiments, nucleic acids of the compositions and methods described herein are incorporated into recombinant AAV (rAAV) vectors and/or virions in order to facilitate their introduction into a cell. rAAV vectors useful in the compositions and methods described herein are recombinant nucleic acid constructs that include (1) a heterologous sequence to be expressed (e.g., a polynucleotide encoding an N-terminal or C-terminal portion of an OTOF protein) and (2) viral sequences that facilitate stability and expression of the heterologous genes. The viral sequences may include those sequences of AAV that are required in cis for replication and packaging (e.g., functional ITRs) of the DNA into a virion. Such rAAV vectors may also contain marker or reporter genes. Useful rAAV vectors have one or more of the AAV WT genes deleted in whole or in part but retain functional flanking ITR sequences. The AAV ITRs may be of any serotype suitable for a particular application. For use in the methods and compositions described herein, the ITRs can be AAV2 ITRs. Methods for using rAAV vectors are described, for example, in Tal et al., J. Biomed. Sci. 7:279 (2000), and Monahan and Samulski, Gene Delivery 7:24 (2000), the disclosures of each of which are incorporated herein by reference as they pertain to AAV vectors for gene delivery.

The nucleic acids and vectors described herein can be incorporated into a rAAV virion in order to facilitate introduction of the nucleic acid or vector into a cell. The capsid proteins of AAV compose the exterior, non-nucleic acid portion of the virion and are encoded by the AAV cap gene. The cap gene encodes three viral coat proteins, VP1, VP2 and VP3, which are required for virion assembly. The construction of rAAV virions has been described, for instance, in U.S. Pat. Nos. 5,173,414; 5,139,941; 5,863,541; 5,869,305; 6,057,152; and 6,376,237; as well as in Rabinowitz et al., J. Virol. 76:791 (2002) and Bowles et al., J. Virol. 77:423 (2003), the disclosures of each of which are incorporated herein by reference as they pertain to AAV vectors for gene delivery.

rAAV virions useful in conjunction with the compositions and methods described herein include those derived from a variety of AAV serotypes including AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S. For targeting cochlear hair cells, AAV1, AAV2, AAV6, AAV9, Anc80, Anc80L65, DJ/9, 7m8, and PHP.B may be particularly useful. Serotypes evolved for transduction of the retina may also be used in the methods and compositions described herein. The first and second nucleic acid vectors in the compositions and methods described herein may have the same serotype or different serotypes. Construction and use of AAV vectors and AAV proteins of different serotypes are described, for instance, in Chao et al., Mol. Ther. 2:619 (2000); Davidson et al., Proc. Nati. Acad. Sci. USA 97:3428 (2000); Xiao et al., J. Virol. 72:2224 (1998); Halbert et al., J. Virol. 74:1524 (2000); Halbert et al., J. Virol. 75:6615 (2001); and Auricchio et al., Hum. Molec. Genet. 10:3075 (2001), the disclosures of each of which are incorporated herein by reference as they pertain to AAV vectors for gene delivery.

Also useful in conjunction with the compositions and methods described herein are pseudotyped rAAV vectors. Pseudotyped vectors include AAV vectors of a given serotype (e.g., AAV9) pseudotyped with a capsid gene derived from a serotype other than the given serotype (e.g., AAV1, AAV2, AAV3, AAV4, AAV5, AAV6, AAV7, AAV8, etc.). Techniques involving the construction and use of pseudotyped rAAV virions are known in the art and are described, for instance, in Duan et al., J. Virol. 75:7662 (2001); Halbert et al., J. Virol. 74:1524 (2000); Zolotukhin et al., Methods, 28:158 (2002); and Auricchio et al., Hum. Molec. Genet. 10:3075 (2001).

AAV virions that have mutations within the virion capsid may be used to infect particular cell types more effectively than non-mutated capsid virions. For example, suitable AAV mutants may have ligand insertion mutations for the facilitation of targeting AAV to specific cell types. The construction and characterization of AAV capsid mutants including insertion mutants, alanine screening mutants, and epitope tag mutants is described in Wu et al., J. Virol. 74:8635 (2000). Other rAAV virions that can be used in methods described herein include those capsid hybrids that are generated by molecular breeding of viruses as well as by exon shuffling. See, e.g., Soong et al., Nat. Genet., 25:436 (2000) and Kolman and Stemmer, Nat. Biotechnol. 19:423 (2001).

Pharmaceutical Compositions

The nucleic acid vectors described herein may be incorporated into a vehicle for administration into a patient, such as a human patient suffering from sensorineural hearing loss or auditory neuropathy, as described herein. Pharmaceutical compositions containing vectors, such as viral vectors, that contain a polynucleotide encoding a portion of an OTOF protein can be prepared using methods known in the art. For example, such compositions can be prepared using, e.g., physiologically acceptable carriers, excipients or stabilizers (Remington's Pharmaceutical Sciences 16th edition, Osol, A. Ed. (1980); incorporated herein by reference), and in a desired form, e.g., in the form of lyophilized formulations or aqueous solutions.

Mixtures of the nucleic acid vectors (e.g., viral vectors) described herein may be prepared in water suitably mixed with one or more excipients, carriers, or diluents. Dispersions may also be prepared in glycerol, liquid polyethylene glycols, and mixtures thereof and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (described in U.S. Pat. No. 5,466, 468, the disclosure of which is incorporated herein by reference). In any case the formulation may be sterile and may be fluid to the extent that easy syringability exists. Formulations may be stable under the conditions of manufacture and storage and may be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For example, a solution containing a pharmaceutical composition described herein may be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated. For local administration to the inner ear, the composition may be formulated to contain a synthetic perilymph solution. An exemplary synthetic perilymph solution includes 20-200 mM NaCl, 1-5 mM KCl, 0.1-10 mM $CaCl_2$, 1-10 mM glucose, and 2-50 mM HEPEs, with a pH between about 6 and 9 and an osmolality of about 300 mOsm/kg. The person responsible for administration will, in any event, determine the appropriate dose for the individual subject. Moreover, for human administration, preparations may meet sterility, pyrogenicity, general safety, and purity standards as required by FDA Office of Biologics standards.

Methods of Treatment

The compositions described herein may be administered to a subject with sensorineural hearing loss or auditory neuropathy by a variety of routes, such as local administration to the inner ear (e.g., administration into the perilymph or endolymph, e.g., through the oval window, round window, or horizontal canal, e.g., administration to a cochlear hair cell), intravenous, parenteral, intradermal, transdermal, intramuscular, intranasal, subcutaneous, percutaneous, intratracheal, intraperitoneal, intraarterial, intravascular, inhalation, perfusion, lavage, and oral administration. The most suitable route for administration in any given case will depend on the particular composition administered, the patient, pharmaceutical formulation methods, administration methods (e.g., administration time and administration route), the patient's age, body weight, sex, severity of the disease being treated, the patient's diet, and the patient's excretion rate. Compositions may be administered once, or more than once (e.g., once annually, twice annually, three times annually, bi-monthly, monthly, or bi-weekly). In some embodiments, the first and second nucleic acid vectors are administered simultaneously (e.g., in one composition). In some embodiments, the first and second nucleic acid vectors are administered sequentially (e.g., the second nucleic acid vector is administered immediately after the first nucleic acid vector, or 5 minutes, 10 minutes, 15 minutes, 20 minutes, 25 minutes, 30 minutes, 45 minutes, 1 hour, 2 hours, 8 hours, 12 hours, 1 day, 2 days, 7 days, two weeks, 1 month or more after the first nucleic acid vector). The first and second nucleic acid vector can have the same serotype or different serotypes (e.g., AAV serotypes).

Subjects that may be treated as described herein are subjects having or at risk of developing sensorineural hearing loss or auditory neuropathy. The compositions and methods described herein can be used to treat subjects having a mutation in OTOF (e.g., a mutation that reduces OTOF function or expression, or an OTOF mutation associated with sensorineural hearing loss), subjects having a family history of autosomal recessive sensorineural hearing loss or deafness (e.g., a family history of OTOF-related hearing loss), or subjects whose OTOF mutational status and/or OTOF activity level is unknown. The methods described herein may include a step of screening a subject for a mutation in OTOF prior to treatment with or administration of the compositions described herein. A subject can be screened for an OTOF mutation using standard methods known to those of skill in the art (e.g., genetic testing). The methods described herein may also include a step of assessing hearing in a subject prior to treatment with or administration of the compositions described herein. Hearing can be assessed using standard tests, such as audiometry, ABR, electrocochleography (ECOG), and otoacoustic emissions. The compositions and methods described herein may also be administered as a preventative treatment to patients at risk of developing hearing loss or auditory neuropathy, e.g., patients who have a family history of inherited hearing loss or patients carrying an OTOF mutation who do not yet exhibit hearing loss or impairment.

Treatment may include administration of a composition containing the nucleic acid vectors (e.g., AAV viral vectors) described herein in various unit doses. Each unit dose will ordinarily contain a predetermined-quantity of the therapeutic composition. The quantity to be administered, and the particular route of administration and formulation, are within the skill of those in the clinical arts. A unit dose need not be administered as a single injection but may include continuous infusion over a set period of time. Dosing may be performed using a syringe pump to control infusion rate in order to minimize damage to the cochlea. In cases in which the nucleic acid vectors are AAV vectors (e.g., AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, or PHP.S vectors), the viral vectors may be administered to the patient at a dose of, for example, from about $1\times10^{10}$ vector genomes (VG) to $1\times10^{15}$ VG (e.g., $1\times10^{10}$ VG, $2\times10^{10}$ VG, $3\times10^{10}$ VG, $4\times10^{10}$ VG, $5\times10^{10}$ VG, $6\times10^{10}$ VG, $7\times10^{10}$ VG, $8\times10^{10}$ VG, $9\times10^{10}$ VG, $1\times10^{11}$ VG, $2\times10^{11}$ VG, $3\times10^{11}$ VG, $4\times10^{11}$ VG, $5\times10^{11}$ VG, $6\times10^{11}$ VG, $7\times10^{11}$ VG, $8\times10^{11}$ VG, $9\times10^{11}$ VG, $1\times10^{12}$ VG, $2\times10^{12}$ VG, $3\times10^{12}$ VG, $4\times10^{12}$ VG, $5\times10^{12}$ VG, $6\times10^{12}$ VG, $7\times10^{12}$ VG, $8\times10^{12}$ VG, $9\times10^{12}$ VG, $1\times10^{13}$ VG, $2\times10^{13}$ VG, $3\times10^{13}$ VG, $4\times10^{13}$ VG, $5\times10^{13}$ VG, $6\times10^{13}$ VG, $7\times10^{13}$ VG, $8\times10^{13}$ VG, $9\times10^{13}$ VG, $1\times10^{14}$ VG, $2\times10^{14}$ VG, $3\times10^{14}$ VG, $4\times10^{14}$ VG, $5\times10^{14}$ VG, $6\times10^{14}$ VG, $7\times10^{14}$ VG, $8\times10^{14}$ VG, $9\times10^{14}$ VG, $1\times10^{15}$ VG) in a volume of 1 µL to 200 µL (e.g., 1, 2, 3, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200 µL).

The compositions described herein are administered in an amount sufficient to improve hearing, increase WT OTOF expression (e.g., expression in a cochlear hair cell, e.g., an inner hair cell), or increase OTOF function. Hearing may be evaluated using standard hearing tests (e.g., audiometry, ABR, electrocochleography (ECOG), and otoacoustic emissions) and may be improved by 5% or more (e.g., 5%, 10%, 15%, 20%, 30%, 40%, 50%, 60%, 70%, 80%, 90%, 100% or more) compared to hearing measurements obtained prior to treatment. In some embodiments, the compositions are administered in an amount sufficient to improve the subject's ability to understand speech. The compositions described herein may also be administered in an amount sufficient to slow or prevent the development or progression of sensorineural hearing loss or auditory neuropathy (e.g., in subjects who carry a mutation in OTOF or have a family history of autosomal recessive hearing loss but do not exhibit hearing impairment, or in subjects exhibiting mild to moderate hearing loss). OTOF expression may be evaluated using immunohistochemistry, Western blot analysis, quantitative real-time PCR, or other methods known in the art for detection protein or mRNA, and may be increased by 5% or more (e.g., 5%, 10%, 15%, 20%, 30%, 40%, 50%, 60%, 70%, 80%, 90%, 100% or more) compared to OTOF expression prior to administration of the compositions described herein. OTOF function may be evaluated directly (e.g., using electrophysiological methods or imaging methods to assess exocytosis) or indirectly based on hearing tests, and may be increased by 5% or more (e.g., 5%, 10%, 15%, 20%, 30%, 40%, 50%, 60%, 70%, 80%, 90%, 100% or more) compared to OTOF function prior to administration of the compositions described herein. These effects may occur, for example, within 1 week, 2 weeks, 3 weeks, 4 weeks, 5 weeks, 6 weeks, 7 weeks, 8 weeks, 9 weeks, 10 weeks, 15 weeks, 20 weeks, 25 weeks, or more, following administration of the compositions described herein. The patient may be evaluated 1 month, 2 months, 3 months, 4 months, 5 months, 6 months or more following administration of the composition depending on the dose and route of administration used for treatment. Depending on the outcome of the evaluation, the patient may receive additional treatments.

Kits

The compositions described herein can be provided in a kit for use in treating sensorineural hearing loss or auditory neuropathy (e.g., hearing loss associated with a mutation in OTOF). Compositions may include nucleic acid vectors described herein (e.g., a first nucleic acid vector containing a polynucleotide that encodes and N-terminal portion of an OTOF protein and a second nucleic acid vector containing a polynucleotide that encodes a C-terminal portion of an OTOF protein), optionally packaged in an AAV virus capsid (e.g., AAV1, AAV9, Anc80L65, DJ/9, or 7m8). The kit can further include a package insert that instructs a user of the kit, such as a physician, to perform the methods described herein. The kit may optionally include a syringe or other device for administering the composition.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1: Generation of Nucleic Acid Vectors that Recombine to Produce Full-Length OTOF Gene fragments were synthesized and sub-cloned into an AAV2/cis-plasmid using restriction enzyme sites. Plasmids were maxi prepped to generate 1 mg of transfection grade plasmid. Inner ear-derived HEI-OC1 cells were seeded into a 12-well tissue culture dish 24 hours before plasmid transfection at a density of 200,000 cells/well. One microgram of each plasmid was transfected using Lipofectamine 3000 according to standard manufacturer's protocol. For wells that received both 5' and 3' plasmids, 1 µg of each was transfected for a total of 2 µg of DNA. As a positive control, full-length Otoferlin cDNA was also transfected. Cells were incubated with plasmid for 48 hours.

For PCR to check for recombination at the DNA level, genomic DNA was extracted from each well using Qiagen's DNeasy Blood and Tissue kit, according to standard manufacturer's protocol. PCR primers were designed to anneal to the plasmid outside of the region of overlap or splicing to generate an amplicon of ~1200 bp. PCR was performed using My Taq 2× mastermix according to manufacturer's recommendations: annealing temperature of 58° C., elongation step of 30 seconds, and cycle number of 35×. Ten microliters of PCR product was run on a pre-cast 1.2% agarose E-gel and imaged on a BioRad gel doc imaging station. Both dual hybrid vectors (FIG. 20A) and overlapping vectors (FIG. 20B) showed evidence of recombination when the 5' and 3' plasmids were transfected together.

For immunofluorescence to check for recombination and generation of protein, cells were fixed with cold 4% PFA for 20 minutes at room temperature. Cells were washed three times with PBS and then permeabilized in a blocking solution of PBS with 10% normal donkey serum and 0.01% TritonX100. Cells were incubated in primary antibody overnight (mouse-anti-Otoferlin, Abcam ab53233) at a concentration of 1:1000 at 4° C. Cells were washed three times with PBS and incubated in secondary antibody for three hours at room temperature (donkey-anti-mouse Alexa Fluor 647, ThermoFisher A-31571). Cells were washed three times in PBS and stained with DAPI for 15 minutes at room temperature. Cells were imaged using a Zeiss inverted Apotome microscope. Increased staining was observed in cells transfected with both 5' and 3' plasmids compared to transfection of the 5' or 3' plasmid alone, indicating that the dual hybrid vector (FIG. 21A), trans-splicing vector (FIG. 21B), and overlapping vector (FIG. 21C) systems recombined in HEI-OC1 cells and generated OTOF protein.

Example 2: Administration of a Composition Containing Dual Hybrid Vectors that Express OTOF to Mice Restores Electrophysiological Signatures of Hearing Function Homozygous (HOM) OTOF-Q828X mice (a mouse model of human OTOF mutation p.Gln828Ter) were either left untreated or treated (by injection through the round window membrane) with 4E10 ($4 \times 10^{10}$) vector genomes (vg)/ear of an AAV1-Myo15 (SEQ ID NO: 38)-hOTOF (isoform 5, SEQ ID NO: 5) dual hybrid vector system in which exons 1-20 of the polynucleotide encoding the N-terminal portion of the OTOF protein and exons 21-46 and 48 of the polynucleotide encoding the C-terminal portion of the OTOF protein were delivered in separate vectors (FIG. 22A). An AP recombinogenic region (SEQ ID NO: 65) was included in both vectors of the dual hybrid vector system. Auditory brainstem response (ABR) thresholds were used to assess hearing function. Untreated animals (untreated Otof HOM) showed no detectable recovery in hearing function, whereas treated animals exhibited a robust recovery, which was consistent from four weeks post-treatment (Otof HOM at 4 weeks after treatment) to eight weeks post-treatment (Otof HOM at 8-11 weeks after treatment). ABR thresholds in heterozygous animals (Otof HET) were also tested.

In a separate set of experiments, homozygous OTOF-Q828X mice were either left untreated or treated (by injection through the round window membrane) with 4E10 ($4 \times 10^{10}$) vg/ear of an AAV1-truncated chimeric CMV-chicken β-actin (smCBA)-hOTOF (isoform 5, SEQ ID NO: 5) dual hybrid vector system as described above (FIG. 22B). The first vector contained exons 1-20 of the polynucleotide encoding the N-terminal portion of the OTOF protein and exons 21-46 and 48 of the polynucleotide encoding the C-terminal portion of the OTOF protein and both vectors contained an AP recombinogenic region (SEQ ID NO: 65). Untreated animals had no detectable recovery in hearing function, whereas treated animals exhibited a robust recovery at 4 weeks post-treatment (Otof HOM at 4 weeks after treatment). When these same animals were evaluated at 8 weeks post-treatment (Otof HOM at 8 weeks after treatment), ABR thresholds increased, suggesting less durable recovery with the smCBA promoter. ABR thresholds in heterozygous animals were also tested.

In yet another set of experiments, homozygous OTOF-Q828X mice were either left untreated or treated (by injection through the round window membrane) with an AAV1-smCBA-hOTOF (isoform 5, SEQ ID NO: 5) dual hybrid vector, as described above, at either 8E9 ($8 \times 10^9$) vg/ear (low dose), 1.6E10 ($1.6 \times 10^{10}$) vg vg/ear (mid dose), or 6.4E10 ($6.4 \times 10^{10}$) vg/ear (high dose). The first vector contained exons 1-20 of the polynucleotide encoding the N-terminal portion of the OTOF protein and exons 21-46 and 48 of the polynucleotide encoding the C-terminal portion of the OTOF protein and both vectors contained an AP recombinogenic region (SEQ ID NO: 65). ABR thresholds were used to assess hearing function at four weeks and eight weeks post-treatment (FIG. 22C). A dose-dependent recovery in ABR was observed at both timepoints. When comparing the eight weeks versus the four weeks timepoint, recovery of hearing function was steady for the low and mid doses but decreased for the high dose animals. ABR thresholds in heterozygous animals were also tested.

Example 3: Administration of a Composition Containing Overlapping Dual Vectors that Express OTOF to a Subject with Sensorineural Hearing Loss According to the methods disclosed herein, a physician of skill in the art can treat a patient, such as a human patient, with sensorineural hearing loss (e.g., sensorineural hearing loss associated with a mutation in OTOF) so as to improve or restore hearing. To this end, a physician of skill in the art can administer to the human patient a composition containing a first AAV vector (e.g., AAV1 or AAV9) containing a Myo15 promoter (e.g., SEQ ID NO: 36) operably linked to exons 1-21 of a polynucleotide encoding an OTOF protein (e.g., human OTOF, e.g., SEQ ID NO: 1 or SEQ ID NO: 5) and the 500 kb immediately 3' of the exon 21/22 boundary, and a second AAV vector (e.g., AAV1 or AAV9) containing the 500 kb immediately 5' of the exon 21/22 boundary and exons 22-48 of a polynucleotide encoding an OTOF protein (e.g., human OTOF, e.g., SEQ ID NO: 1 or SEQ ID NO: 5) and a bGH poly(A) sequence. The composition containing the overlapping dual AAV vectors may be administered to the patient, for example, by local administration to the inner ear (e.g., injection into the perilymph), to treat sensorineural hearing loss.

Following administration of the composition to a patient, a practitioner of skill in the art can monitor the expression of OTOF, and the patient's improvement in response to the therapy, by a variety of methods. For example, a physician can monitor the patient's hearing by performing standard tests, such as audiometry, ABR, electrocochleography (ECOG), and otoacoustic emissions following administration of the composition. A finding that the patient exhibits improved hearing in one or more of the tests following administration of the composition compared to hearing test results prior to administration of the composition indicates that the patient is responding favorably to the treatment. Subsequent doses can be determined and administered as needed.

Example 4: Administration of a Composition Containing Trans-Splicing Dual Vectors that Express OTOF to a Subject with Sensorineural Hearing Loss According to the methods disclosed herein, a physician of skill in the art can treat a patient, such as a human patient, with sensorineural hearing loss (e.g., sensorineural hearing loss associated with a mutation in OTOF) so as to improve or restore hearing. To this end, a physician of skill in the art can administer to the human patient a composition containing a first AAV vector (e.g., AAV1 or AAV9) containing a Myo15 promoter (e.g., SEQ ID NO: 36) operably linked to exons 1-19 of a polynucleotide encoding an OTOF protein (e.g., human OTOF, e.g., SEQ ID NO: 1 or SEQ ID NO: 5) and a splice donor sequence (e.g., SEQ ID NO: 20 or SEQ ID NO: 68) 3' of the polynucleotide sequence, and a second AAV vector (e.g., AAV1 or AAV9) containing a splice acceptor sequence (e.g., SEQ ID NO: 21 or SEQ ID NO: 69) 5' of exons 20-48 of a polynucleotide encoding an OTOF protein (e.g., human OTOF, e.g., SEQ ID NO: 1 or SEQ ID NO: 5) and a bGH poly(A) sequence. The composition containing the trans-splicing dual AAV vectors may be administered to the patient, for example, by local administration to the inner ear (e.g., injection into the perilymph), to treat sensorineural hearing loss.

Following administration of the composition to a patient, a practitioner of skill in the art can monitor the expression of OTOF, and the patient's improvement in response to the therapy, by a variety of methods. For example, a physician can monitor the patient's hearing by performing standard tests, such as audiometry, ABR, electrocochleography (ECOG), and otoacoustic emissions following administration of the composition. A finding that the patient exhibits improved hearing in one or more of the tests following administration of the composition compared to hearing test results prior to administration of the composition indicates that the patient is responding favorably to the treatment. Subsequent doses can be determined and administered as needed.

Example 5: Administration of a Composition Containing Dual Hybrid Vectors that Express OTOF to a Subject with Sensorineural Hearing Loss According to the methods disclosed herein, a physician of skill in the art can treat a patient, such as a human patient, with sensorineural hearing loss (e.g., sensorineural hearing loss associated with a mutation in OTOF) so as to improve or restore hearing. To this end, a physician of skill in the art can administer to the human patient a composition containing a first AAV vector (e.g., AAV1 or AAV9) containing a Myo15 promoter (e.g., SEQ ID NO: 36) operably linked to exons 1-19 of a polynucleotide encoding an OTOF protein (e.g., human OTOF, e.g., SEQ ID NO: 1 or SEQ ID NO: 5), a splice donor sequence (e.g., SEQ ID NO: 20 or SEQ ID NO: 68) 3' of the polynucleotide sequence, and an F1 phage recombinogenic region (e.g., an F1 phage AK gene, SEQ ID NO: 19) 3' of the splice donor sequence, and a second nucleic acid vector containing an F1 phage recombinogenic region (e.g., an F1 phage AK gene, SEQ ID NO: 19), a splice acceptor sequence (e.g., SEQ ID NO: 21 or SEQ ID NO: 69) 3' of the recombinogenic region, a polynucleotide 3' of the splice acceptor sequence that contains exons 20-48 of a polynucleotide encoding an OTOF protein (e.g., human OTOF, e.g., SEQ ID NO: 1 or SEQ ID NO: 5), and a bGH poly(A) sequence. The first and second dual hybrid AAV vectors can optionally include a degradation signal sequence (e.g., SEQ ID NO: 22) positioned 3' of the recombinogenic region in the first nucleic acid vector, and positioned between the recombinogenic region and the splice acceptor sequence in the second nucleic acid vector. The composition containing the dual hybrid AAV vectors may be administered to the patient, for example, by local administration to the inner ear (e.g., injection into the perilymph), to treat sensorineural hearing loss.

Following administration of the composition to a patient, a practitioner of skill in the art can monitor the expression of OTOF, and the patient's improvement in response to the therapy, by a variety of methods. For example, a physician can monitor the patient's hearing by performing standard tests, such as audiometry, ABR, electrocochleography (ECOG), and otoacoustic emissions following administration of the composition. A finding that the patient exhibits improved hearing in one or more of the tests following administration of the composition compared to hearing test results prior to administration of the composition indicates that the patient is responding favorably to the treatment. Subsequent doses can be determined and administered as needed.

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. Other embodiments are in the claims.

The invention claimed is:

1. A dual vector system comprising:
a first nucleic acid vector comprising a myosin 15 (Myo15) promoter operably linked to a first coding polynucleotide that encodes an N-terminal portion of an otoferlin (OTOF) protein; and
a second nucleic acid vector comprising a second coding polynucleotide that encodes a C-terminal portion of an OTOF protein and a polyadenylation (poly(A)) sequence positioned at a 3' end of the second coding polynucleotide;
wherein the Myo15 promoter has at least 95% sequence identity to SEQ ID NO: 38, wherein neither the first nor second nucleic acid vector encodes a full-length OTOF protein, and, when introduced into a mammalian cell, the first and second nucleic acid vectors undergo homologous recombination or concatemerization to form a recombined nucleic acid that encodes a full-length OTOF protein.

2. The dual vector system of claim 1, wherein
the first nucleic acid vector further comprises a splice donor signal sequence positioned at a 3' end of the first coding polynucleotide; and
the second nucleic acid vector further comprises a splice acceptor signal sequence positioned 5' of the second coding polynucleotide;
wherein the first coding polynucleotide and the second coding polynucleotide do not overlap.

3. The dual vector system of claim 2, wherein
the first nucleic acid vector further comprises a first recombinogenic region positioned 3' of the splice donor signal sequence; and
the second nucleic acid vector further comprises a second recombinogenic region positioned 5' of the splice acceptor signal sequence positioned.

4. The dual vector system of claim 3, wherein the first and second recombinogenic regions have the same nucleic acid sequence.

5. The dual vector system of claim 1, wherein the first and second nucleic acid vectors are adeno-associated virus (AAV) vectors.

6. The dual vector system of claim 1, wherein the first and second coding polynucleotides that encode the OTOF protein do not comprise introns.

7. The dual vector system of claim 1, wherein the Myo15 promoter has the sequence of SEQ ID NO: 38.

8. The dual vector system of claim 3, wherein each of the first and second recombinogenic regions is an AP gene fragment or an F1 phage AK gene.

9. The dual vector system of claim 1, wherein the OTOF protein is a human OTOF protein.

10. The dual vector system of claim 5, wherein the first and second nucleic acid vectors comprise an inverted terminal repeat (ITR) at each end of the nucleic acid sequence.

11. The dual vector system of claim 10, wherein the ITR is an AAV2 ITR.

12. The dual vector system of claim 1, wherein the poly(A) sequence is a bovine growth hormone (bGH) poly(A) signal sequence.

13. The dual vector system of claim 7, wherein the OTOF protein is a human OTOF protein.

14. The dual vector system of claim 13, wherein the first and second coding polynucleotides that encode the OTOF protein do not comprise introns.

15. The dual vector system of claim 14, wherein
the first nucleic acid vector further comprises a splice donor signal sequence positioned at a 3 'end of the first coding polynucleotide; and
the second nucleic acid vector further comprises a splice acceptor signal sequence positioned 5' of the second coding polynucleotide;
wherein the first coding polynucleotide and the second coding polynucleotide do not overlap.

16. The dual vector system of claim 15, wherein
the first nucleic acid vector further comprises a first recombinogenic region positioned 3' of the splice donor signal sequence; and
the second nucleic acid vector further comprises a second recombinogenic region positioned 5' of the splice acceptor signal sequence positioned.

17. The dual vector system of claim 16, wherein the first and second recombinogenic regions have the same nucleic acid sequence.

18. The dual vector system of claim 17, wherein each of the first and second recombinogenic regions is an AP gene fragment or an F1 phage AK gene.

19. The dual vector system of claim 16, wherein the first and second nucleic acid vectors are adeno-associated virus (AAV) vectors.

* * * * *